(12) United States Patent
Lin et al.

(10) Patent No.: US 11,135,306 B2
(45) Date of Patent: Oct. 5, 2021

(54) ANTIBODY-DRUG CONJUGATES

(71) Applicant: CHO Pharma Inc., Taipei (TW)

(72) Inventors: Nan-Horng Lin, Vernon Hills, IL (US); Charng-Sheng Tsai, Taipei (TW); Ting-Chun Hung, Taipei (TW); Hong-Yang Chuang, Taipei (TW)

(73) Assignee: CHO PHARMA INC., Taipei (TW)

( * ) Notice: Subject to any disclaimer, the term of this patent is extended or adjusted under 35 U.S.C. 154(b) by 47 days.

(21) Appl. No.: 15/812,811

(22) Filed: Nov. 14, 2017

(65) Prior Publication Data

US 2018/0133340 A1 May 17, 2018

Related U.S. Application Data

(60) Provisional application No. 62/421,429, filed on Nov. 14, 2016.

(51) Int. Cl.
| | |
|---|---|
| *A61K 47/68* | (2017.01) |
| *A61K 47/61* | (2017.01) |
| *A61K 47/54* | (2017.01) |
| *A61K 31/40* | (2006.01) |
| *A61P 35/00* | (2006.01) |
| *A61K 38/08* | (2019.01) |
| *C07K 16/32* | (2006.01) |

(52) U.S. Cl.
CPC .......... *A61K 47/6889* (2017.08); *A61K 31/40* (2013.01); *A61K 38/08* (2013.01); *A61K 47/542* (2017.08); *A61K 47/545* (2017.08); *A61K 47/549* (2017.08); *A61K 47/61* (2017.08); *A61K 47/6803* (2017.08); *A61K 47/6807* (2017.08); *A61K 47/6849* (2017.08); *A61K 47/6855* (2017.08); *A61K 47/6863* (2017.08); *A61P 35/00* (2018.01); *C07K 16/32* (2013.01); *C07K 2317/24* (2013.01); *C07K 2317/41* (2013.01); *C07K 2317/92* (2013.01)

(58) Field of Classification Search
None
See application file for complete search history.

(56) References Cited

PUBLICATIONS

Remon van Geel et al., Bioconjugate Chem. 2015, 26, 2233-2242 (Year: 2015).*
Parsons et al., Angew.Chem. Int.Ed. 2016, 55, 2361-2367 (Year: 2016).*
Tang et al., Org. Biomol. Chem., 2016, 14, 9501-9518 (Year: 2016).*

* cited by examiner

*Primary Examiner* — Karl J Puttlitz

(57) ABSTRACT

An antibody-drug conjugate (ADC) has a structure represented by Formula (I):

$$[D_2\text{-}L_2\text{-}Cn_2]_y\text{-}G_2\text{-}Ab\text{-}Sg_1\text{-}[G_1\text{-}L_1\text{-}D_1]_x \qquad \text{Formula (I)}$$

or a pharmaceutically acceptable salt thereof, wherein
Ab is an antibody without glycans (i.e., the protein portion of an antibody);
$G_1$ and $G_2$ are glycan moieties, which may be the same or different;
$Cn_1$ and $Cn_2$ are conjugation moieties, which may be the same or different;
$L_1$ and $L_2$ are linker moieties, which may be the same or different;
$D_1$ and $D_2$ are drug units which may be the same or different; and
x and y are independently an integer from 0 to 8, provided that x+y≠0.

8 Claims, 7 Drawing Sheets

Figure 2
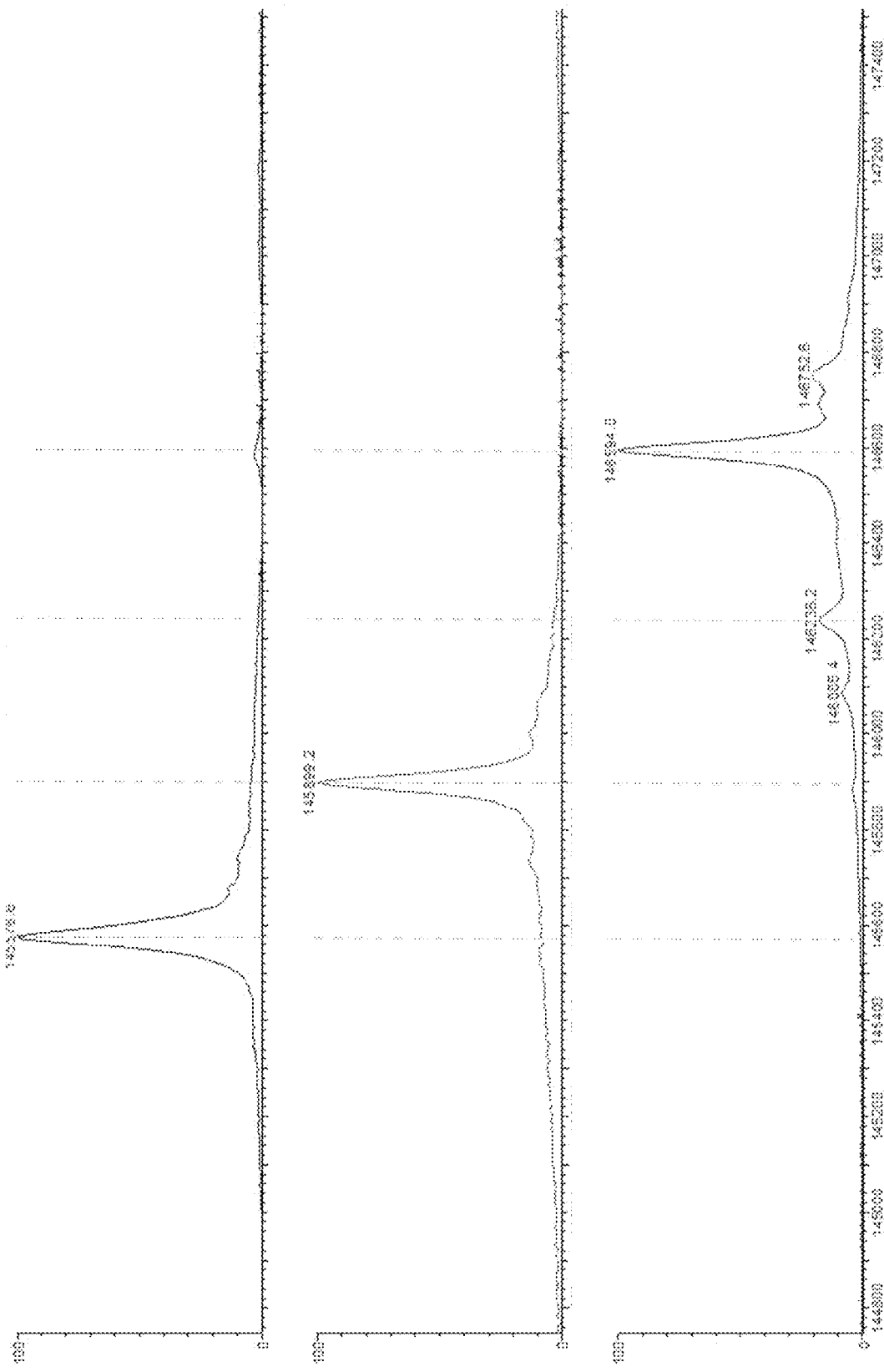

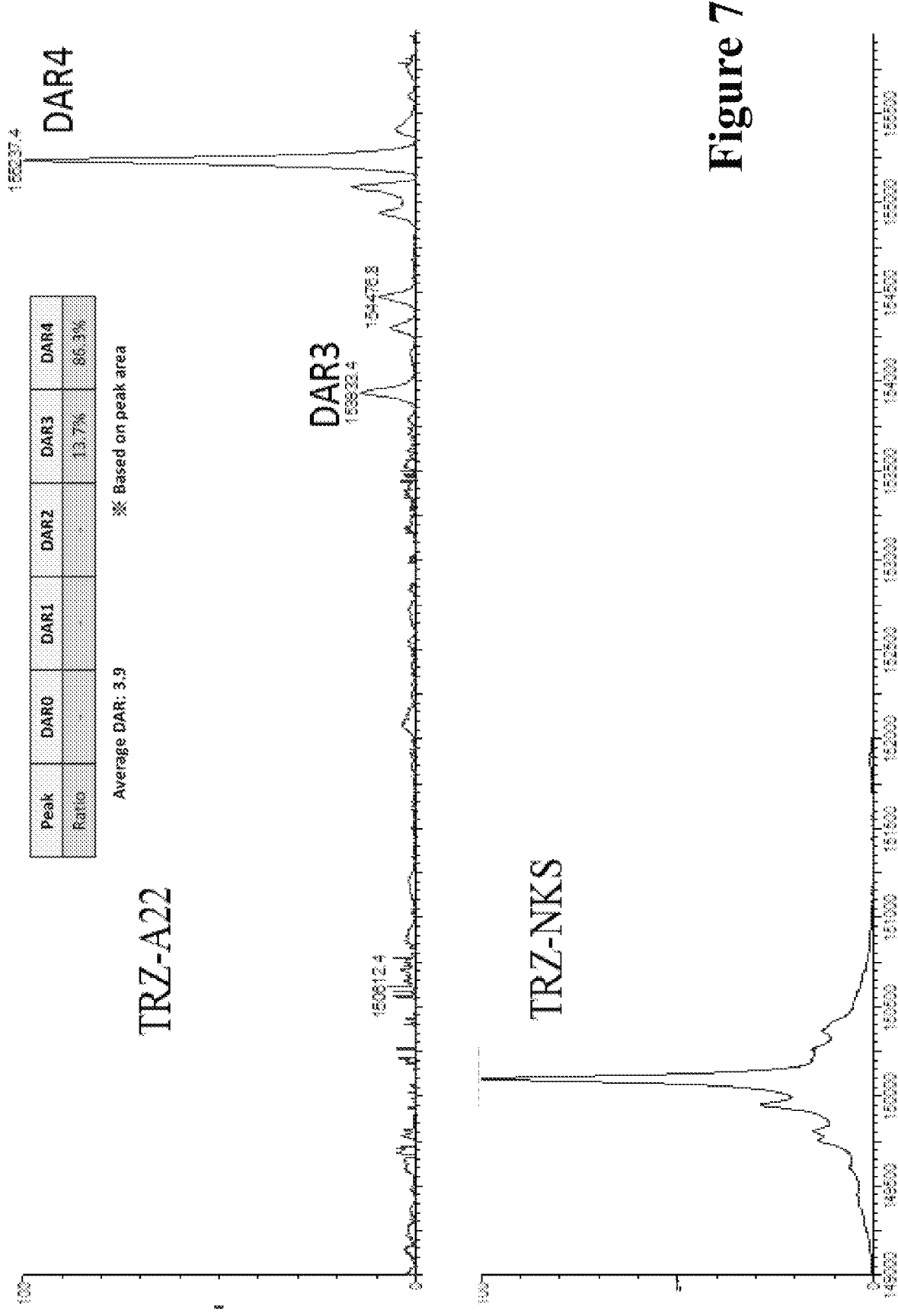

ANTIBODY-DRUG CONJUGATES

CROSS REFERENCE TO RELATED APPLICATIONS

This application claims the benefit of Provisional Application No. 62/421,429, filed on Nov. 14, 2016, the disclosure of which is incorporated by reference in its entirety.

BACKGROUND OF INVENTION

Field of the Invention

The present invention relates to antibody-drug conjugates (ADC), particularly to ADCs in which the drug moieties are site-specifically linked to the antibodies via glycans.

Background Art

Antibody-drug conjugates (ADCs) can provide targeted therapy to treat various diseases or conditions, such as cancer. ADCs are complex molecules comprising antibodies linked to biologically active agents, such as cytotoxic agents or drugs. By combining unique targeting of the antibodies with the therapeutic effects of the drugs, antibody-drug conjugates can distinguish between normal and cancer cells, thereby minimizing the side effects.

ADC typically comprises an anticancer drug (e.g. a cytotoxin) coupled to an antibody that specifically targets a marker, e.g., a tumor marker. Antibodies track these proteins down in the body and attach themselves to the surface of cancer cells. The biochemical reaction between the antibody and the target protein (antigen) triggers a signal in the tumor cell, which then internalizes the ADC. After the ADC is internalized, the cytotoxic drug is released and kills the cancer. Due to this targeting, the drug has lower side effects.

A stable link between the antibody and cytotoxic (anti-cancer) agent is important for ADC. Linkers may be cleavable or non-cleavable. With a non-cleavable linker, the entire antibody, linker and cytotoxic (anti-cancer) agent enters the targeted cancer cell where the antibody may be degraded and the cytotoxic agent is released inside the cells. In contrast, with cleavable linkers, the cytotoxic agent may be released outside the target cells, which may result in "bystander killing" of the neighboring cancer cells.

In early development of ADCs, a range of conjugated chemistries have been explored. The drug moieties are often attached to the lysine or cysteine side-chains of the antibodies in a non-selective manner. As a result of the non-selective conjugation, the ADCs typically contain mixtures of molecules that can have different drug-antibody ratios, leading to different pharmacokinetic profiles.

More recent biotechnological advancements allow site-specific conjugation sites to fix the number and precise location of attachment of linkers and cytotoxic payloads. This approach involves, for example, thio-engineered antibodies or other similar antibodies with engineered binding sites.

An alternative approach that provides site-specific attachments is to attach the payload to the glycan moieties of the antibodies. Even though this approach can provide site-specific attachments, it may not produce homogeneous ADCs due to heterogeneity of the glycan moieties on the antibodies.

A typical IgG contains N-glycans at Asn297 of Fc domain. The N-linked glycans are typically a biantennary complex type with considerable structural heterogeneities, in which the core pentasaccharides can be differentially decorated with core fucose (Fuc), bisecting N-acetyl glucosamine (GlcNAc), terminal galactose (Gal), and terminal sialic acid (Sia). The compositions of N-glycans could influence the Fc domain conformations, thereby modulating the properties of an antibody, such as stability, immunogenicity, effector functions, antibody-mediated inflammation, and complement activation.

The site-specific ADC formation based on the heterogeneous glycan results in the highly variable drug antibody ratio (DAR) and pharmacokinetic profile. Thus, there is a need for better approaches to site-specific antibody-drug conjugates that are substantially homogeneous in composition.

SUMMARY OF INVENTION

Embodiments of the present invention relate to antibody-drug conjugates that use glycan moieties for the attachments of the payloads. The glycan of the antibodies may be modified to be substantially homogeneous. Such glycan modifications may use endoglycosidases. For example, the glycans on native antibodies may be trimmed with glycosidases down to one or several glycan residues. Then, glycans having defined structures may be coupled on the remaining glycan residues to produce antibodies having substantially homogeneous glycan structures. These antibodies are then used for the preparation of ADCs.

ADCs of the invention are substantially homogeneous. They will have favorable properties in the manufacturing, quality control, and in vivo pharmacokinetic profiles (especially, for designing and monitoring the dosing regimen).

Due to unique preparation processes, embodiments of the invention have relatively high average DAR numbers. In accordance with embodiments of the invention, the average DAR numbers of antibodies with two biantennary glycans are 3.0 or higher. In contrast, those in the prior art are typically 2.0 or less. The average DAR numbers of antibodies with two monoantennary glycans are 1.5~2.0. The high average DAR numbers mean each antibody molecule carries more payload, and the ADCs of the invention would be more efficacious as therapeutic agents, as evidenced by the tests set forth in this description. In addition, ADCs of the invention are more cost effective because smaller amounts of antibodies are needed to achieve the same payload delivery. Because antibody drugs are expensive, this can save patients substantial amounts in treatment costs.

In accordance with embodiments of the invention, the glycan moiety having a defined structure may be coupled with a linker-drug moiety prior to conjugation with the trimmed antibodies. Alternatively, the glycan moiety having a defined structure may be conjugated with the trimmed antibody first, which is then further conjugated with a linker-drug moiety.

In accordance with some embodiments of the invention, the "linker-drug" moiety may not be formed prior to conjugation with the glycan moiety. Instead, the linker may be first linked to the glycan moiety, followed by attachment of the drug moiety to the resulting products.

In accordance with embodiments of the invention, an antibody-drug conjugate (ADC) may have a structure represented by Formula (I):

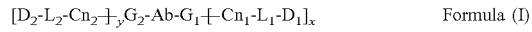

Formula (I)

or a pharmaceutically acceptable salt thereof, wherein
Ab is an antibody without glycans (i.e., the protein portion of an antibody);

G₁ and G₂ are glycan moieties, which may be the same or different;

Cn₁ and Cn₂ are conjugation moieties, which may be the same or different;

L₁ and L₂ are linker moieties, which may be the same or different;

D₁ and D₂ are drug units, which may be the same or different; and x and y are independently an integer from 0 to 8, provided that x+y≠0.

In accordance with some embodiments of the invention, the antibody in the ADC binds to a target selected from the group consisting of CD19, CD22, CD27, CD30, CD33, CD37, CD56, CD70, CD74, CD79b, CD138, CD142, CA6, p-Cadherin, CEACAM5, C4.4a, DLL3, EGFR, EGFRVIII, ENPP3, EphA2, EphrinA, FLOR1, FGFR2, GCC, HER2, cKIT, LIV1, MSLN, MUC16, NaPi2b, Nectin4, gpNMB, PSMA, SLITRK6, STEAP1, TROP2, 5T4, SSEA4, GloboH, Gb5, STn and Tn.

In accordance with some embodiments of the invention, the glycan moiety may be selected from the group consisting of di-, tri-, tetra-, penta-, hexyl-, hepta-, octyl-, nona-, deca- and undeca-saccharide In accordance with preferred embodiments of the invention, the glycan moiety may have a structure shown as Formula (II-1a) or Formula (II-2a):

wherein $R_{N1a}$, $R_{N1b}$, $R_{N2a}$, and $R_{N2b}$ are independently selected from the group consisting of hydrogen, optionally substituted C1-C6 alkyl, optionally substituted C1-C6 acyl, and a nitrogen protecting group, wherein the nitrogen protecting group can be any suitable protecting group known in the art, such as isotertbutyloxycarboxy group (t-BOC), 9-fluorenylmethoxycarbonyl group (Fmoc), benzyl group (Bn), benzyloxycarbonyl group (Cbz), allyloxycarbonyl group (Aloc), 2-(trimethylsilyl)ethoxycarbonyl group (Teoc), 2,2,2-trichloroethoxycarbonyl (Troc), diphenylmethyl group (Dpm), trityl group (Tr), 9-phenylfluorenyl group (PhFI), and p-methoxybenzyl group (PMB);

[Ab] indicates the attachment site for the antibody;

[Cn] indicated the attachment site for the conjugation moiety.

In accordance with preferred embodiments of the invention, the glycan moiety may have a structure shown as Formula (II-1b) or Formula (II-2b):

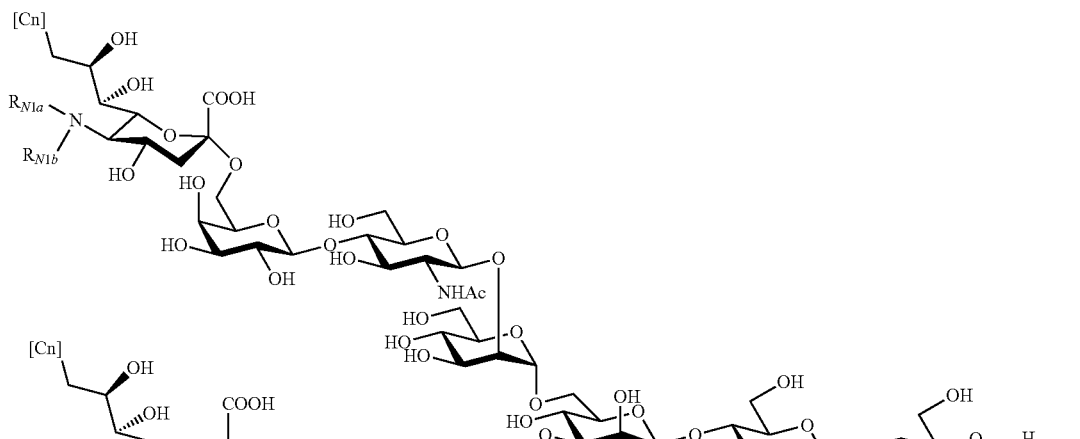

Formula (II-1a)

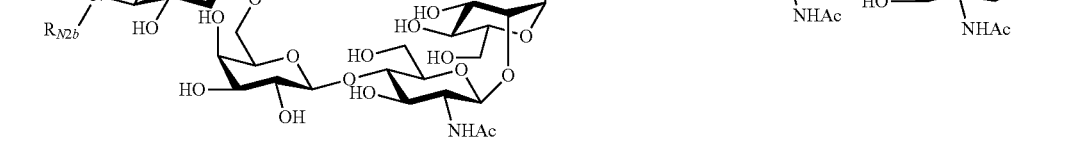

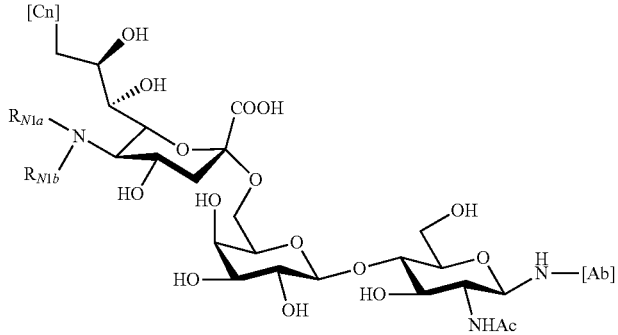

Formula (II-2a)

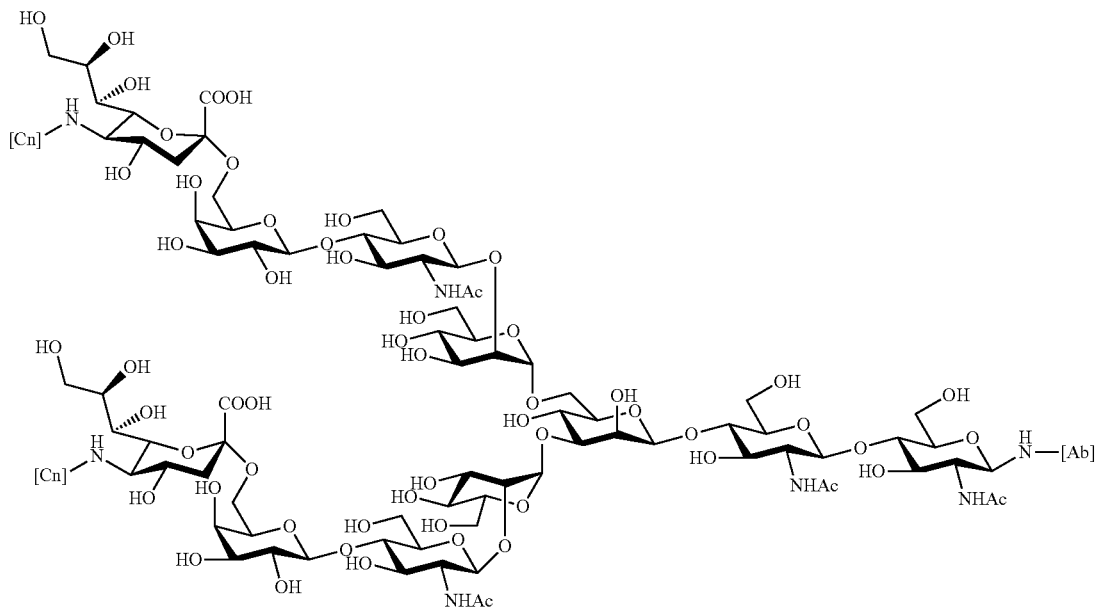

Formula (II-1b)

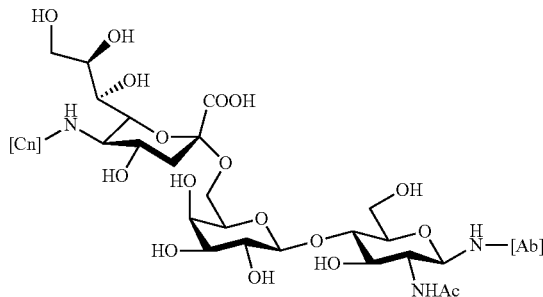

Formula (II-2b)

wherein

[Ab] indicates the attachment site for the antibody;

[Cn] indicates the attachment site for the conjugation moiety;

In accordance with some embodiments of the invention, the conjugation moiety may be selected from the group consisting of the structures of Formula (III-1), Formula (III-2a), Formula (III-2b), Formula (III-2c), Formula (III-2d), Formula (III-3), Formula (III-4a), Formula (III-4b), Formula (III-4c), and Formula (III-4d):

Formula (III-1)

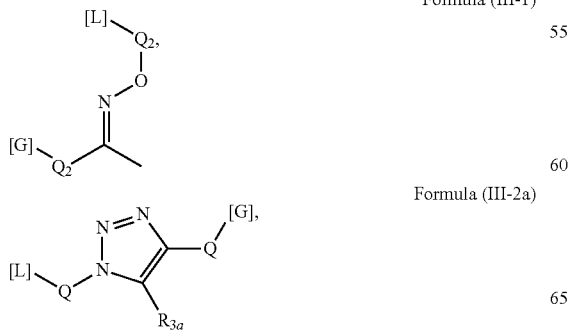

Formula (III-2a)

-continued

Formula (III-2b)

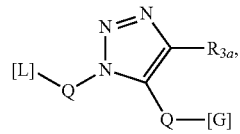

Formula (III-2c)

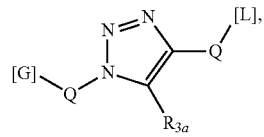

Formula (III-2d)

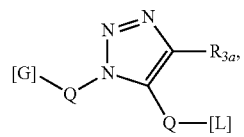

-continued

Formula (III-3)

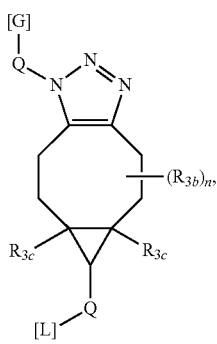

Formula (III-4a)

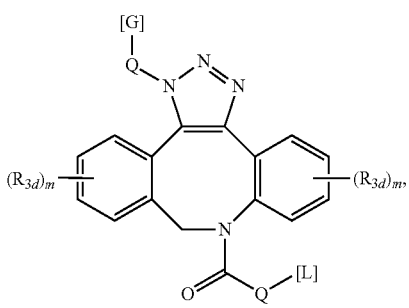

Formula (III-4b)

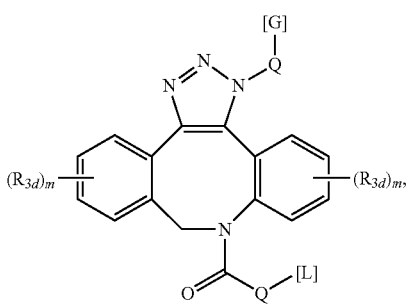

Formula (III-4c)

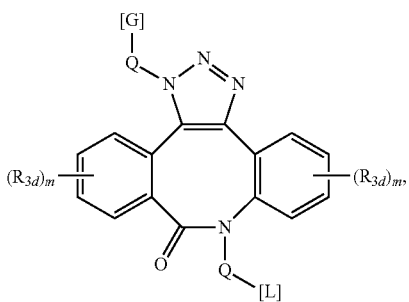

Formula (III-4d)

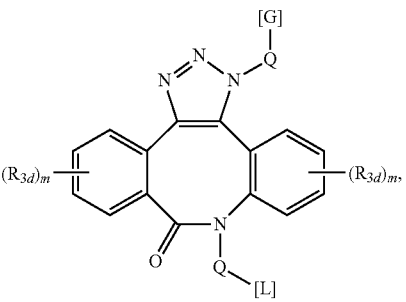

wherein each of Q, $Q_1$ and $Q_2$ is a Y1+Y2 spacer, wherein Y1 and Y2 are independently selected from the group consisting of a direct bond, —$(CH_2)_n$—, —O—, —NH—, —C(O)—, —C(O)NH—, —NHC(O)—, —$(CH_2)_nO$—, —$O(CH_2)_n$—, —$(CH_2)_n$—C(O)—, —C(O)$(CH_2)_n$—, —$(CH_2)_n$—NH—, —NH—$(CH_2)_n$—, —$(CH_2)_n$—NHC(O)—, —C(O)$(CH_2)_n$—NHC(O)—, $(CH_2)_nSCH_2C(O)$—, and —$(CH_2CH_2O)_n$—;

$R_{3a}$ is selected from the group consisting of hydrogen, halogen, C1-C6 alkyl group;

$R_{3b}$ is independently selected from the group consisting of hydrogen, halogen, —$NO_2$, and —CN, optionally substituted C1-C6 alkyl group, optionally substituted C1-C6 alkyoxy group, optionally substituted C1-C24 cycloalkyl group, optionally substituted C6-C24 aryl group, optionally substituted C7-C24 aralkyl group, optionally substituted C4-C24 heteroaryl group, optionally substituted C5-C24 heteroaralkyl group;

$R_{3c}$ is independently selected from the group consisting of hydrogen, halogen, optionally substituted C1-C6 alkyl group, optionally substituted C6-C24 aryl group, optionally substituted C7-C24 aralkyl group, optionally substituted C4-C24 heteroaryl group, and optionally substituted C5-C24 heteroaralkyl group;

$R_{3d}$ is independently selected from the group consisting of hydrogen, halogen, —OH, —$NO_2$, and —CN, optionally substituted C1-C6 alkyl group, optionally substituted C1-C6 alkyoxy group;

n is an integer from 1 to 8, inclusive;

m is an integer from 1 to 4, inclusive;

[G] indicates the attachment site for the glycan moiety;

[L] indicated the attachment site for the linker moiety.

In accordance with some embodiments of the invention, the "linker" may be a direct bond. That is, the drug is directly linked to a conjugation moiety without an intervening linker. In accordance with some embodiments of the invention, the linker may be cleavable or non-cleavable. Cleavable linkers, for example, may involve chemical bonds (e.g., esters or amides) that can hydrolyze/degrade or can be cleaved by enzymes in vivo. In accordance with some embodiments of the invention, the linker may be water-soluble or water-insoluble.

In accordance with preferred embodiments of the invention, the linker may be selected from the group consisting of the structure of Formula (IV-1), Formula (IV-2), Formula (IV-3), Formula (IV-4), and Formula (IV-5):

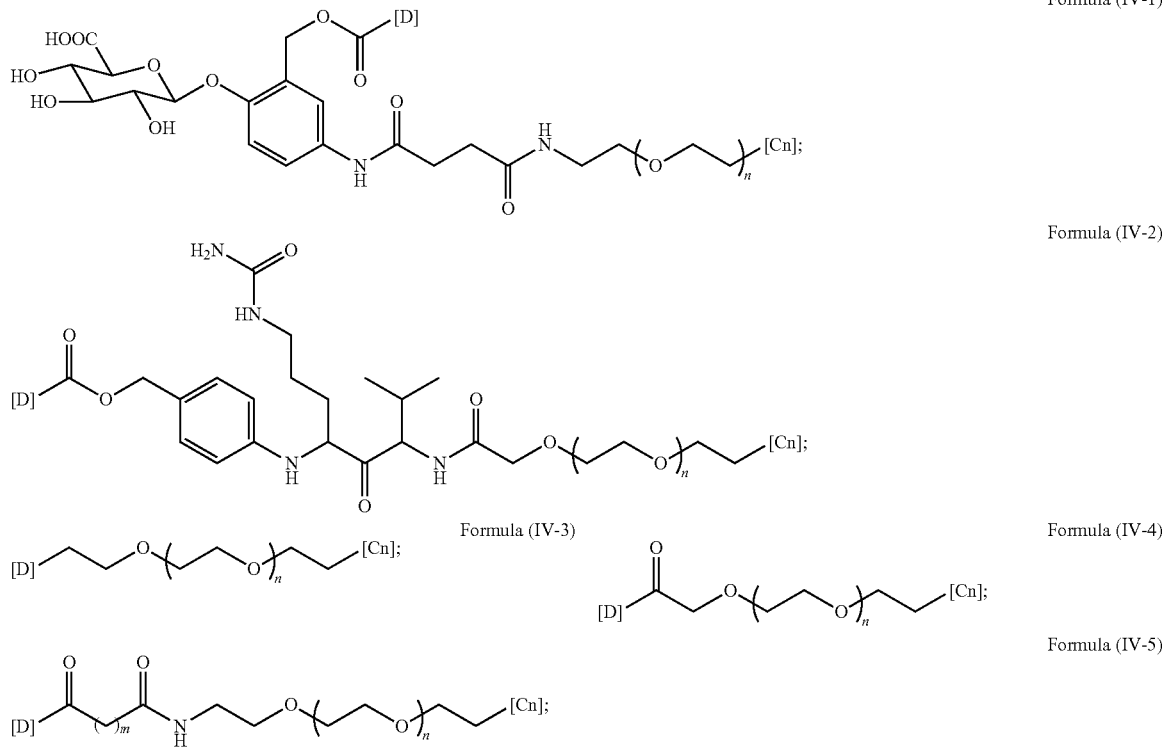

Formula (IV-1)

Formula (IV-2)

Formula (IV-3)

Formula (IV-4)

Formula (IV-5)

wherein

[Cn] indicated the attachment site for the conjugation moiety;

[D] indicates the attachment site for the drug unit;

and each instance of m and n is an integer from 0 to 6, inclusive.

In accordance with some embodiments of the invention, the drugs (payloads) may be selected from the group consisting of Monomethyl auristatin E (MMAE), Monomethyl auristatin F (MMAF), Monomethyl auristatin D (MMAD), Mertansine (Maytansinoid DM1/DM4), Paclitaxel, Docetaxel, Epothilone B, Epothilone A, CYT997, Auristatin tyramine phosphate, Auristatin aminoquinoline, Halocombstatins, Calicheamicin theta, 7-Ethyl-10-hydroxy-camptothecin (SN-38), Pyrrolobenzodiazepine (PBD), Pancratistatin, Cyclophosphate, Cribrostatin-6, Kitastatin, Turbostatin 1-4, Halocombstatins, Silstatins, Pretubulysin D, and Tubulysins (A, B, C, D, E, F, G, H, I, U, V, and Z).

One aspect of the invention relate to methods of using any one of the above ADCs as pharmaceutical compositions for treating cancers. In accordance with some embodiments of the invention, the cancers may be brain, lung, breast, oral, esophageal, stomach, liver, bile duct, pancreatic, colon, kidney, gastric, cervical, ovarian, or prostate cancer.

Other aspects and advantages of the invention will become apparent from the following description and the appended claims.

BRIEF DESCRIPTION OF THE DRAWINGS

FIG. 2 shows mass spectra of TRZ-N, TRZ-NG and TRZ-NGKS (glycoengineered Herceptin with two modified monoantennary glycans), in accordance with embodiments of the invention. Top panel: TRZ-N, Middle panel: TRZ-NG, Bottom panel: TRZ-NGKS.

FIG. 7 shows mass spectra profiles of TRZ-A22 and TRZ-NKS in accordance with embodiments of the invention. Top panel: TRZ-A22. Bottom panel: TRZ-NKS.

DETAILED DESCRIPTION OF THE INVENTION

Figure 6:
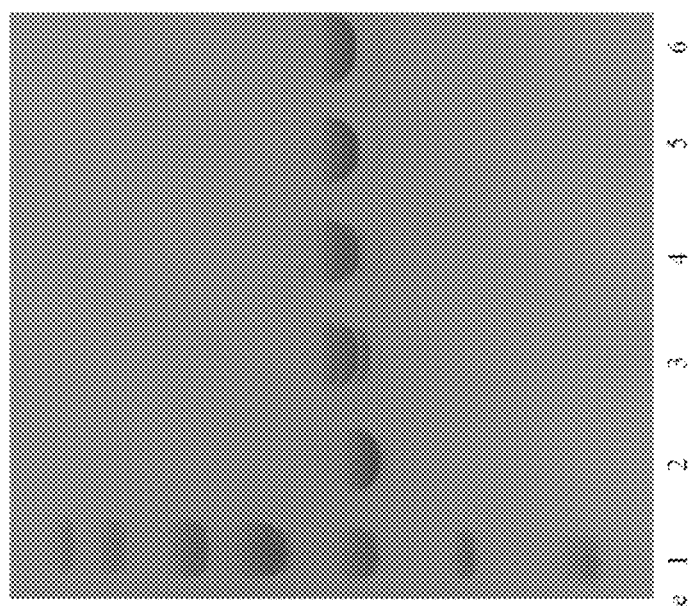
FIG. 6 shows SDS-PAGE profiles of time-dependent, site-specific ADCs formation in accordance with embodiments of the invention. Lane 1: Marker, Lane 2: TRZ-NKS, Lane 3: TRZ-A09 (reaction time: 15 min), Lane 4: TRZ-A09 (reaction time: 30 min), Lane 5: TRZ-A09 (reaction time: 60 min), Lane 6: TRZ-A09 (reaction time: 120 min).

Embodiments of the present invention relate to antibody-drug conjugates that use glycan moieties for the attachments of the payloads. The glycans of the antibodies may be modified to be substantially homogeneous. As used herein, the term "substantially homogeneous" refers to a homogeneity of 80% or higher, preferably 85% or higher, more preferably 90% or higher, and most preferably 95% or higher. Such glycan modifications may use endoglycosidases. For example, the glycans on native antibodies may be trimmed with glycosidases down to one or several glycan residues. Then, glycans having defined structures may be coupled on the remaining glycan residues to produce antibodies having substantially homogeneous glycan structures. These glyco-engineered antibodies are then used for the preparation of ADCs. Alternatively, the glycan having defined structures may have been coupled with a linker or a linker with a drug moiety prior to coupling to the endoglycosidase-trimmed antibodies.

In accordance with embodiments of the invention, the glyco-engineering may involve the use of endoglycosidase S2 (EndoS2) from *Streptococcus pyogenes* or mutants thereof, having improved transglycosylation activities and reduced hydrolyzing activities, to achieve the synthesis of antibodies carrying a broad range of well-defined N-glycans. These antibodies with well-defined N-glycans may then be used to prepare ADCs.

Due to unique preparation processes, embodiments of the invention have relatively high average DAR numbers. In accordance with embodiments of the invention, the average DAR numbers on antibodies with two biantennary glycans are 3.0 or higher. In contrast, those in the prior art are typically 2.0 or less. The average DAR numbers of antibodies with two monoantennary glycans are 1.5~2.0. The high average DAR numbers mean each antibody molecule carries more payload, and the ADCs of the invention would be more efficacious as therapeutic agents, as evidenced by the tests set forth in this description. In addition, ADCs of the invention are more cost effective because smaller amounts of antibodies are needed to achieve the same payload delivery. Because antibody drugs are expensive, this can save the patients substantial amounts in the treatment costs.

In accordance with embodiments of the invention, a drug moiety (payload) in the ADC may be attached to a glycan with or without a linker.

In accordance with embodiments of the invention, an antibody-drug conjugate (ADC) may have a structure represented by Formula (I):

$$[D_2\text{-}L_2\text{-}Cn_2]_y\text{-}G_2\text{-}Ab\text{-}G_1\text{-}[\text{-}G\text{-}L_1\text{-}D_1]_x \qquad \text{Formula (I)}$$

or a pharmaceutically acceptable salt thereof, wherein
Ab is an antibody without glycans (i.e., the protein portion of an antibody);
$G_1$ and $G_2$ are glycan moieties, which may be the same or different;
$Cn_1$ and $Cn_2$ are conjugation moieties, which may be the same or different;
$L_1$ and $L_2$ are linker moieties, which may be the same or different;
$D_1$ and $D_2$ are drug units, which may be the same or different; and
x and y are independently an integer from 0 to 8, provided that $x+y \neq 0$.

In accordance with some embodiments of the invention, the antibody in the ADC may bind to any target of interest, such as CD19, CD22, CD27, CD30, CD33, CD37, CD70, CD74, CD79b, CD138, CD142, CA6, p-Cadherin, CEACAM5, C4.4a, DLL3, EGFR, EGFRVIII, ENPP3, EphA2, EphrinA, FLOR1, FGFR2, GCC, HER2, cKIT, LIV1, MSLN, MUC16, NaPi2b, Nectin4, gpNMB, PSMA, SLITRK6, STEAP1, TROP2, 5T4, SSEA4, GloboH, Gb5, STn or Tn.

In accordance with some embodiments of the invention, the glycan moiety may be selected from the group consisting of di-, tri-, tetra-, penta-, hexyl-, hepta-, octyl-, nona-, deca-, and undeca-saccharides. In accordance with preferred embodiments of the invention, the glycan moiety may have a structure shown as Formula (II-1a) or Formula (II-2a):

Formula (II-1a)

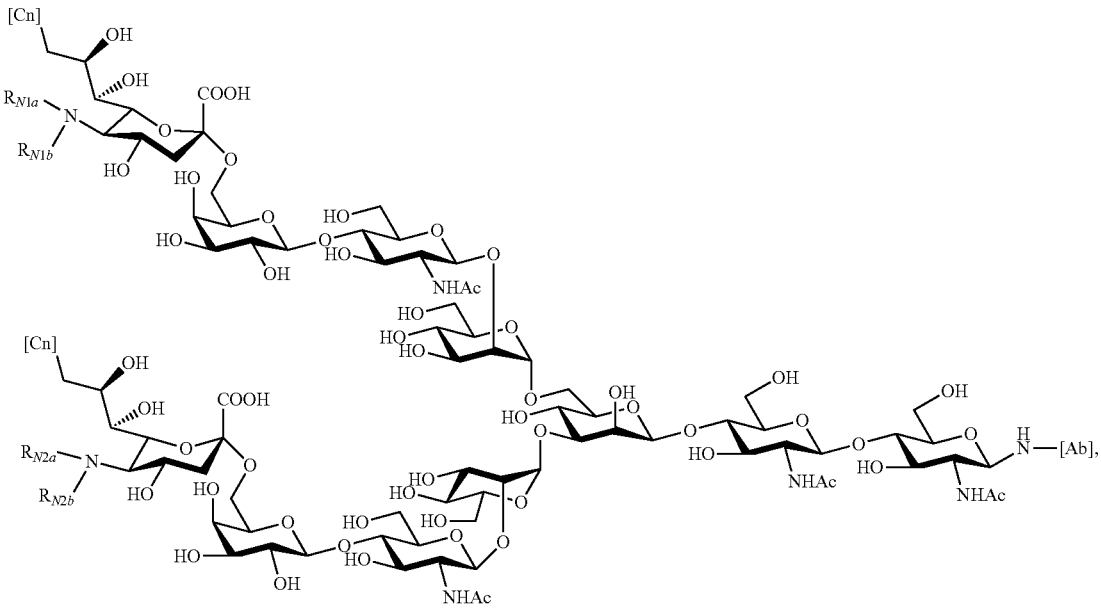

-continued

Formula (II-2a)

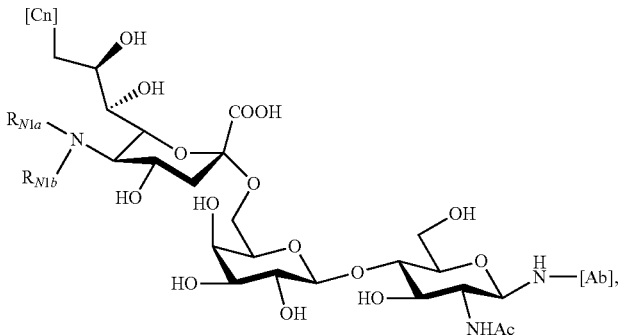

wherein

R$_{N1a}$, R$_{N1b}$, R$_{N2A}$, and R$_{N2b}$ are independently selected from the group consisting of hydrogen, optionally substituted C1-C6 alkyl, optionally substituted C1-C6 acyl, and a nitrogen protecting group, wherein the nitrogen protecting group can be any suitable protecting group known in the art, such as isotertbutyloxycarboxy group (t-BOC), 9-fluorenylmethoxycarbonyl group (Fmoc), benzyl group (Bn), benzyloxycarbonyl group (Cbz), allyloxycarbonyl group (Aloc), 2-(trimethylsilyl)ethoxycarbonyl group (Teoc), 2,2,2-trichloroethoxycarbonyl (Troc), diphenylmethyl group (Dpm), trityl group (Tr), 9-phenylfluorenyl group (PhFl), and p-methoxybenzyl group (PMB);

[Ab] indicates the attachment site for the antibody; and

[Cn] indicates the attachment site for the conjugation moiety;

In accordance with preferred embodiments of the invention, the glycan moiety may have a structure shown as Formula (II-1b) or Formula (II-2b):

Formula (II-1b)

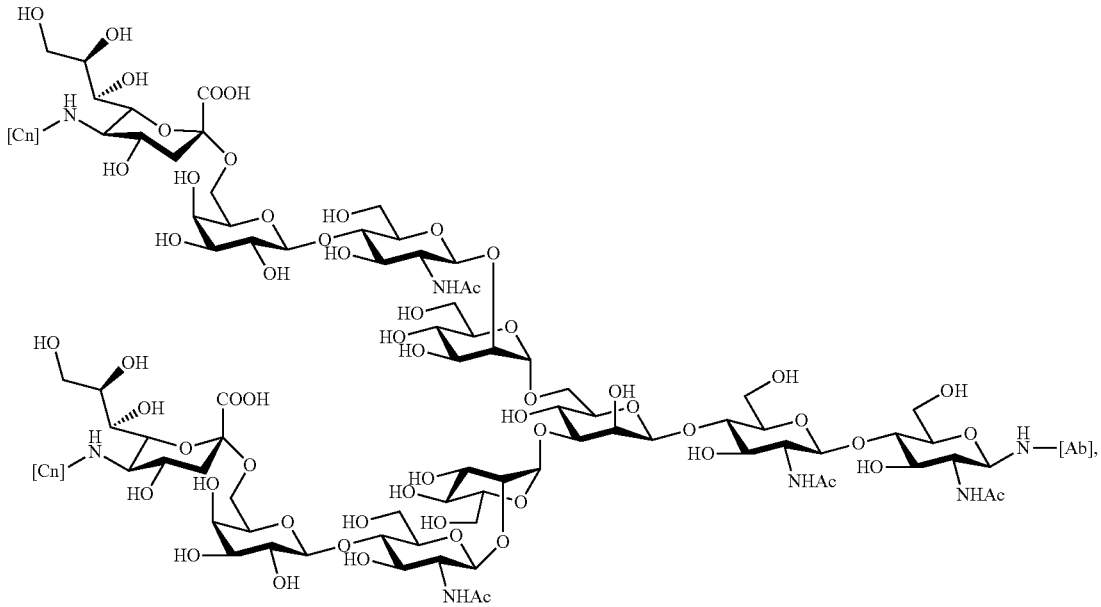

Formula (II-2b)

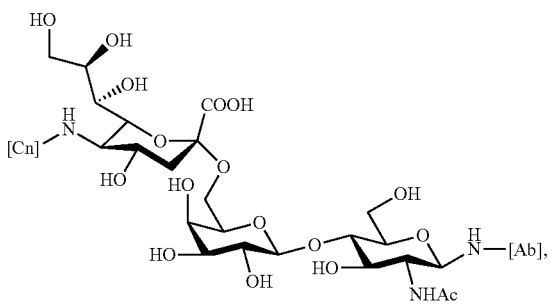

wherein

[Ab] indicates the attachment site for the antibody; and

[Cn] indicates the attachment site for the conjugation moiety;

In accordance with some embodiments of the invention, the conjugation moiety may be selected from the group consisting of the structures of Formula (III-1), Formula (III-2a), Formula (III-2b), Formula (III-2c), Formula (III-2d), Formula (III-3), Formula (III-4a), Formula (III-4b), Formula (III-4c), and Formula (III-4d):

Formula (III-1)

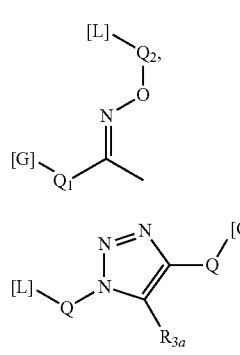

Formula (III-2a)

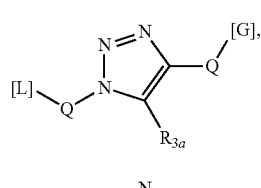

Formula (III-2b)

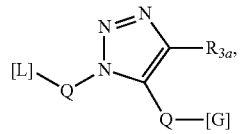

Formula (III-2c)

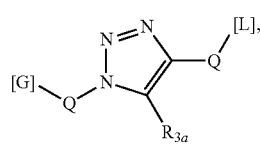

Formula (III-2d)

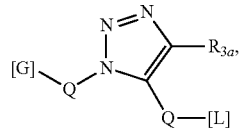

Formula (III-3)

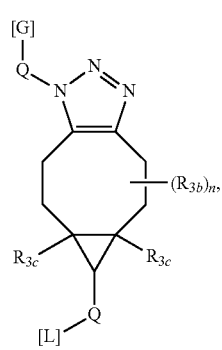

Formula (III-4a)

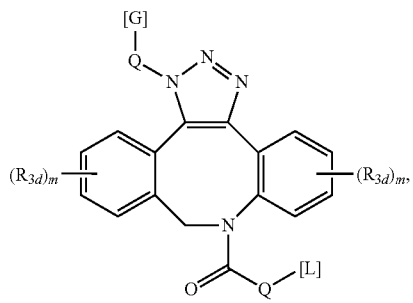

Formula (III-4b)

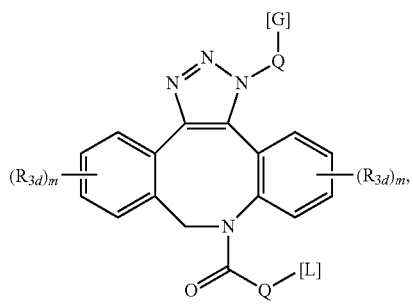

Formula (III-4c)

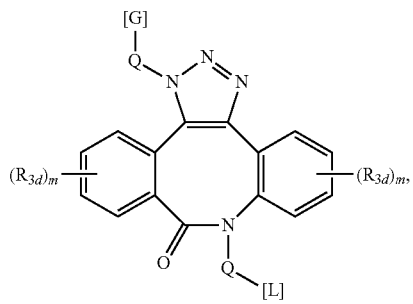

Formula (III-4d)

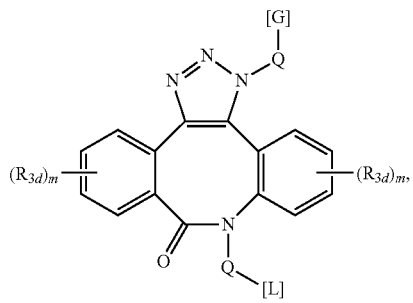

wherein each of Q, $Q_1$ and $Q_2$ is a Y1+Y2 spacer, wherein Y1 and Y2 are independently selected from the group consisting of a direct bond, —(CH$_2$)—, —O—, —NH—, —C(O)—, —C(O)NH—, —NHC(O)—, —(CH$_2$)$_n$O—, —O(CH$_2$)$_n$—, —(CH$_2$)$_n$—(O)—, —C(O)(CH$_2$)$_n$—, —(CH$_2$)$_n$—NH—, —NH—(CH$_2$)$_n$—, —(CH$_2$)$_n$—NHC(O)—, —C(O)(CH$_2$)$_n$—NHC(O)—, —(CH$_2$)$_n$SCH$_2$C(O)—, and —(CH$_2$CH$_2$O)$_m$—;

$R_{3a}$ is selected from the group consisting of hydrogen, halogen, C1-C6 alkyl group;

$R_{3b}$ is independently selected from the group consisting of hydrogen, halogen, —NO$_2$, and —CN, optionally substituted C1-C6 alkyl group, optionally substituted C1-C6 alkyoxy group, optionally substituted C1-C24 cycloalkyl group, optionally substituted C6-C24 aryl group, optionally substituted C7-C24 aralkyl group, optionally substituted C4-C24 heteroaryl group, optionally substituted C5-C24 heteroaralkyl group;

$R_{3c}$ is independently selected from the group consisting of hydrogen, halogen, optionally substituted C1-C6 alkyl group, optionally substituted C6-C24 aryl group, optionally substituted C7-C24 aralkyl group, optionally substituted C4-C24 heteroaryl group, and optionally substituted C5-C24 heteroaralkyl group;

$R_{3d}$ is independently selected from the group consisting of hydrogen, halogen, —OH, —NO₂, and —CN, optionally substituted C1-C6 alkyl group, optionally substituted C1-C6 alkyoxy group;

n is an integer from 1 to 8, inclusive;
m is an integer from 1 to 4, inclusive;
[G] indicates the attachment site for the glycan moiety; and
[L] indicated the attachment site for the linker moiety;

In accordance with preferred embodiments of the invention, the linker may be selected from the group consisting of the structure of Formula (IV-1), Formula (IV-2), Formula (IV-3), Formula (IV-4), and Formula (IV-5):

etaxel, Epothilone B, Epothilone A, CYT997, Auristatin tyramine phosphate, Auristatin aminoquinoline, Halocombstatins, Calicheamicin theta, 7-Ethyl-10-hydroxy-camptothecin (SN-38), Pyrrolobenzodiazepine (PBD), Pancratistatin, Cyclophosphate, Cribrostatin-6, Kitastatin, Turbostatin 1-4, Halocombstatins, Silstatins, Pretubulysin D, and Tubulysins (A, B, C, D, E, F, G, H, I, U, V, and Z).

In accordance with embodiments of the invention, the drug moiety may be first coupled with the linker (if a linker is used), which is then conjugated with (e.g., via a conjugation moiety discussed above) the glycan moiety. If no linker is used, the drug moiety may be directly conjugated with the glycan moiety.

The coupling between the linker and the drug may be accomplished with any suitable methods known in the art. One skilled in the art would appreciate that the particular methods used would depend on the properties of the linkers and the drugs, and one skilled in the art would be able to make these coupling without inventive efforts. Some examples are described herein in later sections. Once the drug-linker moieties are prepared, they can be conjugated with the glycan moieties.

Formula (IV-1)

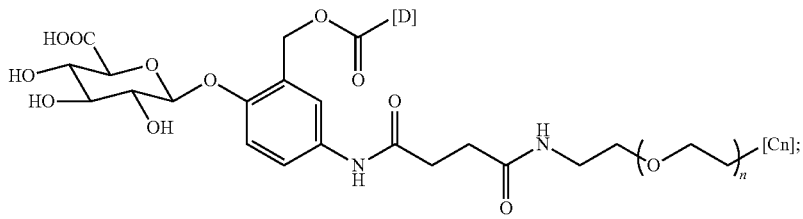

Formula (IV-2)

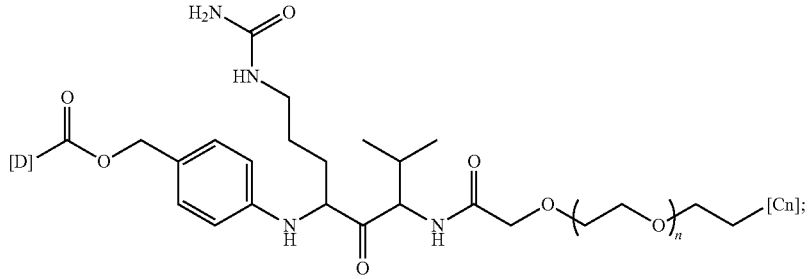

Formula (IV-3)

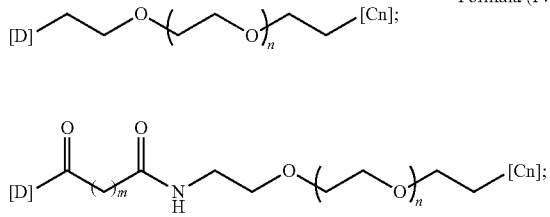

Formula (IV-4)

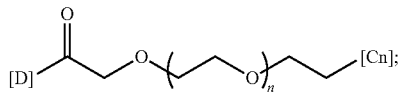

Formula (IV-5)

wherein
[Cn] indicated the attachment site for the conjugation moiety;
[D] indicates the attachment site for the drug unit;
and each instance of m and n is independently an integer from 0 to 6, inclusive.

In accordance with some embodiments of the invention, the drug (payload) may be selected from the group consisting of Monomethyl auristatin E (MMAE), Monomethyl auristatin F (MMAF), Monomethyl auristatin D (MMAD), Mertansine (Maytansinoid DM1/DM4), Paclitaxel, Doc- Alternatively, the linker may be first coupled to the glycan moiety, followed by attachment of the drug moiety to the linker. Again, these methods are conventional and one skilled in the art would be able to perform these reactions without inventive efforts.

Various methods are known in that art that use mild reaction conditions and can be used to couple biomolecules. For example, click chemistry is a class of biocompatible reactions that can be used to couple tags with biomolecules. (H. C. Kolb; M. G. Finn; K. B. Sharpless (2001), "*Click Chemistry: Diverse Chemical Function from a Few Good*

*Reactions*," Angewandte Chemie, Int'l Ed., 40(11): 2004-2021). A particularly useful click chemistry uses copper-free, strain-promoted azide-alkyne cycloaddition, in which the azide group adds to the strained alkyne (e.g., cyclooctyne) to form a new five-membered ring. One example of such a click reaction is illustrated in the following scheme:

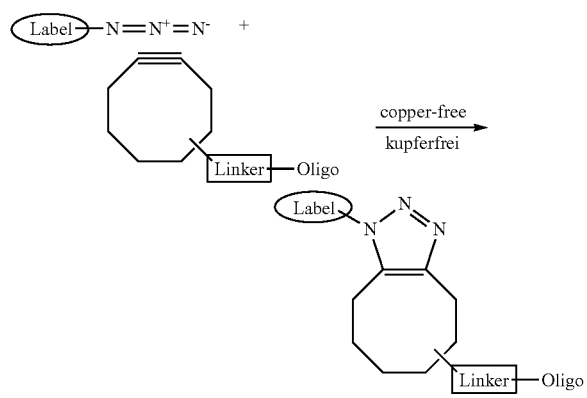

In accordance with some embodiments of the invention, a glycan-linker moiety for ADC may be synthesized using click chemistry. For example, the glycan moiety may contain an azido group and the linker may contain a cyclooctyne group (or a similar alkyne group), or vice versa.

In addition to click chemistry, other commonly used coupling chemistry may also be used with embodiments of the invention. These other methods, for example, may include Schiff base formation (oxime formation) between ketones/aldehydes and amines, covalent bond formation via addition or substitution reactions, etc.

Embodiments of the invention will be further illustrated with the following examples. One skilled in the art would appreciate that these examples are for illustration only and other modifications or variations are possible without departing from the scope of the invention. Furthermore, one skilled in the art would appreciate that in the following examples, specific parameters or quantities may be provided. However, such specific parameters or quantities are for illustration only and are not intended to limit the scope of the invention.

EXAMPLES

Example 1. Preparation and Characterization of Glyco-Engineered Antibody 1.1 Preparation of NKS/NAS Glycan The NKS/NAS glycan was prepared by sialylation of CT (complex type) glycan. The CT glycan was obtained by treating a solution of SCT (sialyl complex type) glycan (50.5 mg, 25 μmol dissolved in 50 mM Tris-HCl buffer, pH 7.4) with sialidase (75 units) at 37° C. for 24 h. and monitored by TLC. After heating the solution at 80° C. for 30 min, the denatured enzyme was removed by filtration and the solution was concentrated in vacuo, and the crude CT glycan was purified by G-20 gel chromatography (elute water, 90% P).

NKS/NAS glycan was prepared from CT glycan by enzymatic method. Briefly, CT (32.8 mg, 18 μmol), CTP (5 μmol), ManNAcN$_3$/ManNAcLev (40 μmol), Sodium Pyruvate (81 μmol), PEP (55 μmol), and ATP (5 μmol), were dissolved in 50 mM Tris-HCl buffer (pH 8.0). Enzymes, α-(2,6)-sialyltransferase (20 units), sialic acid aldolase (20 units), CMK (10 units), Pykf (10 units), PPA (10 units), and Pmcss (10 units), were added to the solution, and the reaction was incubated at 37° C. for 8 hours and monitored by TLC. At the end of reaction, enzymes were denatured by heating at 100° C. for 5 minutes. The desired NKS/NAS was then purified with G25, DEAE, and G25 column (yield: 29.1 mg, 80%). ESI-TOF m/z: 2130.8349 ([M–H⁻]⁻ of NKS), 2100.7804 ([M⁻–H]⁻ of NAS).

Scheme 1: Synthesis of NKS-oxazoline or NAS-oxazoline.

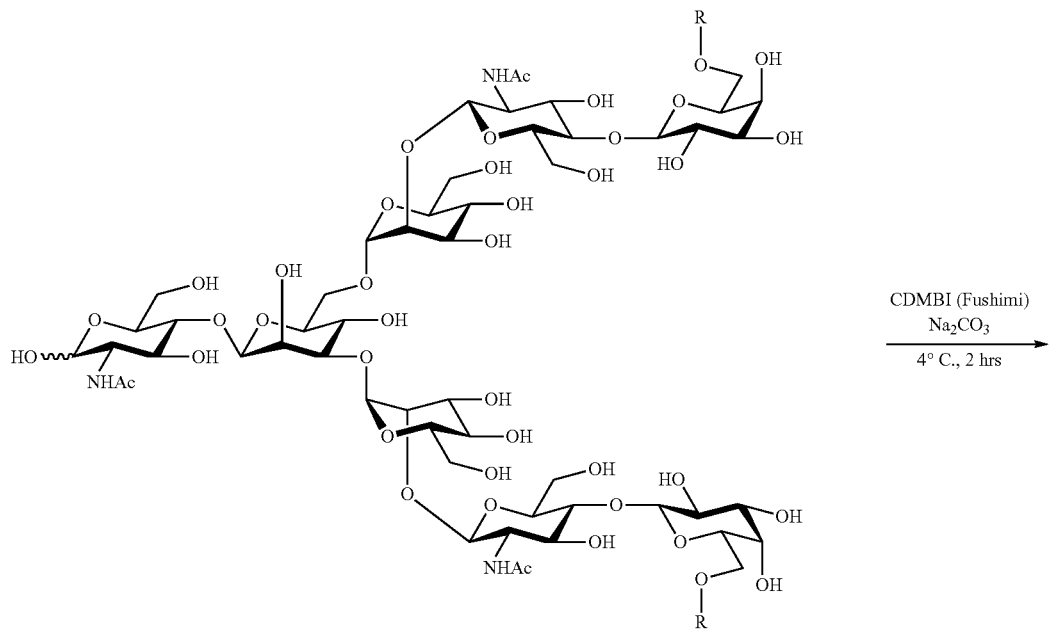

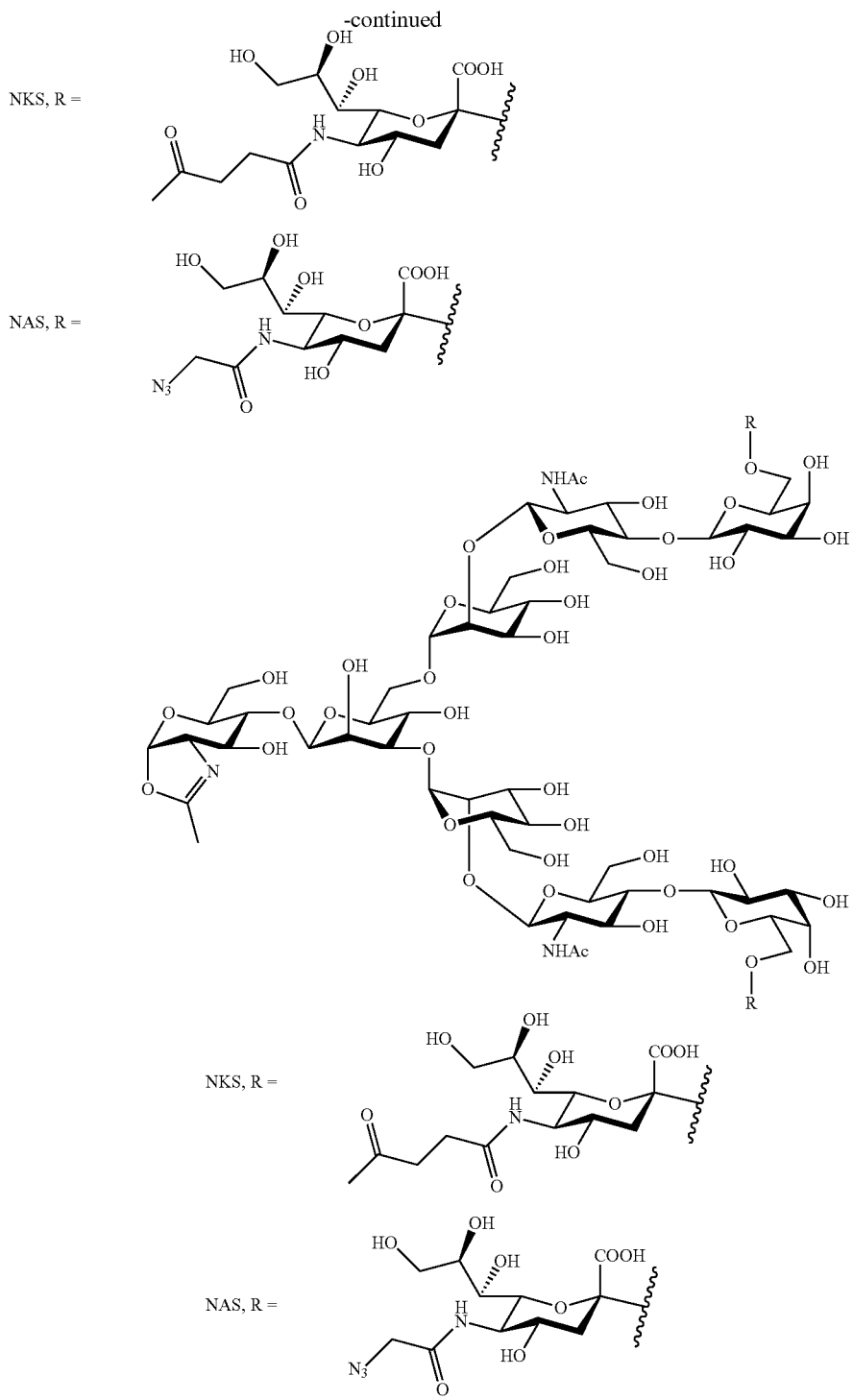

1.2 General Procedure of NKS/NAS-Oxazoline Formation

NKS/NAS glycan (13.6 mg) and Na$_2$CO$_3$ (78.75 mg) was dissolved in H$_2$O (1.16 mL), cooled to 4° C., CDMBI (48 mg) was then added and the reaction was kept shaking (1000 rpm) at 4° C. for 2 hours. The crude solution was centrifuged at 3000 rpm for 2 mins, then the supernatant was collected, for further purification. Size exclusion column (G25), eluted with 0.01% TEA/H$_2$O, then 100% H$_2$O, the product was collected and lyophilized to give NKS-oxazoline (NKS-ox) or NAS-oxazoline (NAS-ox) as white powder.

NAS-ox. $^1$H NMR (400 MHz, CDCl3) δ 6.09 (d, J=7.2 Hz, 1H), 5.12 (s, 1H), 4.96 (s, 1H), 4.8 (d, J=1.2 Hz, 1H), 4.74 (s, 1H), 4.65-4.57 (m, 2H), 4.44 (d, J=7.6 Hz, 1H), 4.38 (t, J=2.8 Hz, 1H), 4.23-4.13 (m, 4H), 4.06 (s, 4H), 4.25-3.46 (61H), 3.45-3.38 (m, 1H), 2.67 (dd, J=4 Hz, 12.8 Hz, 1H), 2.08-2.04 (n, 98), 1.72 (t, J=12.4 Hz, 1H). NKS-ox. $^1$H NMR (400 MHz, CDCl3) δ 6.05 (S, J=7.2 Hz, 1H), 6.05 (s, 1H), 4.92 (s, 1H), 4.65-4.55 (m, 2H), 4.43-4.34 (m, 38), 4.2-4.1

(m, 58), 4.0-3.34 (m, 72H), 2.93-2.75 (m, 4H), 2.63 (dd, J=3.6 Hz, 12.4 Hz, 2H), 2.58-2.4 (m, 5H), 2.19 (s, 7H), 2.07-1.96 (m, 11H), 1.68 (t, J=12.0 Hz, 1H).

1.3 General Procedure of One-Pot Chemoenzymatic Synthesis of Glycoengineered Herceptin with Two Modified Biantennary Glycans (TRZ-NKS and TRZ-NAS)

EndoS2 (or a derivative or mutant of EndoS2) (1-5 µg) was added to Herceptin (10 mg) in 100 mM TES buffer (pH 7.0) to a final antibody concentration of 10 mg/nL. The solution was incubated for 1.0-4.0 h at room temperature, 30° C. or 37° C. Then, the obtained Herceptin-N(F) (monoGlcNAc with or without fucose; N is GlcNAc and F is fucose) was added another portion of EndoS2 (or a derivative or mutant of EndoS2) (10-15 µg) to the reaction, chilled to 30° C., followed by the addition of NKS/NAS-ox (6-8 mg) to a final antibody concentration of 8 mg/mL, and kept reacting for another 1-1.5 hours. After completion, the transglycosylated Herceptin was purified through Protein A affinity column and an anion exchange column Capto S (GE Healthcare). The purified glycoengineered Herceptin (TRZ-NKS, and TRZ-NAS) was analyzed by SDS-PAGE and exchanged buffer to PBS pH 7.4 for further use.

1.4 General Procedure of Glycoengineered Herceptin with Two Modified Monoantennary Glycans (TRZ-NGKS)

50 mg TRZ-N in 50 mM Tris buffer (pH 7.0) with a final concentration of 10 mM $MnCl_2$ were mixed with 1 mg β-1,4-galactosyltransferase, followed by addition of 5 ing of UDP-Gal. The mixture was incubated for 8 hours at 37° C. to generate TRZ-NG. For TRZ-NGKS synthesis, TRZ-NG was mixed with 5 mmol of N-acetylneuraminic acid (Neu5Ac), 0.05 mmol of ATP, 0.5 mmol of CTP, 10 mmol of PEP with 10 mM $MgCl_2$ in 100 mM Tris-HCl buffer (pH 8.0) followed by 50 U of cytidine monophosphate kinase (CMK), 120 U of CMP-sialic acid synthetase (CSS), 100 U of PK, 100 U of PPA, and 150 U of α-2,6-sialyltransferase. The flask was incubated at 25° C. until complete reaction. The reaction material and products were monitored by intact mass spectra (FIG. 2)

1.5 Characterization of Glycan Profile

The GlycoWorks RapiFluor-MS N-Glycan Kit was used to analyze the glycan profile of TRZ-NKS and TRZ-NAS. Glycan was hydrolyzed from antibody and labeled to glycosylamines, according to manufacturer's instructions. After the labeling procedure, the samples were purified using the HILIC SPE µElution plate. The purified glycans were analyzed using Xevo G2-XS QToF coupled to Waters H-class UHPLC. Glycan samples were separated with an ACQUITY UPLC Glycan BEH Amide column (2.1 mm×150 mm, 1.7 µm, Waters Corp, Milford, Mass.) using a 50 min gradient at a flow rate of 0.4 mL/min. Mobile phase A was made up of 50 mM ammonium formate in $ddH_2O$, while mobile phase B was made up of acetonitrile. For the data acquisition during the glycan analysis, the Xevo G2 XS QToF mass spectrometer was operated in FastDDA mode.

Figure 3:
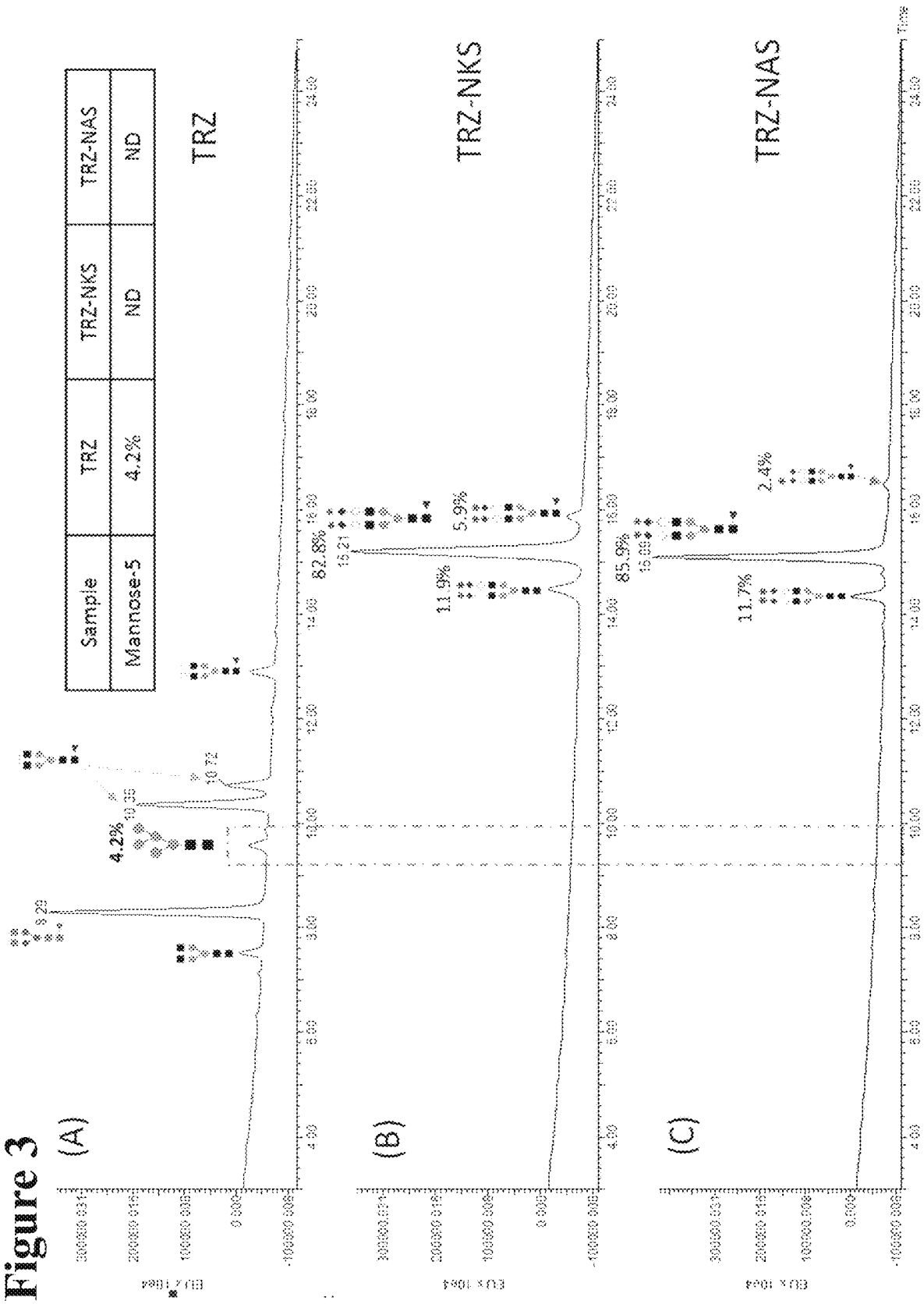
FIG. 3 shows glycan mapping for TRZ (Panel A), TRZ-NKS (Panel B) and TRZ-NAS (Panel C), in accordance with embodiments of the invention. The identity of each glycan peak was confirmed by MS analysis on-line connected to HPLC with fluorescence detection. The table on the right of panel A listed the amount of Man-5 glycan, which were sorted by abundance.

FIG. 3 shows results of comparison of the glycan profiles between TRZ, TRZ-NKS and TRZ-NAS. TRZ exhibits high-mannose type N-glycan profile above 4.2% level. In contrast, TRZ-NKS and TRZ-NAS show no high-mannose type N-glycan. Majority of glycan release from TRZ-NKS and TRZ-NAS are in modified sialyl ($Neu5AcN_3$ and Neu5AcLev) biantennary complex type. glyco-form.

Example 2. Preparation and Characterization of Payloads (A01-A24)

TABLE 1
Designed payloads
| Payload | Structure |
|---|---|
| A01 | 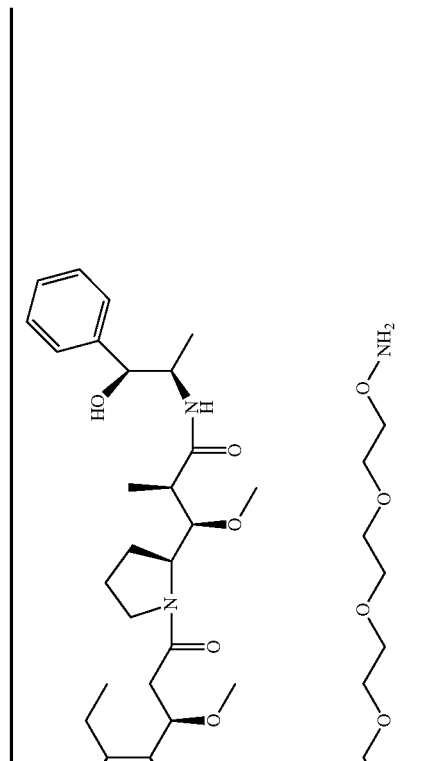 |
| A02 | 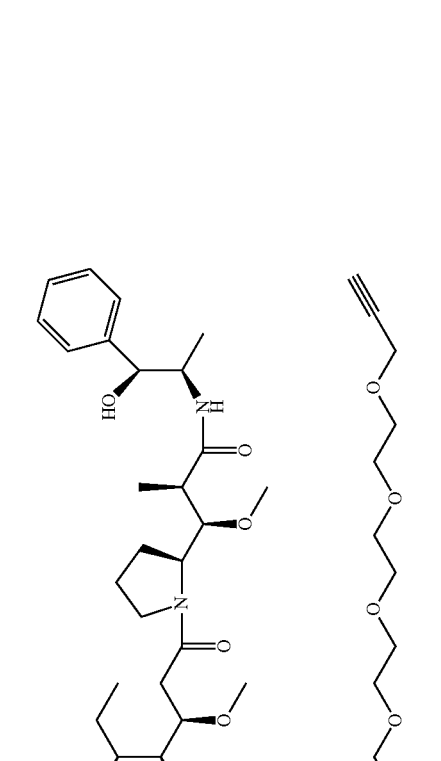 |

TABLE 1-continued

Designed payloads

| Payload | Structure |
|---------|-----------|
| A03 | 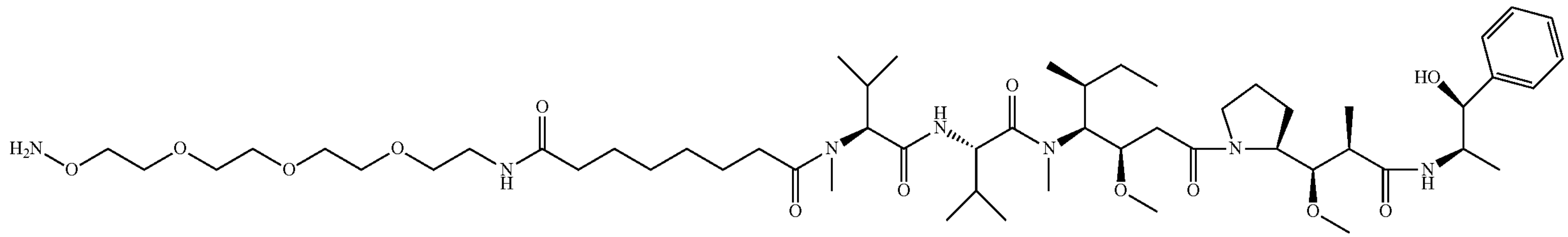 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)CCCCCCC(=O)NCCOCCOCCOCCON)C(C)C] |
| A04 | 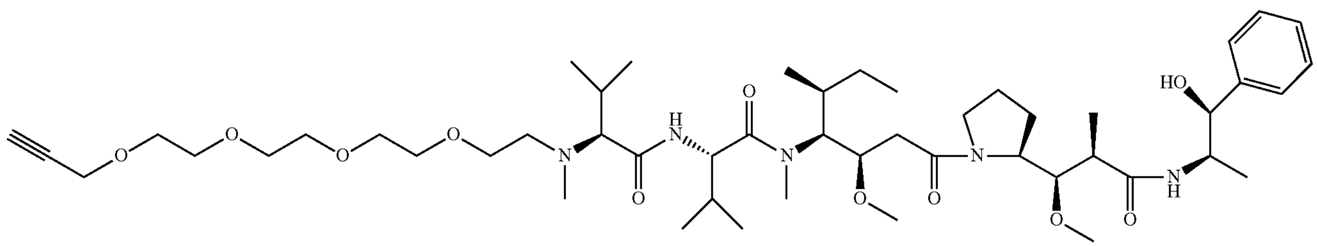 [SMILES: C#CCOCCOCCOCCOCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C] |
| A05 | 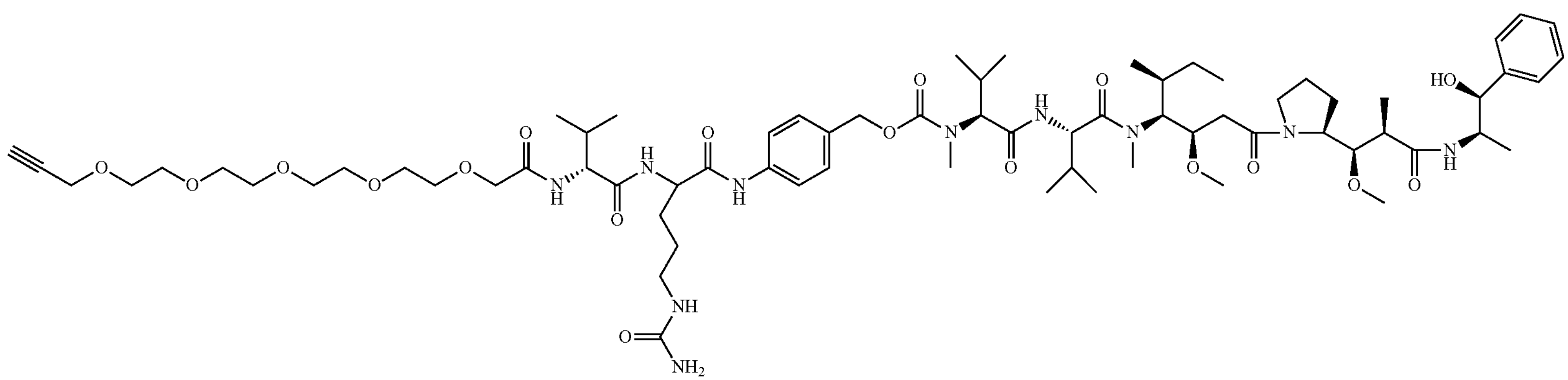 [SMILES: C#CCOCCOCCOCCOCCOCC(=O)N[C@@H](C(=O)NC(CCCNC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1)C(C)C] |

TABLE 1-continued
Designed payloads
| Payload | Structure |
|---|---|
| A06 | 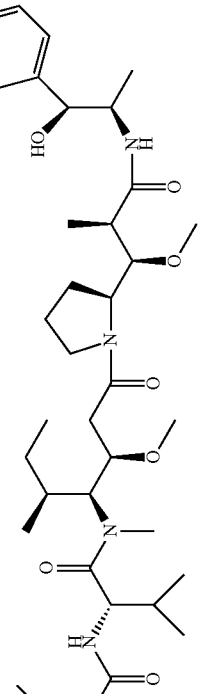 |
| A07 | 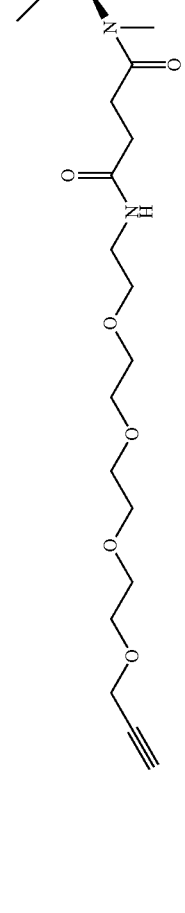 |
| A08 | 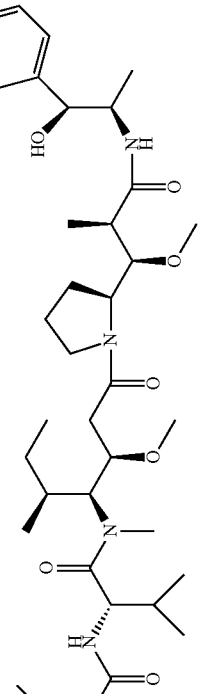 |

TABLE 1-continued
Designed payloads
| Payload | Structure |
|---|---|
| A09 | 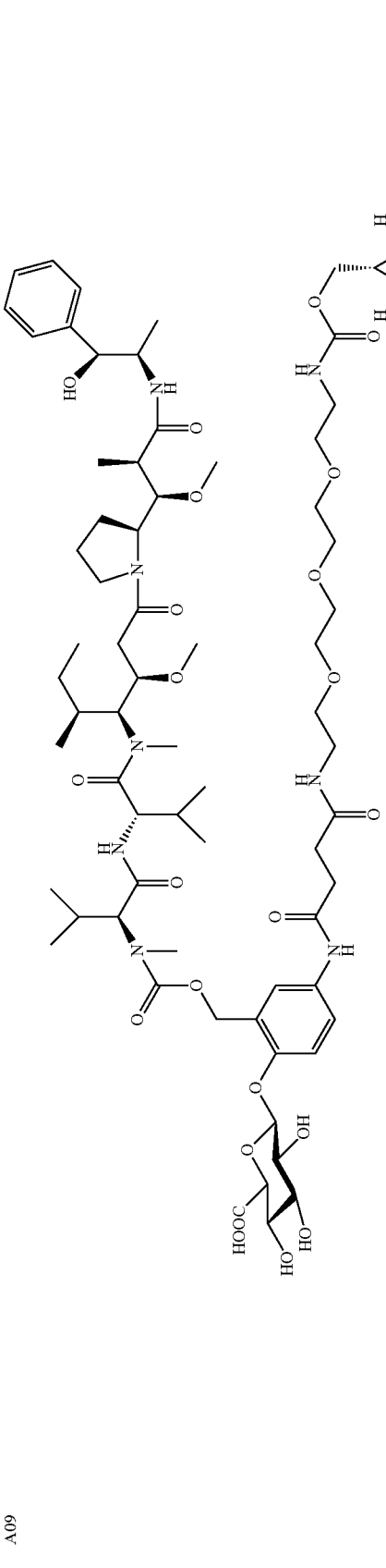 |
| A10 | 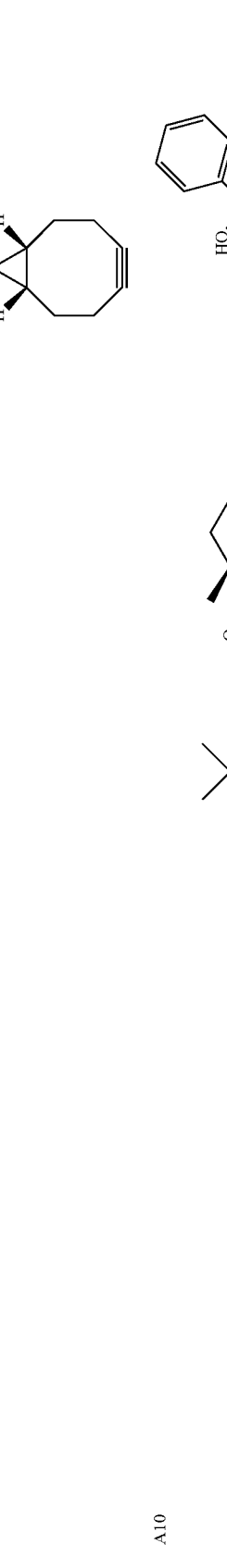 |

TABLE 1-continued

Designed payloads

| Payload | Structure |
|---|---|
| A11 | (chemical structure) |
| A12 | (chemical structure) |
| A13 | (chemical structure) |

TABLE 1-continued
Designed payloads
| Payload | Structure |
|---|---|
| A14 | 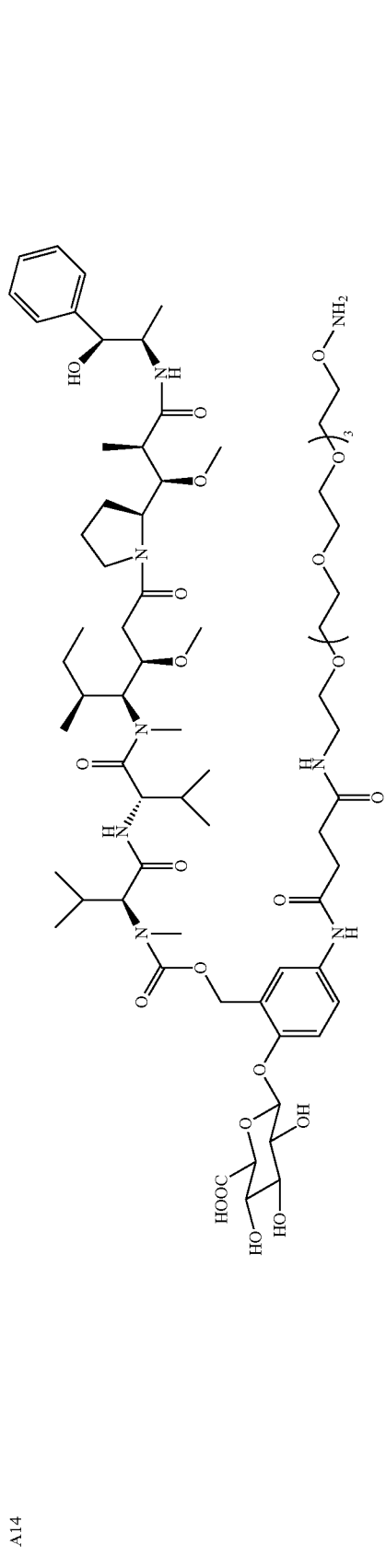 |
| A15 | 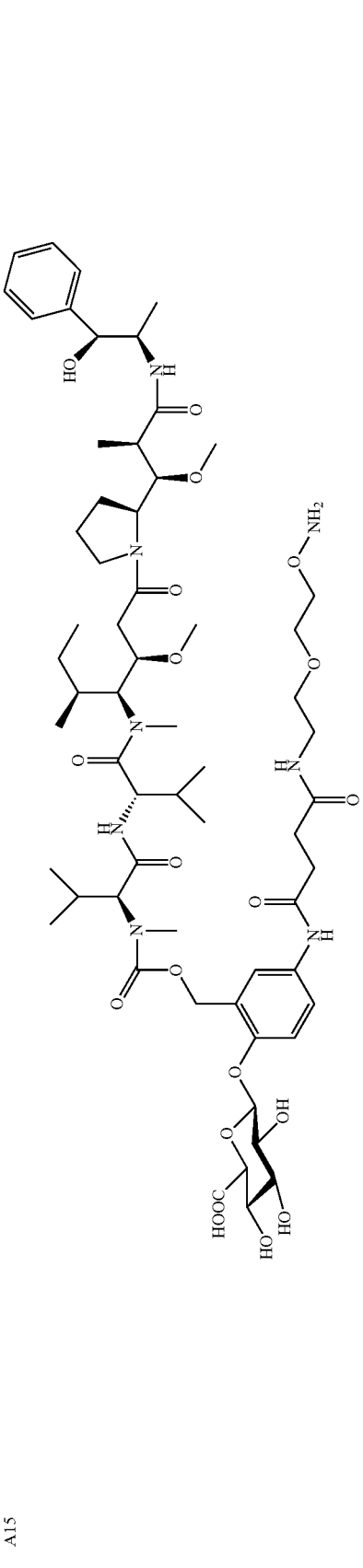 |

TABLE 1-continued
Designed payloads
| Payload | Structure |
|---|---|
| A16 | 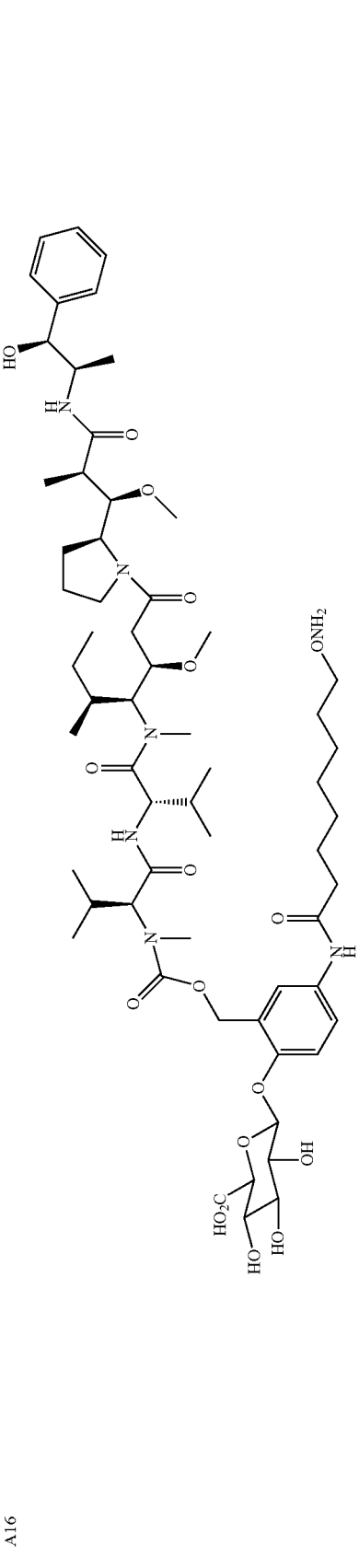 |
| A17 | 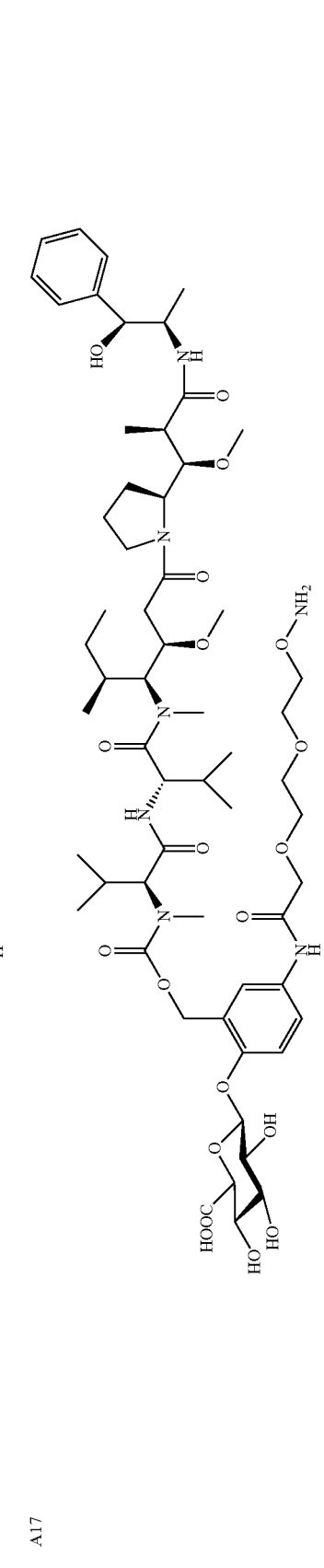 |

TABLE 1-continued
Designed payloads
| Payload | Structure |
|---|---|
| A18 | 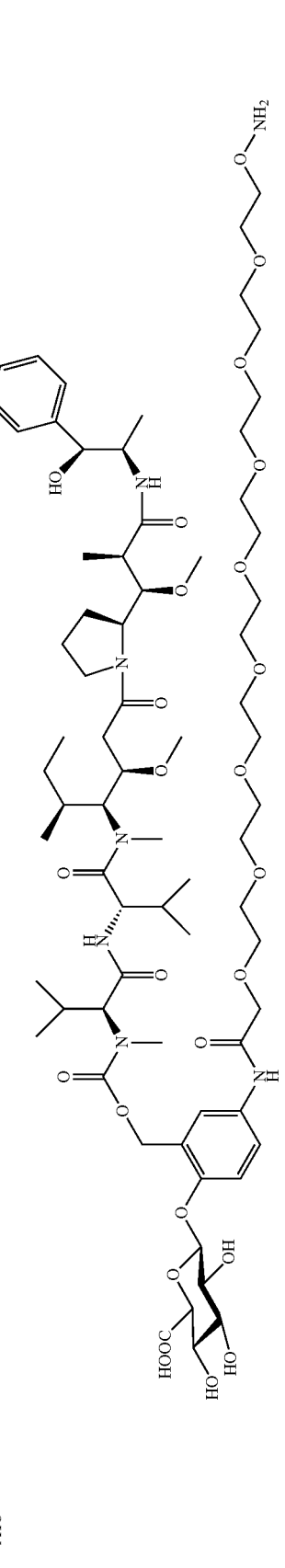 |
| A19 | 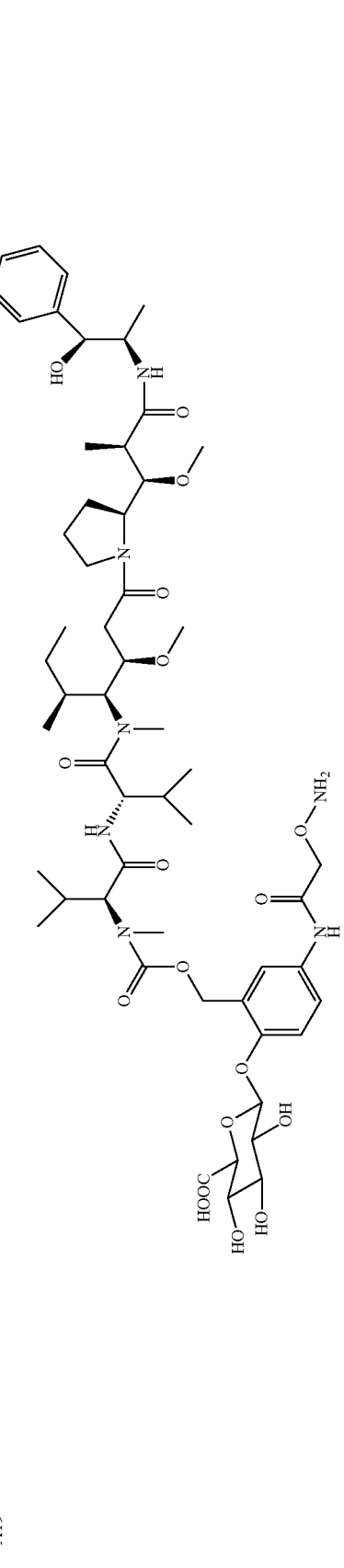 |

TABLE 1-continued
Designed payloads
| Payload | Structure |
|---|---|
| A20 | 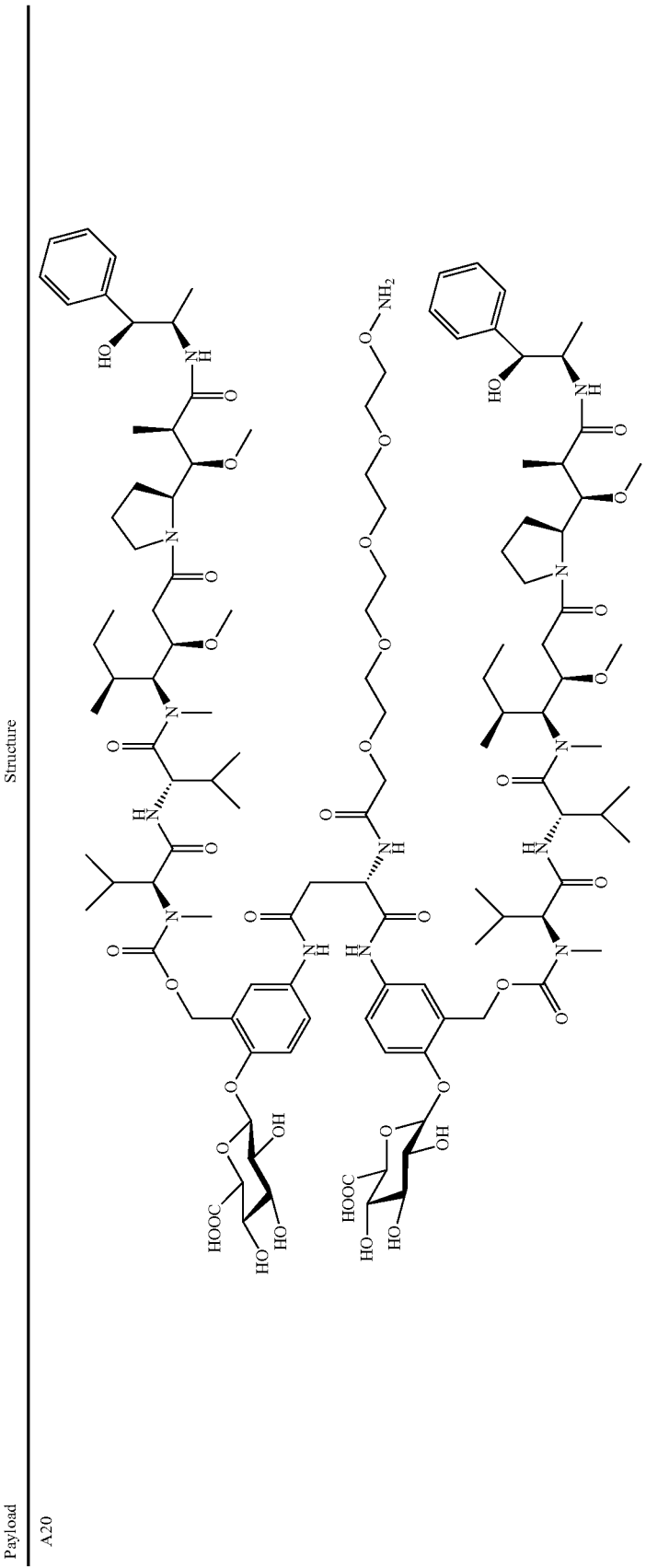 |

TABLE 1-continued
Designed payloads
| Payload | Structure |
|---|---|
| A21 | 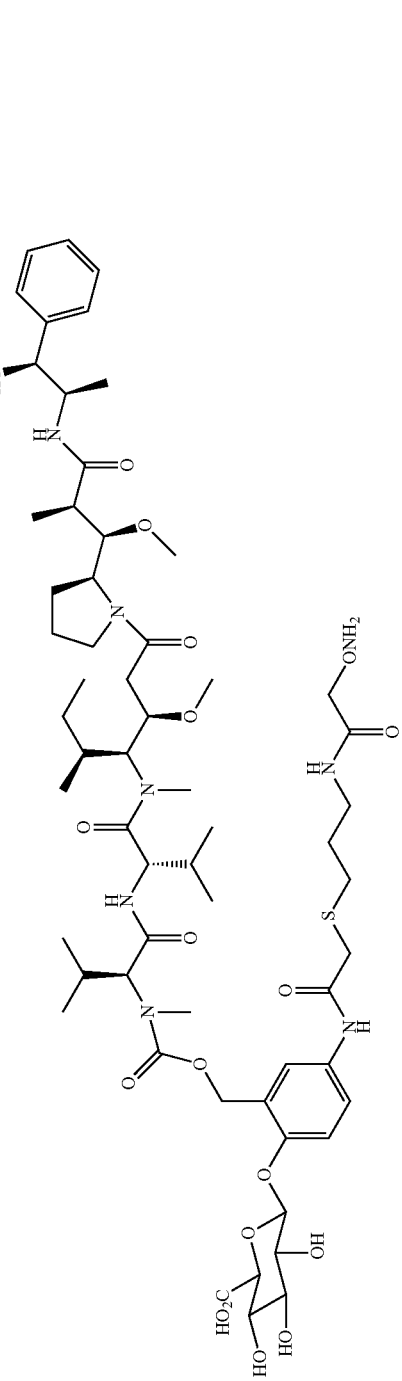 |
| A22 | 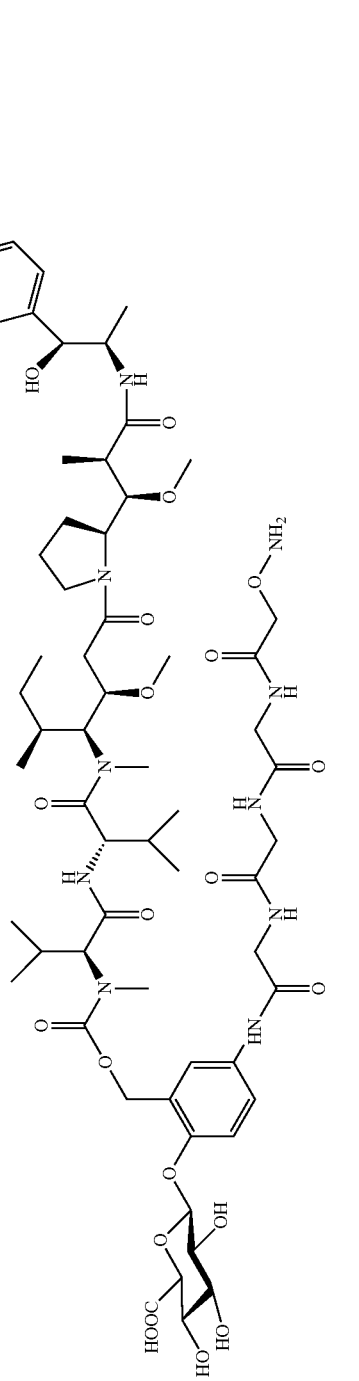 |

TABLE 1-continued
Designed payloads
| Payload | Structure |
|---|---|
| A23 | 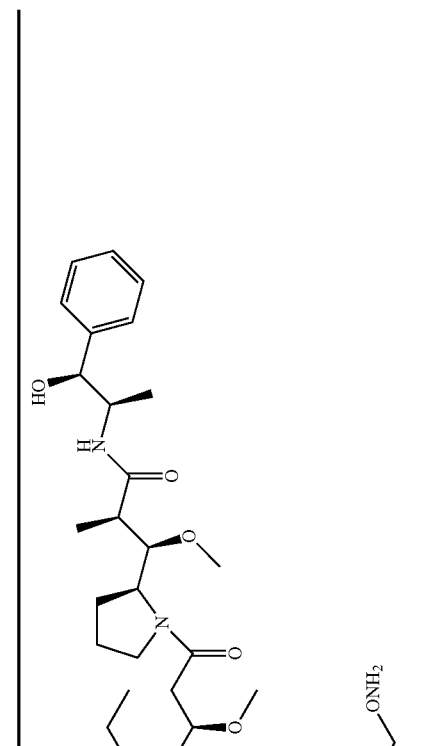 |
| A24 | 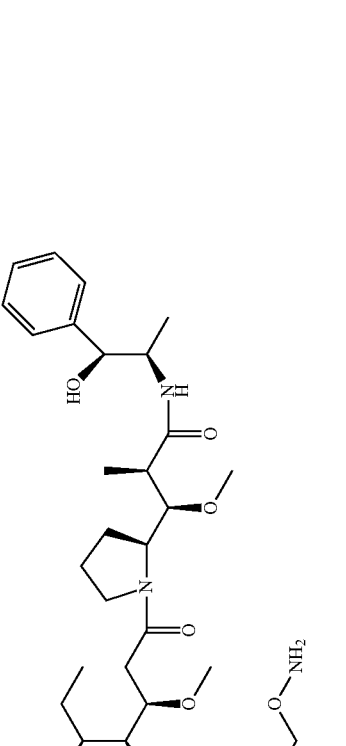 |

2.1 Synthesis and Characterization of Compound 9 (A01)

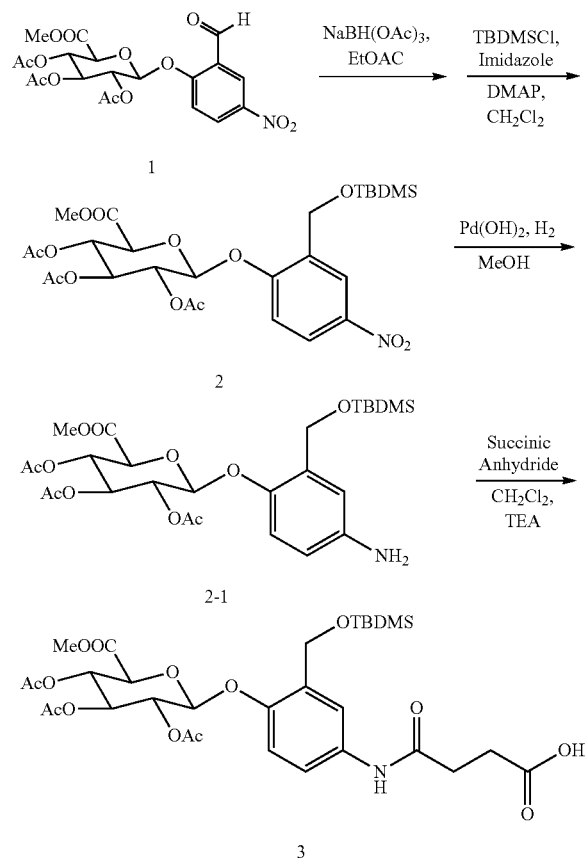

Preparation of Compound (2)

To a solution of compound 1 (500.0 mg, 1.03 mmol) in 20 ml of EtOAc was added NaBH(OAc)$_3$ (500.0 mg, 1.54 mmol). The reaction was stirred at room temperature for 20 h. The resulting mixture was diluted with EtOAc and washed with 1 N HCl, saturated aqueous NaHCO$_3$ and brine. The organic layer extraction was dried by MgSO$_4$ and concentrated to give compound as a yellow solid (485.0 mg) for next step. To a solution of compound obtained above (450.0 mg, 0.93 mmol), Imidazole (69.4 mg, 1.02 mmol) and DMAP (11.4 mg, 0.093 mmol) in 30 ml of CH$_2$Cl$_2$ was added TBDMSCl (154.0 mg, 1.02 mmol). The reaction was stirred at room temperature for 15 h. The resulting mixture was diluted with CH$_2$Cl$_2$ and washed with 1 N HCl, saturated aqueous NaHCO$_3$ and brine. The organic layer extraction was dried by MgSO$_4$ and concentrated to give compound 2 as a yellow solid (490.0 mg). 88% $^1$H NMR (400 MHz, CDCl$_3$) δ 8.37 (t, J=1.6 Hz, 1H), 8.08 (dd, J=2.8, 9.2 Hz, 1H), 7.00 (d, J=9.2 Hz, 1H), 5.33 (m, 3H), 5.23 (d, J=6.8 Hz, 1H), 4.70 (d, J=15.6 Hz, 1H), 4.56 (d, J=15.6 Hz, 1H), 4.23 (d, J=8.8 Hz, 1H), 3.69 (s, 3H), 2.03 (s, 3H), 2.03 (s, 3H), 2.02 (s, 3H), 0.94 (s, 9H), 0.10 (s 3H), 0.10 (s, 3H).

Preparation of Compound (3)

To a solution of compound 2 (1.0 g, 1.67 mmol) in 20 ml of EtOAc/MeOH (9:1) was added Pd(OH)$_2$. The system was evacuated and filled with H$_2$ three times. It was kept under H$_2$ atmosphere with a balloon and stirred at room temperature for 1 h. After the reaction was completed, Pd(OH)$_2$ was filtered out. The filtrate was evaporated to get compound 2-1 (930.0 mg) for next step. To a solution of compound 2-1 (930.0 mg, 1.63 mmol) and succinic anhydride (180.0 mg, 1.80 mmol) in 20 ml of CH$_2$Cl$_2$ was added TEA (272 uL). The reaction was stirred at room temperature for 15 h. The reaction mixture was evacuated and purified by column to give compound 3 as yellow oil (2.78 g). $^1$H NMR (400 MHz, CDCl3) δ 10.09 (s, 1H), 7.59 (dd, J=2.4, 8.8 Hz, 1H), 7.39 (d, J=2.4 Hz, 1H), 6.86 (d, J=8.8 Hz, 1H), 5.27 (m, 3H), 5.01 (d, J=6.8 Hz, 1H), 4.69 (d, J=14.8 Hz, 1H), 4.58 (d, J=14.8 Hz, 1H), 4.09 (d, J=8.4 Hz, 1H), 3.70 (s 3H), 2.88 (q, J=7.2 Hz, 8H), 2.59 (bs, 4H), 2.03 (s, 3H), 2.02 (s, 3H), 2.01 (s, 3H), 1.17 (t, J=7.2 Hz, 9H), 0.92 (s, 9H), 0.08 (s, 6H).

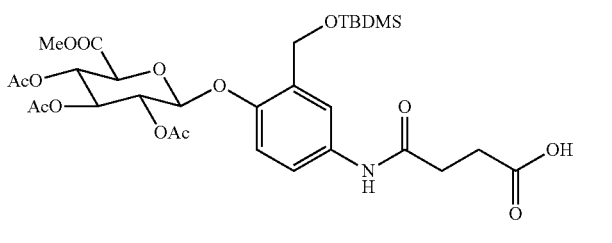

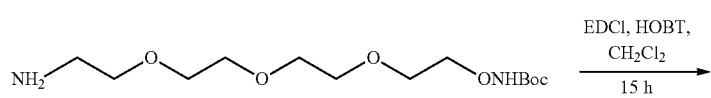

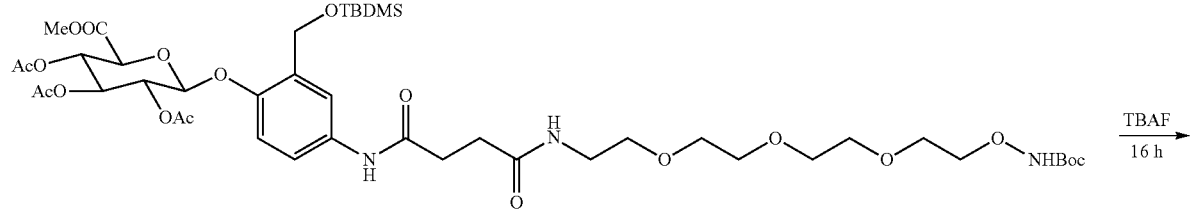

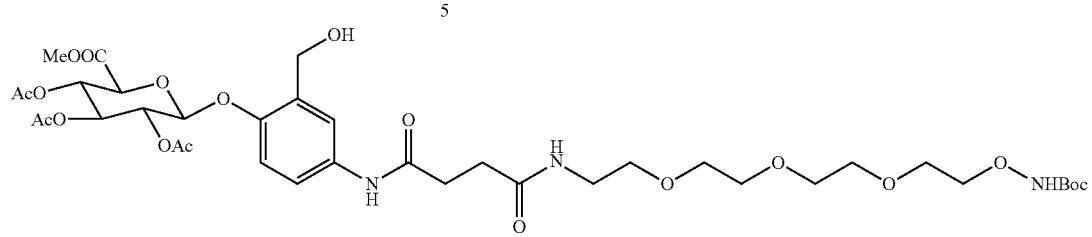

Preparation of Compound (5)

To a solution of compound 3 (289.0 mg, 0.432 mmol), 4 (200 mg, 0.648 mmol), and HOBT (100.0 mg, 0.648 mmol) in CH$_2$Cl$_2$ was added EDCI (100.0 mg, 0.648 mmol). It was stirred at rt for 14 h. The solution was evaporated. The crude product was purified by column to give compound 5 as yellow oil (340.0 mg, 0.35 mmol). $^1$H NMR (400 MHz, CDCl3) δ 8.78 (s, 1H), 8.10 (s, 1H), 7.53 (dd, J=2.4, 8.8 Hz, 1H), 7.41 (d, J=2.4 Hz, 1H), 6.85 (d, J=8.8 Hz, 1H), 6.75 (bs, 1H), 5.30 (m, 3H), 5.01 (d, J=7.2 Hz, 1H), 4.68 (d, J=15.2 Hz, 1H), 4.59 (d, J=15.2 Hz, 1H), 4.10 (m, 1H), 3.95 (m, 2H), 3.70 (s, 3H), 3.70-3.15 (m, 12H), 3.40 (m, 2H), 2.60 (m, 4H), 2.03 (s, 3H), 2.01 (s, 3H), 2.00 (s, 3H), 1.43 (s, 9H), 0.92 (s, 9H), 0.07 (s, 6H).

Preparation of Compound (6)

To a solution of compound 5 (300.0 mg, 0.312 mmol) in 25 mL of THF was added 375 uL of TBAF. It was stirred at rt for 15 h. The solution was evaporated. The crude product was purified by column to give compound 6 as yellow oil (235.0 ing, 0.28 mmol). $^1$H NMR (400 MHz, CDCl3) δ 9.12 (s, 1H), 8.27 (s, 1H), 7.51 (dd, J=2.4, 8.8 Hz, 1H), 7.40 (d, J=2.4 Hz, 1H), 7.15 (bs, 1H), 6.9 (d, J=8.8 Hz, 1H), 5.30 (m, 3H), 5.02 (d, J=7.6 Hz, 1H), 4.68 (d, J=15.2 Hz, 1H), 4.40 (d, J=15.2 Hz, 1H), 4.12 (m, 1H), 3.98 (m, 2H), 3.67 (s, 3H), 3.66-3.50 (m, 12H), 3.40 (m, 2H), 2.60 (m, 4H), 2.04 (s, 3H), 2.02 (s, 3H), 2.01 (s, 3H), 1.42 (s, 9H).

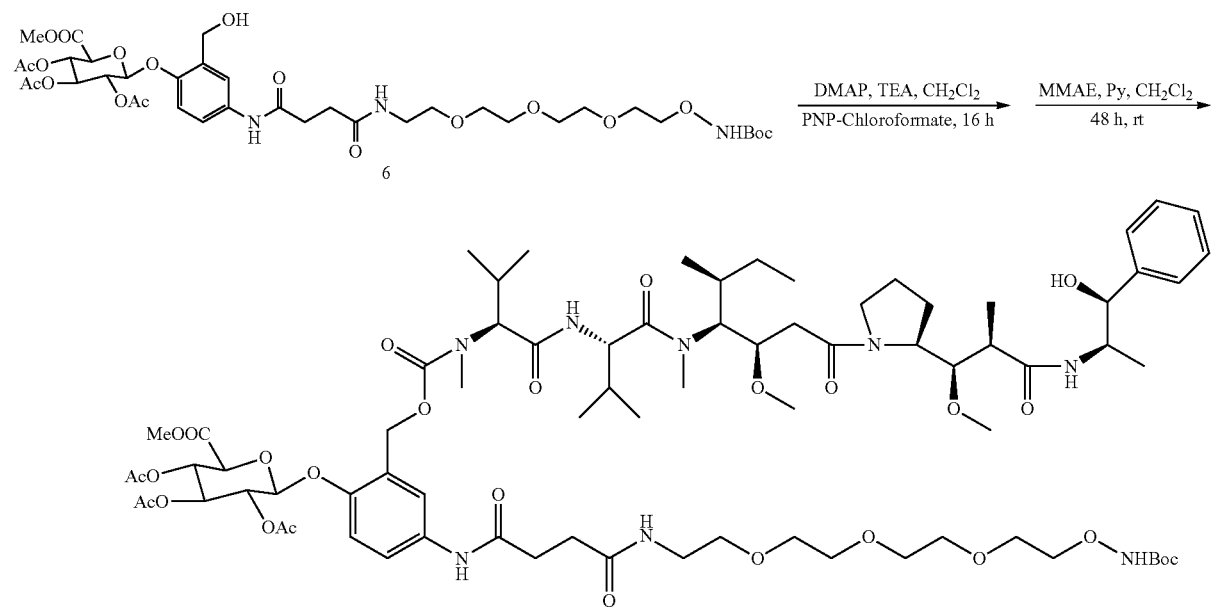

Preparation of Compound (7)

Compound 6 (100.0 mg, 0.12 mmol) was dissolved in 5 mL of CH$_2$Cl$_2$ and cooled to 0° C. TEA (24.0 mg, 0.24 mmol), DMAP (14.7 mg, 0.12 mmol), PNP Chloroformate (47.7 mg, 0.24 mmol) were added and the mixture was stirred in rt for 3 h. The resulting mixture was diluted with CH$_2$Cl$_2$ and washed with 1 N HCl, saturated aqueous NaHCO$_3$ and brine. The organic layer extraction was dried by MgSO$_4$ and concentrated. The crude product was purified by column to give compound A01-6 for next step. A solution of A01-6 (95.0 mg, 0.094 mmol) and MMAE (67.5 mg, 0.094 mmol) in 4 mL of THF was treated with TEA (19.0 mg, 0.188 mmol). The resulting mixture was stirred at RT for 48 h. After the reaction was completed, 35 mL of EA and 20 mL of 0.5N HCl solution were added. The organic layer extraction was dried by MgSO$_4$ and concentrated. The crude product was purified by column to give compound 7 as yellow oil (98.0 mg, 0.06 mmol). ESI-TOF m/z: 1587.8759 [M−H]$^-$.

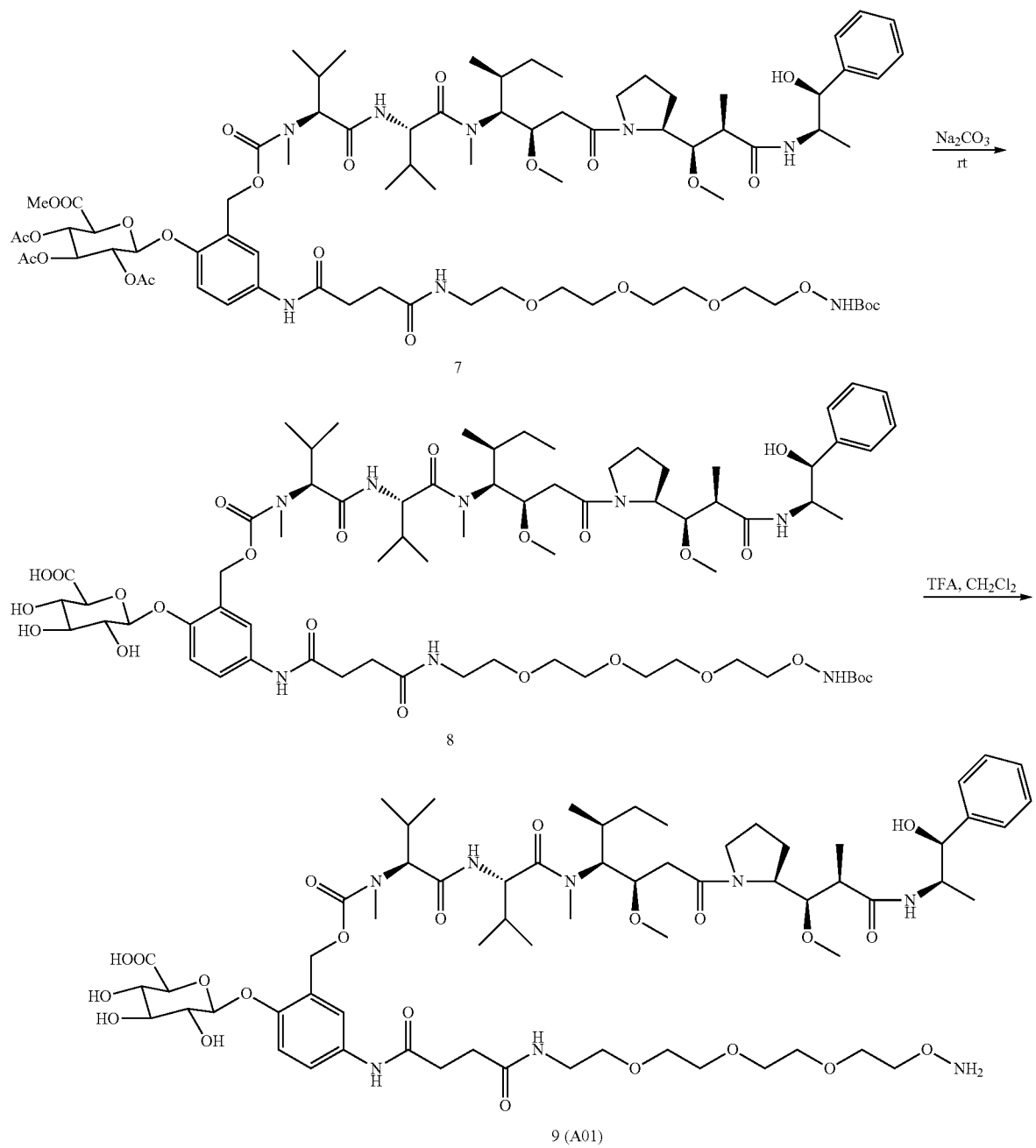

Preparation of Compound (8)

A solution of compound 7 (20.0 mg, 0.013 mmol) in 2.5 mL of solution (MeOH:H$_2$O=4:1) was treated at 0° C. with Na$_2$CO$_3$. The resulting mixture was stirred at rt for 3 h. After the reaction was completed, the organic solution was removed under reduced pressure. The residue was purified by was purified by C18 column to give compound 8 (15.2 mg, 0.010 mmol, 77.0%). ESI-TOF m/z: 1471.7639 [M+Na$^+$]

Preparation of Compound (9)

To a solution of compound 8 (10 mg, 2.99 mmol) was dissolved in 2 ml of CH$_2$Cl$_2$. 0.25 ml of TFA was then added and stirred at room temperature for 1 h. The solution was concentrated and the residue was purified by C18 column to give compound 9 (6.5 mg, 77%). ESI-TOF m/z: 1347.7178 [M−H]$^−$.

2.2 Synthesis and Characterization of Compound 15 (A02)

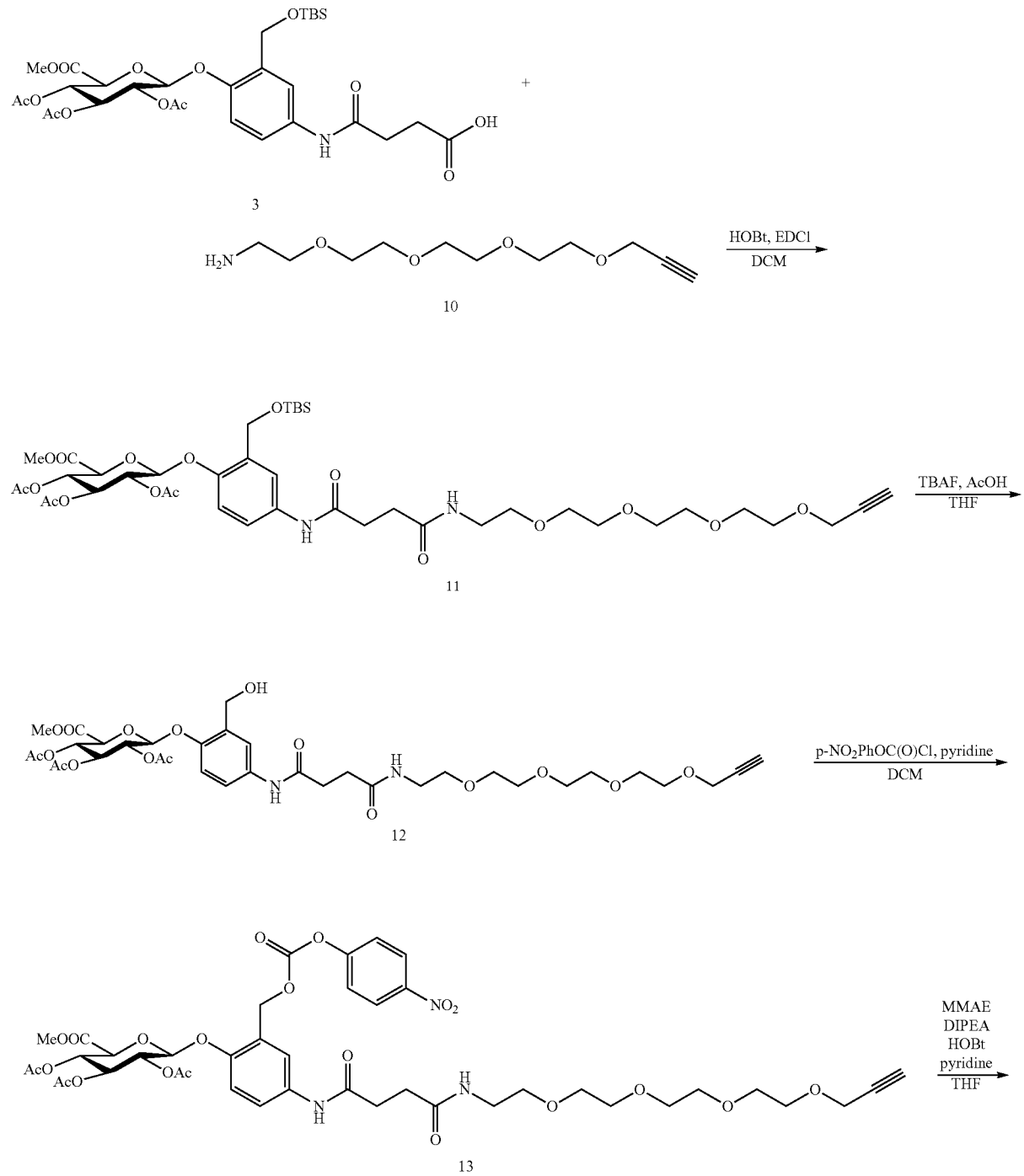

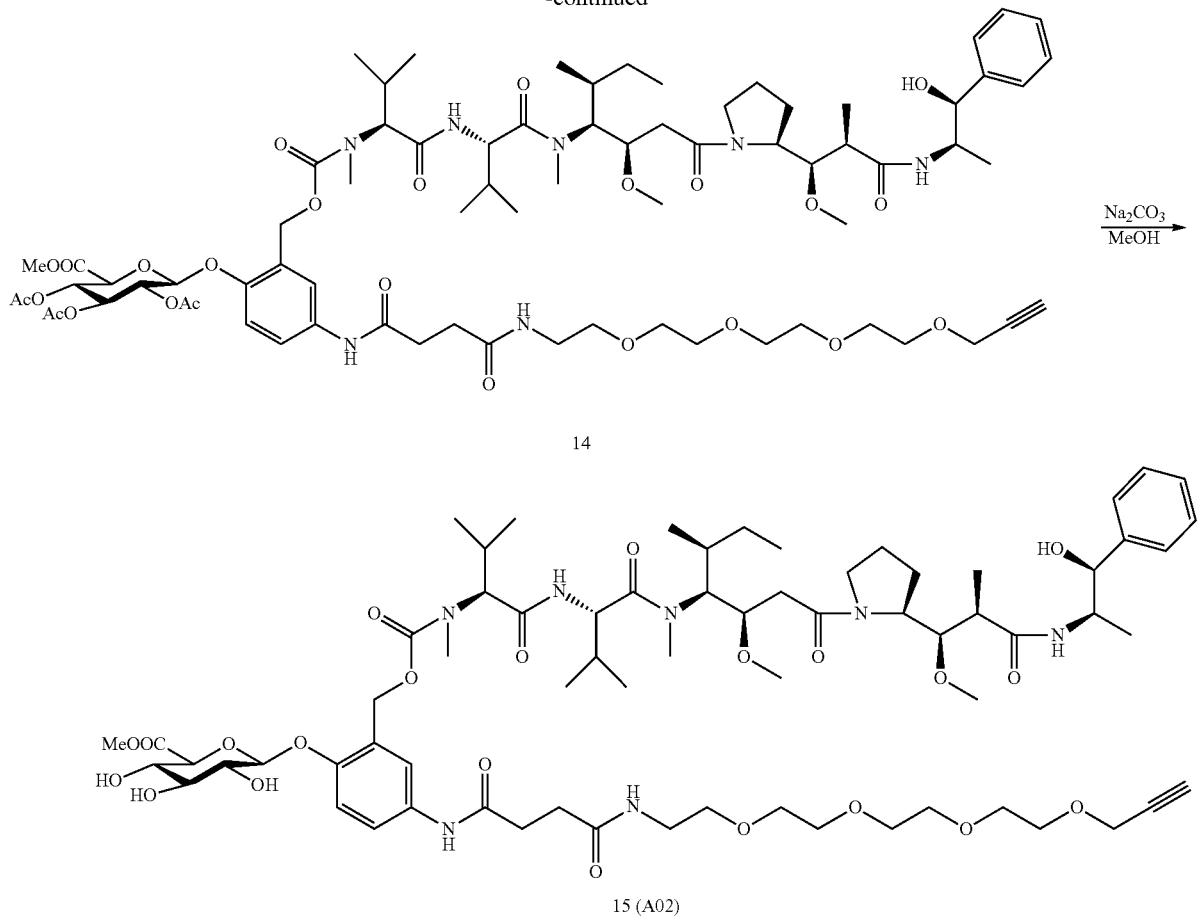

14

15 (A02)

Preparation of Compound (11)

2,3,4-tri-Ac-6-methyl-Glucuranate-2'-OTBS-PAB-succinic acid 3 (109 mg, 0.16 mmol) and alkynyl-PEG4-amine 10 (60 mg, 0.16) was dissolved in $CH_2Cl_2$ (5 mL) followed by the addition of EDCI (46.4 mg, 0.244 mmol), HOBt (2.5 mg, 0.015 mmol) and DMAP (6.2 mg, 0.05 mmol). After 4 hours, the solvent was removed and the reaction mixture was then purified by silica gel chromatography eluting with 20% EA/hexane, then 50% EA/hexane to give 103 mg (73%) of 2,3,4-tri-Ac-6-methyl-Glucuranate-2'-OTBS-PAB-succinate-alkynyl-PEG4 11. Then 11 (95 mg, 0.108 mmol) was dissolved in a mixture of pyridine (9 mL) and acetic acid (3 mL) followed by the addition of TBAF (0.5 mL, 1 M in THF). After 12 hours, the solvent was removed and the reaction mixture was then purified by silica gel chromatography eluting with $CH_2Cl_2$ (100%), then 5% MeOH/$CH_2Cl_2$ to give 66.4 mg (80%) of 2,3,4-tri-Ac-6-methyl-Glucuranate-2'-OH-PAB-succinate-alkynyl-PEG4 12. The obtained compound was suspended in anhydrous $CH_2Cl_2$ (2.6 mL), followed by the addition of pyridine (122 μL, 0.88 mmol) and 4-nitrobenzoyl chloride (74 mg, 0.36 mmol). After 2 hours the solvent was removed and purified by silica gel chromatography eluting with $CH_2Cl_2$ (100%), then 5% MeOH/$CH_2Cl_2$ to give 46.6 mg (58%) of 2,3,4-tri-Ac-6-methyl-Glucuranate-2'-OpNP-PAB-succinate-alkynyl-PEG4 13. $^1$H NMR (400 MHz, CDCl3) δ 9.12 (s, 1H), 8.24 (d, J=2.04 Hz, 2H), 7.57 (d, J=2.44 Hz, 1H), 7.5 (d, J=8.88 Hz, 1H), 7.39 (d, J=7.12 Hz, 1H), 6.98 (d, J=8.88 Hz, 1H), 6.76 (t, J=2.74 Hz, 1H), 5.37-5.28 (m, 3H), 5.24 (dd, J=11.92 Hz, 24.04 Hz, 2H), 5.1 (d, J=14.32 Hz, 1H), 4.16 (d, J=9.08 Hz, 1H), 4.13 (d, J=2.4 Hz, 2H), 3.69 (s, 3H), 3.67-3.6 (m, 8H), 3.59-3.56 (m, 4H), 3.5 (t, J=4.8 Hz, 1H), 3.41 (t, J=4.8 Hz, 1H), 2.62 (ddd, J=4.6 Hz, 7.76 Hz, 16.12 Hz, 4H), 2.41 (t, J=2.36 Hz, 1H), 2.35 (s, 1H), 2.03 (s, 3H), 2.01 (s, 3H), 2.0 (s, 3H).

Preparation of Compound (14)

MMAE (30 mg, 0.043 mmol) was dissolved in a mixture of THF (2.0 mL) and pyridine (0.5 mL) followed by the addition of DIPEA (80 μL), HOBt (1.5 mg, 0.01 mmol) and 2,3,4-tri-Ac-6-methyl-Glucuranate-2'-OpNP-PAB-succinate-alkynyl-PEG4 13 (40 mg, 0.043 mmol). After 48 hours the solvent was removed and the reaction mixture was then purified by silica gel chromatography eluting with $CH_2Cl_2$ (100%), then 7.5% MeOH/$CH_2Cl_2$ to give 38.4 mg (59%) of 2,3,4-tri-Ac-6-methy 1-Glucuranate-2'-MMAE-PAB-succinate-alkynyl-PEG4 14. $^1$H NMR (400 MHz, CDCl3) δ 9.0 (m, 1H), 7.67-7.25 (m, 6H), 7.24-6.9 (m, 3H), 6.81 (s, 1H), 6.7-6.45 (m, 2H), 5.42-5.29 (m, 4H), 5.29-4.88 (m, 4H), 4.8-4.55 (m, 2H), 4.22 (bs, 1H), 4.15 (s, 3H), 4.12-4.0 (m, 3H), 3.85-3.23 (m, 33H), 3.1-2.75 (m, 6H), 2.73-2.5 (m, 5H), 2.42 (d, J=2.0 Hz, 1H), 2.4-2.3 (m, 4H), 2.3-2.16 (m, 2H), 2.15-2.07 (m, 5H), 2.06 (s, 9H), 1.8-1.0 (m, 33H). ESI-TOF m/z: 1408.7366 [M+Na]$^+$.

Preparation of Compound (15)

2,3,4-tri-Ac-6-methyl-Glucuranate-2'-MMAE-PAB-succinate-alkynyl-PEG4 14 (30 mg, 0.02 mmol) was dissolved MeOH (1.0 mL), then Na$_2$CO$_3$ (7 mg, 0.063 mmol) was added. After 1 hour, H$_2$O (40 μL) was added to the reaction mixture and the reaction was kept stirring for another 1 hour. Then the reaction was neutralized by IR-120, after filtered, the crude was evaporated and purified by C18 column eluting with 100% H$_2$O, then 50% acetonitrile/H$_2$O to give 12.3 mg (44.5%) of 6-methyl-Glucuranate-2'-MMAE-PAB-succinate-alkynyl-PEG4 15. $^1$H NMR (400 MHz, CDCl3) δ 8.95 (m, 1H), 7.68 (d, J=7.9 Hz, 1H), 7.5-6.8 (m, 8H), 5.38 (d, J=6.7 Hz, 1H), 5.37-5.15 (m, 1H), 5.0 (d, J=6.7 Hz, 1H), 4.9 (s, 1H), 4.85-4.52 (m, 3H), 4.35-4.16 (bs, 2H), 4.15 (d, J=2.36 Hz, 3H), 4.1-3.2 (m, 32H), 3.14-2.97 (m, 2H), 2.86-2.75 (m, 3H), 2.68-2.54 (m, 41H), 2.43 (t, J=2.36 Hz, 1H), 2.4-1.5 (m, 13H), 1.4-1.23 (m, 1H), 1.22 (s, 2H), 1.2 (s, 1H), 1.12-1.0 (m, 1H), 0.98-0.45 (m, 20H). ESI-TOF m/z: 1408.7366 [M+Na]$^+$.

2.3 Synthesis and Characterization of Compound 23 (A03)

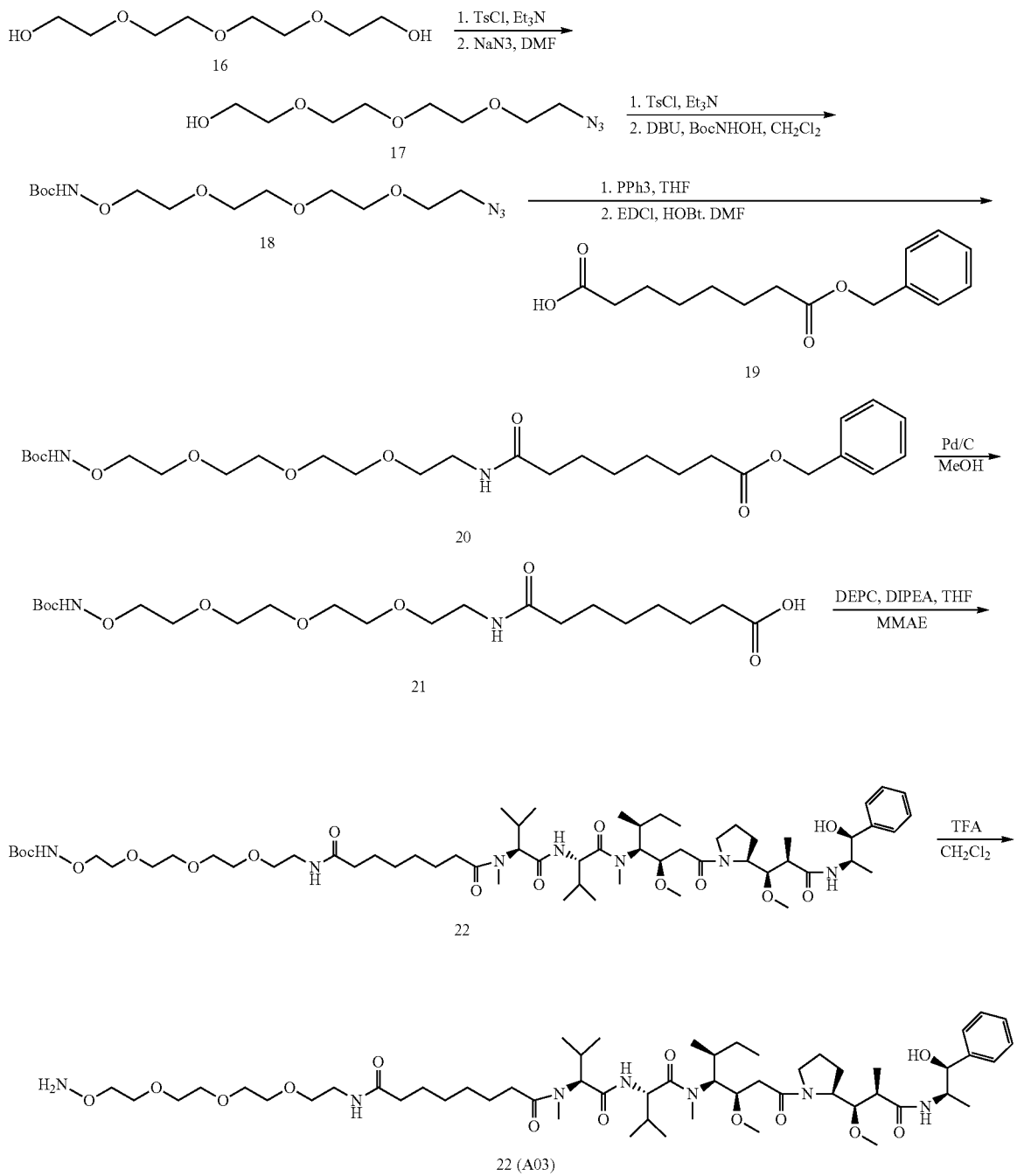

Preparation of Compound (17)

To a dichloromethane (100 mL) solution of the tetraethylene glycol (60 g, 308 mmole) and triethylamine (47 mL, 337 mmole), p-Toluenesulfonyl chloride (30 g, 157 mmole) in $CH_2Cl_2$ (100 mL) was dropwise added into the mixture and solution was stirred at room temperature for 16 hr. The white solid was observed, filtered by the pad of celite, and washed by $CH_2Cl_2$. The filtrate was concentrated in vacuo and the residue was purified by flash column chromatography (silica gel, 10-20% Ethyl acetate in Hexane) to afford an oil intermediate (40 g, 115 mmole). Then, a N,N-Dimethylformamide solution of sodium azide (20 g, 307 mmole) and compound (40 g, 115 mmole) obtained above was stirred for 16 hr at 80° C. The white solid was observed, filtered by the pad of celite, and washed by Ethyl acetate. The filtrate was concentrated in vacuo and the residue was purified by flash column chromatography (silica gel, 50-70% Ethyl acetate in Hexane) to afford the product 17 as an oil (24 g, 109.5 mmole); $^1$H NMR (400 MHz, CDCl3) 3.67 (t, J=4.0 Hz, 2H), 3.62-3.61 (m, 10H), 3.57-3.55 (m, 2H), 3.34 (t, J=2.4 Hz, 2H), 2.66 (s, 1H).

Preparation of compound (18)

To a Dichloromethane (40 mL) solution of the compound 17 (24 g, 109.5 mmole) and triethylamine (19 mL, 136.8 mmole), P-Toluenesulfonyl chloride (26 g, 136.8 mmole) in $CH_2Cl_2$ (40 mL) was dropwisely added into the mixture and solution was stirred at room temperature for 16 hr. The white solid was observed, filtered by the pad of celite, and washed by $CH_2Cl_2$. The filtrate was concentrated in vacuo and the residue was purified by flash column chromatography (silica gel, 25-30% Ethyl acetate in Hexane) to afford the tosylated product as an oil (34.7 g, 93 mmole). Then, a Dichloromethane (30 mL) solution of the N-Boc-hydroxylamine (5.35 g, 40 mmole) and the tosylated compound (10 g, 26.78 mmole) obtained above, and DBU (8.07 mL, 54 mmole) was added into the mixture and solution was stirred at room temperature for 72 hr. When TLC indicated that starting material was fully consumed, the solution was concentrated. Purification of the crude material using column chromatography (silica gel, 35-50% Ethyl acetate in Hexane) afforded the product 18 (5.37 g, 60% yield) as an oil; HRMS (ESI-TOF, MNa+) calculated for C13H26N4O6Na 357.1745, found 357.1736.

Preparation of Compound (20)

To a Dichloromethane (20 mL) solution of triphenylphosphine (2.89 g, 11 mmole) and compound 18 (1.4 g, 4.2 mmole) was stirred. After stirring overnight at room temperature, the solution was concentrated in vacuo and the residue was purified by flash column chromatography (silica gel, 90% Ethyl acetate in Hexane) to afford the product as an oil (1.09 g, 3.53 mmole). The, a solution of the intermediate compound (1.09 g, 3.53 mmole) obtained above and compound 19 (1.46 g, 5.52 mmol, 1.0 eq) in DMF (90 mL) were added EDCI-HCl (1.06 g, 6.83 mmol) and HOBt (0.34 g, 2.52 mmol). The resulting mixture was stirred for 24 h and concentrated in vacuo. The crude product was purified by flash column chromatography (silica gel, 2% MeOH in Ethyl acetate) to afford the product 20 (1.38 g, 2.49 mmole) as an oil; $^1$H NMR (400 MHz, CDCl3) 7.78 (s, 1H), 7.35-7.26 (m, 5H), 6.26 (s, 1H), 5.07 (s, 2H), 3.99-3.97 (m, 2H), 3.70-3.68 (m, 2H), 3.67-3.58 (m, 8H), 3.53 (t, J=4.8 Hz, 2H), 3.42-3.39 (m, 2H), 2.31 (t, J=7.6 Hz, 2H), 2.12 (t, J=7.2 Hz, 2H), 1.64-1.54 (m, 4H), 1.44 (s, 9H), 1.30-1.27 (m, 4H); HRMS (ESI-TOF, MNa+) calculated for C28H46N2O9Na, 577.3096, found 577.3080.

Preparation of Compound (21)

To a Methyl alcohol (10 mL) solution of compound 20 (1.38 g, 2.49 mmole) and Pd/C (0.4 g) was stirred under H2 atmosphere. After stirring overnight for 14 hr, the Pd/C was filtered by the pad of celite, and washed by Methyl alcohol. The solution was concentrated in vacuo and the residue was purified by flash column chromatography (silica gel, 2% MeOH in $CH_2Cl_2$) to afford the product as an oil 21 (0.5146 g, 1.1 mmole); $^1$H NMR (400 MHz, CDCl3) 7.98 (s, 11H), 6.45 (s, 1H), 4.00-3.98 (m, 2H), 3.70-3.68 (m, 2H), 3.64-3.61 (m, 8H), 3.54 (t, J=4.4 Hz, 2H), 3.43-3.41 (m, 2H), 2.30 (t, J=6.8z, 2H), 2.16 (t, J=7.6 Hz, 2H), 1.64-1.54 (m, 4H), 1.45 (s, 9H), 1.32-1.31 (m, 4H); HRMS (ESI-TOF, MNa+) calculated for C21H40N2O9Na 487.2626, found 487.2625.

Preparation of Compound (22)

DEPC (0.31 g, 0.181 mmole) and DIPEA (0.03 mL, 0.181 mmol) were added sequentially to a solution of compounds 21 (30 mg, 0.0646 mmol) and MMAE (35.5 mg, 0.0494 mmol) in DMF (2 mL) at 0° C., and the mixture was stirred at 0° C. to room temperature for 16 h. The reaction mixture was then concentrated in vacuo and the residue was purified by flash column chromatography (silica gel, 6-10% MeOH in $CH_2Cl_2$) to afford the product as an oil 22 (52.6 mg, 0.0452 mmole); HRMS (ESI-TOF, MNa+) calculated for C21H40N2O9Na, 1186.7561, found 1186.7567.

Preparation of Compound (23)

TFA (0.3 mL) was slowly added into a solution of 22 (52.6 mg, 0.0452 mmol) in DCM (0.7 mL) at 0° C. The resulting mixture was stirred at room temperature for 2 h, and concentrated. Purification of the crude material using column chromatography (silica gel, 6-10% MeOH in $CH_2Cl_2$) afforded the product 23 (33.6 mg, 0.032 mmol) as an oil; HRMS (ESI-TOF, MNa+) calculated for C13H26N4O6Na, 1086.7037, found 1086.7113.

2.4 Synthesis and Characterization of Compound 25 (A04)

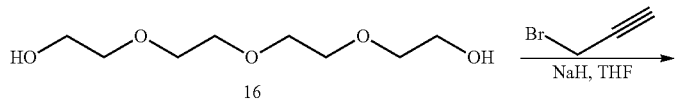

16

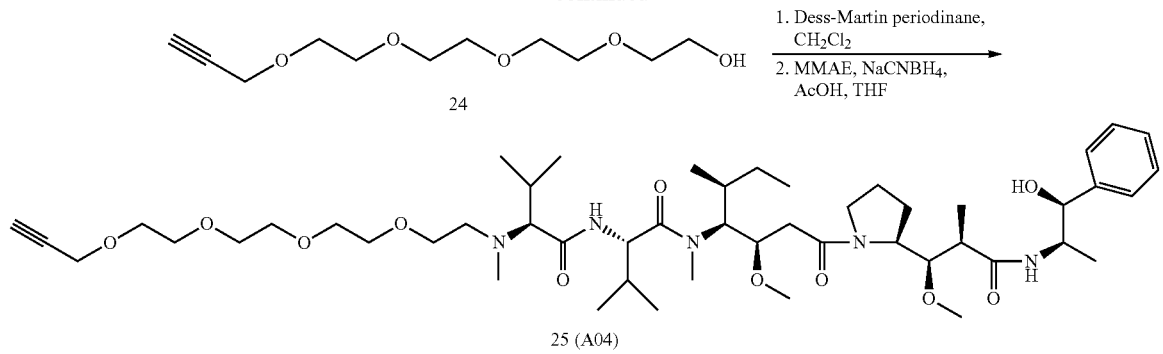

Preparation of Compound (24)

To a Tetrahydrofuran (250 mL) solution of the Sodium hydride (4.8 g, 120 mmole) and tetraethylene glycol 16 (40 g, 207 mmole), propargyl bromide (7.4 mL, 69 mmole) was added into the mixture at 0° C. and solution was stirred at room temperature for 16 hr. When TLC indicated that starting material was fully consumed, the solution was concentrated. The residue was extracted with $CH_2Cl_2$ (4×30 mL) and $H_2O$. The combined organic layers were dried over $MgSO_4$, and filtered. The filtrate was concentrated in vacuo and the residue was purified by flash column chromatography (silica gel, 15% Ethyl acetate in Hexane) to afford the product as an oil 24 (14 g, 60.3 mmole); $^1$H NMR (400 MHz, $CDCl_3$) 4.17-4.16 (m, 2H), 3.70-3.62 (m, 14H), 3.59-3.56 (m, 2H), 2.40 (t, J=2.4 Hz, 1H); HRMS (ESI-TOF, MNa+) calculated for C11H20O5Na 255.1203, found 255.1202.

Preparation of Compound (25)

To a solution of compound 24 (920 mg, 3.96 mmol) in 70 mL of dichloromethane was added Dess-Martin Periodinane (2.25 g, 5.30 mmol). The reaction mixture was stirred at ambient temperature overnight. The reaction was quenched with the solution of sodium bisulfite in 60 mL of saturated sodium bicarbonate. The mixture was separated. The organic layer was washed with saturated sodium bicarbonate, brine, dried over sodium sulfate, filtered, and concentrated in vacuo. The residue was purified by flash column chromatography to give compound (0.54 g, 2.345 mmole); $^1$H NMR (400 MHz, $CDCl_3$) 9.69 (s, 1H), 4.16-4.13 (m, 2H), 3.71-3.62 (m, 14H), 2.40 (t, J=2.4 Hz, 1H). To a solution of MMAE (10 mg, 0.0139 mmol) in 0.286 mL of N,N-Dimethylformamide (DMF) was added compound obtained above (12.8 mg, 0.0556 mmol) and 16 μL of acetic acid, followed by addition of 2 mg of sodium cyanoborohydride. The resulting mixture was stirred at ambient temperature for 2 h. The reaction mixture was concentrated and purified by flash column chromatography to give compound 25 (10 mg, 0.0107 mmole); HRMS (ESI-TOF, MNa+) calculated for C50H85N5O11Na, 954.6138, found 954.6303.

2.5 Synthesis and Characterization of Compound 31 (A05)

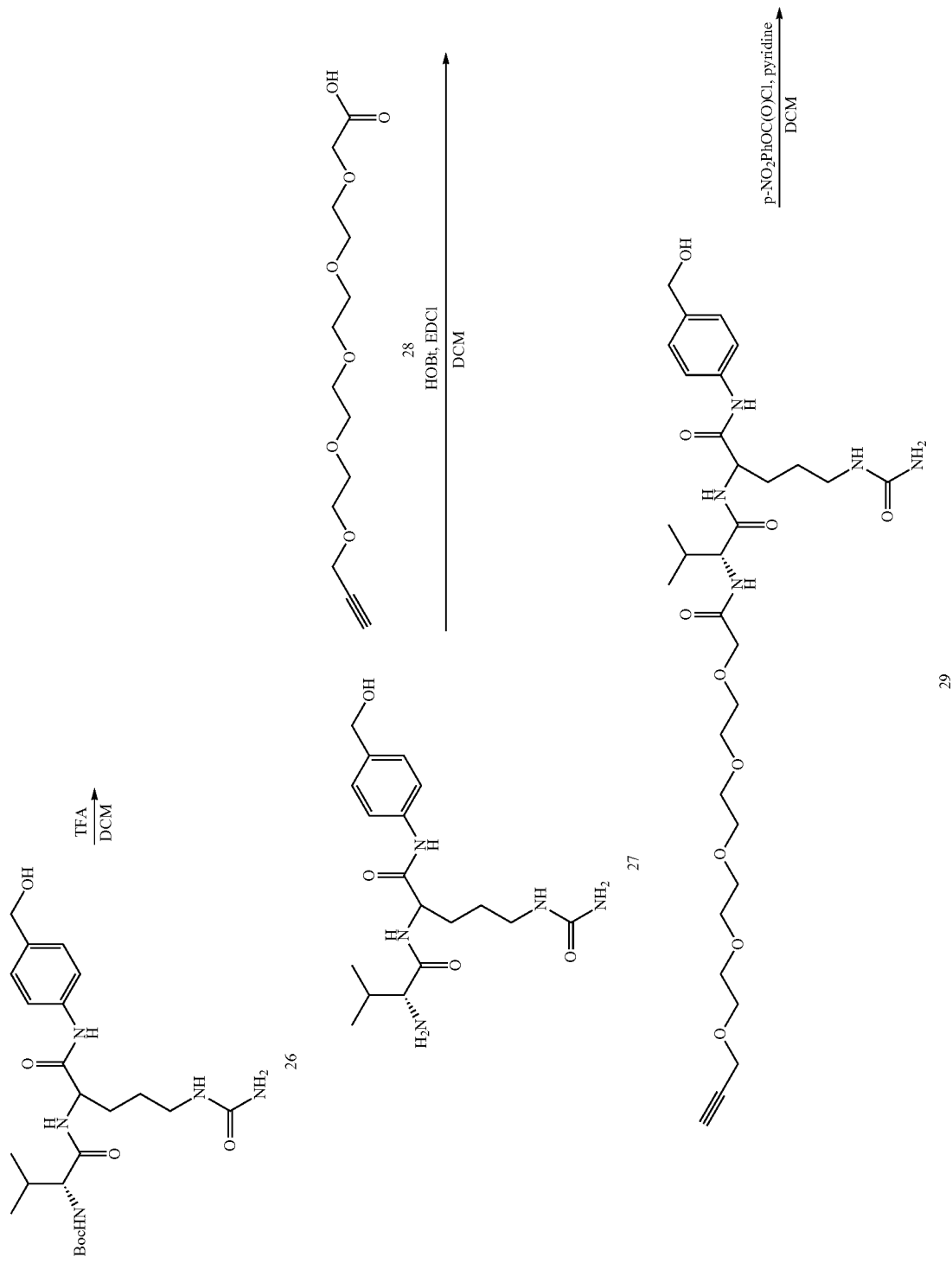

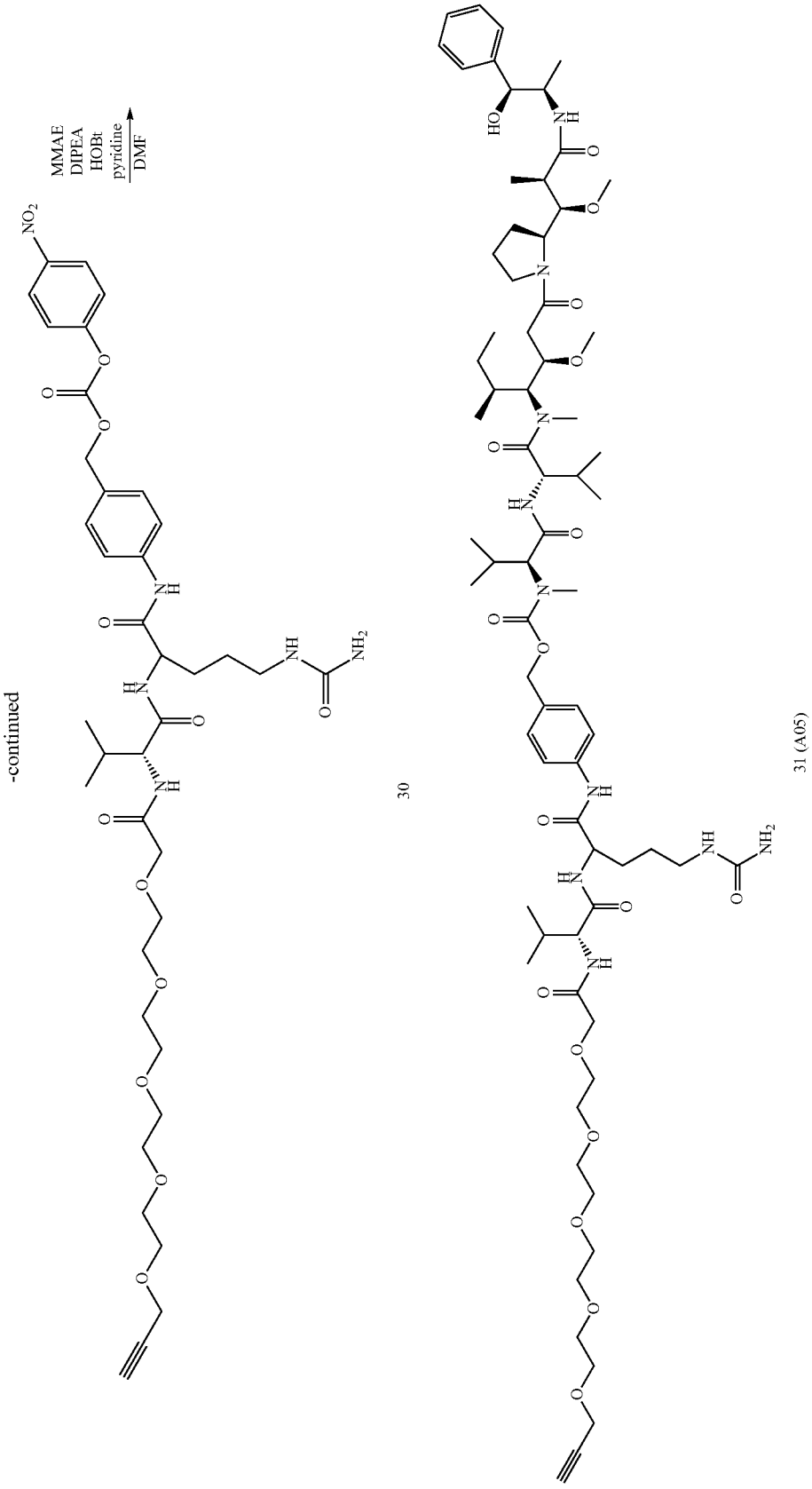

Preparation of Compound (27)

Boc-Val-Cit-PAB-OH 26 (100 mg, 0.2 mmol) was suspended in anhydrous $CH_2Cl_2$ (1.8 mL), and TFA (0.45 mL) was added. The reaction was stirred at 0° C. for 10 min, then warmed to room temperature for another 30 min. The reaction mixture was evaporated to dryness (azeotropic with toluene for 3 times) to get Val-Cit-PAB-OH 27 without further purification. $^1$H NMR (400 MHz, $CDCl_3$) δ 7.3-6.99 (m, 5H), 4.47 (m, 1H), 4.44 (s, 1H), 3.86 (s, 3H), 3.05 (m, 2H), 2.11 (m, 1H), 1.7 (m, 1H), 1.58 (m, 1H), 1.5 (m, 2H), 0.95 (q, 6H).

Preparation of Compound (29)

The obtained compound 27 and alkynyl-PEG4-COOH 28 (58 mg, 0.2 mmol) were suspended in anhydrous $CH_2Cl_2$ (2.0 mL) followed by the addition of HOBt (2.7 mg, 0.02 mmol) and EDCI (57 mg, 0.3 mmol). After 12 hours the solvent was removed and purified by silica gel chromatography eluting with $CH_2Cl_2$ (100%), then 10% MeOH/$CH_2Cl_2$ to give 80.8 mg (62%) of alkynyl-PEG4-Val-Cit-PAB-OH 29. Then compound 29 (80 mg, 0.12 mmol) was suspended in anhydrous DMF (2 mL), followed by the addition of pyridine (58 μL, 0.72 mmol) and 4-nitrobenzoyl chloride (66.8 mg, 0.36 mmol). After 2 hours the solvent was removed and purified by silica gel chromatography eluting with $CH_2Cl_2$ (100%), then 5% MeOH/$CH_2Cl_2$ to give 63.7 mg (65%) of alkynyl-PEG4-Val-Cit-PAB-OpNP 30. Next, MMAE (33.4 mg, 0.047 mmol) was dissolved in a mixture of DMF (1.5 mL) and pyridine (0.5 mL) followed by the addition of DIPEA (72 μL), HOBt (2 mg, 0.014 mmol) and alkynyl-PEG4-Val-Cit-PAB-OpNP 30 (38 mg, 0.047 mmol). After 48 hours the solvent was removed and the reaction mixture was then purified by silica gel chromatography eluting with $CH_2Cl_2$ (100%), then 15% MeOH/$CH_2Cl_2$ to give 30 mg (45%) of alkynyl-PEG4-Val-Cit-PAB-MMAE 31. $^1$H NMR (400 MHz, MeOD) δ 7.48 (d, J=7.88 Hz, 2H), 7.3-7.05 (m, 7H), 5.14-4.9 (m, 2H), 4.6-4.37 (m, 3H), 4.19 (dd, J=2.76 Hz, 7.12 Hz, 1H), 4.15-4.09 (m, 2H), 4.07 (d, J=2.36 Hz, 2H), 3.78 (s, 21), 3.64-3.57 (m, 5H), 3.56-3.53 (m, 8H), 3.51 (s, 4H), 3.3 (t, J=10.8 Hz, 1H), 2.45 (d, J=3.32 Hz, 1H), 3.17 (s, 1H), 3.15-2.95 (m, 3H), 2.85-2.8 (m, 3H), 2.75 (t, J=2.36 Hz, 1H), 2.45-2.35 (m, 2H), 2.15-1.57 (m, 11H), 1.45 (m, 4H), 1.35-1.13 (m, 9H), 1.07 (q, 3H), 1.03 (t, J=7.08 Hz, 3H), 1.0-0.55 (m, 25H). ESI-TOF m/z: 1417.8368 [M+Na]$^+$.

2.6 Synthesis and Characterization of Compound 35 (A06)

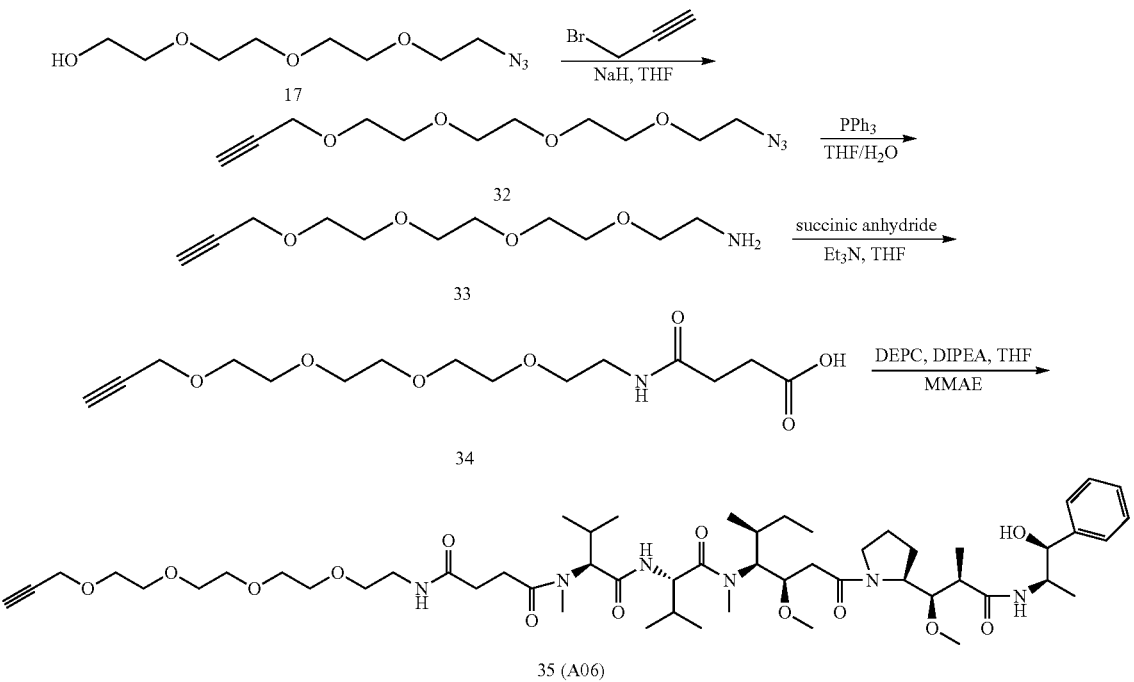

Preparation of Compound (32)

To a Tetrahydrofuran (200 mL) solution of the Sodium hydride (1.93 g, 48.25 mmole) and 1-azido-3,6,9,12-tetraoxapentadecane (5 g, 22.80 mmole), Propargyl bromide (6 mL, 69.6 mmole) was added into the mixture at 0° C. and solution was stirred at room temperature for 16 hr. When TLC indicated that starting material was fully consumed, the solution was concentrated. The residue was extracted with $CH_2Cl_2$ (4×30 mL) and $H_2O$. The combined organic layers were dried over $MgSO_4$, and filtered. The filtrate was concentrated in vacuo and the residue was purified by flash column chromatography (silica gel, 35% Ethyl acetate in Hexane) to afford the product as an oil 32 (5.4 g, 20.9 mmole); $^1$H NMR (400 MHz, $CDCl_3$) 4.17 (d, J=2.4 Hz, 2H), 3.67-3.64 (m, 14H), 3.36 (t, J=5.2 Hz, 2H), 2.40 (t, J=2.4 Hz, 1H); HRMS (ESI-TOF, MNa+) calculated for C11H19N3O4Na, 280.1268, found 280.1270.

Preparation of Compound (33)

To a Tetrahydrofuran (40 mL) solution of triphenylphosphine (3.68 g, 14 mmole) and compound 32 (2.9 g, 11.3 mmole) was stirred. After stirring overnight at room temperature, the solution was concentrated in vacuo and the residue was purified by flash column chromatography (silica gel, 80% MeOH in $CH_2Cl_2$) to afford the product as an oil 33 (2.4 g, 10.376 mmole); 1H NMR (400 MHz, $CDCl_3$) 4.17-4.16 (m, 21), 3.65-3.57 (m, 14H), 2.83 (t, J=4.8 Hz, 2H), 2.40 (t, J=2.0 Hz, 1H); HRMS (ESI-TOF, MNa+) calculated for C11H21NO4Na 232.1543, found 232.1615.

Preparation of Compound (34)

Compound 33 (0.34 g, 1.47 mmole) and succinic anhydride (0.18 g, 1.79 mmole) were dissolved in Tetrahydrofuran (12 mL) followed by addition of triethylamine (0.35 mL, 2.51 mmole) at room temperature and the solution was stirred at room temperature for 2 hr. The solution was concentrated and the residue was purified by flash column chromatography (silica gel, 5-6% MeOH in $CH_2Cl_2$) to afford the product as an oil 34 (2.4 g, 10.376 mmole); $^1$H NMR (400 MHz, $CDCl_3$) 6.79 (s, 1H), 4.16 (d, J=2.4 Hz, 1H), 3.68-3.58 (m, 12H), 3.52 (t, J=4.8 Hz, 2H), 3.43-3.39 (m, 2H), 2.64 (t, J=6 Hz, 2H), 2.51 (t, J=7.2 Hz, 2), 2.42 (t, J=2.4 Hz, 1H); HRMS (ESI-TOF, MNa+) calculated for C15H25NO7Na, 354.1523, found 354.1548.

Preparation of Compound (35)

DEPC (0.014 g, 0.0863 mmole) and DIPEA (0.021 mL, 0.127 mmol) were added sequentially to a solution of compounds 34 (24.5 mg, 0.0739 mmol) and MMAE (30 mg, 0.0418 mmol) in DMF (2.75 mL) at 0° C., and the mixture was stirred at 0° C. to room temperature for 16 h. The reaction mixture was then concentrated in vacuo and the residue was purified by flash column chromatography (silica gel, 4-7% MeOH in $CH_2Cl_2$) to afford the product as an oil 35 (25.9 mg, 0.0251 mmole); HRMS (ESI-TOF, MNa+) calculated for C54H90N6O13Na, 1053.6458, found 1053.6604.

Preparation of Compound (36)

To a Tetrahydrofuran (24 mL) solution of the Sodium hydride (0.245 g, 6.125 mmole) and compound 24 (1.14 g, 4.908 mmole), methyl bromoacetate (0.67 mL, 6.865 mmole) was dropwise added into the mixture at 0° C. and solution was stirred at room temperature for 16 hr. When TLC indicated that starting material was fully consumed, the solution was quenched with MeOH, filtered through a pad of celite, and the celite was washed with MeOH. The combined filtrates and washings were concentrated under reduced pressure and the residue was purified by flash column chromatography (silica gel, 70% Ethyl acetate in Hexane) to afford the product as an oil 36 (1.18 g, 3.877 mmole); $^1$H NMR (400 MHz, $CDCl_3$) 4.10 (d, J=2.4 Hz, 1H), 4.07 (s, 2H), 3.65 (s, 3H), 3.64-3.56 (m, 16H), 2.36 (t, J=2.4 Hz, 1H); HRMS (ESI-TOF, MH+) calculated for C14H25O7 305.1595, found 305.1599.

Preparation of Compound (37)

To a Tetrahydrofuran (10 mL) solution of compound 36 (1.18 g, 3.877 mmole), $H_2O$ (6 mL), and LiOH (0.188 g, 7.85 mmole) was stirred. After stirring for 2 hr at room temperature, the solution was quenched with 1N HCl (10 mL), and partitioned between ethyl acetate and brine. The organic phase was collected and the aqueous phase was extracted with ethyl acetate (50 mL×4). The combined organic layer were concentrated and the residue was purified by flash column chromatography (silica gel, 10-15% MeOH in $CH_2Cl_2$) to afford the product as an oil 37 (0.6 g, 2.07 mmole); $^1$H NMR (400 MHz, $CDCl_3$) 4.01 (d, J=2.4 Hz, 1H), 3.99 (s, 2H), 3.56-3.48 (m, 16H), 2.35 (t, J=2.0 Hz, 1H); HRMS (ESI-TOF, MNa+) calculated for C13H22O7Na, 313.1258, found 313.1261.

Preparation of Compound (38)

DEPC (0.0334 g, 0.206 mmole) and DIPEA (0.034 mL, 0.206 mmol) were added sequentially to a solution of compounds 37 (38.8 mg, 0.1337 mmol) and MMAE (51 mg, 0.071 mmol) in DMF (4 mL) at 0° C., and the mixture was stirred at 0° C. to room temperature for 16 h. The reaction 2.7 Synthesis and Characterization of Compound 38 (A07)

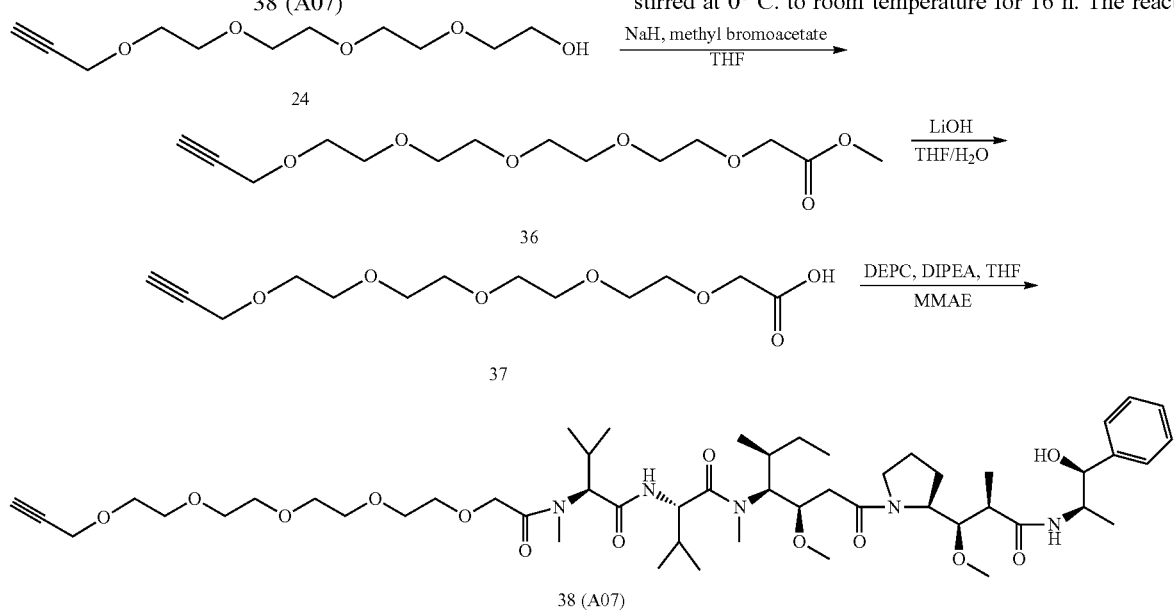

mixture was then concentrated in vacuo and the residue was purified by flash column chromatography (silica gel, 4-6% MeOH in CH$_2$Cl$_2$) to afford the product as an oil 38 (49.2 mg, 0.0497 mmole); HRMS (ESI-TOF, MNa+) calculated for C52H87N5O13Na, 1012.6193, found 1012.6186.
2.8 Synthesis and Characterization of Compound 44 (A08)
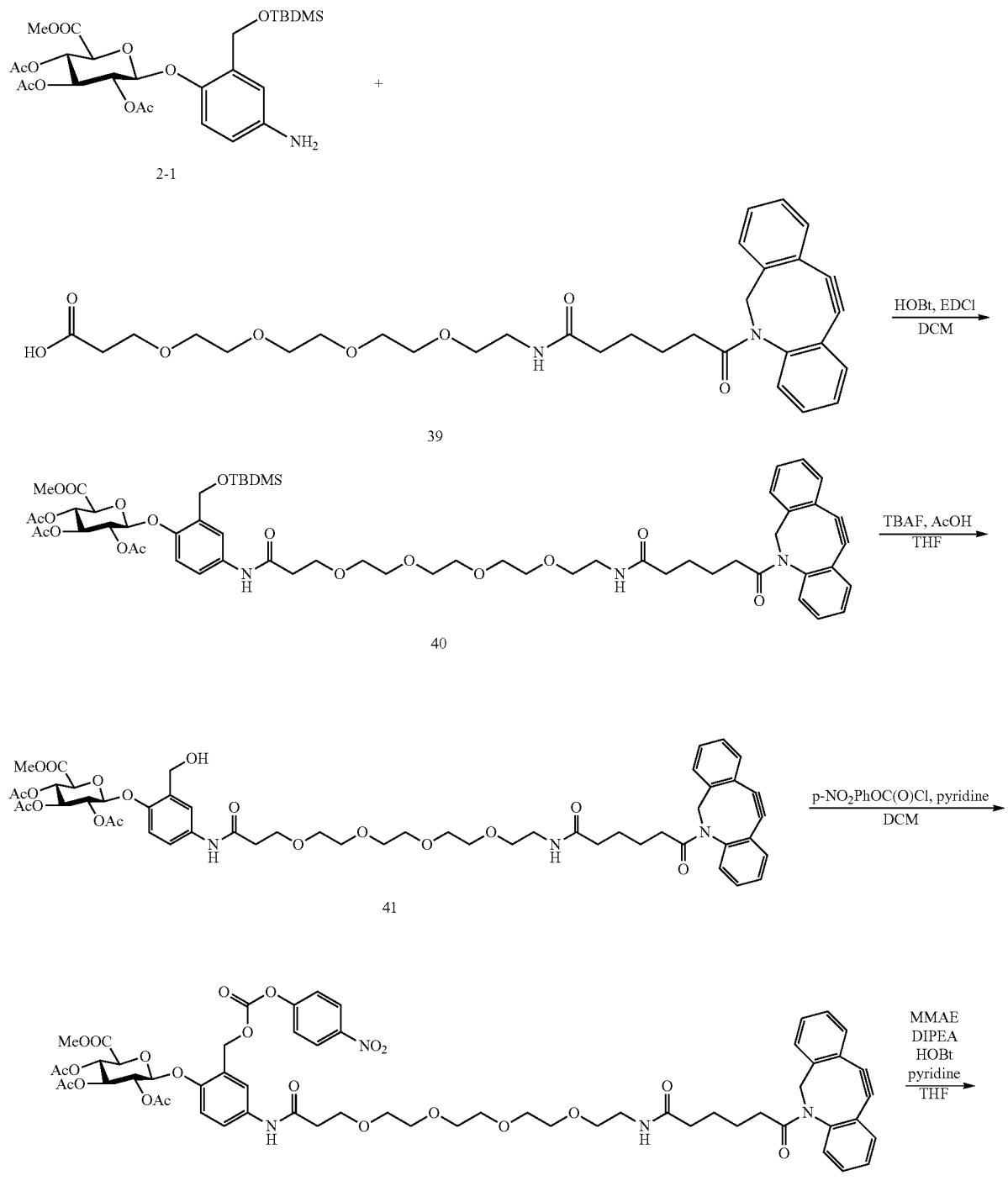

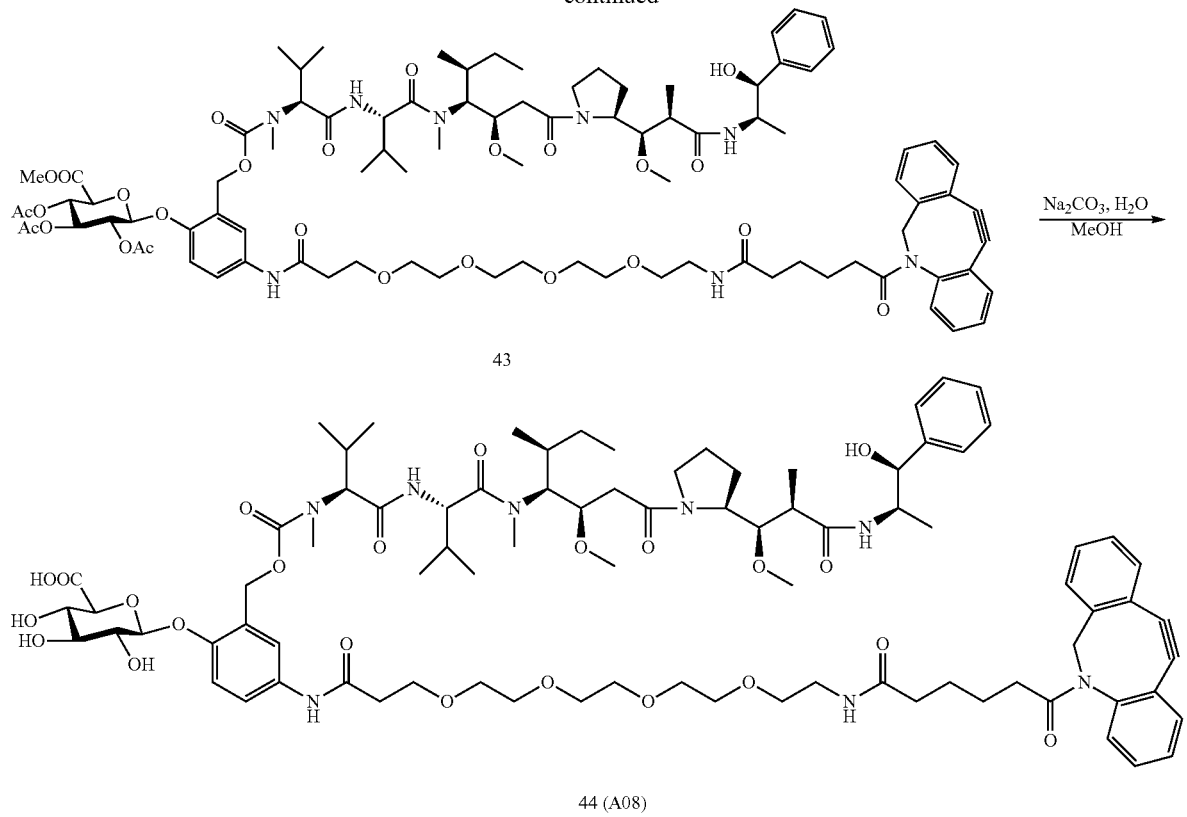

43

44 (A08)

Preparation of Compound (40)

2,3,4-tri-Ac-6-methyl-Glucuranate-2'-OTBS-PAB-amine 2-1 (44 mg, 0.077 mmol) and DBCO-PEG4-acid 39 (45 mg, 0.077) was dissolved in $CH_2Cl_2$ (4 mL) followed by the addition of EDCI (22.5 mg, 0.117 mmol), HOBt (1.2 mg, 0.008 mmol) and DMAP (3 mg, 0.025 mmol). After 6 hours, the solvent was removed and the reaction mixture was then purified by silica gel chromatography eluting with 20% EA/hexane, then 75% EA/hexane to give 56.7 mg (64.8%) of 2,3,4-tri-Ac-6-methyl-Glucuranate-2'-OTBS-PAB-PEG4-DBCO 40. $^1$H NMR (400 MHz, $CDCl_3$) δ 7.65-7.59 (m, 1H), 7.58-7.55 (m, 1H), 7.46 (t, J=2.52 Hz, 2H), 7.4-7.26 (m, 5H), 7.23-7.18 (m, 1H), 6.87 (dd, J=1.04 Hz, 8.8 Hz, 1H), 5.35-5.21 (m, 4H), 5.1 (dd, J=1.36 Hz, 13.84 Hz, 1H), 5.04 (dd, J=4.4 Hz, 7.12 Hz, 1H), 4.64 (dd, J=14.84 Hz, 44.64 Hz, 1H), 4.12 (dd, J=3.25 Hz, 9.08 Hz, 1H), 3.84-3.68 (m, 5H), 3.68-3.49 (m, 12H), 3.43 (t, J=5.28 Hz, 2H), 3.31 (t, J=2.36 Hz, 2H), 2.47 (q, J=6.36 Hz, 1H), 2.37-2.13 (m, 2H), 2.03 (s, 3H), 2.01 (s, 3H), 2.0 (s, 3H), 1.97-1.91 (m, 2H), 2.91-1.8 (m, 1H), 1.48-1.17 (m, 6H), 0.91 (s, 9H), 0.07 (s, 6H).

Preparation of Compound (41)

2,3,4-tri-Ac-6-methyl-Glucuranate-2'-OTBS-PAB-PEG4-DBCO 40 (56 mg, 0.05 mmol) was dissolved in a mixture of pyridine (0.63 mL) and acetic acid (0.42 mL) followed by the addition of TBAF (72 μL, 1 M in THF). After 12 hours, the solvent was removed and the reaction mixture was then purified by silica gel chromatography eluting with 20% EA/hexane, then 85% EA/hexane to give 50.2 mg (98.6%) of 2,3,4-tri-Ac-6-methyl-Glucuranate-2'-OH-PAB-PEG4-DBCO 41. $^1$H NMR (400 MHz, $CDCl_3$) δ 9.01 (s, 1H), 7.64 (dd, J=5.7 Hz, 9.9 Hz, 2H), 7.45-7.28 (m, 6H), 6.89 (dd, J=1.07 Hz, 7.9 Hz, 1H), 5.37-5.29 (m, 1H), 5.24 (d, J=8.16 Hz, 2H), 5.18 (d, J=12.2 Hz, 2H), 5.06 (t, J=4.36 Hz, 1H), 4.65 (d, J=13.2 Hz, 1H), 4.38 (dd, J=1.07 Hz, 8.9 Hz, 1H), 4.0 (dd, J=8.07 Hz, 8.9 Hz, 1H), 3.73 (t, J=5.68 Hz, 1H), 3.67 (s, 3H), 3.65-3.46 (m, 13H), 3.42 (t, J=5.12 Hz, 2H), 3.28 (d, J=4.6 Hz, 2H), 2.53 (t, J=5.65 Hz, 1H), 2.22-2.12 (m, 1H), 2.05 (s, 3H), 2.02 (s, 2H), 2.01 (s, 3H), 2.0 (s, 3H), 1.93-1.89 (q, J=4.1 Hz, 2H), 1.87-1.69 (m, 2H), 1.45-1.15 (m, 8H).

Preparation of Compound (42)

2,3,4-tri-Ac-6-methyl-Glucuranate-2'-OH-PAB-PEG4-DBCO 41 (50 mg, 0.049 mmol) was suspended in anhydrous $CH_2Cl_2$ (1 mL), followed by the addition of pyridine (40 μL, 0.49 mmol) and 4-nitrobenzoyl chloride (41.4 mg, 0.197 mmol). After 2 hours the solvent was removed and purified by silica gel chromatography eluting with 20% EA/hexane, then 60% EA/hexane to give 36.3 mg (62.2%) of 2,3,4-tri-Ac-6-methyl-Glucuranate-2'-OpNP-PAB-PEG4-DBCO 42. Then MMAE (25.3 mg, 0.035 mmol) was dissolved in a mixture of THF (1.6 mL) and pyridine (0.4 mL) followed by the addition of DIPEA (48 μL), HOBt (2 mg, 0.014 mmol) and 2,3,4-tri-Ac-6-methyl-Glucuranate-2'-OpNP-PAB-PEG4-DBCO 42 (36 mg, 0.03 mmol). After 48 hours the solvent was removed and the reaction mixture was then purified by silica gel chromatography eluting with $CH_2Cl_2$ (100%), then 5% $MeOH/CH_2Cl_2$ to give 29 mg (55%) of 2,3,4-tri-Ac-6-methyl-Glucuranate-2'-MMAE-PAB-PEG4-DBCO 43. $^1$H NMR (400 MHz, $CDCl_3$) δ 8.8 (m, 1H), 7.7-7.18 (m, 14H), 7.17-6.87 (m, 1H), 6.66-6.3 (m, 2H), 5.5-5.2 (m, 4H), 5.5-4.88 (m, 2H), 4.87-4.59 (m, 2H), 4.35-3.95 (m, 6H), 3.85 (d, J=9.2 Hz, 1H), 3.79-3.68 (m, 7H), 3.68-3.47 (m, 16H), 3.44 (t, J=5.16 Hz, 2H), 3.37 (s, 3H), 3.36-3.3 (m, 2H), 3.27 (s, 3H), 2.98 (s, 2H), 2.88 (s, 2H), 2.67-2.02 (m, 18H), 2.01 (s, 9H), 1.92 (bs, 2H), 1.81 (bs, 2H), 1.77-1.59 (m, 3H), 1.5-1.15 (m, 11H), 1.14-0.76 (m, 20H), 0.65 (d, J=3.34 Hz, 1H). ESI-TOF m/z: 1784.8878 [M+Na]$^+$.

Preparation of Compound (44)

2,3,4-tri-Ac-6-methyl-Glucuranate-2'-MMAE-PAB-PEG4-DBCO 43 (10 ing 0.005 mmol) was dissolved MeOH (0.5 mL), then Na$_2$CO$_3$ (1.62 ing, 0.015 mmol) was added. After 1 hour, H$_2$O (48 µL) was added to the reaction mixture and the reaction was kept stirring for another 1 hour. Then the reaction was neutralized by IR-120, after filtered, the crude was evaporated and purified by C18 column eluting with 100% H$_2$O, then 30% acetonitrile/H$_2$O to give 5 mg (62%) of Glucuranate-2'-MMAE-PAB-PEG4-DBCO compound 44 ESI-TOF m/z: 1619.8361 [M−H]$^-$.

2.9 Synthesis and Characterization of Compound 50 (A09)

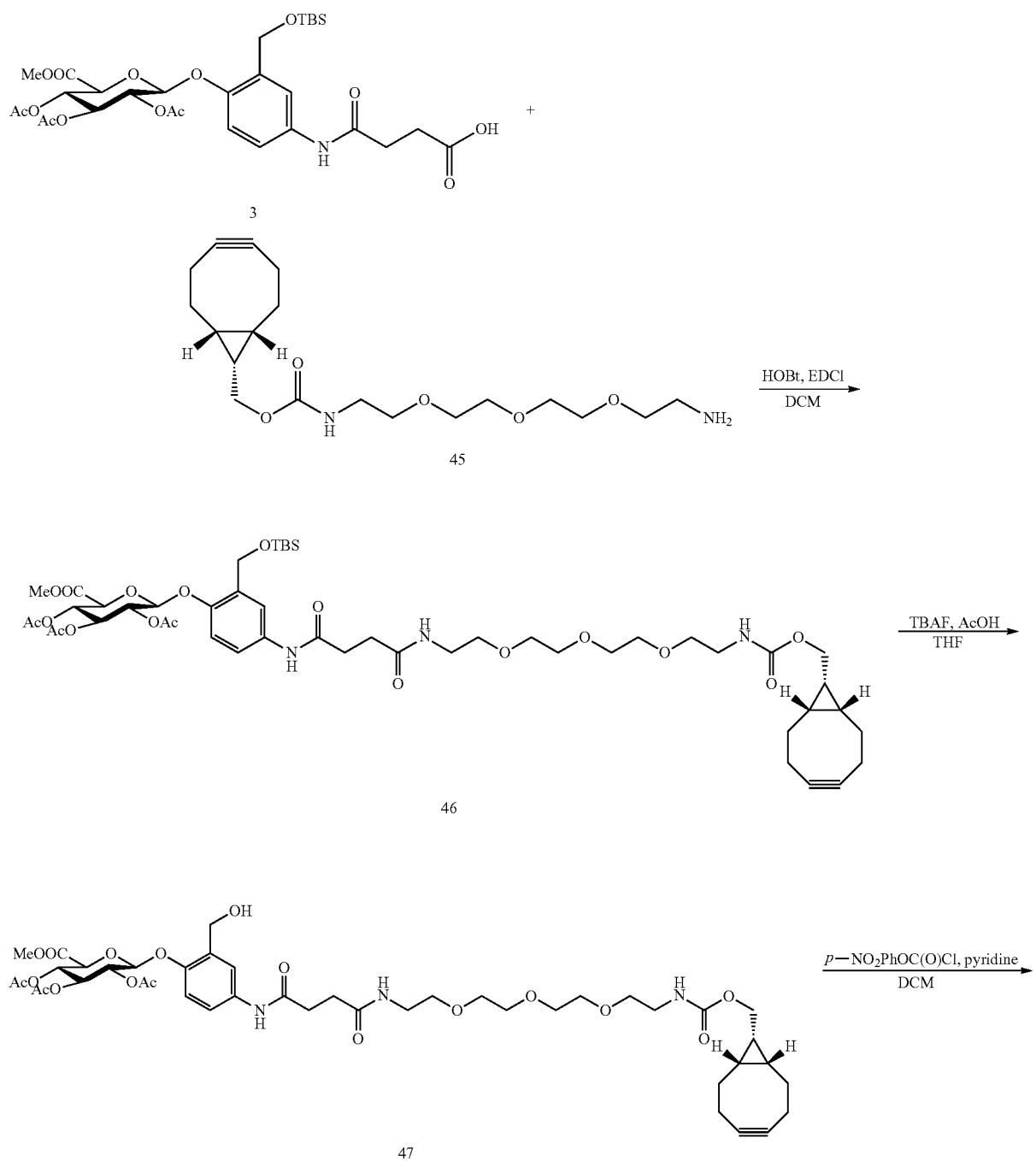

-continued

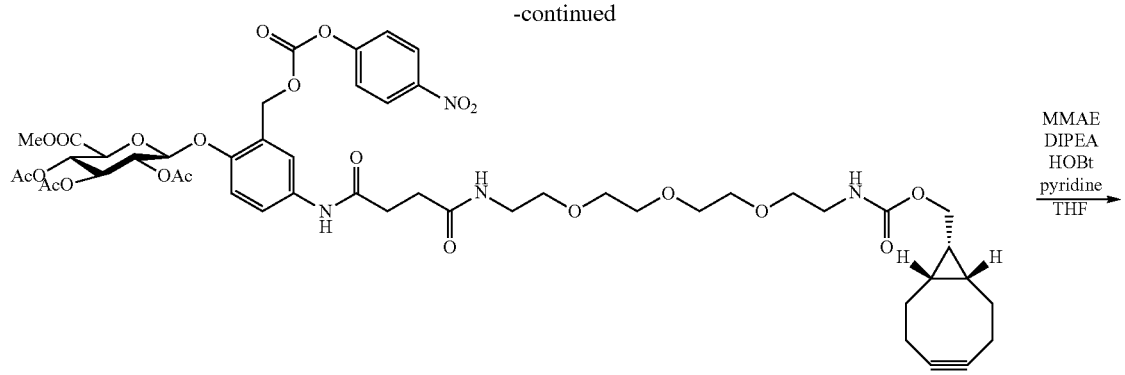

48

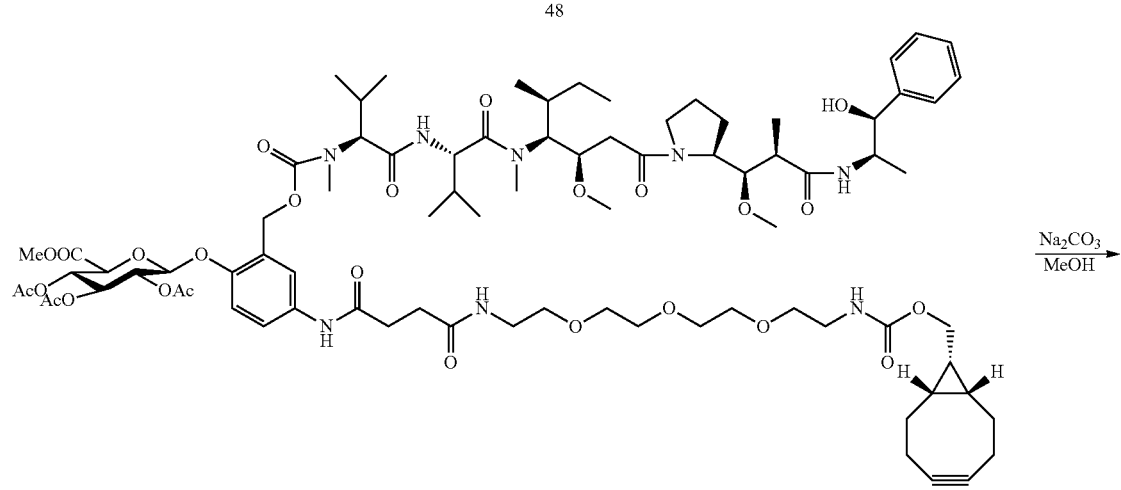

49

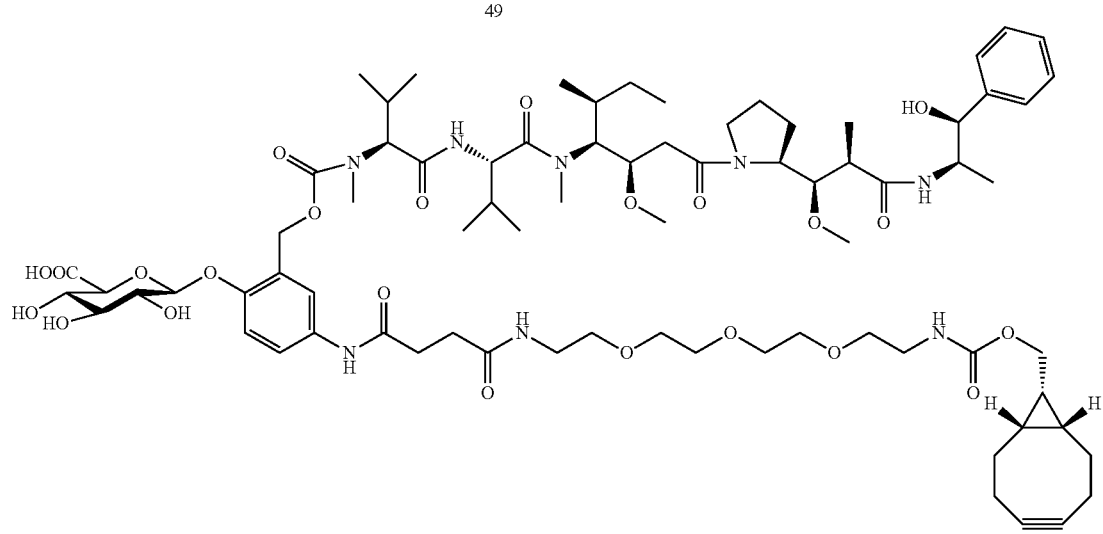

50(A09)

Preparation of Compound (46)

2,3,4-tri-Ac-6-methyl-Glucuranate-2'-OTBS-PAB-succinic acid 3 (136 mg, 0.2 mmol) and BCN-PEG4-amine 45 (74.4 mg, 0.2 mmol) was dissolved in CH$_2$Cl$_2$ (7.8 mL) followed by the addition of EDCI (58 mg, 0.305 mmol), HOBt (3.1 mg, 0.019 mmol) and DMAP (7.8 mg, 0.063 mmol). After 4 hours, the solvent was removed and the reaction mixture was then purified by silica gel chromatography eluting with 20% EA/hexane, then 60%/6 EA/hexane to give 135 mg (65%) of 2,3,4-tri-Ac-6-methyl-Glucuranate-2'-OTBS-PAB-succinate-PEG4-BCN 46. The compound obtained above was dissolved in a mixture of pyridine (9 mL) and acetic acid (3 mL) followed by the addition of TBAF (0.5 mL, 1 M in THF). After 12 hours, the solvent was removed and the reaction mixture was then purified by silica gel chromatography eluting with CH$_2$Cl$_2$ (100%), then 5% MeOH/CH$_2$Cl$_2$ to give 100 mg (85%) of 2,3,4-tri-Ac-6- methyl-Glucuranate-2'-OH-PAB-succinate-PEG4-BCN 47. ESI-TOF m/z: 928.3738 [M+Na]+.

Preparation of Compound (48)

2,3,4-tri-Ac-6-methyl-Glucuranate-2'-OH-PAB-succinate-PEG4-BCN 47 (100 mg, 0.11 mmol) was suspended in anhydrous $CH_2Cl_2$ (3.24 mL), followed by the addition of pyridine (89.6 μL, 1.1 mmol) and 4-nitrobenzoyl chloride (92.7 mg, 0.45 mmol). After 2 hours the solvent was removed and purified by silica gel chromatography eluting with $CH_2Cl_2$ (100%), then 5% MeOH/$CH_2Cl_2$ to give 82.3 mg (69.8%) of 2,3,4-tri-Ac-6-methyl-Glucuranate-2'-OpNP-PAB-succinate-PEG4-BCN 48. Then, MMAE (63.3 mg, 0.088 mmol) was dissolved in a mixture of THF (4.0 mL) and pyridine (1.0 mL) followed by the addition of DIPEA (120 μL), HOBt (3 mg, 0.021 mmol) and 2,3,4-tri-Ac-6-methyl-Glucuranate-2'-OpNP-PAB-succinate-PEG4-BCN 48 (82.3 mg, 0.0768 mmol). After 48 hours the solvent was removed and the reaction mixture was then purified by silica gel chromatography eluting with $CH_2Cl_2$ (100%), then 7.5% MeOH/$CH_2Cl_2$ to give 50 mg (34.4%) of 2,3,4-tri-Ac-6-methyl-Glucuranate-2'-MMAE-PAB-succinate-PEG4-BCN 49. 2,3,4-tri-Ac-6-methyl-Glucuranate-2'-MMAE-PAB-succinate-PEG4-BCN 49 (50 mg, 0.03 mmol) was dissolved MeOH (1.2 mL), then $Na_2CO_3$ (10 mg, 0.095 mmol) was added. After 1 hour, $H_2O$ (60 μL) was added to the reaction mixture and the reaction was kept stirring for another 1 hour. Then the reaction was neutralized by IR-120, after filtered, the crude was evaporated and purified by C18 column eluting with 100% $H_2O$, then 35% acetonitrile/$H_2O$ to give 14.2 mg (31.4%) of Glucuranate-2'-MMAE-PAB-succinate-PEG4-BCN 50 $^1$H NMR (400 MHz, $D_2O$) δ 7.62-7.17 (m, 8H), 5.26 (s, 2H), 5.01 (s, 1H), 4.75-4.42 (m, 2H), 4.4-4.17 (m, 2H), 4.01 (bs, 3H), 3.83 (bs, 1H), 3.73-3.51 (m, 18H), 3.5-3.26 (m, 128), 3.15 (s, 2H), 3.05 (d, J=6.44 Hz, 2H), 3.01-2.9 (m, 3H), 2.84-2.42 (m, 68), 2.21 (s, 3H), 2.16 (bs, 6H), 1.92-1.77 (m, 2H), 1.72-1.56 (m, 1H), 1.54-1.39 (m, 3H), 1.39-1.23 (m, 4H), 1.22-1.12 (m, 3H), 1.08 (d, J=6.48 Hz, 2H), 0.98 (d, J=6.55 Hz, 2H), 0.95-0.6 (m, 19H). ESI-TOF m/z: 1507.8027 [M−H]−.

2.10 Synthesis and Characterization of Compound 54 (A10)

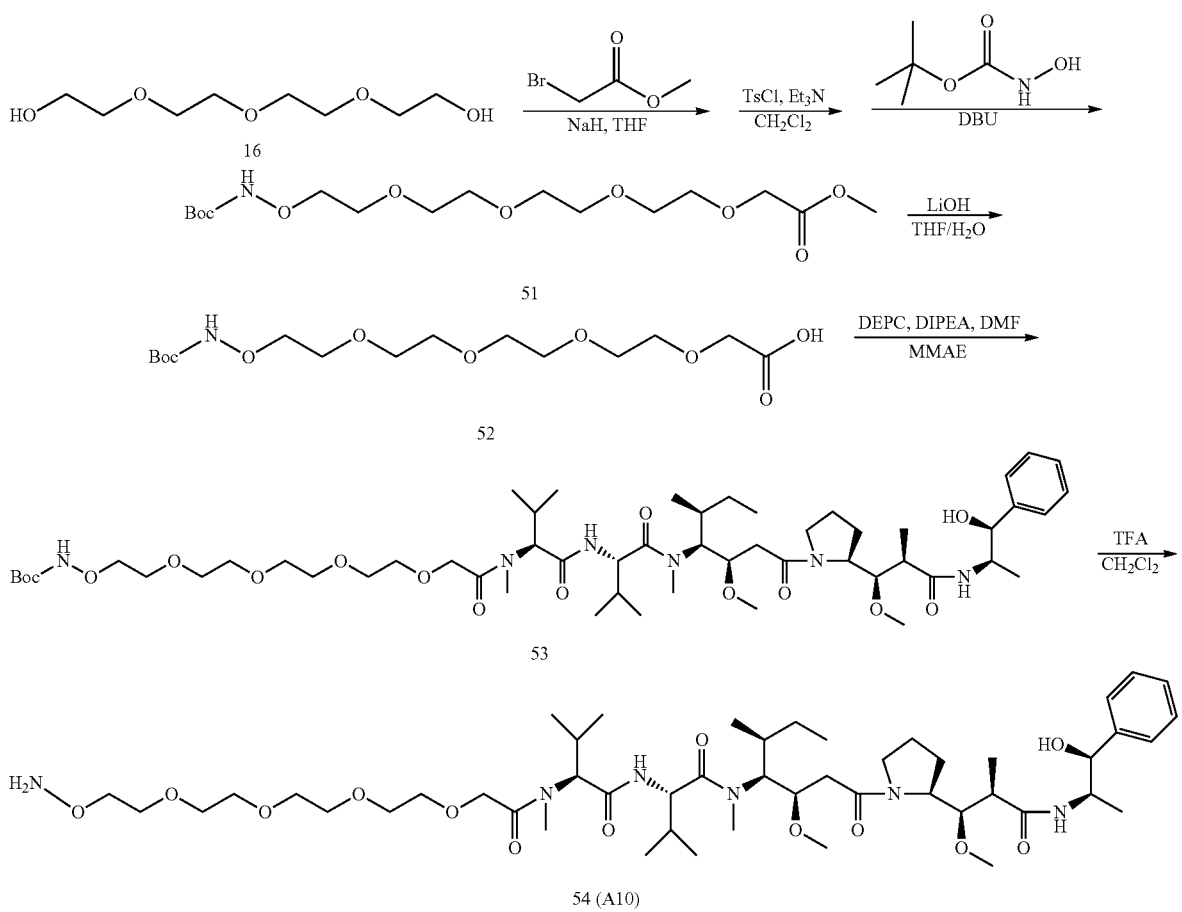

Preparation of Compound (51)

To a Tetrahydrofuran (120 mL) solution of the Sodium hydride (0.42 g, 10.50 mmole) and tetraethylene glycol 16 (6 g, 30.89 mmole), methyl bromoacetate (1.25 mL, 10.5 mmole) was dropwise added into the mixture at ° C. and solution was stirred at room temperature for 16 hr. When TLC indicated that starting material was fully consumed, the solution was quenched with MeOH, filtered through a pad of celite, and the celite was washed with MeOH. The combined filtrates and washings were concentrated under reduced pressure and the residue was purified by flash column chromatography (silica gel, 4-6% MeOH in CH$_2$Cl$_2$) to afford the product as an oil (1.843 g, 6.92 mmole).

To a Dichloromethane (10 mL) solution of the compound (0.49 g, 1.84 mmole) obtained above and triethylamine (0.7 mL, 5.02 mmole), P-Toluenesulfonyl chloride (0.56 g, 2.937 mmole) in CH$_2$Cl$_2$ (20 mL) was added into the mixture and solution was stirred at room temperature for 16 hr. The white solid was observed, filtered by the pad of celite, and washed by CH$_2$Cl$_2$. The filtrate was concentrated in vacuo and the residue was purified by flash column chromatography (silica gel, 75-85% Ethyl acetate in Hexane) to afford the product as an oil (0.367 g, 0.872 mmole).

To a Tetrahydrofuran (4 mL) solution of the N-Boc-hydroxylamine (0.1762 g, 1.323 mmole) and compound (0.367 g, 0.873 mmole) obtained above, DBU (0.26 mL, 1.74 mmole) was added into the mixture and solution was stirred at room temperature for 72 hr. When TLC indicated that starting material was fully consumed, the solution was concentrated. Purification of the crude material using column chromatography (silica gel, Ethyl acetate) afforded the product 51 (0.14 g, 0.367 mmole) as an oil; $^1$H NMR (400 MHz, CDCl$_3$) 4.14 (s, 2H), 4.00-3.98 (m, 1H), 3.72 (s, 3H), 3.70-3.61 (m, 15H), 1.45 (s, 9H); HRMS (ESI-TOF, MNa+) calculated for C16H31NO9 Na, 404.1891, found 404.1901.

Preparation of Compound (52)

To a Tetrahydrofuran (1.00 mL) solution of compound 51 (68.4 mg, 0.179 mmole), H$_2$O (0.05 mL), and LiOH (7.7 mg, 0.183 mmole) was stirred. After stirring for 2 hr at room temperature, the solution was quenched with 1N HCl (10 mL), and partitioned between ethyl acetate and brine. The organic phase was collected and the aqueous phase was extracted with ethyl acetate (50 mL×4). The combined organic layer were concentrated and the residue was purified by flash column chromatography (silica gel, 12-20% MeOH in CH$_2$Cl$_2$) to afford the product as an oil 52 (34.5 mg, 0.0939 mmole); $^1$H NMR (400 MHz, CDCl$_3$) 9.29 (s, 1H), 3.98 (s, 2H), 3.86 (s, 2H), 3.65-3.61 (m, 14H), 1.45 (s, 9H); HRMS (ESI-TOF, MNa+) calculated for C15H29NO9Na 390.1735, found 390.1742.

Preparation of Compound (53)

DEPC (30.6 mg, 0.189 mmole) and DIPEA (0.030 mL, 0.182 mmol) were added sequentially to a solution of compounds 52 (44.8 mg, 0.1219 mmol) and MMAE (46.5 mg, 0.065 mmol) in DMF (2.7 mL) at 0° C., and the mixture was stirred at 0° C. to room temperature for 16 h. The reaction mixture was then concentrated in vacuo and the residue was purified by flash column chromatography (silica gel, 3-6% MeOH in CH$_2$Cl$_2$) to afford the product as an oil 53 (48.6 mg, 0.0455 mmole); HRMS (ESI-TOF, MNa+) calculated for C54H94N6O15Na, 1089.6669, found 1089.6660.

Preparation of Compound (54)

TFA (0.35 mL) was slowly added into a solution of 53 (52.6 mg, 0.0493 mmol) in DCM (0.65 mL) at 0° C. The resulting mixture was stirred at room temperature for 2 h, and concentrated. Purification of the crude material using column chromatography (silica gel, 6-10% MeOH in CH$_2$Cl$_2$) afforded the product 54 (29 mg, 0.030 mmol) as an oil; HRMS (ESI-TOF, MNa+) calculated for C49H86N6O13Na, 967.6326, found 967.6353.

2.11 Synthesis and Characterization of Compound 59 (A11)

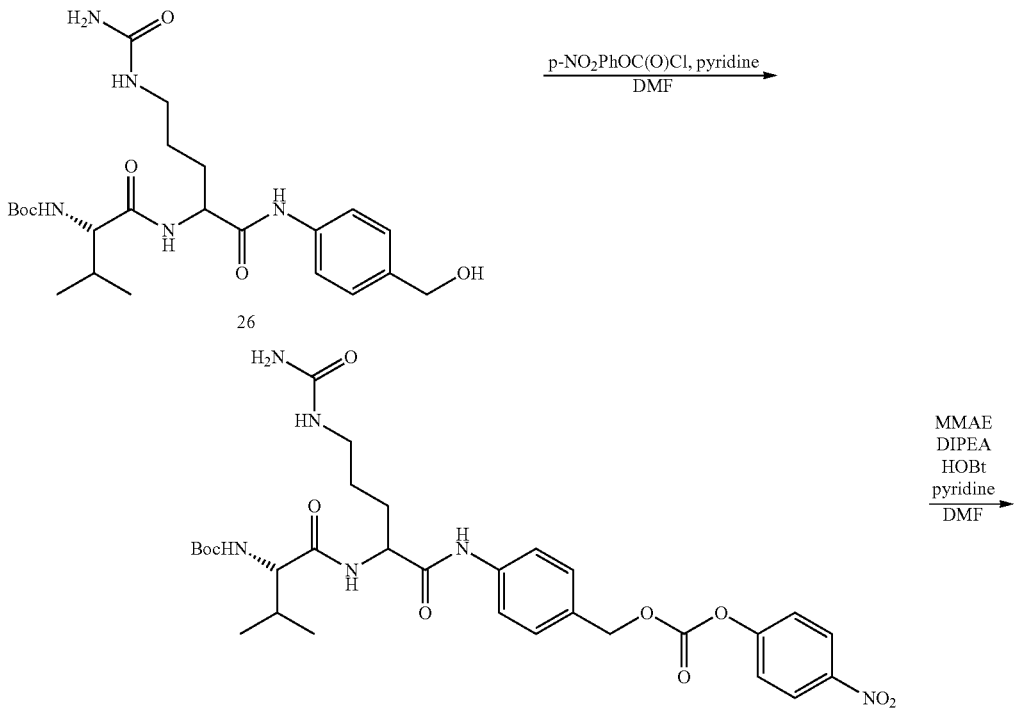

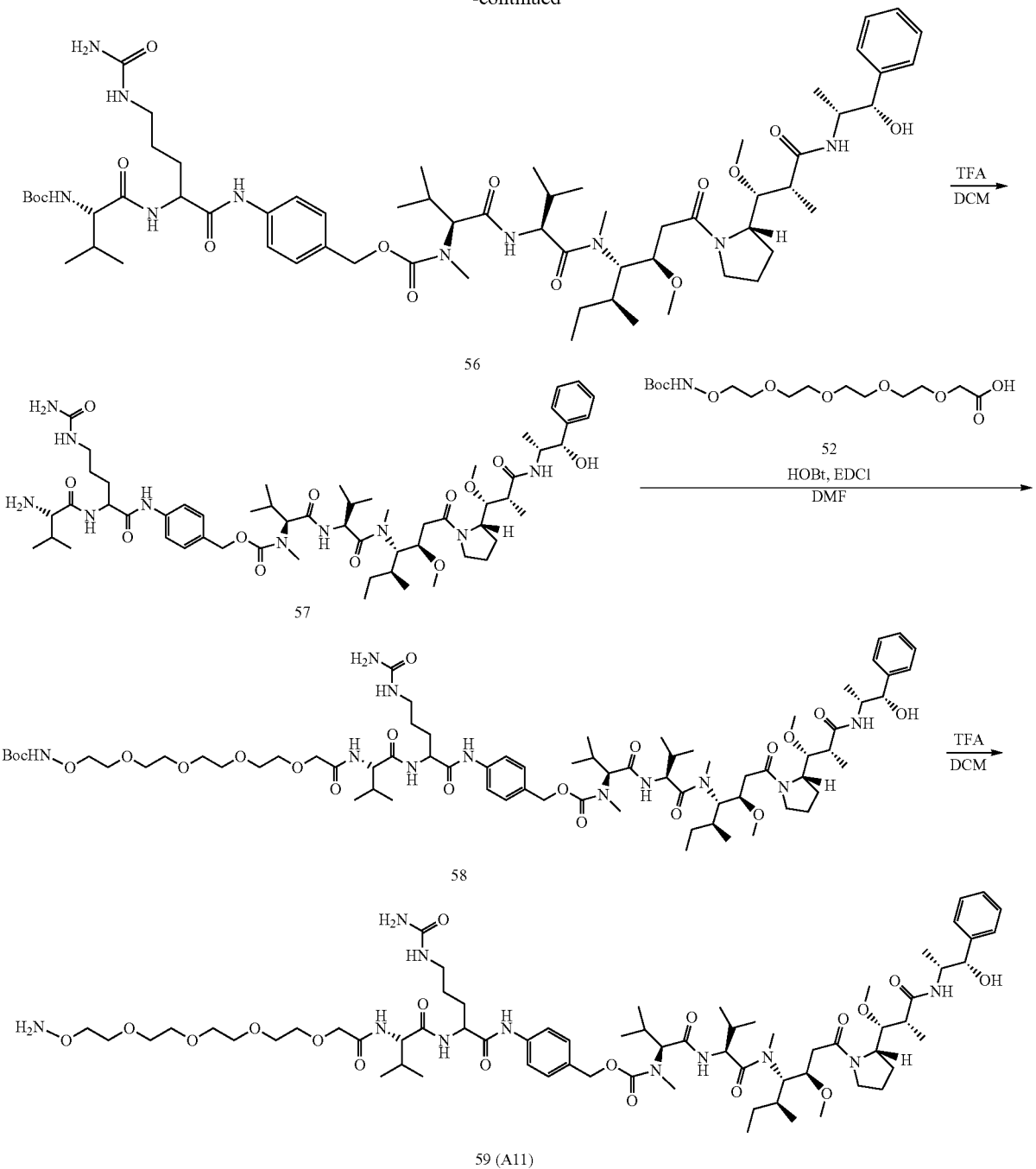

Preparation of Compound (55)

Boc-Val-Cit-PAB-OH 26. (100 m&, 0.2 mmol) was suspended in a mixture of anhydrous DMF (1 mL), THF (2 mL) and CH$_2$Cl$_2$ (1 mL), followed by the addition of pyridine (97 μL, 1.2 mmol) and 4-nitrobenzoyl chloride (115 mg, 0.62 mmol). After 2 hours the solvent was removed and purified by silica gel chromatography eluting with CH$_2$Cl$_2$ (100%), then 5% MeOH/CH$_2$Cl$_2$ to give 89 mg (69%) of Boc-Val-Cit-PAB-OpNP 55. Then, MMAE (88.6 mg, 0.123 mmol) was dissolved in a mixture of THF (2.8 mL) and pyridine (0.7 mL) followed by the addition of DIPEA (212 μL), HOBt (5.6 mg, 0.039 mmol) and Boc-Val-Cit-PAB-OpNP 55 (89 mg, 0.138 mmol). After 48 hours the solvent was removed and the reaction mixture was then purified by silica gel chromatography eluting with CH$_2$Cl$_2$ (100%), then 15% MeOH/CH$_2$Cl$_2$ to give 30 mg (45%) of Boc-Val-Cit-PAB-MMAE 56. $^1$H NMR (400 MHz, CDCl$_3$) δ 7.49 (t, J=7.2 Hz, 2H), 7.29-7.08 (m, 11H), 5.13-4.94 (m, 2H), 4.69-4.4 (m, 5H), 4.2-4.05 (m, 4H), 4.97 (bs, 1H), 3.81 (dd, J=2.5 Hz, 6.56 Hz, 1H), 3.77 (dt, J=9.2 Hz, 1.8 Hz, 1H), 3.63-3.55 (m, 2H), 3.44 (m, 1H), 3.35-3.15 (m, 20H), 3.14-3.04 (m, 2H), 3.5-2.95 (m, 3H), 2.9-2.75 (m, 4H), 2.41-2.34 (m, 3H), 2.45 (s, 1H), 2.21 (s, 1H), 2.16-1.55 (m, 16H), 1.54-1.39 (m, 4H), 1.34 (s, 9H), 1.3 (bs, 2H), 1.11-0.95 (m, 11H), 0.9-0.6 (m, 42H).

Preparation of
Boc-Hydroxylamino-PEG4-Val-Cit-PAB-MMAE
Compound (58)

Boc-Val-Cit-PAB-MMAE 56 (66 mg, 0.054 mmol) was suspended in anhydrous $CH_2Cl_2$ (4.0 mL), and TFA (1.0 mL) was added. The reaction was stirred at 0° C. for 10 min, then warmed to room temperature for another 30 min. The reaction mixture was evaporated to dryness (azeotropic with toluene for 3 times) to get Val-Cit-PAB-MMAE 57 without further purification. The obtained compound 29 was dissolved in anhydrous DMF (1.5 mL) followed by the addition of TEA (75 μL), DMAP (0.66 mg), HOBt (0.73 mg), and Boc-hydroxylamino-PEG4-COOH 51 (20 mg, 0.054 mmol). After 16 hours the solvent was removed and purified by silica gel chromatography eluting with 1% $MeOH/CH_2Cl_2$, then 10% $MeOH/CH_2Cl_2$ to give 32.6 mg (41%) of Boc-hydroxylamino-PEG4-Val-Cit-PAB-MMAE 58. $^1$H NMR (400 MHz, $CDCl_3$) δ 7.89-7.05 (m, 101), 5.11-4.95 (m, 2H), 4.6-4.38 (m, 3H), 4.21 (dd, J=2.76 Hz, 7.0 Hz, 1H), 4.18-4.04 (m, 2H), 3.98 (s, 2H), 3.82 (dd, J=3.36 Hz, 5.72 Hz, 2H), 3.63-3.4 (m, 16H), 3.35-3.15 (m, 15H), 3.0 (s, 2H), 2.83 (dd, J=2.66 Hz, 11.1 Hz, 3H), 2.43-1.4 (m, 13H), 1.07 (t, J=5.92 Hz, 3H), 1.03 (t, J=7.08 Hz, 3H), 0.95-0.6 (m, 26H). ESI-TOF m/z: 1494.8684 [M+Na]$^+$.

Preparation of
Hydroxylamino-PEG4-Val-Cit-PAB-MMAE
Compound (59)

Boc-hydroxylamino-PEG4-Val-Cit-PAB-MMAE 58 (32 mg, 0.021 mmol) was suspended in anhydrous $CH_2Cl_2$ (2.0 mL), and TFA (0.5 mL) was added. The reaction was stirred at 0° C. for 10 min, then warmed to room temperature for another 30 min. The reaction mixture was evaporated to dryness, then pass through a C18 column eluting with 100% $H_2O$, then 40% acetonitrile/$H_2O$ to get 18 mg (65%) of hydroxylamino-PEG4-Val-Cit-PAB-MMAE 59. $^1$H NMR (400 MHz, MeOD) δ 7.9-6.9 (m, 11H), 5.25-4.95 (m, 2H), 4.65-4.37 (m, 2H), 4.21-3.9 (m, 6H), 3.73 (bs, 1H), 3.65-3.48 (m, 12H), 3.42-3.15 (m, 6H), 3.01 (s, 2H), 2.82 (d, J=10.5 Hz, 2H), 2.45-1.25 (m, 11H), 1.1-0.5 (m, 32H). ESI-TOF m/z: 1394.8241 [M+Na]$^+$.

2.12 Synthesis and Characterization of Compound
60 (A12)

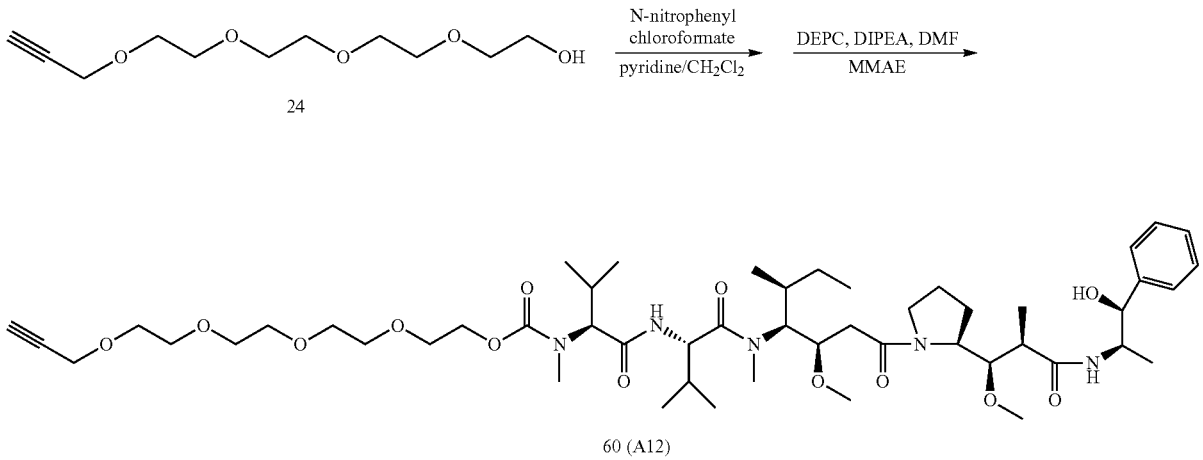

60 (A12)

Preparation of Compound (60)

To a Dichloromethane (5.00 mL) solution of compound 24 (46.4 mg, 0.150 mmole), 4-Nitrophenylchloroformate (150 mg, 0.744 mmole), and pyridine (0.12 mL, 1.497 mmole) was stirred. After stirring for 2 hr at room temperature, the solution was concentrated and the residue was purified by flash column chromatography (silica gel, 35% Ethyl acetate in Hexane) to afford the product as a solid (53 mg, 0.112 mmole); $^1$H NMR (400 MHz, $CDCl_3$) 8.28-8.24 (m, 2H), 7.39-7.35 (m, 2H), 4.43-4.41 (m, 2H), 4.18 (d, J=2.4 Hz, 2H), 3.80-3.78 (m, 2H), 3.67-3.64 (m, 12H), 2.40 (t, J=2.4 Hz, 1H). To a Dimethylformamide (7.5 mL) solution of compound. (28 mg, 0.0705 mmole) obtained above, MMAE (50 mg, 0.0696 mmole), DIPEA (0.110 mL, 0.631 mmole), HOBT (9.5 mg, 0.0703 mmole), and pyridine (2.0 mL) was stirred. After stirring for 72 hr at room temperature, the solution was concentrated and the residue was purified by flash column chromatography (silica gel, 4% MeOH in $CH_2Cl_2$) to afford the product as a solid 60 (47 mg, 0.0481 mmole); HRMS (ESI-TOF, MNa+) calculated for $C_{51}H_{85}N_5O_{13}Na$ 998.6036, found 998.6051.

2.13 Synthesis and Characterization of Compound 64 (A13)

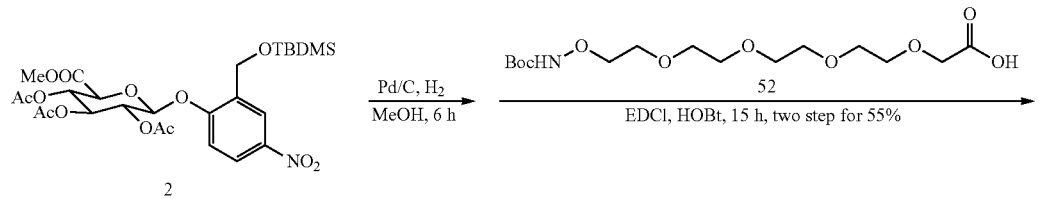

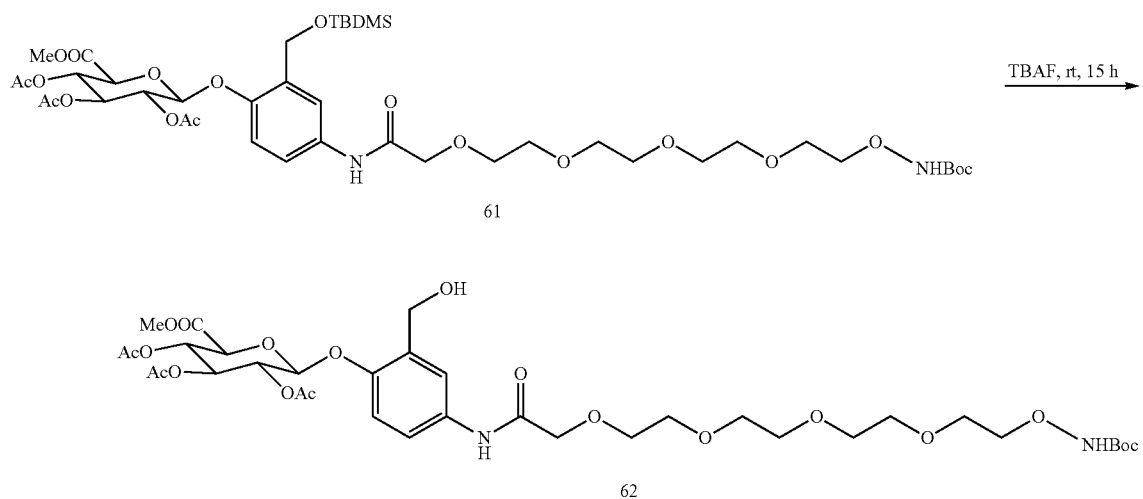

Preparation of Compound (61)

To a solution of compound 2 (300.0 mg, 0.50 mmol) in 30 ml of EtOAc/MeOH (9:1) was added Pd/C. The system was evacuated and filled with H2 three times. It was kept under H$_2$ atmosphere with a balloon and stirred at room temperature for 1 h. After the reaction was completed, Pd/C was filtered out. The filtrate was evaporated to get compound (265.0 mg, 0.47 mmol) for next step. To a solution of compound (265.0 mg, 0.46 mmol), 2 (170 mg, 0.47 mmol), and HOBT (105.0 mg, 0.70 mmol) in CH$_2$Cl$_2$ was added EDCI (108.0 mg, 0.70 mmol). It was stirred at rt for 14 h. The solution was evaporated. The crude product was purified by column to give compound 61 as yellow oil (300.0 mg, 0.33 mmol). $^1$H NMR (400 MHz, CDCl$_3$) δ 8.71 (s, 1H), 7.78 (s, 1H), 7.54 (d, J=1.6 Hz, 1H), 7.44 (dd, J=1.6, 8.8 Hz, 1H), 6.86 (d, J=8.8 Hz, 1H), 5.31-5.15 (m, 3H), 5.02 (d, J=7.6 Hz, 1H), 4.65 (d, J=14.8 Hz, 1H), 4.53 (d, J=14.8 Hz, 1H), 4.11 (d, J=9.2 Hz, 1H), 4.03 (s, 2H), 3.88 (m, 2H), 3.75-3.43 (m, 17H), 1.98 (s, 3H), 1.96 (s, 3H), 1.94 (s, 3H), 1.38 (s, 9H), 0.87 (s, 9H), 0.05 (s, 6H).

Preparation of Compound (62)

To a solution of 61 (300.0 mg, 0.33 mmol) in 15 mL of solution (Pyridine:HOAc=3:2) was added 2 mL of TBAF. It was stirred at rt for 14 h. The solution was evaporated. The crude product was purified by column to give compound 62 as yellow oil (220.0 mg, 0.27 mmol). $^1$H NMR (400 MHz, CDCl$_3$) δ 8.89 (s, 1H), 7.72 (s, 1H), 7.67 (dd, J=2.0, 8.8 Hz, 1H), 7.43 (s, 1H), 6.95 (d, J=8.8 Hz, 1H), 5.33-5.21 (m, 3H), 5.05 (d, J=7.6 Hz, 1H), 4.67 (d, J=9.6 Hz, 1H), 4.42 (d, J=13.6 Hz, 1H), 4.11 (d, J=9.6 Hz, 1H), 4.05 (s, 2H), 3.90 (m, 2H), 3.71-3.53 (m, 17H), 2.05 (s, 3H), 2.00 (s, 3H), 1.99 (s, 3H), 1.42 (s, 9H).

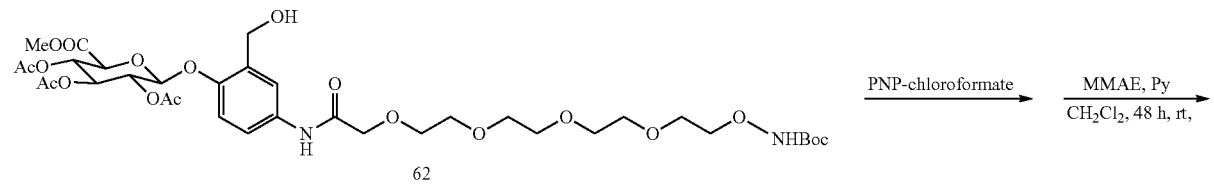

-continued

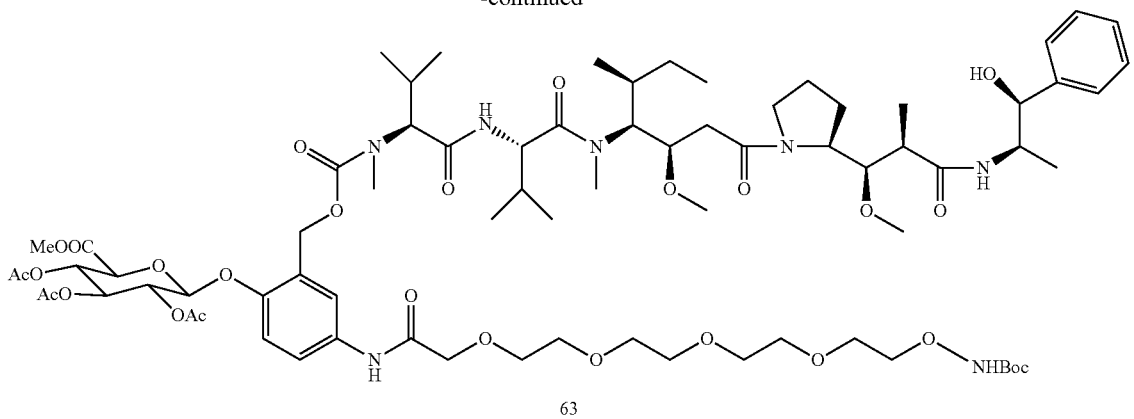

63

Preparation of Compound (63)

Compound 62 (220.0 ing, 0.27 mmol) was dissolved in 8 mL of CH₂Cl₂ and cooled to 0° C. Pyridine (0.20 mL) and PNP Chloroformate were added and the mixture was stirred in rt for 3 h. The solution was evaporated. The crude product was purified by column to give compound (80.0 mg, 0.082 mmol) for next step. A solution of compound from last step (80.0 mg, 0.082 mmol) and MMAE (60.0 mg, 0.082 mmol) in 5 mL of THF was treated with TEA (0.1 mL). The resulting mixture was stirred at rt for 48 h. After the reaction was completed, 35 mL of EA and 20 mL of 0.5N HCl solution were added. The organic layer extraction was dried by MgSO₄ and concentrated. The crude product was purified by column to give compound 63 as yellow oil (70.0 mg, 0.05 mmol). ESI-TOF m/z: 1570.7932 [M+Na⁺].

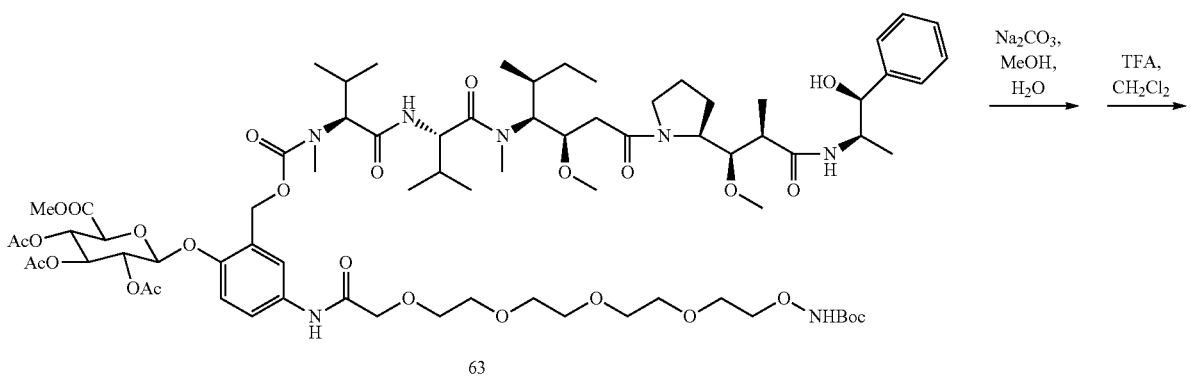

63

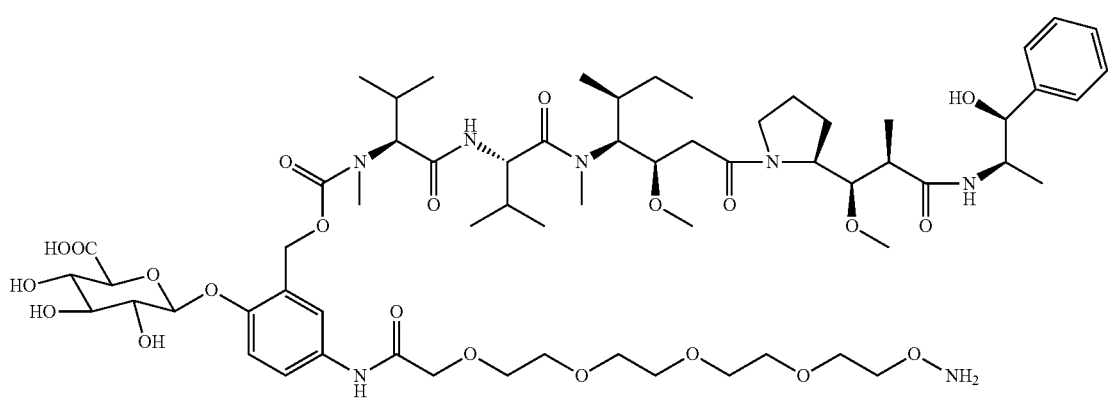

64 (A13)

Preparation of Compound (64)

A solution of 63 (20.0 mg, 0.013 mmol) in 2.5 mL of solution (MeOH:H2O=4:1) was treated at 0° C. with Na$_2$CO$_3$. The resulting mixture was stirred at rt for 3 h. After the reaction was completed, the organic solution was removed under reduced pressure. The residue was purified by was purified by C18 column to give compound A01-8 for next step. To a solution of compound from last step was dissolved in 1.6 ml of CH$_2$Cl$_2$. 0.40 ml of TFA was then added and stirred at room temperature for 1 h. The solution was concentrated and the residue was purified by C18 column to give 64 (11.2 mg, 0.0085 mmol). ESI-TOF m/z: 1306.6916 [M−H]$^-$.

2.14 Synthesis and Characterization of Compound 60 (A14)

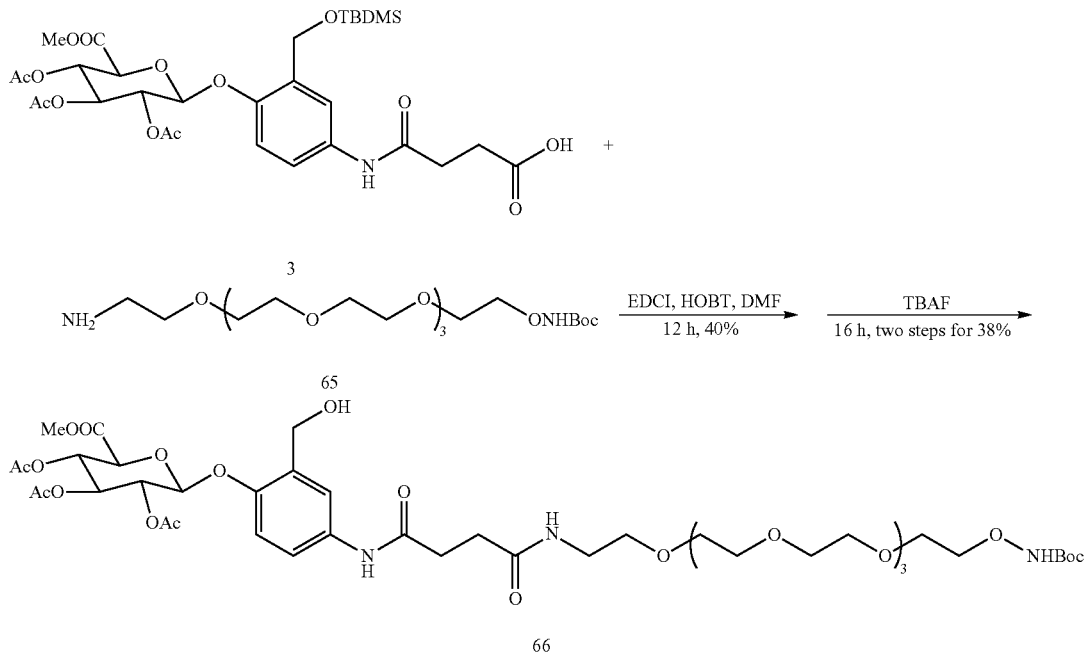

Preparation of Compound (66)

To a solution of 3 (315.0 mg, 0.47 mmol), 65 (220 mg, 0.43 mmol), and HOBT (87.0 mg, 0.65 mmol) in DMF was added EDCI (87.0 mg, 0.56 mmol). It was stirred at rt for 12 h. The solution was evaporated. The crude product was purified by column to give compound as yellow oil (200.0 mg, 0.18 mmol) for next step. To a solution from last step (200.0 mg, 0.33 mmol) in 15 mL of solution (Pyridine: HOAc=3:2) was added 2 mL of TBAF. It was stirred at rt for 16 h. The solution was evaporated. The crude product was purified by column to give compound 66 as yellow oil (176.0 mg, 0.17 mmol, two steps for 38%). $^1$H NMR (400 MHz, CDCl$_3$) δ 8.05 (s, 1H), 7.67 (dd, J=2.4, 8.8 Hz, 1H), 7.47 (s, 1H), 6.94 (d, J=8.8 Hz, 1H), 5.40-5.25 (m, 3H), 5.06 (d, J=7.6 Hz, 1H), 4.72 (d, J=12.8 Hz, 1H), 4.42 (d, J=12.8 Hz, 1H), 3.99 (m, 2H), 3.75-3.52 (m, 27H), 2.05 (s, 3H), 2.04 (s, 3H), 1.94 (s, 3H), 1.46 (s, 9H).

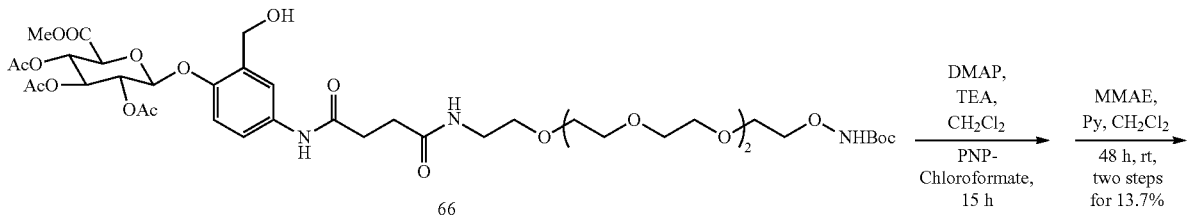

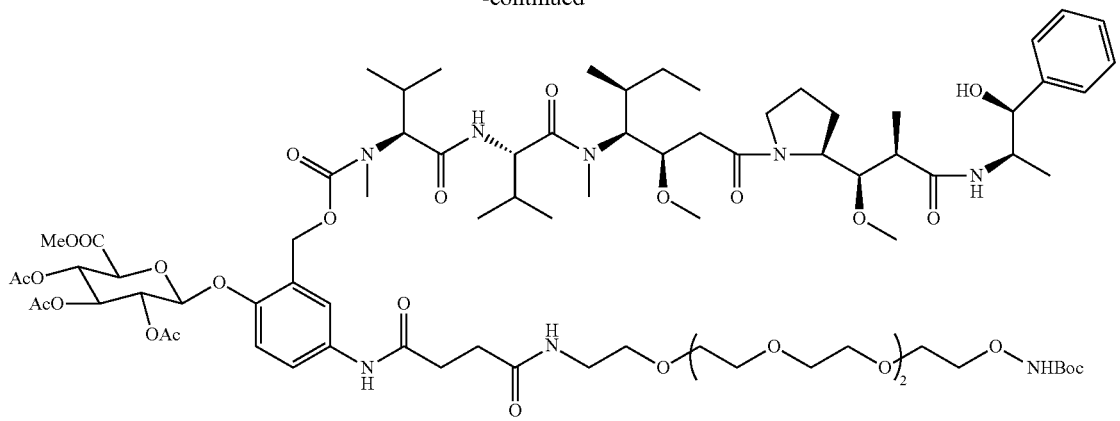

67

Preparation of Compound (67)

Compound 66 (176.0 mg, 0.17 mmol) was dissolved in 5 mL of $CH_2Cl_2$ and cooled to 0° C. Pyridine (27 uL) and PNP Chloroformate (52 mg, 0.26 mmol) were added and the mixture was stirred in rt for 3 h. The resulting mixture was diluted with $CH_2Cl_2$ and washed with 1 N HCl, saturated aqueous $NaHCO_3$ and brine. The organic layer extraction was dried by $MgSO_4$ and concentrated. The crude product was purified by column to give compound for next step. A solution of compound from last step (128.0 mg, 0.108 mmol) and MMAE (78.0 mg, 0.108 mmol) in 4 mL of DMF was treated with TEA (100 uL) and pyridine (87 uL). The resulting mixture was stirred at rt for 48 h. The solution was evaporated. The crude product was purified by column to give compound 67 as yellow oil (40.0 mg, 0.02 mmol). ESI-TOF m/z: 1787.9224 [M+Na$^+$].

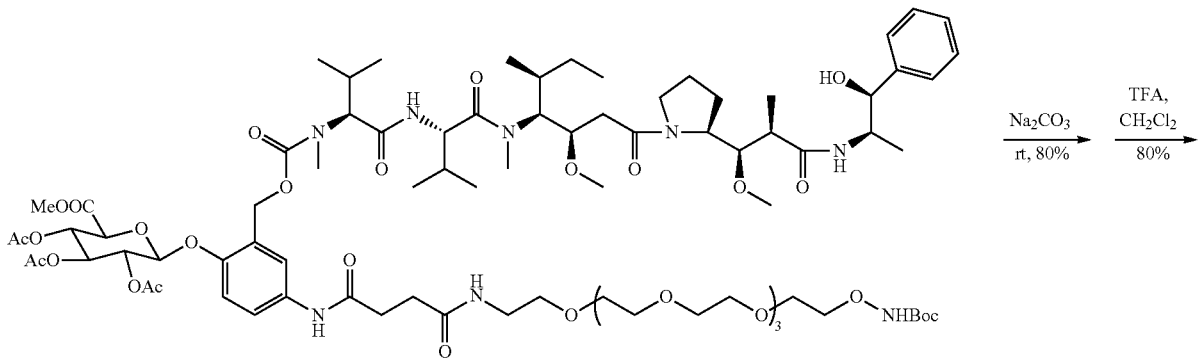

67

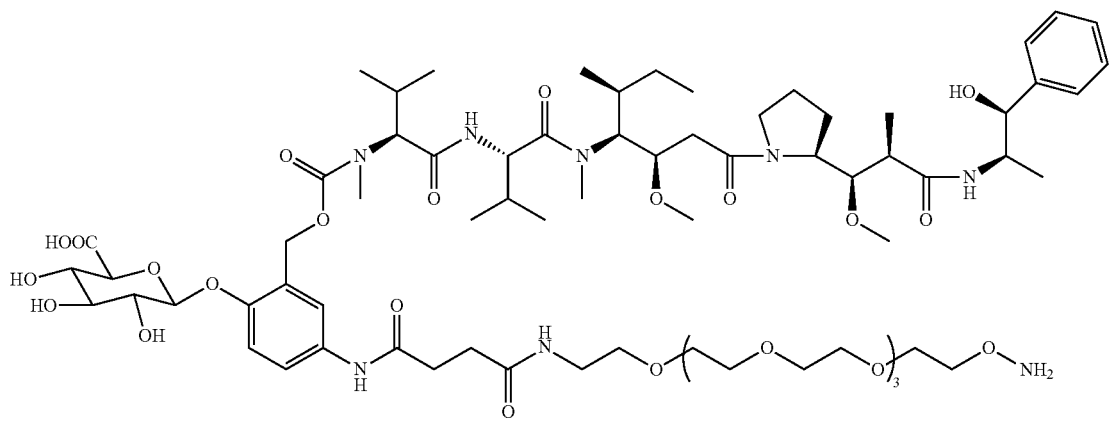

68 (A14)

Preparation of Compound (68)

A solution of 67 (10.0 mg, 0.013 mmol) in 1.25 mL of solution (MeOH:H$_2$O=4:1) was treated at 0° C. with Na$_2$CO$_3$ (1.8 mg, 0.017 mmol). The resulting mixture was stirred at rt for 3 h. After the reaction was completed, the organic solution was removed under reduced pressure. The residue was purified by was purified by C18 column to give compound for next step. To a solution of compound from last step was dissolved in 1.6 ml of CH$_2$Cl$_2$. 0.40 ml of TFA was then added and stirred at room temperature for 1 h. The solution was concentrated and the residue was purified by C18 column to give 68 (4.0 mg). ESI-TOF m/z: 1307.5170 [M−H]$^-$.

2.15 Synthesis and Characterization of Compound 80 (A15)

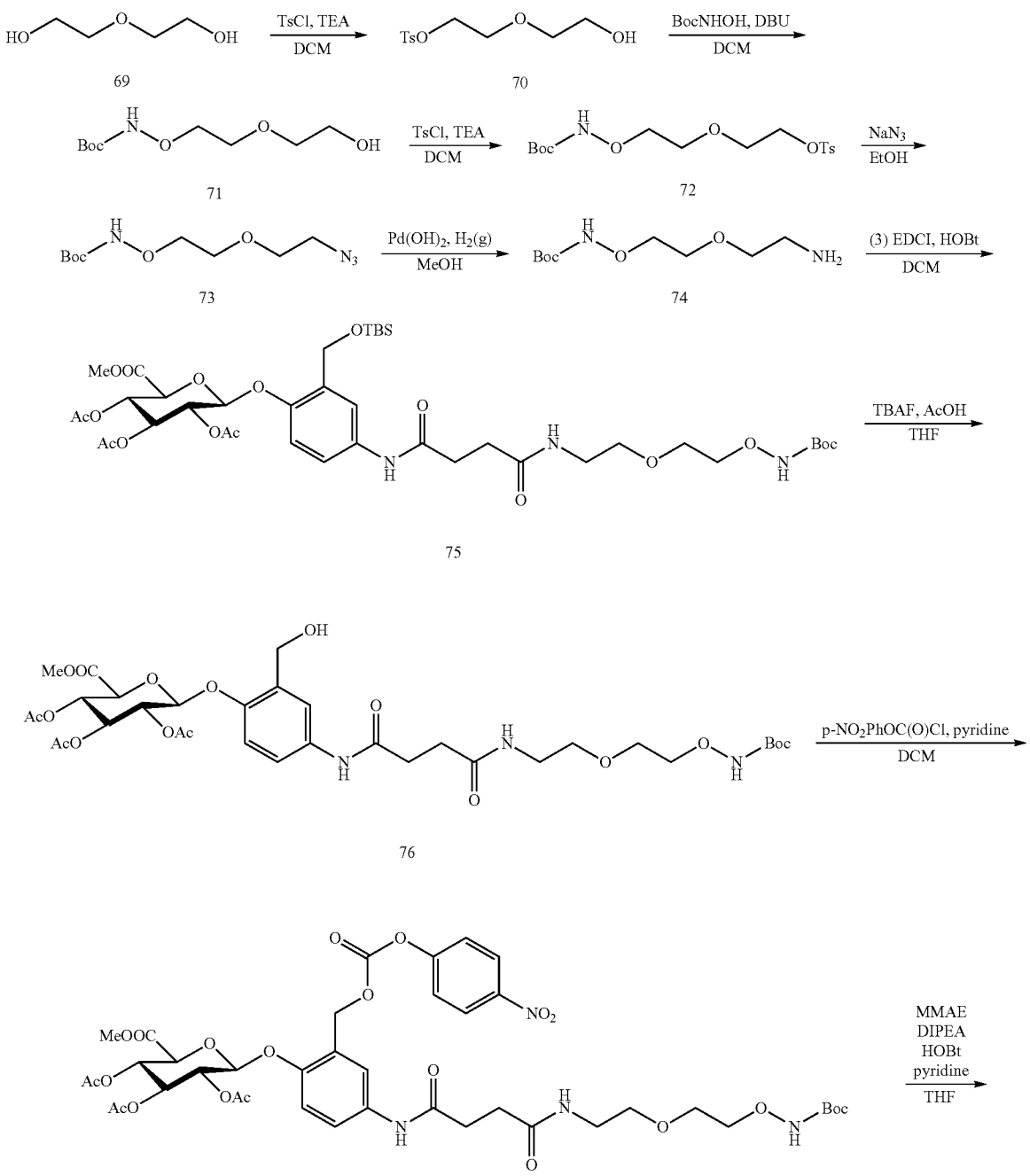

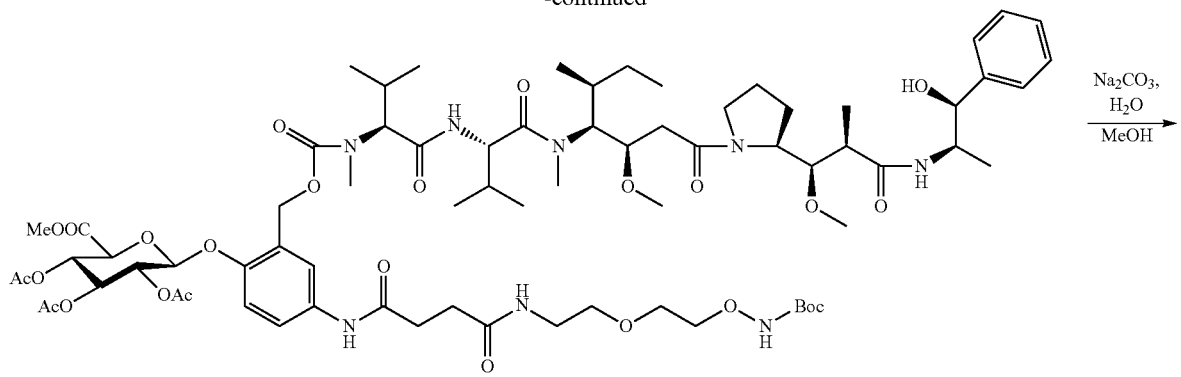

78

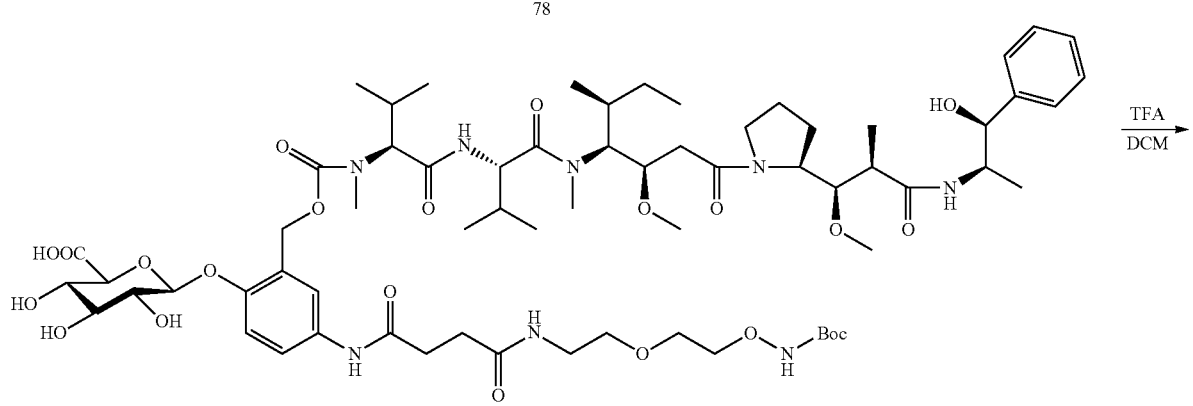

79

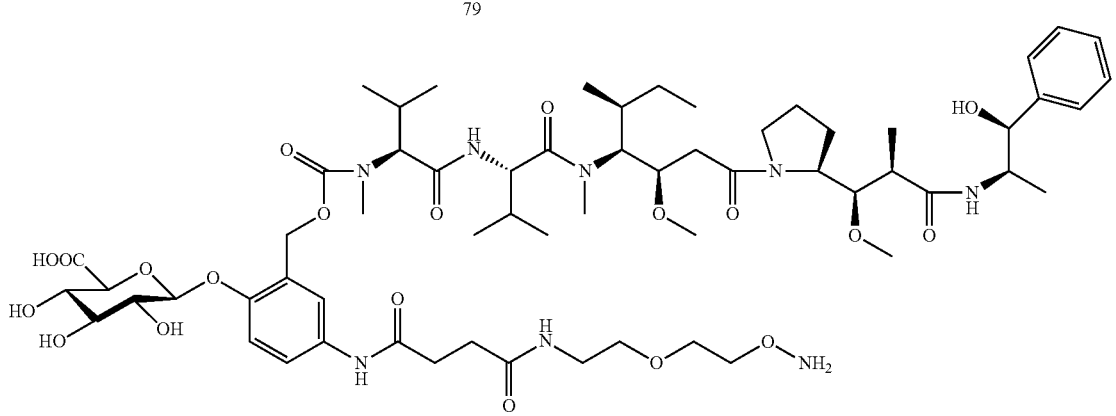

80 (A15)

Preparation of Compound (70)

Diethylene glycol 69 (208 g, 0.188 mol) was dissolved in CH$_2$Cl$_2$ (500 mL) followed by the addition of TEA (29 mL, 0.207 mol), then cooled with an ice bath. TsCl (20 g, 0.094 mol) in CH$_2$Cl$_2$ (100 mL) was added drop-wise during a period of 30 min. Slowly warmed to room temperature and kept reacting for another 1 hour. The solvent was removed and purified by silica gel chromatography eluting with 20% EA/hexane, then 66% EA/hexane to give 14.4 g (29.5%) of diethylene glycol mono-Ts 70. Then, the obtained compound above diethylene glycol mono-Ts 70 (12.61 g, 44.2 mmol) and N-Boc-hydroxylamine (8.25 g, 62 mmd) were dissolved in CH$_2$Cl$_2$ (400 mL) followed by the addition of DBU (13.5 mL, 88.4 mol). After 48 hours reaction, the reaction was diluted with 400 mL of CH$_2$Cl$_2$, washed with 1N HCl (100 mL, twice), H$_2$O (100 mL) and brine (200 mL), the organic layer was dried over anhydrous MgSO$_4$ and evaporated. The crude was purified by silica gel chromatography eluting with 33% EA/hexane, then 50% EA/hexane containing 5% MeOH to give 1.5 g (16.1%) of diethylene glycol mono-Ts 71. The product was dissolved in CH$_2$Cl$_2$ (70 mL) followed by the addition of TEA (2.96 mL, 21.3 mmol), then cooled with an ice bath. TsCl (2 g, 9.4 mmol) in CH$_2$Cl$_2$ (20 mL) was added drop-wise during a period of 30 min. Slowly warmed to room temperature and kept reacting for another 1 hour. The solvent was removed and purified by silica gel chromatography eluting with 10%

EA/hexane, then 40% EA/hexane to give 1.31 g (49%) of OTs-diethylene glycol hydroxylamie-Boc 72. Finally, OTs-diethylene glycol hydroxylamie-Boc 72 (1.3 g, 3.48 mmol) was dissolved in anhydrous ethanol (50 mL) followed by the addition of sodium azide (680 mg, 10.4 mmol), then refluxed overnight. The solvent was removed, diluted with EA (200 mL), washed with H$_2$O (50 mL) and brine (50 mL), the organic layer was dried over anhydrous MgSO$_4$ and evaporated. The crude was purified by silica gel chromatography eluting with 10% EA/hexane, then 40% EA/hexane to give 728 mg (85%) of Azido-diethylene glycol hydroxylamie-Boc 73. $^1$H NMR (400 MHz, CDCl$_3$) δ 3.85-3.82 (m, 2H), 3.54-3.51 (m, 2H), 3.48 (d, J=4.88 Hz, 2H), 3.21 (d, J=5.2 Hz, 2H), 1.28 (s, 3H).

Preparation of Compound (74)

Azido-diethylene glycol hydroxylamie-Boc 73 (168.5 mg, 0.684 mmol) was dissolved in a mixture of methanol (0.68 mL) and EA (6.2 mL) then the solution was degassed by N$_{2(g)}$. Pd(OH)$_2$ (59 mg) was added and purged with H$_{2(g)}$ for 5 min, then the reaction was reacted for 2 hours under the same condition. After completion, the crude was filtered through a pad of celite then concentrated to dryness to give 145 mg (96.2%) of amino-diethylene glycol hydroxylamie-Boc 74 without further purification. Then, 2,3,4-tri-Ac-6-methyl-Glucuranate-2'-OTBS-PAB-succinic acid 3 (322.6 mg, 0.482 mmol) and the above compound 74 (127.3 mg, 0.578 mmol) was dissolved in CH$_2$C$_2$ (5 mL) followed by the addition of EDCI (138.5 mg, 0.723 mmol), HOBt (74 mg, 0.48 mmol). After 8 hours, the solvent was removed and the reaction mixture was then purified by silica gel chromatography eluting with 15% EA/hexane, then 60% EA/hexane to give 312.2 mg (74%) of 2,3,4-tri-Ac-6-methyl-Glucuranate-2'-OTBS-PAB-succinate-PEG2-hydroxylamie-Boc 75. The obtained compound 75 was dissolved in a mixture of pyridine (2.7 mL) and acetic acid (1.8 mL) followed by the addition of TBAF (0.3 mL, 1 M in THF). After 12 hours, the solvent was removed and the reaction mixture was then purified by silica gel chromatography eluting with CH$_2$C2 (100%), then 5% MeOH/CH$_2$Cl$_2$ to give 218.1 mg (80.4%) of 2,3,4-tri-Ac-6-methyl-Glucuranate-2'-OH-PAB-succinate-PEG2-hydroxylamie-Boc 76. 2,3,4-tri-Ac-6-methyl-Glucuranate-2'-OH-PAB-succinate-PEG2-hydroxylamie-Boc 76 (218.1 mg, 0.288 mmol) was suspended in anhydrous CH$_2$Cl$_2$ (5.5 mL), followed by the addition of pyridine (240 µL, 2.95 mmol) and 4-nitrobenzoyl chloride (260 mg, 1.26 mmol). After 2 hours the solvent was removed and purified by silica gel chromatography eluting with CH$_2$C2 (100%), then 5% MeOH/CH$_2$Cl$_2$ to give 155.6 mg (58.7%) of 2,3,4-tri-Ac-6-methyl-Glucuranate-2'-OpNP-PAB-succinate-PEG2-hydroxylamie-Boc 77. Then, MMAE (108.3 mg, 0.15 mmol) was dissolved in a mixture of THF (3.45 mL) and pyridine (0.86 mL) followed by the addition of DIPEA (260 µL), HOBt (6.9 mg, 0.048 mmol) and 2,3,4-tri-Ac-6-methyl-Glucuranate-2'-OpNP-PAB-succinate-PEG2-hydroxylamie-Boc 77 (155.6 mg, 0.169 mmol). After 48 hours the solvent was removed and the reaction mixture was then purified by silica gel chromatography eluting with CH$_2$Cl$_2$ (100%), then 7.5% MeOH/CH$_2$Cl$_2$ to give 145.7 mg (57.4%) of 2,3,4-tri-Ac-6-methyl-Glucuranate-2'-MMAE-PAB-succinate-PEG2-hydroxylamie-Boc 78. $^1$H NMR (400 MHz, CDCl$_3$) δ 9.22 (s, 1H), 8.2-7.95 (m, 2H), 7.6-6.5 (m, 12H), 5.4-5.15 (m, 5H), 5.15-4.92 (m, 3H), 4.85 (d, J=2.48 Hz, 1H), 4.82-4.5 (m, 3H), 4.49-3.98 (m, 71), 3.95-3.17 (m, 27H), 3.14-2.46 (m, 13H), 2.45-1.45 (m, 24H), 1.39 (s, 9H), 1.17 (d, J=7.2 Hz, 1H), 1.05-0.45 (m, 30H).

Preparation of Compound (79)

2,3,4-tri-Ac-6-methyl-Glucuranate-2'-MMAE-PAB-succinate-PEG2-hydroxylamie-Boc 78 (145.7 mg, 0.097 mmol) was dissolved MeOH (3.9 mL), then Na$_2$CO$_3$ (32.3 mg, 0.31 mmol) was added. After 1 hour, H$_2$O (194 µL) was added to the reaction mixture and the reaction was kept stirring for another 1 hour. Then the reaction was neutralized by IR-120, after filtered through a pad of celite, the crude was evaporated and purified by C18 column eluting with 100% H$_2$O, then 40% acetonitrile/H$_2$O to give 85 mg (65.5%) of Glucuranate-2'-MMAE-PAB-succinate-PEG2-hydroxylamie-Boc 79. 20 mg of Glucuranate-2'-MMAE-PAB-succinate-PEG2-hydroxylamie-Boc was suspended in anhydrous CH$_2$Cl$_2$ (1.0 mL), and TFA (0.25 mL) was added. The reaction was stirred at 0° C. for 10 min, then warmed to room temperature for another 30 min. The reaction mixture was evaporated to dryness, then pass through a C18 column eluting with 100% H$_2$O, then 20% acetonitrile/H$_2$O to get 13 mg (72%) of Glucuranate-2'-MMAE-PAB-succinate-PEG2-hydroxylamie 80. $^1$H NMR (400 MHz, D$_2$O) δ 8.22-7.9 (m, 1H), 7.54-7.1 (m, 8H), 5.4-5.1 (m, 2H), 5.04 (s, 1H), 4.73-4.25 (m, 2H), 4.18 (d, J=8.28 Hz, 1H), 4.05 (bs, 3H), 3.9 (s, 1H), 3.7-3.59 (m, 5H), 3.54 (m, 2H), 3.5-3.24 (m, 9H), 3.18 (s, 1H), 3.07 (d, J=3.08 Hz, 2H), 2.97 (s, 1H), 2.93 (d, J=2.52 Hz, 2H), 2.82-2.24 (m, 6H), 2.2-1.9 (m, 2H), 1.83 (s, 2H), 1.8-1.56 (m, 21), 1.55-1.47 (m, 1H), 1.27 (d, J=6.4 Hz, 3H), 1.18 (d, J=7.2 Hz, 1H), 1.13 (d, J=9.58 Hz, 1H), 1.06 (d, J=8.9 Hz, 2H), 0.94 (d, J=7.54 Hz, 2H), 0.94-0.5 (m, 14H). ESI-TOF m/z: 1283.6622 [M+Na]$^+$.

2.16 Synthesis and Characterization of Compound 86 (A16)

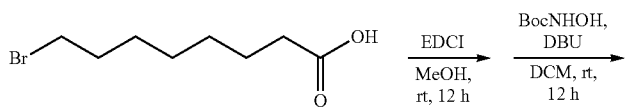

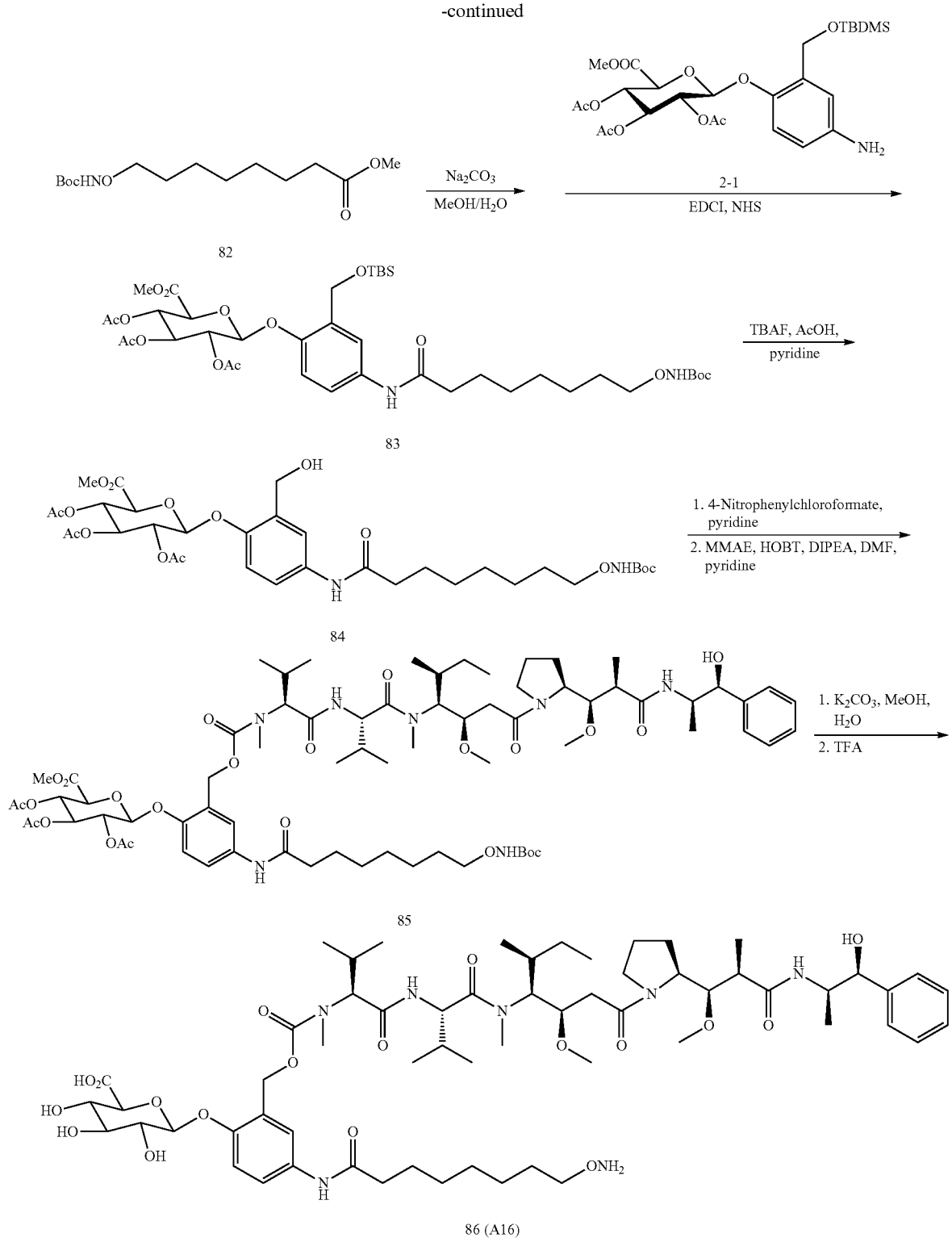

Preparation of Compound (82)

To a Methyl alcohol (20 mL) solution of compound 81 (1.5 g, 6.756 mmole) and EDCI (1.26 g, 8.1 mmole) was stirred. After stirring for 16 hr at room temperature, the solution was concentrated and the residue was purified by flash column chromatography to afford the product as an oil (1.51 g, 6.4 mmole) for next step. To a Dichloromethane (30 mL) solution of the N-Boc-hydroxylamine (1.28 g, 9.6 mmole) and compound (1.51 g, 6.4 mmole) from last step, DBU (1.95 g, 12.8 mmole) was added into the mixture and solution was stirred at room temperature for 16 hr. The solution was concentrated. Purification of the crude material using column chromatography afforded the product 82 (1.22 g, 4.22 mmole) as an oil; $^1$H NMR (400 MHz, CDCl$_3$) 7.09 (s, 1H), 3.83 (t, J=6.8 Hz, 2H), 3.66 (s, 3H), 2.29 (t, J=7.6 Hz, 2H), 1.64-1.49 (m, 4H), 1.45 (s, 9H), 1.39-1.30 (m, 6H).

Preparation of Compound (83)

To a Methyl alcohol (9 mL) solution of compound 82 (1.22 g, 4.22 mmole), H$_2$O (1.0 mL), and Na$_2$CO$_3$ (2.24 g, 21.1 mmole) was stirred. After stirring for 24 hr at room temperature, the solution was concentrated. The residue was extracted with 1N HCl (10 mL) and ethyl acetate. The organic phase was concentrated to afford the product as oil (0.22 g, 0.8 mmole) for next step. EDCI (0.16 g, 1.04 mmole) and HOBT (0.162 g, 1.2 mmol) were added sequentially to a solution of compounds (0.22 g, 0.8 mmol) obtained above and compound 2-1 (0.5 g, 0.88 mmol) in Dichloromethane (16 mL), and the mixture was stirred at room temperature for 12 h. The reaction mixture was then concentrated in vacuo and the residue was purified by flash column chromatography to afford the product as an oil 83 (0.28 g, 0.34 mmole). $^1$H NMR (400 MHz, CDCl$_3$) δ 7.64 (dd, J=2.8, 8.8 Hz, 1H), 7.31 (d, J=2.8 Hz, 1H), 7.23 (s, 1H), 7.15 (s, 1H), 6.91 (d, J=8.8 Hz, 1H), 5.34-5.25 (m, 3H), 5.05 (d, J=6.8 Hz, 1H), 4.72 (d, J=14.8 Hz, 1H), 4.60 (d, J=14.8 Hz, 1H), 4.13 (d, J=9.6 Hz, 1H), 3.84 (t, J=6.4 Hz, 2H), 3.73 (s, 3H), 2.34 (m, 1H), 2.08 (s, 3H), 2.05 (s, 3H), 2.04 (s, 3H), 1.72-1.61 (m, 4H), 1.47 (s, 9H), 1.40-1.33 (m, 6H), 0.96 (s, 3H), 0.12 (s, 6H).

Preparation of Compound (84)

To a solution of compound 83 (0.28 g, 0.34 mmole), TBAF (0.36 mL, 0.36 mmole), AcOH (2.1 mL), and pyridine (3.2 mL) was stirred. After stirring for 12 hr at room temperature, the solution was concentrated and the residue was purified by flash column chromatography to afford the product as a solid 84 (0.18 g, 0.253 mmole). $^1$H NMR (400 MHz, CDCl$_3$) δ 7.61 (dd, J=2.4, 8.4 Hz, 1H), 7.39 (s, 1H), 7.35 (d, J=2.4 Hz, 1H), 7.18 (s, 1H), 6.97 (d, J=8.4 Hz, 1H), 5.40-5.23 (m, 3H), 5.07 (d, J=7.2 Hz, 1H), 4.74 (d, J=12.8 Hz, 1H), 4.41 (d, J=13.2 Hz, 1H), 4.10 (d, J=9.6 Hz, 1H), 3.84 (t, J=6.4 Hz, 2H), 3.71 (s, 3H), 2.34 (t, J=7.6 Hz, 1H), 2.10 (s, 3H), 2.05 (s, 3H), 2.03 (s, 3H), 1.68-1.56 (m, 4H), 1.47 (s, 9H), 1.40-1.35 (m, 6H).

Preparation of Compound (85)

To a Dichloromethane (10 mL) solution of compound 84 (180 mg, 0.253 mmole), 4-Nitrophenylchloroformate (76 mg, 0.379 mmole), and pyridine (0.04 mL, 0.506 mmole) was stirred for 12 hr at room temperature. The solution was concentrated and the residue was purified by flash column chromatography to get the product as a solid (162 mg, 0.185 mmole) for next step. To a Dimethylformamide (6 mL) solution of compound (70.8 mg, 0.080 mmole) obtained above, MMAE (146 mg, 0.203 mmole), DIPEA (0.185 mL, 0.925 mmole), HOBT (9.65 mg, 0.0714 mmole), and pyridine (0.146 mL) was stirred. After stirring for 48 hr at room temperature, the solution was concentrated and the residue was purified by flash column chromatography to afford the product as a solid 85 (95 ng, 0.065 mmole); HRMS (ESI-TOF, MNa+) calculated for C73H113N7O23Na, 1478.7780, found 1478.7828.

Preparation of Compound (86)

A solution of 85 (20.0 mg, 0.015 mmol) in 5 mL of solution (MeOH:H$_2$O=4:1) was treated at 0° C. with Na$_2$CO$_3$ (4.0 mg, 0.0371 mmol). The resulting mixture was stirred at rt for 3 h. After the reaction was completed, the organic solution was removed under reduced pressure. The residue was purified by was purified by C18 column to give compound for next step. To a solution of compound from last step was dissolved in 1.6 ml of CH$_2$Cl$_2$. 0.40 ml of TFA was then added and stirred at room temperature for 1 h. The solution was concentrated and the residue was purified by C18 column to give 86 (10.1 mg, 0.0076 mmol). ESI-TOF m/z: 1214.6890 [M-H]$^-$.

2.17 Synthesis and Characterization of Compound 90 (A17)

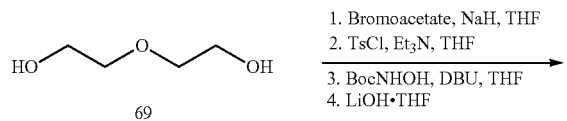

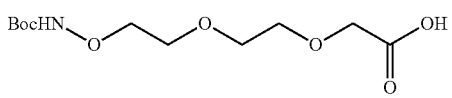

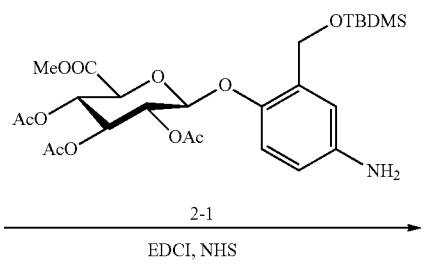

-continued

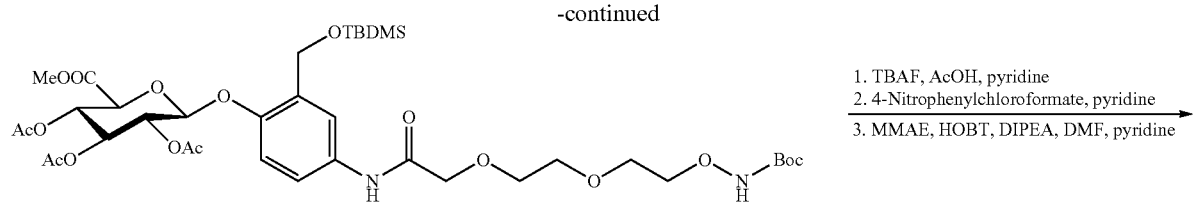

1. TBAF, AcOH, pyridine
2. 4-Nitrophenylchloroformate, pyridine
3. MMAE, HOBT, DIPEA, DMF, pyridine

88

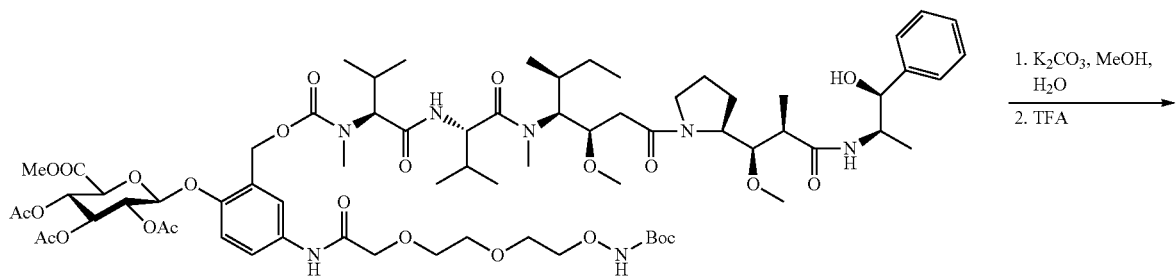

1. K₂CO₃, MeOH, H₂O
2. TFA

89

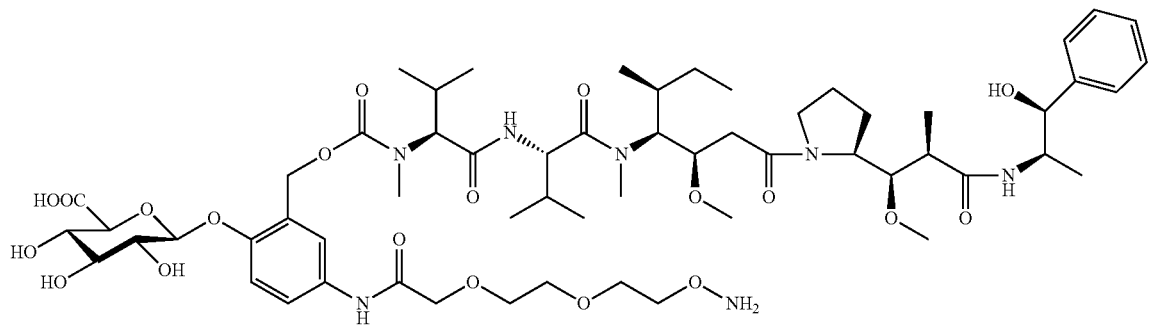

90 (A17)

Preparation of Compound (87)

To a Tetrahydrofuran (300 mL) solution of the Sodium hydride (6.2 g 155 mmole) and Diethylene glycol 69 (26 g, 245 mmole), methyl bromoacetate (25 g, 163 mmole) was dropwise added into the mixture at 0° C. and solution was stirred at room temperature for 16 hr. When TLC indicated that starting material was fully consumed, the solution was quenched with MeOH, filtered through a pad of celite, and the celite was washed with MeOH. The combined filtrates and washings were concentrated under reduced pressure and the residue was purified by flash column chromatography (silica gel, 2% MeOH in $CH_2Cl_2$) to afford the product as an oil (8 g, 44.92 mmole); H NMR (400 MHz, MeOD) δ 4.11-4.10 (m, 2H), 3.70-3.65 (m, 9H), 3.56-3.54 (m, 2H). To a Dichloromethane (100 mL) solution of the compound (8 g, 44.92 mmole) obtained above and triethylamine (12 mL, 86.33 mmole), P-Toluenesulfonyl chloride (11.53 g, 60.48 mmole) in $CH_2Cl_2$ (100 mL) was added into the mixture and solution was stirred at room temperature for 16 hr. The white solid was observed, filtered by the pad of celite, and washed by $CH_2Cl_2$. The filtrate was concentrated in vacuo and the residue was purified by flash column chromatography (silica gel, 35% Ethyl acetate in Hexane) to afford the product as an oil (12 g, 36.10 mmole); $^1$H NMR (400 MHz, $CDCl_3$) 7.77 (d, J=8.4 Hz, 2H), 7.31 (d, J=8.0 Hz, 2H), 4.13 (t, J=4.8 Hz, 2H), 4.09 (s, 2H), 3.72 (s, 3H), 3.67-3.58 (m, 6H), 2.42 (s, 3H). To a Tetrahydrofuran (160 mL) solution of the N-Boc-hydroxylamine (5.87 g, 44.09 mmole) and compound (8.9 g, 26.78 mmole) obtained above, DBU (7.0 mL, 46.85 mmole) was added into the mixture and solution was stirred at room temperature for 72 hr. When TLC indicated that starting material was fully consumed, the solution was concentrated. Purification of the crude material using column chromatography (silica gel, Ethyl acetate) afforded the product (4.05 g, 13.80 mmole) as an oil. To a Tetrahydrofuran (12 mL) solution of compound (1 g, 3.41 mmole) obtained above, $H_2O$ (0.5 mL), and LiOH (0.172 g, 4.099 mmole) was stirred. After stirring for 2 hr at room temperature, the solution was quenched with 1N HCl (10 mL), and partitioned between ethyl acetate and brine. The organic phase was collected and the aqueous phase was extracted with ethyl acetate (50 mL×4). The combined organic layer were concentrated and the residue was purified by flash column chromatography (silica gel, 20% MeOH in $CH_2Cl_2$) to afford the product as an oil 87 (0.87 g, 3.11 mmole); $^1$H NMR (400 MHz, $CDCl_3$) 3.95 (m, 4H), 3.66-3.62 (m, 6H), 3.32 (s, 1H), 1.41 (s, 9H); HRMS (ESI-TOF, MNa+) calculated for $C_{11}H_{21}NO_7$ Na, 302.1210, found 302.1233.

Preparation of Compound (88)

EDCI (0.22 g, 1.417 mmole) and HOBT (0.126 g, 0.932 mmol) were added sequentially to a solution of compounds 87 (0.4 g, 1.432 mmol) and compound 2-1 (0.532 g, 0.934 mmol) in Dichloromethane (16 mL), and the mixture was stirred at room temperature for 16 h. The reaction mixture was then concentrated in vacuo and the residue was purified by flash column chromatography (silica gel, 67% Ethyl acetate in Hexane) to afford the product as an oil 88 (0.4676 g, 0.562 mmole); $^1$H NMR (400 MHz, CDCl$_3$) 8.69 (s, 1H), 7.61 (s, 1H), 7.56 (dd, J=2.8, 8.8 Hz, 1H), 7.47 (d, J=2.8 Hz, 1H), 6.91 (d, J=8.8 Hz, 1H), 5.31-5.25 (m, 3H), 5.04 (d, J=6.8 Hz, 1H), 4.73 (d, J=15.2 Hz, 1H), 4.61 (d, J=14.8 Hz, 1H), 4.12-4.06 (m, 4H), 4.00-3.98 (m, 2H), 3.76-3.68 (m, 8H), 2.03 (s, 3H), 2.01 (s, 3H), 2.01 (s, 3H), 1.41 (s, 9H), 0.92 (s, 9H), 0.09 (s, 6H); HRMS (ESI-TOF, MNa+) calculated for C37H58N2O17SiNa, 853.3397, found 853.3385.

Preparation of Compound (89)

To a solution of compound 88 (0.4676 g, 0.562 mmole), TBAF (0.56 mL, 0.56 mmole), AcOH (3.4 mL), and pyridine (5.5 mL) was stirred. After stirring for 12 hr at room temperature, the solution was concentrated and the residue was purified by flash column chromatography (silica gel, Ethyl acetate) to afford the product as a solid (0.36 g, 0.5 mmole); $^1$H NMR (400 MHz, CDCl$_3$) 8.81 (s, 1H), 7.95 (s, 1H), 7.82-7.79 (m, 1H), 7.33 (d, J=2.8 Hz, 1H), 6.95 (d, J=8.8 Hz, 1H), 5.35-5.23 (m, 3H), 5.03 (d, J=7.2 Hz, 1H), 4.74 (d, J=13.2 Hz, 1H), 4.41 (d, J=12.8 Hz, 1H), 4.11-4.02 (m, 71), 3.77-3.68 (m, 8H), 2.07 (s, 3H), 2.02 (s, 3H), 2.01 (s, 3H), 1.41 (s, 9H). To a Dichloromethane (9 mL) solution of compound (90 mg, 0.126 mmole) obtained above, 4-Nitrophenylchloroformate (100 mg, 0.495 mmole), and pyridine (0.11 mL, 1.423 mmole) was stirred. After stirring for 2 hr at room temperature, the solution was concentrated and the residue was purified by flash column chromatography (silica gel, 35% Ethyl acetate in Hexane) to afford the product as a solid (70.8 mg, 0.080 mmole). To a Dimethylformamide (6 mL) solution of compound (70.8 ing, 0.080 mmole) obtained above, MMAE (58 mg, 0.08 mmole), DIPEA (0.125 mL, 0.7175 mmole), HOBT (9.65 mg, 0.0714 mmole), and pyridine (2.0 mL) was stirred. After stirring for 72 hr at room temperature, the solution was concentrated and the residue was purified by flash column chromatography (silica gel, 4% MeOH in CH$_2$Cl$_2$) to afford the product as a solid 89 (75 mg, 0.051 mmole); HRMS (ESI-TOF, MNa+) calculated for C71H109N7O25 Na, 1482.7365, found 1482.7334.

Preparation of Compound (90)

To a Methyl alcohol (2 mL) solution of compound 89 (75 mg, 0.051 mmole), K2C03 (42 mg, 0.304 mmole), and H$_2$O (0.4 mL) was stirred. After stirring for 6 hr at room temperature, the solution was quenched with AcOH and then concentrated. The residue was purified by C18 column to afford the product as a solid (44 mg, 0.0333 mmole); HRMS (ESI-TOF, MNa+) calculated for C64H101N7O22Na, 1342.6892, found 1342.6881. TFA (0.35 mL) was slowly added into a solution of compound (44 mg, 0.0333 mmol) obtained above in DCM (0.65 mL) at 0° C. The resulting mixture was stirred at room temperature for 2 h, and concentrated. Purification of the crude material using C18 column to afforded the product 90 (36 mg, 0.029 mmol) as an oil; HRMS (ESI-TOF, M-H) calculated for C59H92N7O20 1218.6392, found 1218.6324.

2.18 Synthesis and Characterization of Compound 94 (A18)

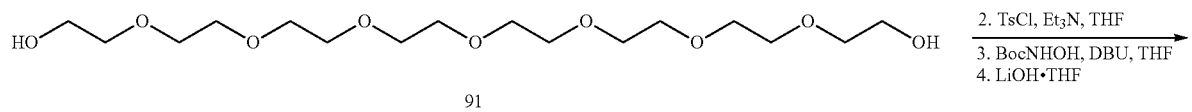

91

1. Bromoacetate, NaH, THF
2. TsCl, Et$_3$N, THF
3. BocNHOH, DBU, THF
4. LiOH·THF

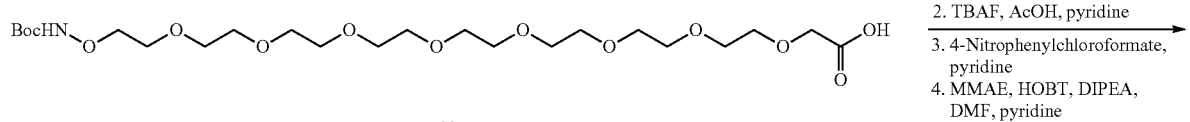

92

1. (2-1) EDCI, NHS
2. TBAF, AcOH, pyridine
3. 4-Nitrophenylchloroformate, pyridine
4. MMAE, HOBT, DIPEA, DMF, pyridine

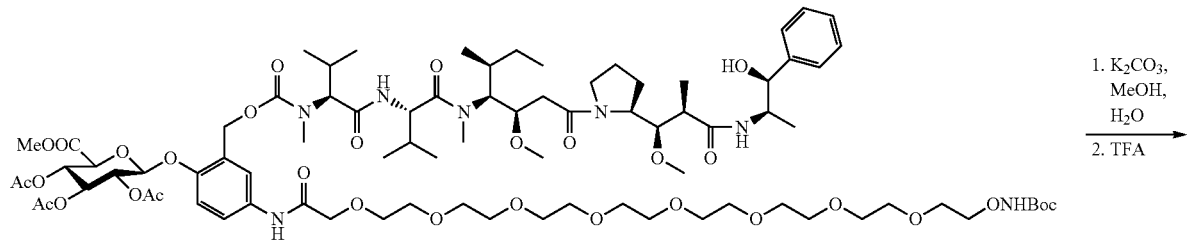

93

1. K$_2$CO$_3$, MeOH, H$_2$O
2. TFA

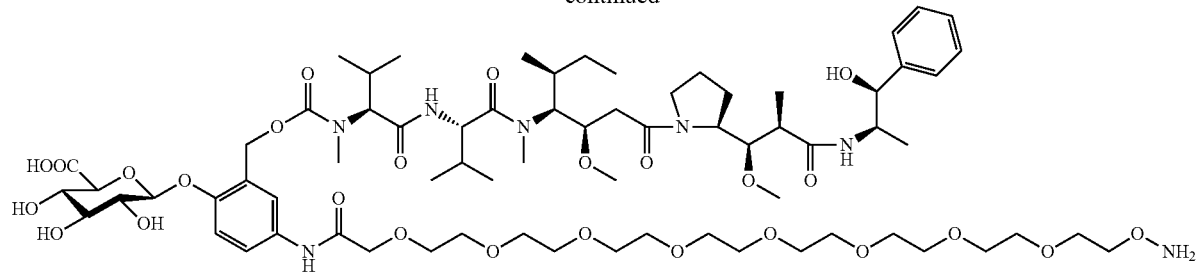

94 (A18)

Preparation of Compound (92)

To a Tetrahydrofuran (200 mL) solution of the Sodium hydride (0.7 g, 17.5 mmole) and Octoethylene glycol 91 (10 g, 26.99 mmole), methyl bromoacetate (1.7 ML, 16.67 mmole) was dropwise added into the mixture at 0° C. and solution was stirred at room temperature for 16 hr. When TLC indicated that starting material was fully consumed, the solution was quenched with MeOH, filtered through a pad of celite, and the celite was washed with MeOH. The combined filtrates and washings were concentrated under reduced pressure and the residue was purified by flash column chromatography (silica gel, 2% MeOH in $CH_2Cl_2$) to afford the product as an oil (2.7 g, 15.16 mmole); $^1$H NMR (400 MHz, $CDCl_3$) 4.09 (d, J=1.2 Hz, 2H), 3.67-3.53 (m, 34H). To a Dichloromethane (30 mL) solution of the compound (2.7 g, 15.16 mmole) obtained above and triethylamine (3 mL, 21.58 mmole), P-Toluenesulfonyl chloride (2.8 g, 14.69 mmole) in $CH_2Cl_2$ (20 mL) was added into the mixture and solution was stirred at room temperature for 16 hr. The white solid was observed, filtered by the pad of celite, and washed by $CH_2Cl_2$. The filtrate was concentrated in vacuo and the residue was purified by flash column chromatography (silica gel, 2% MeOH in $CH_2Cl_2$) to afford the product as an oil (2.16 g, 3.62 mmole); $^1$H NMR (400 MHz, $CDCl_3$) 7.73 (d, J=8.4 Hz, 2H), 7.28 (d, J=8.0 Hz, 2H), 4.10 (t, J=4.8 Hz, 2H), 4.10 (s, 2H), 3.69-3.52 (m, 35H), 2.39 (s, 3H). To a Tetrahydrofuran (40 mL) solution of the N-Boc-hydroxylamine (1 g, 7.51 mmole) and compound (2.16 g, 3.62 mmole) obtained above, DBU (1.45 mL, 9.705 mmole) was added into the mixture and solution was stirred at room temperature for 72 hr. When TLC indicated that starting material was fully consumed, the solution was concentrated. Purification of the crude material using column chromatography (silica gel, 12% MeOH in $CH_2C$) afforded the product (0.6 g, 1.076 mmole) as an oil. To a Tetrahydrofuran (3 mL) solution of compound (0.6 g, 1.076 mmole) obtained above, $H_2O$ (0.15 mL), and LiOH (0.056 g, 1.335 mmole) was stirred. After stirring for 2 hr at room temperature, the solution was quenched with 1N HCl (10 mL), and partitioned between ethyl acetate and brine. The organic phase was collected and the aqueous phase was extracted with ethyl acetate (50 mL×4). The combined organic layer were concentrated and the residue was purified by flash column chromatography (silica gel, 20% MeOH in $CH_2Cl_2$) to afford the product as an oil 92 (0.46 g, 0.846 mmole); HRMS (ESI-TOF, MNa+) calculated for $C_{23}H_{45}NO_{13}Na$, 566.2783, found 566.2768.

Preparation of Compound (93)

EDCI (0.18 g, 1.16 mmole) and HOBT (0.114 g, 0.843 mmol) were added sequentially to a solution of compounds 92 (0.46 g, 0.846 mmol) and compound I (0.683 g, 1.2 mmol) in Dichloromethane (0.51 mL), and the mixture was stirred at room temperature for 16 h. The reaction mixture was then concentrated in vacuo and the residue was purified by flash column chromatography (silica gel, 5% MeOH in $CH_2Cl_2$) to afford the product as an oil (0.51 g, 0.465 mmole); $^1$H NMR (400 MHz, $CDCl_3$) 8.67 (s, 1H), 7.70 (s, 1H), 7.55 (d, J=2.0 Hz, 1H), 7.48 (dd, J=2.0, 8.8 Hz, 1H), 6.90 (d, J=8.8 Hz, 1H), 5.30-5.25 (m, 3H), 5.04 (d, J=6.8 Hz, 1H), 4.70 (d, J=15.2 Hz, 1H), 4.59 (d, J=15.2 Hz, 1H), 4.13-4.08 (m, 3H), 3.99-3.97 (m, 2H), 3.73-3.55 (m, 33H), 2.03 (s, 3H), 2.01 (s, 3H), 2.01 (s, 3H), 1.44 (s, 9H), 0.92 (s, 9H), 0.08 (s, 6H). To a solution of compound (0.51 g, 0.465 mmole) obtained above, TBAF (0.49 mL, 0.49 mmole), AcOH (3 mL), and pyridine (5 mL) was stirred. After stirring for 12 hr at room temperature, the solution was concentrated and the residue was purified by flash column chromatography (silica gel, 5% MeOH in $CH_2Cl_2$) to afford the product as a solid (0.49 g, 0.499 mmole); $^1$H NMR (400 MHz, $CDCl_3$) 8.91 (s, 1H), 7.81 (s, 11H), 7.48 (dd, J=2.4, 8.8 Hz, 1H), 7.42 (d, J=2.4 Hz, 1H), 6.95 (d, J=8.8 Hz, 1H), 5.32-5.23 (m, 3H), 5.05 (d, J=7.6 Hz, 1H), 4.69 (d, J=13.2 Hz, 1H), 4.43 (d, J=13.2 Hz, 1H), 4.10-4.07 (m, 3H), 3.98-3.96 (m, 2H), 3.72-3.56 (m, 33H), 3.44 (s, 1H), 2.07 (s, 3H), 2.02 (s, 3H), 2.01 (s, 3H), 1.43 (s, 9H). To a Dichloromethane (24 mL) solution of compound (122.5 in, 0.125 mmole) obtained above, 4-Nitrophenylchloroformate (100 mg, 0.495 mmole), and pyridine (0.11 mL, 1.423 mmole) was stirred. After stirring for 2 hr at room temperature, the solution was concentrated and the residue was purified by flash column chromatography (silica gel, 35% Ethyl acetate in Hexane) to afford the product as a solid (59 in, 0.051 mmole); $^1$H NMR (400 MHz, $CDCl_3$) 8.90 (s, 1H), 8.26-8.23 (m, 2H), 7.74 (s, 1H), 7.66 (d, J=2.4 Hz, 1H), 7.60 (dd, J=2.4, 9.2 Hz, 1H), 0.7.41-7.38 (m, 2H), 7.04 (d, J=9.2 Hz, 1H), 5.32-5.26 (m, 4H), 5.19-5.10 (m, 2H), 4.16 (d, J=9.2 Hz, 1H), 4.08 (s, 2H), 3.99-3.96 (m, 2H), 3.73-3.56 (m, 33H), 2.04 (s, 3H), 2.02 (s, 3H), 2.01 (s, 3H), 1.43 (s, 9H). To a Dimethylformamide (6 mL) solution of compound (90 mg, 0.0785 mmole) obtained above, MMAE (60 mg, 0.084 mmole), DIPEA (0.14 mL, 0.8037 mmole), HOBT (22 in, 0.163 mmole), and pyridine (2.0 mL) was stirred. After stirring for 72 hr at room temperature, the solution was concentrated and the residue was purified by flash column chromatography (silica gel, 3% MeOH in $CH_2Cl_2$) to afford the product as a solid 93 (80 mg, 0.046 mmole); HRMS (ESI-TOF, M2Na+) calculated for $C_{83}H_{133}N_7O_{31}$ Na2 884.9415, found 884.9360.

Preparation of Compound (94)

To a Methyl alcohol (2.5 mL) solution of compound 93 (80 mg, 0.046 mmole), K2CO3 (38 mg, 0.276 mmole), and $H_2O$ (0.5 mL) was stirred. After stirring for 6 hr at room temperature, the solution was quenched with AcOH and then concentrated. The residue was purified by C18 column to afford the product as a solid (15 mg, 0.0095 mmole); HRMS (ESI-TOF, M2Na+) calculated for C76H125N7O28Na2 814.9178, found 814.9132. TFA (0.35 mL) was slowly added into a solution of compound (15 mg, 0.0095 mmole) obtained above in DCM (0.65 mL) at 0° C. The resulting mixture was stirred at room temperature for 2 h, and concentrated. Purification of the crude material using C18 column to afforded the product 94 (12 mg, 0.0081 mmol) as an oil; HRMS (ESI-TOF, M2Na+) calculated for C71H117N7O26Na2 764.8916, found 764.9085.

2.19 Synthesis and Characterization of Compound 99 (A19)

(143 mg, 0.746 mmol) in $CH_2Cl_2$ was added EDCI (173.0 mg, 1.12 mmol). It was stirred at rt for 15 h. The solution was evaporated. The crude product was purified by column to give compound 96 as yellow oil (350.0 mg, 0.47 mmol). $^1H$ NMR (400 MHz, $CDCl_3$) δ 10.19 (s, 1H), 8.04 (s, 1H), 7.71 (dd, J=2.0, 8.4 Hz, 1H), 7.62 (d, J=2.0 Hz, 1H), 6.90 (d, J=8.4 Hz, 1H), 5.30-5.20 (m, 3H), 5.04 (d, J=7.2 Hz, 1H), 4.69 (d, J=14.8 Hz, 1H), 4.58 (d, J=14.8 Hz, 1H), 4.37 (s, 2H), 4.12 (d, J=8.8 Hz, 1H), 3.68 (s, 3H), 2.01 (s, 3H), 1.99 (s, 3H), 1.99 (s, 3H), 1.43 (s, 9H), 0.9 (s, 9H), 0.07 (s, 6H).

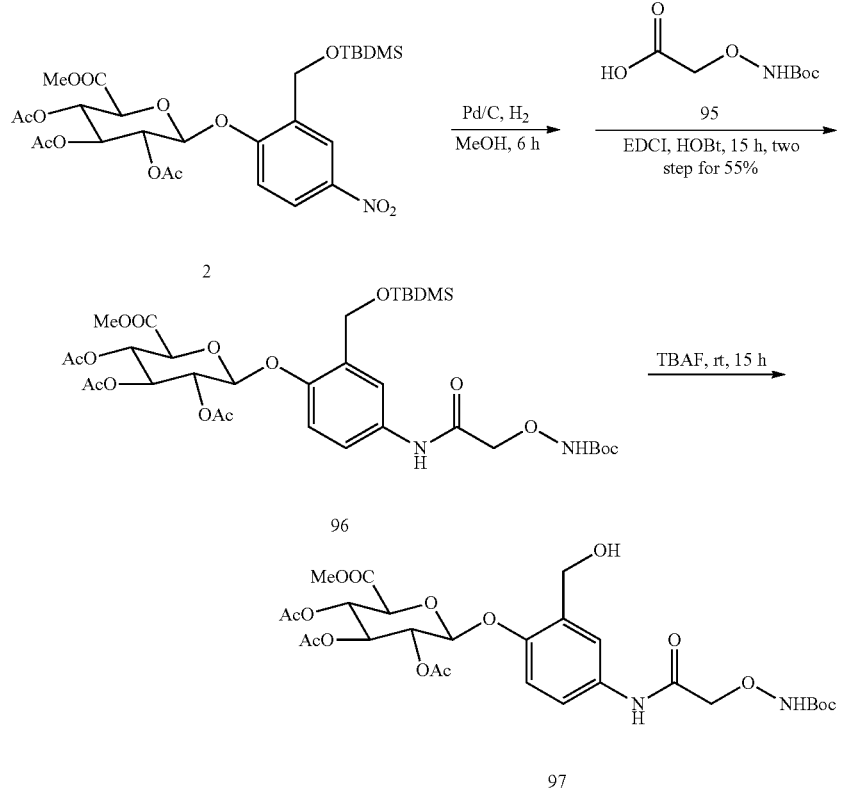

Preparation of Compound (96)

To a solution of compound 2 (500.0 mg, 0.83 mmol) in 35 ml of EtOAc/MeOH (6:1) was added Pd/C. The system was evacuated and filled with H2 three times. It was kept under $H_2$ atmosphere with a balloon and stirred at room temperature for 1 h. After the reaction was completed, Pd/C was filtered out. The filtrate was evaporated to get compound for next step. To a solution of compound from last step and 95

Preparation of Compound (97)

To a solution of 96 (350.0 mg, 0.471 mmol) in 15 mL of THF was added 0.50 mL of TBAF. It was stirred at rt for 14 h. The solution was evaporated. The crude product was purified by column to give compound 97 as yellow oil (280.0 mg, 0.45 mmol). ESI-TOF m/z: 627.2003

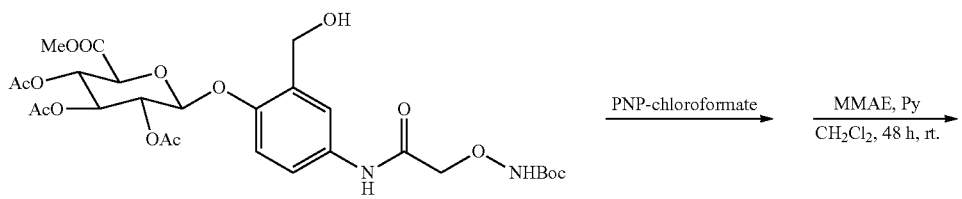

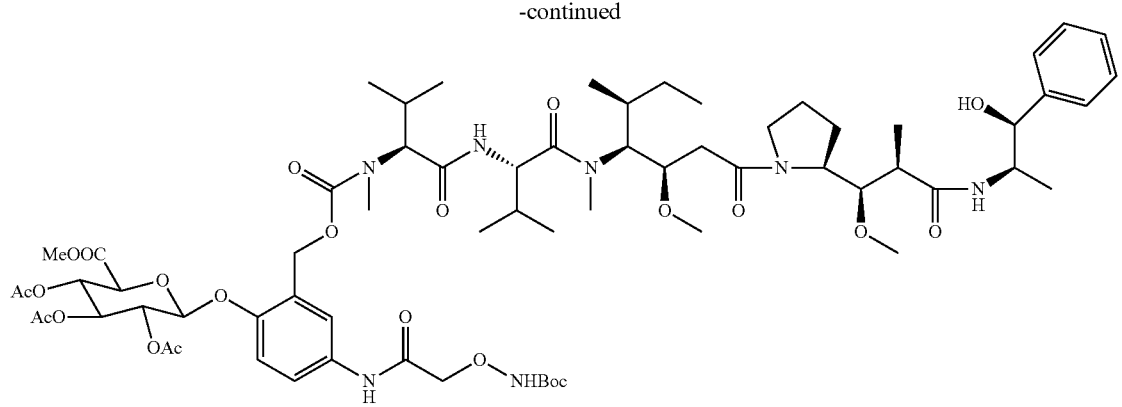

98

Preparation of Compound (98)

Compound 97 (275.0 mg, 0.27 mmol) was dissolved in 8 mL of $CH_2Cl_2$ and cooled to 0° C. Pyridine (0.50 mL) and PNP Chloroformate (176.0 mg, 0.87 mmol) were added and the mixture was stirred in rt for 3 h. The solution was evaporated. The crude product was purified by column to give compound (120.0 mg, 0.15 mmol) for next step. A solution of compound from last step (120.0 mg, 0.15 mmol) and MMAE (120.0 mg, 0.16 mmol) in 5 mL of THF was treated with TEA (0.5 mL). The resulting mixture was stirred at rt for 48 h. After the reaction was completed, 50 mL of EA and 30 mL of 0.5 N HCl were added. The organic layer extraction was dried by $MgSO_4$ and concentrated. The crude product was purified by column to give compound 98 as yellow oil (85.0 mg, 0.062 mmol). ESI-TOF nm/z: 1587.8759 $[M^--H]^-$.

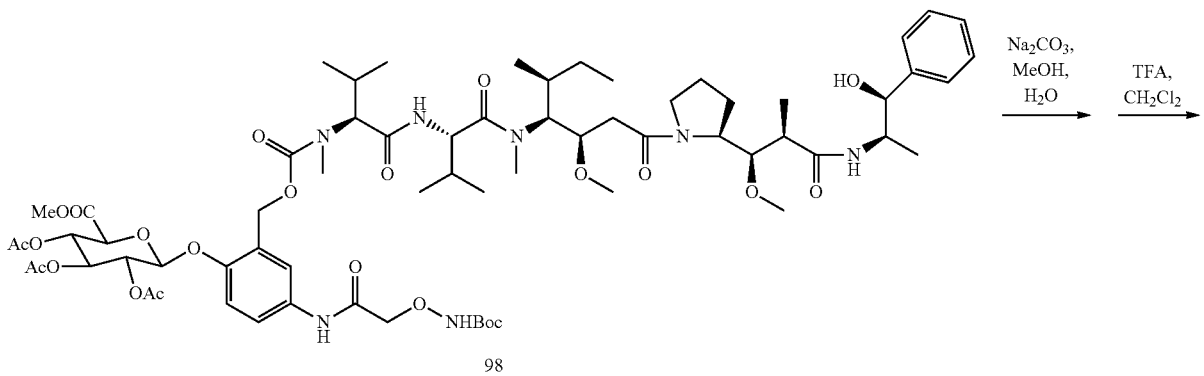

98

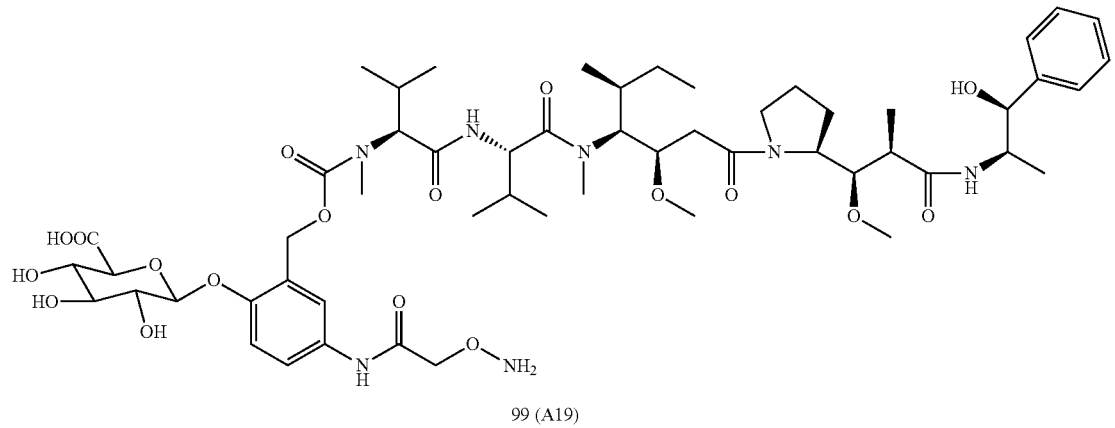

99 (A19)

Preparation of Compound (99)

A solution of 98 (20.0 mg, 0.015 mmol) in 2.5 mL of solution ($MeOH:H_2O=4:1$) was treated at 0° C. with $Na_2CO_3$. The resulting mixture was stirred at rt for 3 h. After the reaction was completed, the organic solution was removed under reduced pressure. The residue was purified by was purified by C18 column to give compound for next step. To a solution of compound from last step was dissolved in 1.6 ml of CH$_2$Cl$_2$. 0.40 ml of TFA was then added and stirred at room temperature for 1 h. The solution was concentrated and the residue was purified by C18 column to give 99 (10.3 mg, 0.0085 mmol). ESI-TOF m/z: 1130.5896 [M−H]$^-$.
2.20 Synthesis and Characterization of Compound 108 (A20)
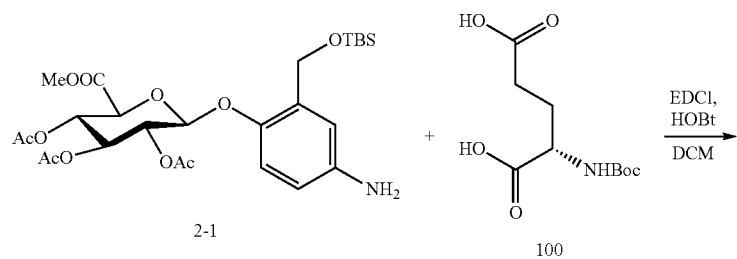
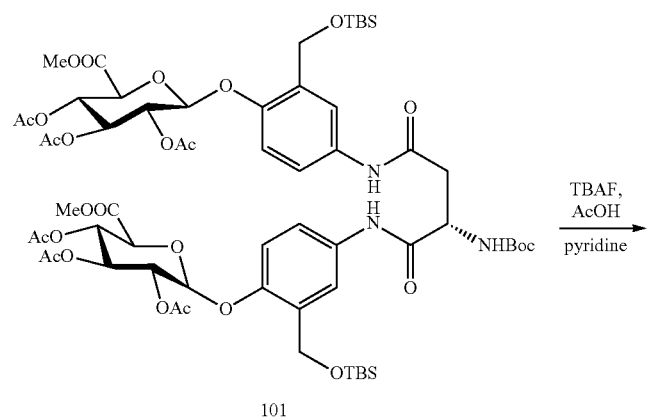
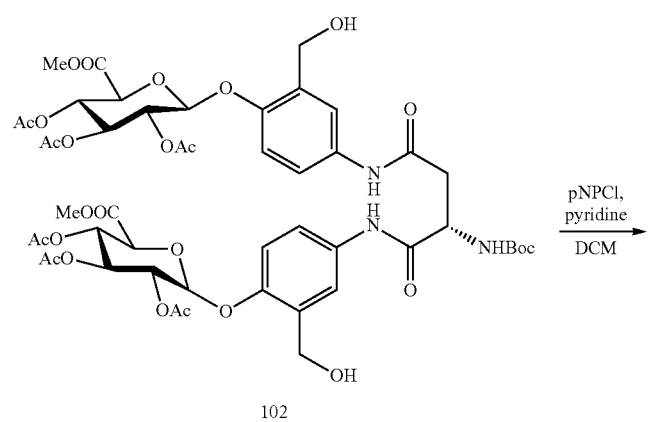

-continued
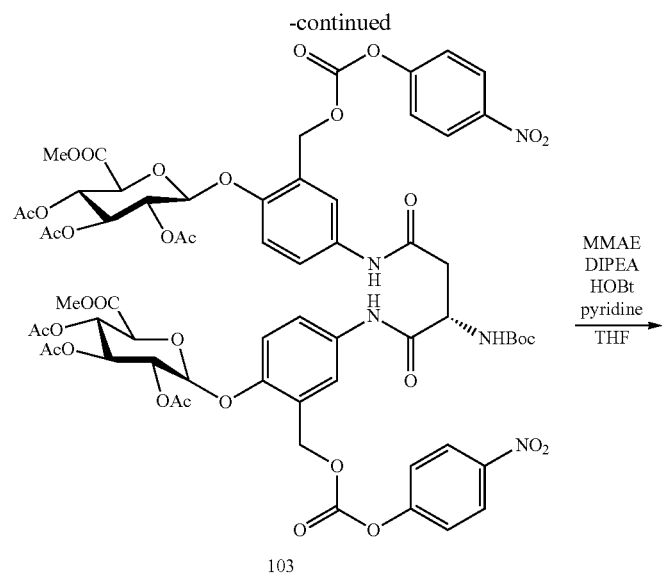
103
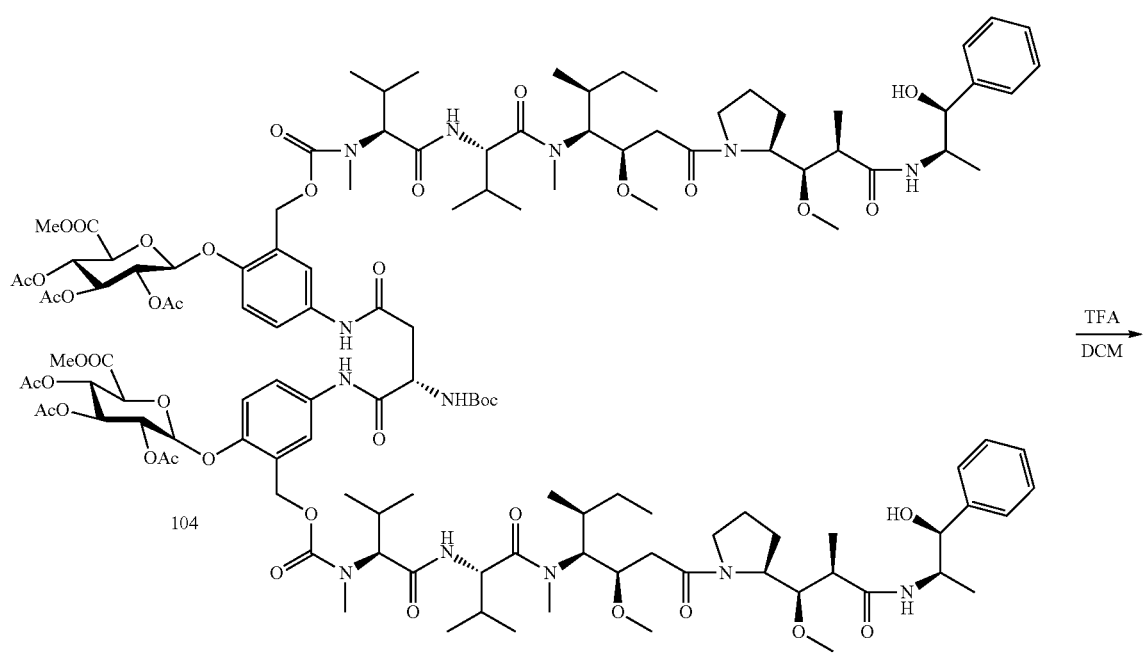
104

-continued
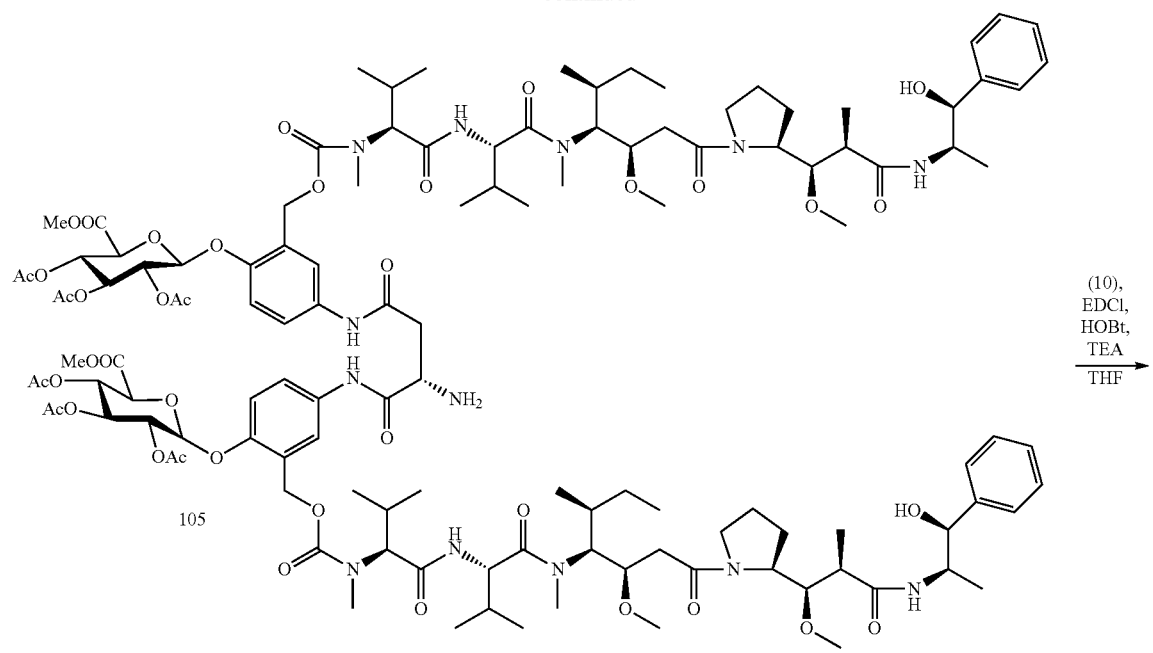
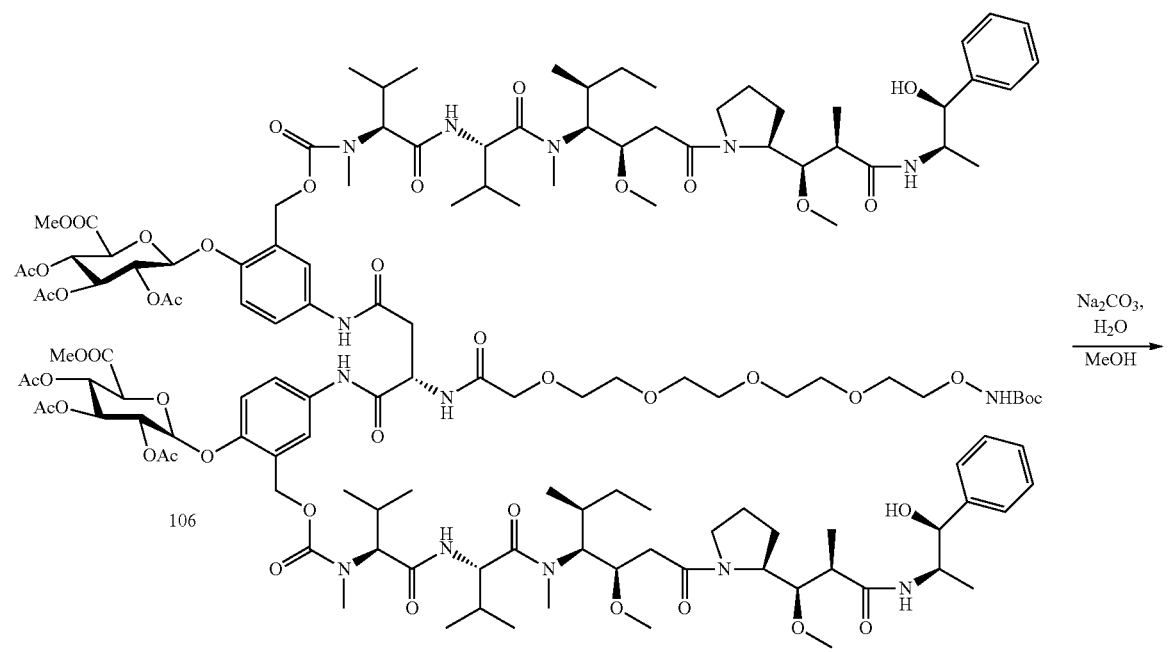

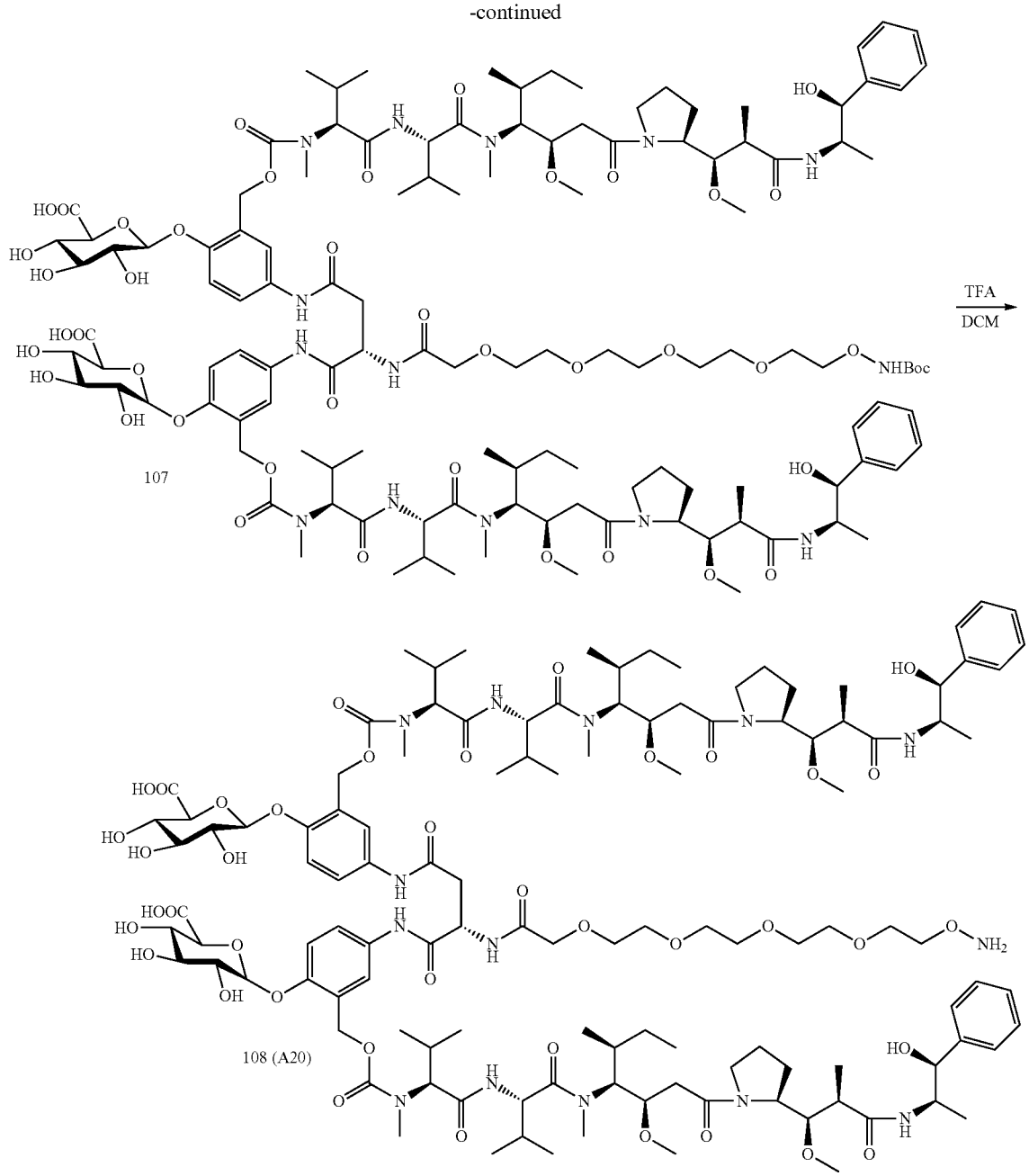

Preparation of Compound (101)

2,3,4-tri-Ac-6-methyl-Glucuranate-2'-OTBS-PAB-amine 2-1 (1.9 g, 3.34 mmol) and Glutamic acid 100 (412 mg, 1.67 mmol) were dissolved in $CH_2Cl_2$ (25 mL) followed by the addition of EDCI (1 g, 5.22 mmol), HOBt (13 mg, 0.083 mmol). After 8 hours, the solvent was removed and the reaction mixture was then purified by silica gel chromatography eluting with 5% EA/hexane, then 20% EA/hexane to give 1.07 g (48%) of Di-(2,3,4-tri-Ac-6-methyl-Glucuranate-2'-OTBS-PAB)-glutamic-N-Boc 101. $^1H$ NMR (400 MHz, $CDCl_3$) δ 8.72 (bs, 1H), 8.19 (bs, 1H), 7.62 (dd, J=1.84 Hz, 8.72 Hz, 1H), 7.53 (dd, J=2.6 Hz, 8.72 Hz, 1H), 7.42 (dd, J=2.16 Hz, 10.64 Hz, 2H), 6.9 (dd, J=5.32 Hz, 8.8 Hz, 2H), 5.28 (m, 7H), 5.03 (d, J=6.84 Hz, 2H), 4.69 (dd, J=2.4 Hz, 15.16 Hz, 2H), 4.58 (d, J=14.96 Hz, 2H), 4.28 (bs, 1H), 4.12 (q, J=4.2 Hz, 2H), 3.71 (s, 3H), 3.7 (s, 3H), 2.62-2.45 (m, 2H), 2.32-2.18 (m, 1H), 2.08-2.0 (m, 18H), 1.75 (s, 3H), 1.43 (s, 9H), 0.92 (s, 9H), 0.91 (s, 9H), 0.09 (s, 6H), 0.08 (s, 6H).

Preparation of Compound (102)

Di-(2,3,4-tri-Ac-6-methyl-Glucuranate-2'-OTBS-PAB)-glutamic-N-Boc 101 (1.07, 0.792 mmol) was dissolved in a mixture of pyridine (9.0 mL) and acetic acid (6.0 mL) followed by the addition of TBAF (1.0 mL, 1 M in THF). After 12 hours, the solvent was removed and the reaction mixture was then purified by silica gel chromatography eluting with $CH_2Cl_2$ (100%), then 8.3% MeOH/$CH_2Cl_2$ to give 658 mg (75%) of Di-(2,3,4-tri-Ac-6-methyl-Glucuranate-2'-OH-PAB)-glutamic-N-Boc 102 [1] H NMR (400 MHz, CDCl$_3$) δ 7.5-7.33 (m, 4H), 6.87 (dd, J=5.68 Hz, 8.8 Hz, 2H), 5.91 (d, J=7.64 Hz, 1H), 5.35 (dd, J=1.32 Hz, 9.44 Hz, 2H), 5.3-5.18 (m, 4H), 5.04 (d, J=7.64 Hz, 2H), 4.6 (d, J=13.2 Hz, 2H), 4.35 (d, J=13.32 Hz, 2H), 4.16 (dd, J=3.64 Hz, 9.76z, 2H), 3.66 (, J=1.72 Hz, 6H), 3.43 (s, 4H), 2.98-2.92 (m, 1H), 2.38 (bs, 2H), 2.054 (s, 3H), 2.051 (s, 3H), 2.01 (s, 12H), 1.37 (s, 9H), 1.36 (s, 9H).

Preparation of Compound (103)

Di-(2,3,4-tri-Ac-6-methyl-Glucuranate-2'-OH-PAB)-glutamic-N-Boc 102 (160 mg, 0.143 mmol) was suspended in anhydrous CH$_2$Cl$_2$ (2.5 mL), followed by the addition of pyridine (200 μL, 2.86 mmol) and 4-nitrobenzoyl chloride (230 mg, 1.14 mmol). After 2 hours the solvent was removed and purified by silica gel chromatography eluting with CH$_2$Cl$_2$ (100%), then 4% MeOH/CH$_2$Cl$_2$ to give 131.4 mg (63%) of Di-(2,3,4-tri-Ac-6-methyl-Glucuranate-2'-OpNP-PAB)-glutamic-N-Boc 103. Then, MMAE (162 mg, 0.225 mmol) was dissolved in a mixture of THF (4.0 mL) and pyridine (1.0 mL) followed by the addition of DIPEA (280 μL), HOBt (6.0 mg, 0.042 mmol) and Di-(2,3,4-tri-Ac-6-methyl-Glucuranate-2'-OpNP-PAB)-glutamic-N-Boc 103 (131 mg, 0.09 mmol). After 48 hours the solvent was removed and the reaction mixture was then purified by silica gel chromatography eluting with CH$_2$Cl$_2$ (100%), then 9% MeOH/CH$_2$Cl$_2$ to give 119.3 mg (51.6%) of Di-(2,3,4-tri-Ac-6-methyl-Glucuranate-2'-MMAE-PAB)-glutamic-N-Boc 104. $^1$H NMR (400 MHz, CDCl$_3$) δ 9.5-8.8 (m, 2H), 8.2-6.3 (m, 22H), 5.4-5.28 (m, 8H), 5.16-4.49 (m, 12H), 4.48-388 (m, 15H), 3.7 (d, J=2.87 Hz, 21), 3.74-3.6 (m, 8H), 3.45 (s, 2H), 3.4-3.15 (m, 17H), 3.09 (s, 1H), 3.02-2.88 (m, 6H), 2.88-2.74 (m, 6H), 2.73-2.52 (m, 4H), 2.5-2.24 (m, 8H), 2.24-1.85 (m, 38H), 1.84-1.45 (m, 8H), 1.45-1.23 (m, 12H), 1.2-1.05 (m, 10H), 1.03-0.4 (m, 60H).

Preparation of Compound (106)

Di-(2,3,4-tri-Ac-6-methyl-Glucuranate-2'-MMAE-PAB)-glutamic-N-Boc 104 (119 mg, 0.046 mmol) was suspended in anhydrous CH$_2$Cl$_2$ (2.8 mL), and TFA (0.7 mL) was added. The reaction was stirred at 0° C. for 10 min, then warmed to room temperature for another 30 min. The reaction mixture was evaporated to dryness (azeotropic with toluene for 3 times) to get Di-(2,3,4-tri-Ac-6-methyl-Glucuranate-2'-MMAE-PAB)-glutamic-amine 105 without further purification. The obtained compound 105 and PEG4-hydroxylamie-N-Boc acid 52 (4.7 mg, 0.02 mmol) were suspended in anhydrous THF (1.5 mL) followed by the addition of TEA (27.8 μL, 0.2 mmol), HOBt (0.14 mg, 0.001 mmol) and EDCI (6 mg, 0.03 mmol). After 12 hours the solvent was removed and purified by silica gel chromatography eluting with CH$_2$Cl$_2$ (100%), then 15% MeOH/CH$_2$Cl$_2$ to give 50 mg (87%) of Di-(2,3,4-tri-Ac-6-methyl-Glucuranate-2'-MMAE-PAB)-glutamic-PEG4-hydroxylamine-N-Boc 106. The above compound was dissolved MeOH (2.7 mL), then Na$_2$CO$_3$ (24.2 mg, 0.23 mmol) was added. After 2 hour, H$_2$O (170 μL) was added to the reaction mixture and the reaction was kept stirring for another 2.5 hour. Then the reaction was neutralized by IR-120, after filtered through a pad of celite, the crude was evaporated and purified by C18 column eluting with 100% H$_2$O, then 30% acetonitrile/H$_2$O to give 27.9 mg (62%) of Di-(Glucuranate-2'-MMAE-PAB)-glutamic-PEG4-hydroxylamie-N-Boc 107. Then 15 mg of 107 was suspended in anhydrous CH$_2$Cl$_2$ (0.8 mL), and TFA (0.2 mL) was added. The reaction was stirred at 0° C. for 10 min, then warmed to room temperature for another 30 min. The reaction mixture was evaporated to dryness, then pass through a C18 column eluting with 100% H$_2$O, then 25% acetonitrile/H$_2$O to get 10 mg (69.5%) of Di-(Glucuranate-2'-MMAE-PAB)-glutamic-PEG4-hydroxylamie 108. $^1$H NMR (400 MHz, MeOD) δ 7.7-7.0 (m, 26H), 5.35-5.1 (m, 6H), 4.7-4.45 (m, 8H), 4.22-4.17 (m, 81-1), 4.05-3.9 (m, 4H), 3.88-3.75 (m, 4H), 3.7-3.4 (m, 26H), 3.38-3.15 (m, 19H), 3.15-2.85 (m, 18H), 2.6-2.3 (m, 10H), 2.28-1.2 (m, 37H), 1.15-1.0 (m, 18H), 1.0-0.5 (m, 60H).

2.21 Synthesis and Characterization of Compound 114 (A21)

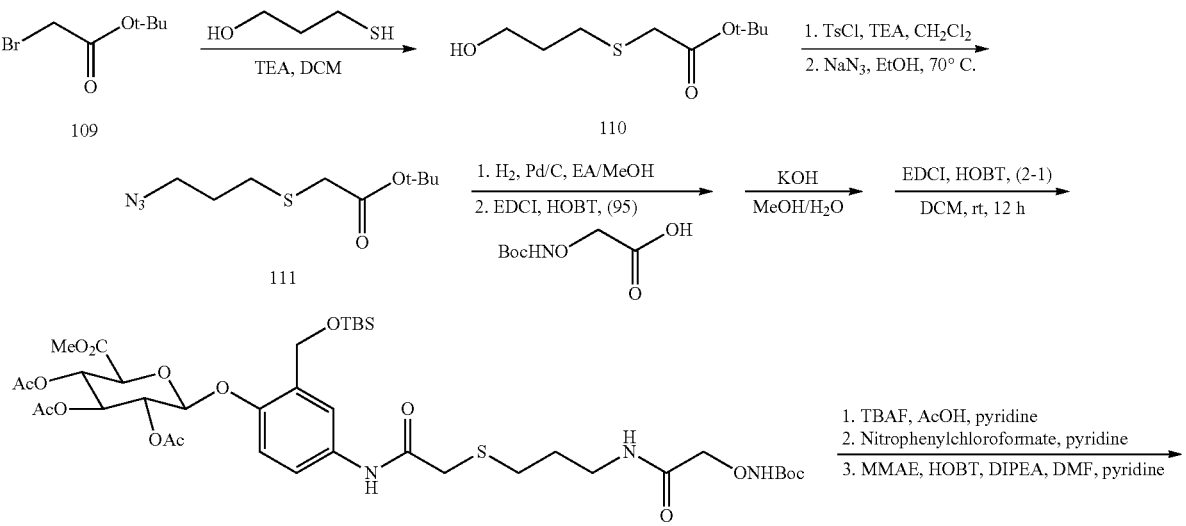

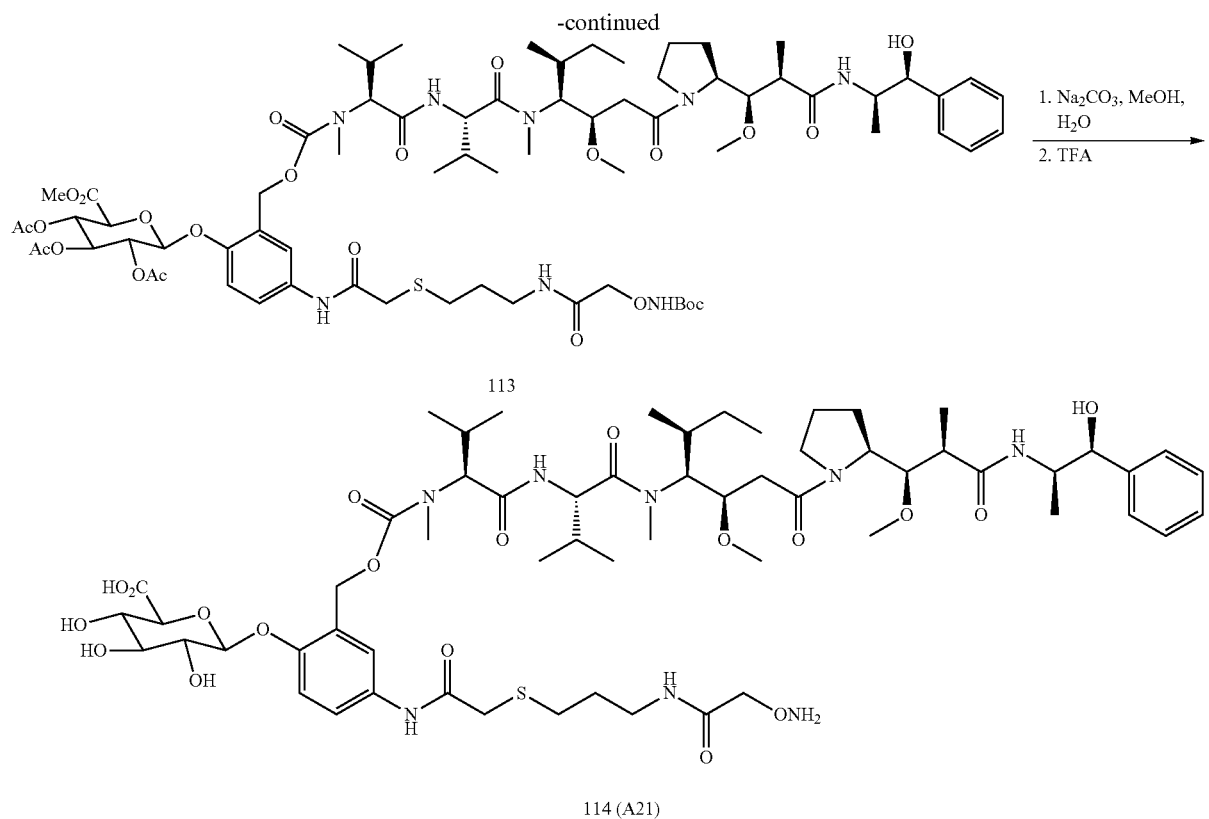

Preparation of Compound (110)

3-Mercaptopropanol (1.04 g, 11.34 mmole) was added to a solution of compounds 109 (2.0 g, 10.31 mmol) and Triethylamine (1.56 g; 15.46 mmol) in Dichloromethane (50 mL), and the mixture was stirred at room temperature for 12 h. When TLC indicated that starting material was fully consumed, the solution was concentrated. The residue was extracted with $CH_2Cl_2$ and 1N HCl, Saturated —$NaHCO_3$ (aq), and brine, respectively. The combined organic layers were concentrated in vacuo and the residue was purified by flash column chromatography to get the product as an oil 110 (1.0 g, 4.8 mmole). $^1$H NMR (400 MHz, $CDCl_3$) δ 3.76 (t, J=6.0 Hz, 2H), 3.15 (s, 2H), 2.77 (t, J=7.2 Hz, 2H), 1.87 (m, 2H), 1.47 (s, 9H).

Preparation of Compound (111)

To a Dichloromethane (50 mL) solution of compound 110 (1.0 g, 4.8 mmole), Triethylamine (1 mL, 9.7 mmole), and P-Toluenesulfonyl chloride (1.39 g, 7.275 mmole) was stirred. After stirring for 16 hr at room temperature, the solution was concentrated to afford the product as an oil. To an Ethanol solution of sodium azide (0.25 g, 3.83 mmole) and compound (0.5 g, 1.28 mmole) obtained above was stirred for 16 hr at 80° C. The solution was concentrated and the residue was extracted with EA and brine. The organic layers were concentrated in vacuo to get 111 (0.27 g, 1.17 mmole). $^1$H NMR (400 MHz, $CDCl_3$) δ 3.42 (t, J=6.8 Hz, 2H), 3.12 (s, 21), 2.72 (t, J=7.2 Hz, 2H), 1.89 (m, 2H), 1.47 (s, 9H).

Preparation of Compound (112)

To a Methyl alcohol (5 mL) solution of compound 111 (1.38 g, 2.49 mmole), Ethyl acetate (5 mL), and Pd/C (0.5 g) was stirred under H2 atmosphere. After stirring overnight for 12 hr, the Pd/C was filtered by the pad of celite, and washed by Methyl alcohol. The solution was concentrated in vacuo to afford the product as an oil. EDCI (0.236 g, 1.521 mmole) and HOBT (0.206 g, 1.521 mmol) were added sequentially to a solution of compounds obtained above and compound 95 (0.24 g, 1.17 mmole) in Dichloromethane (15 mL), and the mixture was stirred at room temperature for 12 h. The reaction mixture was then concentrated in vacuo and the residue was purified by flash column chromatography to afford the product as an oil (0.42 g, 1.11 mmole). To a Methyl alcohol (9 mL) solution of compound from last step (0.42 g, 1.11 mmole), $H_2O$ (1 mL), and KOH (0.28 g, 4.98 mmole) was stirred. After stirring for 16 hr at room temperature, the solution was quenched with 1N HCl and the solution was extracted with $CH_2Cl_2$ and 1N HCl, and brine, respectively. The combined solutions were concentrated to afford the product as oil for next step (0.357 g, 1.11 mmole). EDCI (0.223 g, 1.44 mmole) and HOBT (0.195 g, 1.44 mmol) were added sequentially to a solution of compounds from last step (0.357 g, 1.11 mmole) and compound 2-1 (0.666 g, 1.17 mmole) in Dichloromethane (20 mL), and the mixture was stirred at room temperature for 16 h. The reaction mixture was then concentrated in vacuo and the residue was purified by flash column chromatography to afford the product as an oil 112 (0.39 g, 0.447 mmole). $^1$H NMR (400 MHz, $CDCl_3$) δ 8.71 (s, 1H), 8.23 (s, 1H), 7.94 (s, 1H), 7.53-7.49 (m, 2H), 6.92 (d, J=8.8 Hz, 1H), 5.35-5.23 (m, 3H), 5.06 (d, J=7.2 Hz, 1H), 4.72 (d, J=15.2 Hz, 1H), 4.60 (d, J=15.2 Hz, 1H), 4.23 (s, 2H), 4.15 (d, J=9.6 Hz, 1H), 3.71 (s, 3H), 3.40 (m, 2H), 3.33 (s, 2H), 2.64 (t, J=7.2 Hz, 2H), 2.07 (s, 3H), 2.04 (s, 3H), 2.02 (s, 3H), 1.86 (m, 2H), 1.42 (s, 9H), 0.92 (s, 9H), 0.09 (s, 6H).

Preparation of Compound (113)

To a solution of compound 112 (0.39 g, 0.447 mmole), TBAF (0.5 mL, 0.5 mmole), AcOH (3 mL), and pyridine (4.5 mL) was stirred. After stirring for 12 hr at room temperature, the solution was concentrated and the residue was purified by flash column chromatography to afford the product as a solid (0.29 g, 0.382 mmole). To a Dichloromethane (20 mL) solution of compound (0.29 g, 0.382 mmole) obtained above, 4-Nitrophenylchloroformate (231 mg, 1.146 mmole), and pyridine (0.155 mL, 1.91 mmole) was stirred. After stirring for 12 hr at room temperature, the solution was concentrated and the residue was purified by flash column chromatography to afford the product as a solid (110 mg, 0.12 mmole). To a Dimethylformamide (10 mL) solution of compound (110 mg, 0.12 mmole) obtained above, MMAE (94 mg, 0.131 mmole), DIPEA (0.104 mL, 0.595 mmole), HOBT (18 in, 0.131 mmole), and pyridine (94 in, 1.19 mmole) was stirred. After stirring for 72 hr at room temperature, the solution was concentrated and the residue was purified by flash column chromatography to afford the product as a solid 113 (52 mg, 0.035 mmole); HRMS (ESI-TOF, MNa+) calculated for C72H110N8O24SNa, 1525.7246, found 1525.7189.

Preparation of Compound (114)

A solution of 113 (20.0 in, 0.0133 mmol) in 2.5 mL of solution (MeOH:H$_2$O=4:1) was treated at 0° C. with Na$_2$CO$_3$ (4.2 mg, 0.0399 mmol). The resulting mixture was stirred at rt for 3 h. After the reaction was completed, the organic solution was removed under reduced pressure. The residue was purified by was purified by C18 column to give compound for next step. To a solution of compound from last step was dissolved in 4 ml of CH$_2$Cl$_2$. 1.0 ml of TFA was then added and stirred at room temperature for 1 h. The solution was concentrated and the residue was purified by C18 column to give 114 (7.3 mg, 0.0057 mmol). ESI-TOF m/z: 1301.6356 [M−H]−.

2.22 Synthesis and Characterization of Compound 119 (A22)

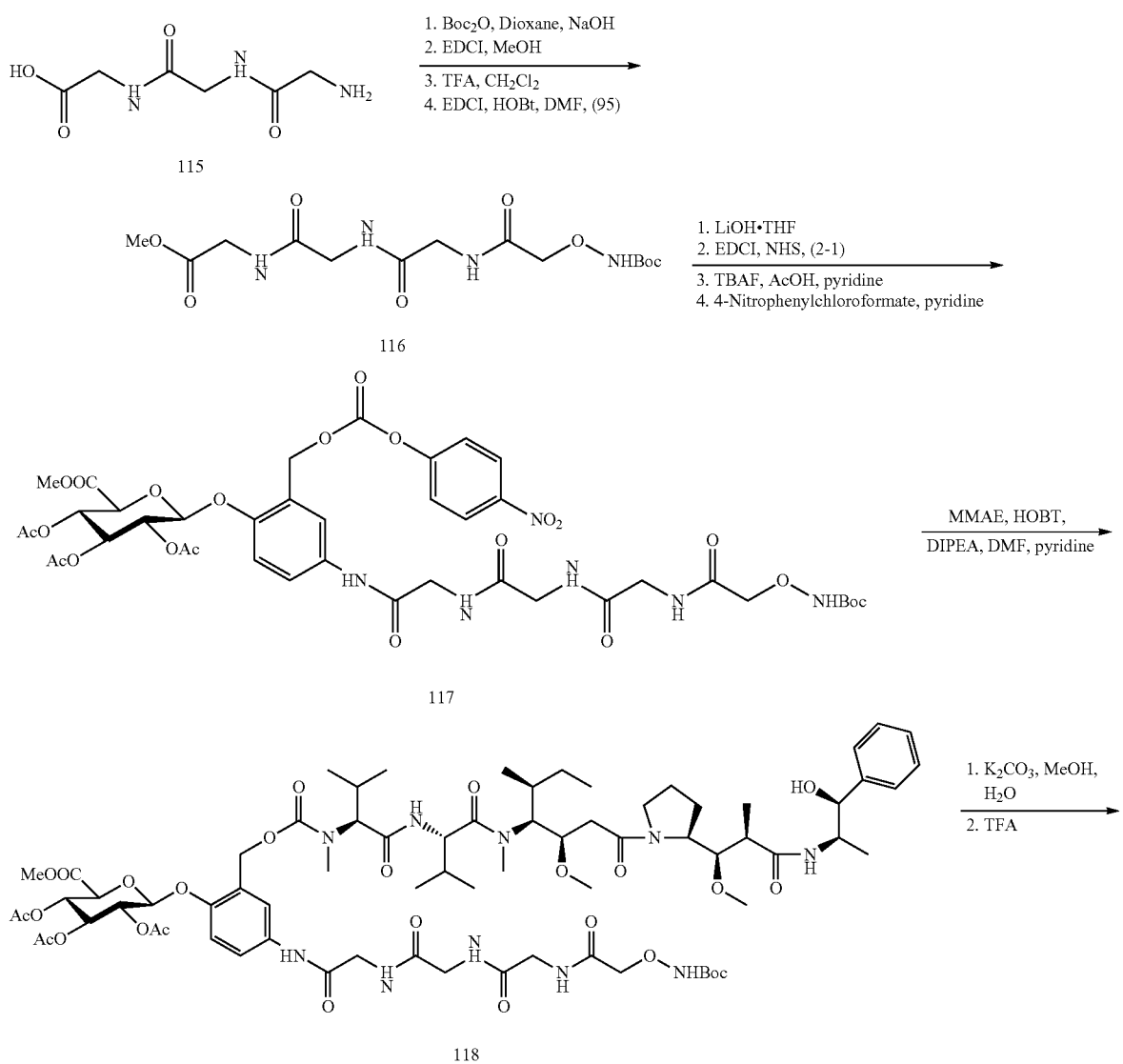

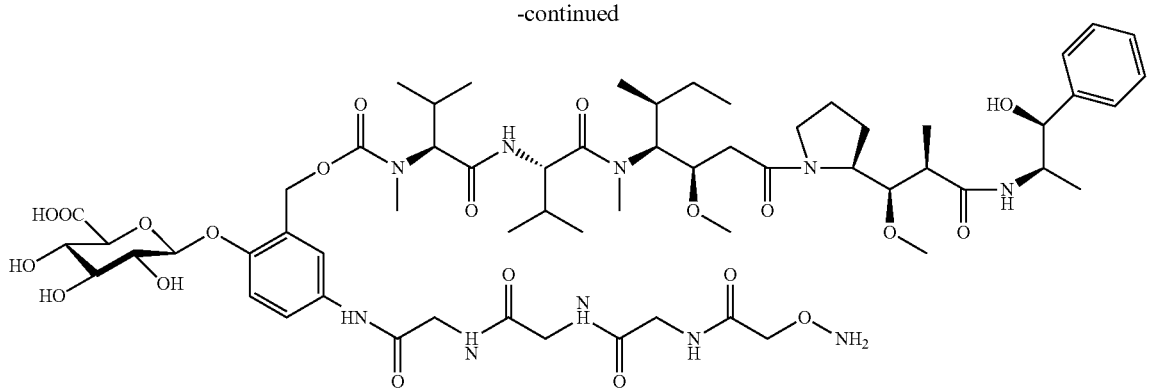

119 (A22)

Preparation of Compound (116)

A solution of Tri-glycine 115 (10 g, 52.86 mmol) in a mixture of dioxane (120 mL), water (60 mL) and 1 M NaOH (60 mL) was stirred and cooled in an ice-water bath. Di-tertbutylpyrocarbonate (17.3 g, 79.29 mmol) was added and stirring continued at room temperature (RT) for 6 h. Then the solution was concentrated in vacuum to about 10-15 mL, cooled in an ice-water bath, covered with a layer of ethyl acetate (about 50 mL) and acidified with a dilute solution of HCl to pH 2-3. The aqueous phase was extracted with ethyl acetate and this was done repeatedly. The ethyl acetate extracts were pooled, washed with water, dried over anhydrous $Na_2SO_4$ and evaporated in a vacuum. The pure material was obtained as a waxy solid (12.5 g, 43.20 mmol). To a Methyl alcohol (24 mL) solution of compound (12.5 g, 43.20 mmole) and EDCI (8.04 g, 51.79 mmole) was stirred. After stirring for 16 hr at room temperature, the solution was concentrated and the residue was purified by flash column chromatography (silica gel, 8% MeOH in $CH_2Cl_2$) to afford the product as a solid (10.45 g, 34.44 mmole). TFA (35 mL) was slowly added into a solution of compound (10.45 g, 34.44 mmole) obtained above in DCM (65 mL) at 0° C. The resulting mixture was stirred at room temperature for 2 h, and concentrated to afforded the product (5.88 g, 28.92 mmole) as an oil; $^1$H NMR (400 MHz, MeOD) δ 4.04-3.59 (m, 4H), 3.38-3.83 (m, 2H), 3.71 (s, 3H). EDCI (1.3 g, 8.37 mmole) and HOBT (1 g, 7.40 mmol) were added sequentially to a solution of compounds (1.5 g, 7.381 mmol) and compound 95 (1.62 g, 8.473 mmol) in Dimethylformamide (25 mL), and the mixture was stirred at room temperature for 48 h. The reaction mixture was then concentrated in vacuo and the residue was purified by flash column chromatography (silica gel, 6% MeOH in $CH_2Cl_2$) to afford the product as an oil 116 (1.5 g, 3.99 mmole); $^1$H NMR (400 MHz, MeOD) δ 4.34 (s, 2H), 3.98-3.93 (m, 6H), 3.72 (s, 3H), 1.47 (s, 9H); HRMS (ESI-TOF, MNa+) calculated for C14H24N4O8Na, 399.1486, found 399.1488.

Preparation of Compound (117)

To a Methyl alcohol (10 mL) solution of compound 116 (0.28 g, 0.739 mmole), $H_2O$ (0.5 mL), and LiOH (0.037 g, 0.881 mmole) was stirred. After stirring for 2 hr at room temperature, the solution was concentrated and the residue was purified by flash column chromatography (silica gel, 50% MeOH in $CH_2Cl_2$) to afford the product as an oil (0.24 g, 0.662 mmole). EDCI (0.18 g, 1.16 mmole) and HOBT (0.114 g, 0.843 mmol) were added sequentially to a solution of compounds (0.46 g, 0.846 mmol) obtained above and compound (2-1) (0.51 g, 0.895 mmol) in Dimethylformamide (20 mL), and the mixture was stirred at room temperature for 48 h. The reaction mixture was then concentrated in vacuo and the residue was purified by flash column chromatography (silica gel, 5% MeOH in $CH_2Cl_2$) to afford the product as an oil (0.42 & 0.460 mmole); $^1$H NMR (400 MHz, MeOD) δ 7.72 (d, J=2.4 Hz, 1H), 7.74 (dd, J=2.4, 9.2 Hz, 1H), 7.02 (d, J=9.2 Hz, 1H), 5.45 (t, J=9.6 Hz, 1H), 5.36 (d, J=7.6 Hz, 1H), 5.22-5.17 (m, 2H), 4.68 (q, J=24.8 Hz, 2H), 4.47 (d, J=9.6 Hz, 1H), 4.32 (s, 2H), 4.01 (s, 2H), 4.00 (s, 2H), 3.94 (s, 21), 3.71 (s, 3H), 2.05 (s, 3H), 2.02 (s, 3H), 2.02 (s, 3H), 1.46 (s, 9H), 0.96 (s, 9H), 0.12 (s, 6H). To a solution of compound (0.42 g, 0.460 mmole) obtained above, TBAF (0.48 mL, 0.48 mmole), AcOH (3 mL), and pyridine (5 mL) was stirred. After stirring for 12 hr at room temperature, the solution was concentrated and the residue was purified by flash column chromatography (silica gel, 9% MeOH in $CH_2Cl_2$) to afford the product as a solid (0.35 g, 0.438 mmole). To a Dichloromethane (24 mL) solution of compound (117 mg, 0.146 mmole) obtained above, 4-Nitrophenylchloroformate (100 mg, 0.495 mmole), and pyridine (0.11 mL, 1.423 mmole) was stirred. After stirring for 2 hr at room temperature, the solution was concentrated and the residue was purified by flash column chromatography (silica gel, 6% MeOH in $CH_2C2$) to afford the product as a solid 117 (100 mg, 0.107 mmole); H NMR (400 MHz, MeOD) δ 8.32-8.29 (m, 2H), 7.76 (d, J=2.4 Hz, 1H), 7.61 (dd, J=2.4, 8.8 Hz, 1H), 7.52-7.50 (m, 2H), 7.16 (d, J=8.8 Hz, 1H), 5.49-5.43 (m, 2H), 5.41-5.19 (m, 4H), 4.51 (d, J=10.0 Hz, 1H), 4.31 (s, 2H), 4.01 (s, 2H), 4.00 (s, 21), 3.93 (s, 2H), 3.72 (s, 3H), 2.06 (s, 3H), 2.02 (s, 3H), 2.02 (s, 3H), 1.45 (s, 9H).

Preparation of Compound (118)

To a Dimethylformamide (7 mL) solution of compound 116 (100 mg, 0.107 mmole), MMAE (69 mg, 0.096 mmole), DIPEA (0.173 mL, 0.995 mmole), HOBT (12 mg, 0.092 mmole), and pyridine (2.5 mL) was stirred. After stirring for 72 hr at room temperature, the solution was concentrated and the residue was purified by flash column chromatography (silica gel, 7% MeOH in $CH_2C2$) to afford the product as a solid 118 (79 mg, 0.051 mmole); HRMS (ESI-TOF, MNa+) calculated for C73H110N10O26Na, 1565.7485, found 1565.7471.

Preparation of Compound (119)

To a Methyl alcohol (2.5 mL) solution of compound 118 (79 mg, 0.051 mmole), K2CO3 (38 mg, 0.276 mmole), and H$_2$O (0.5 mL) was stirred. After stirring for 6 hr at room temperature, the solution was quenched with AcOH and then concentrated. The residue was purified by C18 column to afford the product as a solid (70 mg, 0.0499 mmole); HRMS (ESI-TOF, MNa+) calculated for C66H102N10O23Na, 1425.7012, found 1425.7016. TFA (0.35 mL) was slowly added into a solution of compound (70 mg, 0.0499 mmole) obtained above in DCM (0.65 mL) at 0° C. The resulting mixture was stirred at room temperature for 2 h, and concentrated. Purification of the crude material using C18 column to afforded the product 119 (48 mg, 0.0368 mmol) as an oil; HRMS (ESI-TOF, MNa+) calculated for C61H94N10O21Na, 1325.6487, found 1325.6540.

2.23 Synthesis and Characterization of Compound 125 (A23)

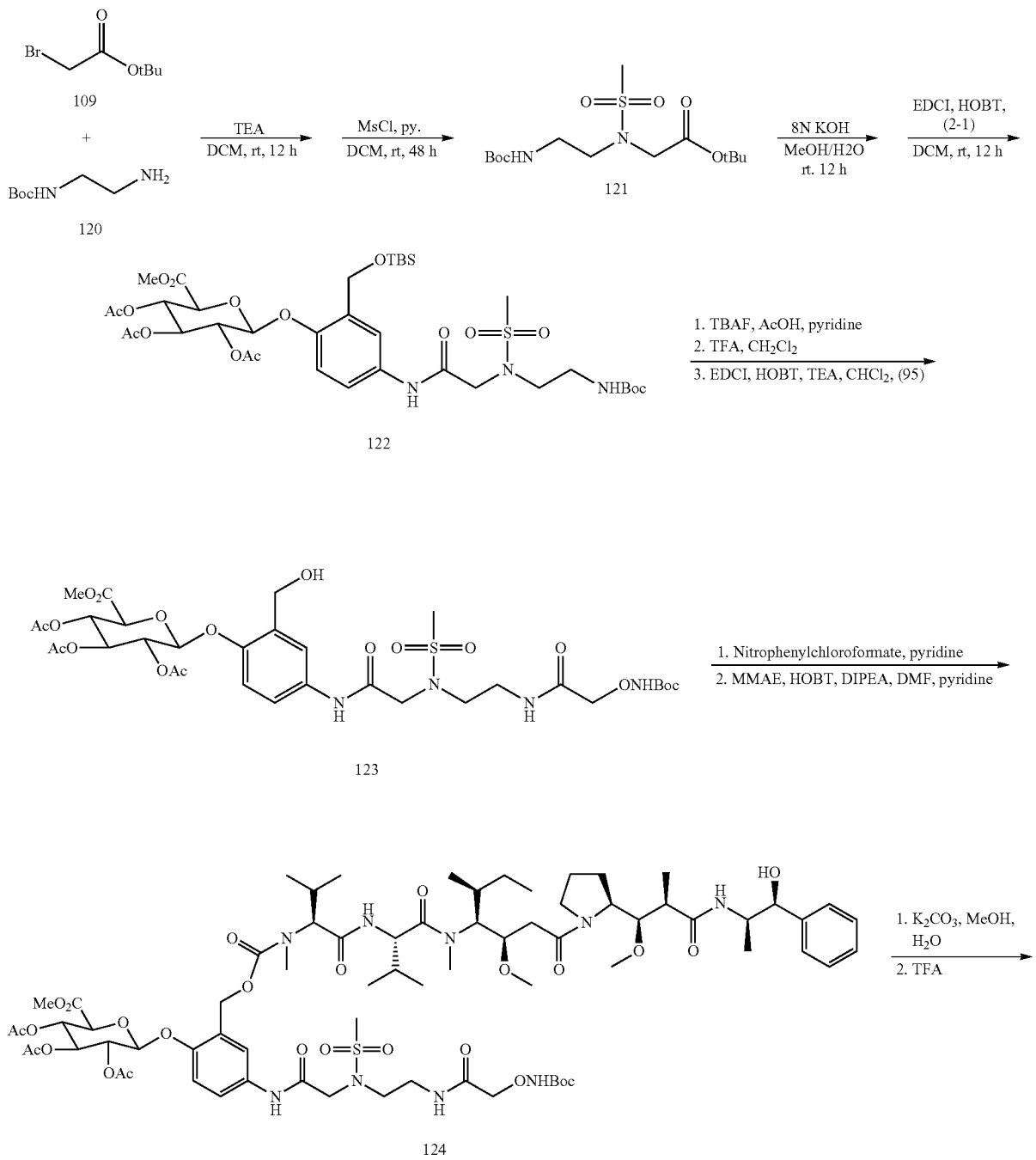

-continued

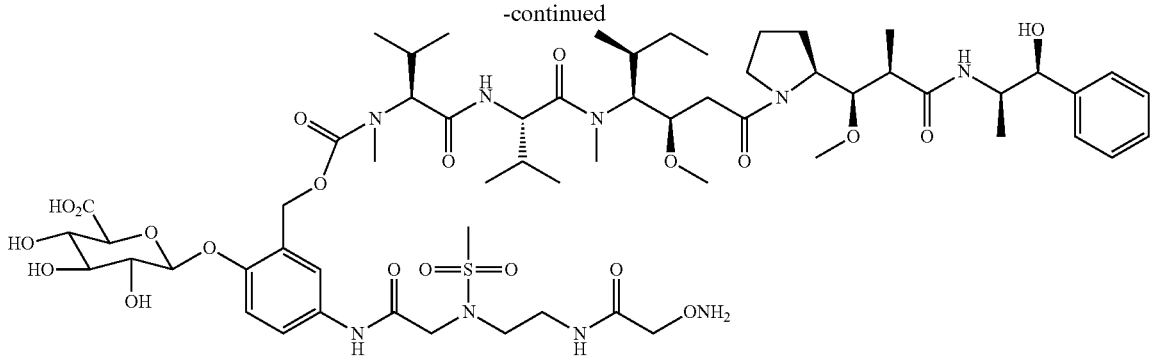

125 (A23)

Preparation of Compound (121)

t-Butyl bromoacetate 109 (2.0 g, 10.25 mmole) was added to a solution of compounds 120 (1.97 g, 12.3 mmol) and Triethylamine (1.56 g, 15.38 mmol) in Dichloromethane (25 mL) at 0° C., and the mixture was stirred at 0° C. to room temperature for 16 h. The reaction mixture was then concentrated in vacuo and the residue was purified by flash column chromatography to get the product as oil for next step (1.9 g, 6.93 mmol). To a Dichloromethane (30 mL) solution of the compound from last step (1.9 g, 6.93 mmole) and pyridine (1.66 mL, 20.8 mmole), Methanesulfonyl chloride (1.03 g, 9.0 mmole) was added into the mixture and solution was stirred at room temperature for 16 hr. When TLC indicated that starting material was fully consumed, the solution was concentrated. The residue was purified by flash column chromatography (silica gel, 35% Ethyl acetate in Hexane) to afford the product as an oil 121 (1.72 g, 4.88 mmole). $^1$H NMR (400 MHz, CDCl$_3$) δ 5.07 (s, 1H), 4.02 (s, 2H), 3.38 (t, J=5.2 Hz, 2H), 3.29 (t, J=5.2 Hz, 2H), 3.01 (s, 3H), 1.47 (s, 9H).

Preparation of Compound (122)

To a Methyl alcohol (10 mL) solution of compound 121 (1.72 g, 4.88 mmole), H$_2$O (10 mL), and KOH (2.19 g, 39.04 mmole) was stirred. After stirring for 16 hr at room temperature, the solution was quenched with IR-120 and the IR-120 was filtered. The IR-120 was washed by the Methyl alcohol and the combined solutions were concentrated to afford the product as an oil. EDCI (1.0 g, 6.441 mmole) and HOBT (1.0 g, 7.40 mmol) were added sequentially to a solution of compounds obtained above and compound I (2.91 g, 5.12 mmol) in Dichloromethane (30 mL), and the mixture was stirred at room temperature for 16 h. The reaction mixture was then concentrated in vacuo and the residue was purified by flash column chromatography to afford the product as an oil 122 (1.2 g, 1.416 mmole). $^1$H NMR (400 MHz, CDCl$_3$) δ 8.50 (s, 1H), 7.56 (s, 1H), 7.37 (dd, J=2.4, 8.8 Hz, 1H), 6.88 (d, J=8.8 Hz, 1H), 5.37-5.20 (m, 4H), 5.04 (d, J=7.2 Hz, 1H), 4.66 (d, J=15.2 Hz, 1H), 4.55 (d, J=15.2 Hz, 1H), 4.14 (d, J=9.2 Hz, 1H), 4.08 (s, 2H), 3.67 (s, 3H), 3.37 (m, 2H), 3.23 (m, 2H), 3.00 (s, 3H), 2.00 (s, 3H), 1.99 (s, 3H), 1.98 (s, 3H), 1.36 (s, 9H), 0.87 (s, 9H), 0.07 (s, 6H).

Preparation of Compound (123)

To a solution of compound 122 (1.2 g, 1.416 mmole), TBAF (1.5 mL, 1.5 mmole), AcOH (9 mL), and pyridine (13.5 mL) was stirred. After stirring for 12 hr at room temperature, the solution was concentrated and the residue was purified by flash column chromatography to afford the product as a solid (0.98 g, 1.33 mmole). And then, TFA (0.35 mL) was slowly added into a solution of compound (0.98 g, 1.33 mmole) obtained above in DCM (0.65 mL) at 0° C. The resulting mixture was stirred at room temperature for 2 h, and concentrated to afford the product. Triethylamine (0.175 g, 1.729 mmole), EDCI (0.268 g, 1.729 mmole), and HOBT (0.233 g, 1.729 mmol) were added sequentially to a solution of compounds obtained above and compound (95) (0.35 g, 1.60 mmole) in Dichloromethane (10 mL), and the mixture was stirred at room temperature for 16 h. The reaction mixture was then concentrated in vacuo and the residue was purified by flash column chromatography to get the product as an oil 123 (0.2 g, 0.25 mmole). $^1$H NMR (400 MHz, CDCl$_3$) δ 8.80 (s, 1H), 8.03 (s, 1H), 7.53 (m, 1H), 7.40 (dd, J=2.4, 32.4 Hz, 1H), 6.97 (dd, J=4.0, 8.8 Hz, 1H), 5.40-5.21 (m, 3H), 5.10 (t, J=7.6 Hz, 1H), 4.72 (d, J=12.8 Hz, 1H), 4.42 (m, 1H), 4.30 (s, 1H), 4.11 (s, 2H), 3.69 (d, J=2.8 Hz, 1H), 3.51 (m, 2H), 3.42 (m, 2H), 3.03 (s, 3H), 2.05 (s, 3H), 2.04 (s, 3H), 2.04 (s, 3H), 1.46 (s, 9H).

Preparation of Compound (125)

To a Dichloromethane (20 mL) solution of 123 (0.2 g, 0.25 mmole), 4-Nitrophenylchloroformate (151 mg, 0.75 mmole), and pyridine (0.103 mL, 1.25 mmole) was stirred. After stirring for 12 hr at room temperature, the solution was concentrated and the residue was purified by flash column chromatography to afford the product as a solid (220 mg, 0.206 mmole). To a Dimethylformamide (6 mL) solution of compound (100 mg, 0.103 mmole) obtained above, MMAE (81.3 mg, 0.1133 mmole), DIPEA (66.6 mg, 0.515 mmole), HOBT (15.3 mg, 0.1133 mmole), and pyridine (81.5 mg, 1.03 mmole) was stirred. After stirring for 48 hr at room temperature, the solution was concentrated and the residue was purified by flash column chromatography to afford the product as a solid 124 (50 mg, 0.032 mmole); HRMS (ESI-TOF, MNa+) calculated for C72H111N9O26SNa, 1572.7253, found 1572.7324. To a Methyl alcohol (2 mL) solution of compound 124 (50 mg, 0.032 mmole), K$_2$CO$_3$ (25 mg, 0.182 mmole), and H$_2$O (0.3 mL) was stirred. After stirring for 6 hr at room temperature, the solution was quenched with AcOH and then concentrated. The residue was purified by C18 column to afford the product as a solid. And then, TFA (0.35 mL) was slowly added into a solution of compound (44 mg, 0.0333 mmol) obtained above in DCM (0.65 mL) at 0° C. The resulting mixture was stirred at room temperature for 2 h, and concentrated. Purification of the crude material using C18 column to afforded the product 125 as an oil. ESI-TOF m/z: 1308.6360 [M−H]⁻.

2.24 Synthesis and Characterization of Compound 130 (A24)

Preparation of Compound (127)

A solution of Di-glycine 126 (5 g, 37.84 mmol) in a mixture of dioxane (60 mL), water (30 mL) and 1 M NaOH (30 mL) was stirred and cooled in an ice-water bath. Di-tertbutylpyrocarbonate (12.38 g, 56.76 mmol) was added and stirring continued at room temperature (RT) for 6 h. Then the solution was concentrated in vacuum to about

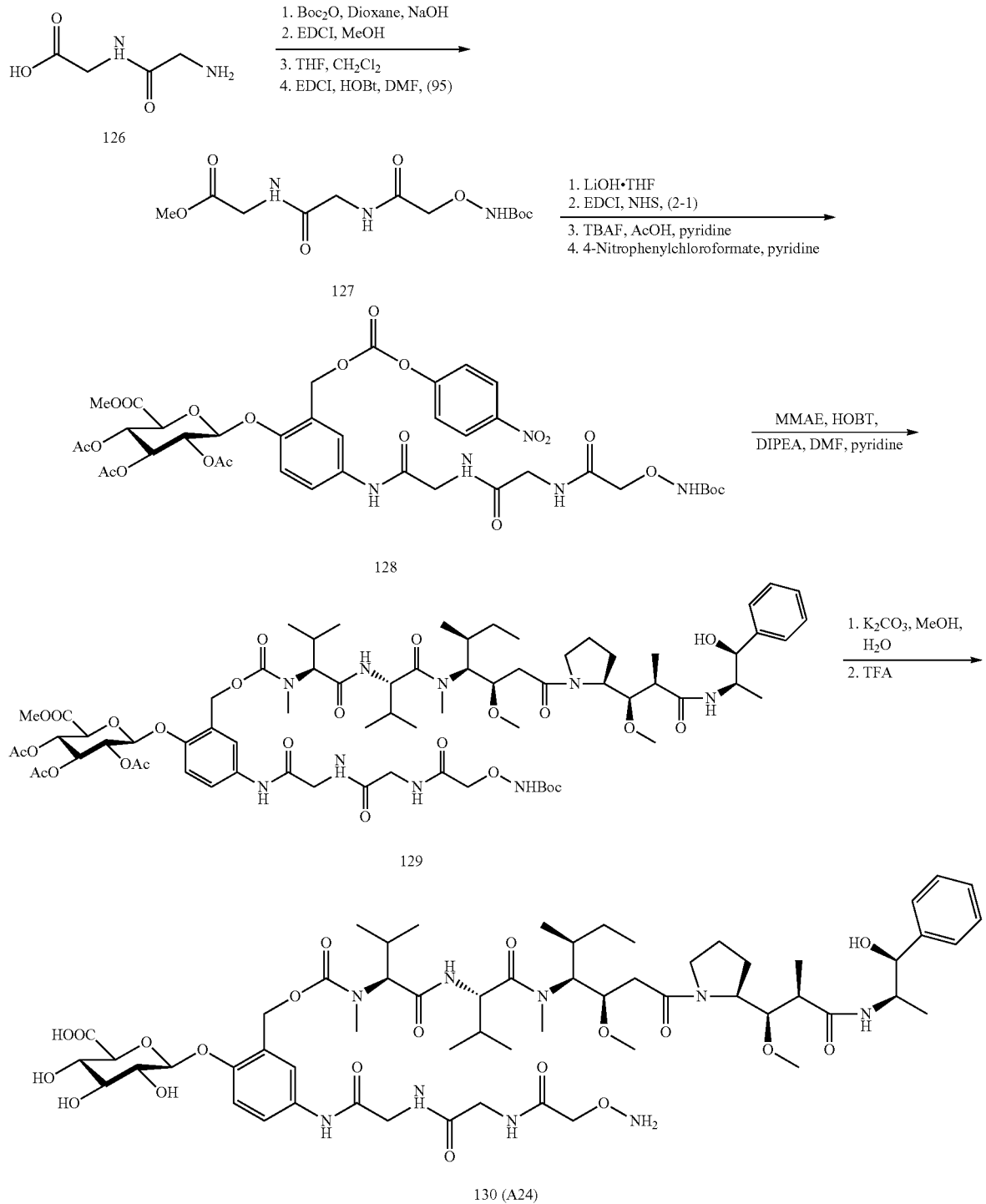

10-15 mL, cooled in an ice-water bath, covered with a layer of ethyl acetate (about 50 mL) and acidified with a dilute solution of HCl to pH 2-3. The aqueous phase was extracted with ethyl acetate and this was done repeatedly. The ethyl acetate extracts were pooled, washed with water, dried over anhydrous $Na_2SO_4$ and evaporated in a vacuum. The pure material was obtained as a waxy solid (5.2 g, 17.97 mmol). To a Methyl alcohol (24 mL) solution of compound (5.2 g, 17.97 mmol) obtained above and EDCI (3.38 g, 21.60 mmole) was stirred. After stirring for 16 hr at room temperature, the solution was concentrated and the residue was purified by flash column chromatography (silica gel, 4% MeOH in $CH_2Cl_2$) to afford the product as a solid (3.5 g, 11.54 mmole). TFA (18 mL) was slowly added into a solution of compound (3.5 g, 11.54 mmole) obtained above in DCM (33 mL) at 0° C. The resulting mixture was stirred at room temperature for 2 h, and concentrated to afforded the product (1.4 g, 9.58 mmol) as an oil. EDCI (1.3 g, 8.374 mmole) and HOBT (1 g, 7.40 mmol) were added sequentially to a solution of compounds (1.106 g, 7.568 mmol) and compound 95 (1.6 g, 8.369 mmole) in Dimethylformamide (24 mL), and the mixture was stirred at room temperature for 48 h. The reaction mixture was then concentrated in vacuo and the residue was purified by flash column chromatography (silica gel, 4% MeOH in $CH_2Cl_2$) to afford the product as an oil 127 (0.41 g, 1.284 mmole); $^1$H NMR (400 MHz, MeOD) δ 4.34 (s, 2H), 3.99 (s, 2H), 3.97 (s, 2H), 3.71 (s, 3H), 1.47 (s, 9H); HRMS (ESI-TOF, MNa+) calculated for C12H21N3O7Na, 342.1278, found 342.1281.

Preparation of Compound (128)

To a Methyl alcohol (10 mL) solution of compound 127 (0.41 g, 0.739 mmole), $H_2O$ (0.8 mL), and LiOH (0.065 g, 1.548 mmole) was stirred. After stirring for 2 hr at room temperature, the solution was concentrated and the residue was purified by flash column chromatography (silica gel, 50% h MeOH in $CH_2Cl_2$) to afford the product as an oil (0.35 g, 1.146 mmole); $^1$H NMR (400 MHz, MeOD) δ 4.34 (s, 2H), 3.98 (s, 2H), 3.80 (s, 2H), 1.47 (s, 9H). EDCI (0.22 g, 1.417 mmole) and HOBT (0.155 g, 1.147 mmol) were added sequentially to a solution of compounds (0.35 g, 1.146 mmol) obtained above and compound 2-1 (0.76 g, 1.334 mmol) in Dimethylformamide (20 mL), and the mixture was stirred at room temperature for 16 h. The reaction mixture was then concentrated in vacuo and the residue was purified by flash column chromatography (silica gel, Ethyl acetate) to afford the product as an oil (0.67 g, 0.780 mmole); $^1$H NMR (400 MHz, MeOD) 7.68 (d, J=2.4 Hz, 1H), 7.48 (dd, J=2.4, 8.8 Hz, 1H), 7.02 (d, J=8.8 Hz, 1H), 5.45 (t, J=9.6 Hz, 1H), 5.35 (d, J=8.0 Hz, 1H), 5.23-5.18 (m, 2H), 4.68 (q, J=24.8 Hz, 2H), 4.47 (d, J=10.0 Hz, 1H), 4.35 (s, 2H), 4.03 (s, 2H), 4.00 (s, 2H), 3.71 (s, 3H), 2.05 (s, 3H), 2.02 (s, 3H), 2.01 (s, 3H), 1.46 (s, 9H), 0.96 (s, 9H), 0.12 (s, 6H); HRMS (ESI-TOF, MNa+) calculated for C37H56N4O17SiNa, 879.3302, found 879.3272. To a solution of compound (0.668 g, 0.78 mmole) obtained above, TBAF (1.05 mL, 1.05 mmole), AcOH (5.6 mL), and pyridine (10 mL) was stirred. After stirring for 12 hr at room temperature, the solution was concentrated and the residue was purified by flash column chromatography (silica gel, 7% MeOH in $CH_2Cl_2$) to afford the product as a solid (0.55 g, 0.74 mmole); $^1$H NMR (400 MHz, $CDCl_3$) 9.03 (s, 1H), 8.83 (s, 1H), 8.31 (s, 1H), 7.76 (s, 1H), 7.44 (s, 1H), 7.40-7.38 (m, 1H), 6.86 (d, J=8.8 Hz, 1H), 5.33 (t, J=9.2 Hz, 1H), 5.21 (t, J=9.6 Hz, 1H), 5.05 (d, J=7.6 Hz, 1H), 4.57 (d, J=13.6 Hz, 1H), 4.39-4.32 (m, 3H), 4.21 (d, J=10.0 Hz, 1H), 3.92 (s, 2H), 3.92 (s, 2H), 3.66 (s, 3H), 2.05 (s, 3H), 2.01 (s, 3H), 2.00 (s, 3H), 1.40 (s, 9H). To a Dichloromethane (20 mL) solution of compound (183 mg, 0.247 mmole) obtained above, 4-Nitrophenylchloroformate (210 mg, 1.042 mmole), and pyridine (0.3 mL, 3.709 mmole) was stirred. After stirring for 2 hr at room temperature, the solution was concentrated and the residue was purified by flash column chromatography (silica gel, 5% MeOH in $CH_2Cl_2$) to afford the product as a solid 128 (116 mg, 0.128 mmole);
$^1$H NMR (400 MHz, $CDCl_3$) 8.65-8.58 (m, 3H), 8.25-8.23 (m, 2), 7.28 (s, 1H), 7.67-7.64 (m, 2H), 7.58 (dd, J=2.4, 8.8 Hz, 1H), 7.40-7.38 (m, 2H), 7.28-7.26 (m, 1H), 7.17-7.14 (m, 1H), 7.01 (d, J=8.8 Hz, 1H), 5.32-5.28 (m, 2H), 5.26-5.05 (m, 3H), 4.39 (s, 2H), 4.03 (d, J=6.0 Hz, 2H), 3.99 (d, J=6.0 Hz, 2H), 3.71 (s, 3H), 2.05 (s, 3H), 2.03 (s, 3H), 2.02 (s, 3H), 1.44 (s, 9H); HRMS (ESI-TOF, MNa+) calculated for C38H45N5O21Na, 930.2499, found 930.2468.

Preparation of Compound (129)

To a Dimethylformamide (8 mL) solution of compound 128 (6 mg, 0.128 mmole), MMAE (83 mg, 0.116 mmole), DIPEA (0.203 mL, 1.167 mmole), HOBT (18 mg, 0.131 mmole), and pyridine (0.8 mL) was stirred. After stirring for 72 hr at room temperature, the solution was concentrated and the residue was purified by flash column chromatography (silica gel, 8% MeOH in $CH_2Cl_2$) to afford the product as a solid 129 (81 mg, 0.054 mmole); HRMS (ESI-TOF, MNa+) calculated for C71H107N9O25Na, 1508.7270, found 1508.7298.

Preparation of Compound (130)

To a Methyl alcohol (3 mL) solution of compound 129 (81 mg, 0.054 mmole), $K_2CO_3$ (38 mg, 0.276 mmole), and H2O (0.5 mL) was stirred. After stirring for 6 hr at room temperature, the solution was quenched with AcOH and then concentrated. The residue was purified by C18 column to afford the product as a solid (70 mg, 0.0499 mmole); HRMS (ESI-TOF, MNa+) calculated for C64H99N9O22Na, 1368.6797, found 1368.6902. TFA (0.35 mL) was slowly added into a solution of compound (70 mg, 0.0499 mmole) obtained above in DCM (0.65 mL) at 0° C. The resulting mixture was stirred at room temperature for 2 h, and concentrated. Purification of the crude material using C18 column to afforded the product 130 (48 mg, 0.0368 mmol) as an oil; HRMS (ESI-TOF, MH+) calculated for C59H92N9O20 1246.6453, found 1246.6609.

Example 3. Formation and Characterization of Antibody-Drug Conjugate (ADC)

Figure 5:
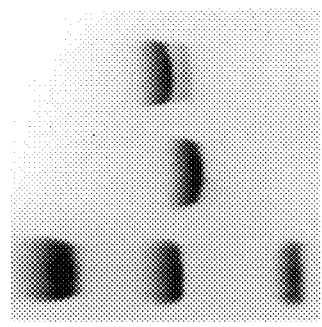
FIG. 5 shows SDS-PAGE profiles of site-specific ADCs in accordance with embodiments of the invention. Lane 1: Marker, Lane 2: TRZ-NGKS, Lane 3: TRZ-A11-$D_2$.
Figure 4:
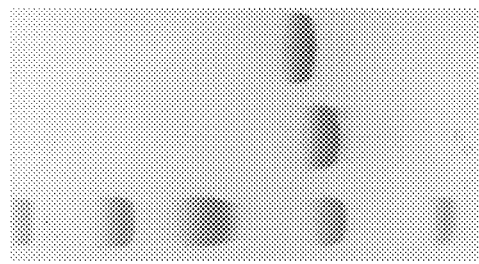
FIG. 4 shows SDS-PAGE profiles of site-specific ADCs in accordance with embodiments of the invention. Lane 1: Marker, Lane 2: TRZ-NKS, Lane 3: TRZ-A22.
Figure 1:
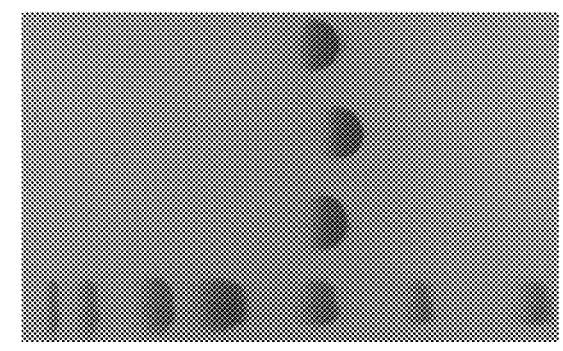
FIG. 1 shows SDS-PAGE profile of TRZ (native Herceptin), TRZ-N(F) (trimmed Herceptin), and TRZ-NAS/fRZ-NKS (glycoengineered Herceptin with two modified bianennary glycans) in accordance with embodiments of the invention. Lane 1: Marker, Lane 2: TRZ, Lane 3: TRZ-N(F), Lane 4: TRZ-NASfRZ-NKS.

3.1 General Procedure of Oxime-Ligation Site-Specific Antibody-Drug Conjugations Via TRZ-NKS or TRZ-NKS-$D_2$ Oxime ligation between ketone on the antibody and alkoxyamine-cleavable payload (A22) was carried out in 100 mM acetate buffer pH 4.5 with TRZ-NKS (5 mg/mL) and 3 mM payload A22 for 3d at 37° C. Buffer exchange with acetate buffer was done in an Amicon concentrator with 10,000 MWCO. Excess small molecule was removed by continuous washing through a 10,000 MWCO Amicon concentrator with PBS (pH 7.4). The result of TRZ-A22 and TRZ-A11-$D_2$ was analyzed by SDS-PAGE, respectively (FIGS. 4 and 5).

3.2 General Procedure of Click Chemistry Site-Specific Antibody-Drug Conjugations Via TRZ-NAS Click reaction via Cu (+) catalyst between azido group on the antibody and alkynyl-cleavable payload (A09) was carried out in 1×PBS buffer (pH 7.4 containing 5-10% DMSO) with TRZ-NAS (3-5 mg/mL) containing 400 μM of alkynyl-cleavable linker, 45 mM of $CuSO_4$, 45 mM of sodium ascorbate for 2-8 hours at 37° C. After completion, the reaction was quenched with 10 mM EDTA. Buffer exchange with 1×PBS buffer was done in an Amicon concentrator with 10,000 MWCO. Excess small molecule was removed by continuous washing through a 10,000 MWCO Amicon concentrator with PBS (pH 7.4). The result was analyzed by SDS-PAGE (FIG. 6).

3.3 Characterization DAR Number of ADC

The total loading of the payload to the antibody to make an ADC is referred to as the Drug Antibody Ratio or DAR. The DAR was calculated for each of the ADCs made by intact mass spectrometer. ADC samples were desalted against $ddH_2O$ during three concentration/dilution cycles on a 10 kDa ultracentrifugation device. Mass spectrometry experiments were performed in positive mode, on a Xevo G2-XS QTOF instrument (Waters, Manchester, UK). The instrument was equipped with an ESI source and with capillary voltage at 3.0 kV and sample cone at 150 V. Full scan spectra were collected over the m/z range of 700-4000. Waters MassLynx software was used to control the instrument and for data processing. TRZ-A22 exhibits a major peak corresponding to an ADC having the number of DAR=4, with a smaller peak corresponding to an ADC having an DAR=3 (FIG. 7). The following equation was used to establish the average DAR number:

$$\text{Average } DAR \text{ number} = \sum_{0}^{n} n \times y \ \%$$

Where the indicated variables are the relative abundance of: n=number of payload (drug) on the antibody, y %=peak area ratio of each ADC calculated based on each peak area. The average drug antibody ratio (DAR) of TRZ-A22 is shown in Table 1 and all average DARs of ADCs are shown in Table 2.

TABLE 1

The ratio of each DAR number (TRZ-A22).

| Peak  | DAR0 | DAR1 | DAR2 | DAR3  | DAR4  |
|-------|------|------|------|-------|-------|
| Ratio | —    | —    | —    | 13.7% | 86.3% |

Average DAR: 3.9
X:Based peak area

TABLE 2

The DAR numbers are calculated based on the intensity percentage of each found mass of ADC in MS spectra

| ADCs      | Average DAR | ADCs    | Average DAR |
|-----------|-------------|---------|-------------|
| TRZ-A01   | 3.5         | TRZ-A12 | 3.8         |
| TRZ-A01-D2| 1.8         | TRZ-A13 | 3.2         |
| TRZ-A02   | 4.0         | TRZ-A14 | 3.0         |
| TRZ-A03   | 3.0         | TRZ-A15 | 3.7         |
| TRZ-A04   | 3.3         | TRZ-A17 | 3.5         |
| TRZ-A05   | 4.0         | TRZ-A18 | 3.4         |
| TRZ-A06   | 3.1         | TRZ-A20 | 5.8         |
| TRZ-A09   | 3.9         | TRZ-A21 | 3.0         |
| TRZ-A10   | 3.8         | TRZ-A22 | 3.9         |
| TRZ-A11   | 3.6         | TRZ-A23 | 3.8         |
| TRZ-A11-D2| 1.9         | TRZ-A24 | 3.5         |

Due to unique preparation processes, embodiments of the invention have relatively high average DAR numbers. In accordance with embodiments of the invention, the average DAR numbers of antibodies with two biantennary glycans are 3.0 or higher. In contrast, those in the prior art are typically 2.0 or less. The average DAR numbers of antibodies with two monoantennary glycans are 1.5-2.0. The high average DAR numbers mean each antibody molecule carries more payload, and the ADCs of the invention would be more cost efficient and more efficacious as therapeutic agents, as evidenced by the tests set forth in this description.

Example 4. The Binding Ability of CHO-A01 to HER2 by ELISA Assay

Her2 binding ELISA was conducted to evaluate if the binding of TRZ was attenuated after linker-drug conjugation. The human HER2 recombinant protein extracellular domain (ECD) (0.025 μg/ml; Sino Biological Inc.) in a carbonate coating buffer (pH 10.0) was coated onto a 96-well plate (Corning) at 4° C. for overnight. After wash, the blocking buffer containing 2% bovine serum albumin and 0.05% Tween20 in PBS was added into the plate for 2 hours. Subsequently, after another wash, a serial dilution of TRZ/TRZ-NKS/TRZ-A01 ranging from 0.00001 μg/ml to 3 μg/ml in a 3-fold dilution of assay buffer was added and incubated for 1 hr, followed by 30-minute incubation with anti-human IgG HRP (Jackson Immuno Research Inc.). Finally, 100 μl of substrate, 3,3',5,5'-tetramethylbenzidine (TMB) was added for color development, and the reaction was stopped by adding 100 μL of 2.5 N sulfuric acid. Absorbance at 450 nm was measured with a Spectra Max M5 microplate reader (Molecular Devices), and data were analyzed using the four-parameter nonlinear regression equation (4PL) for curve fitting. The representative binding curve of TRZ-A01 was shown in FIG. 8. Quantitatively, the EC50 of TRZ-A01 and its functionalized TRZ-NKS compared to TRZ in terms of binding affinity with Her2 (ECD) was also shown in Table 3. The result showed that the binding affinity of TRZ-A01, TRZ-NKS and TRZ to antigen are comparable, suggesting that the payload conjugation wouldn't change the antigen binding affinity. Similar results were observed with the rest of payloads (A02~A24). These results showed the binding property of TRZ-A01~A24 to Her2 was not affected after ADC conjugation.

TABLE 3

EC 50 values (μg/mL) of mAbs to Her2 (ECD).

| mAb | EC$_{50}$ (μg/mL) | R$^2$ |
|---|---|---|
| Roche-TRZ | 0.021 | 0.99 |
| TRZ-A01 | 0.024 | 0.99 |
| TRZ-NKS | 0.026 | 0.99 |

Figure 8:
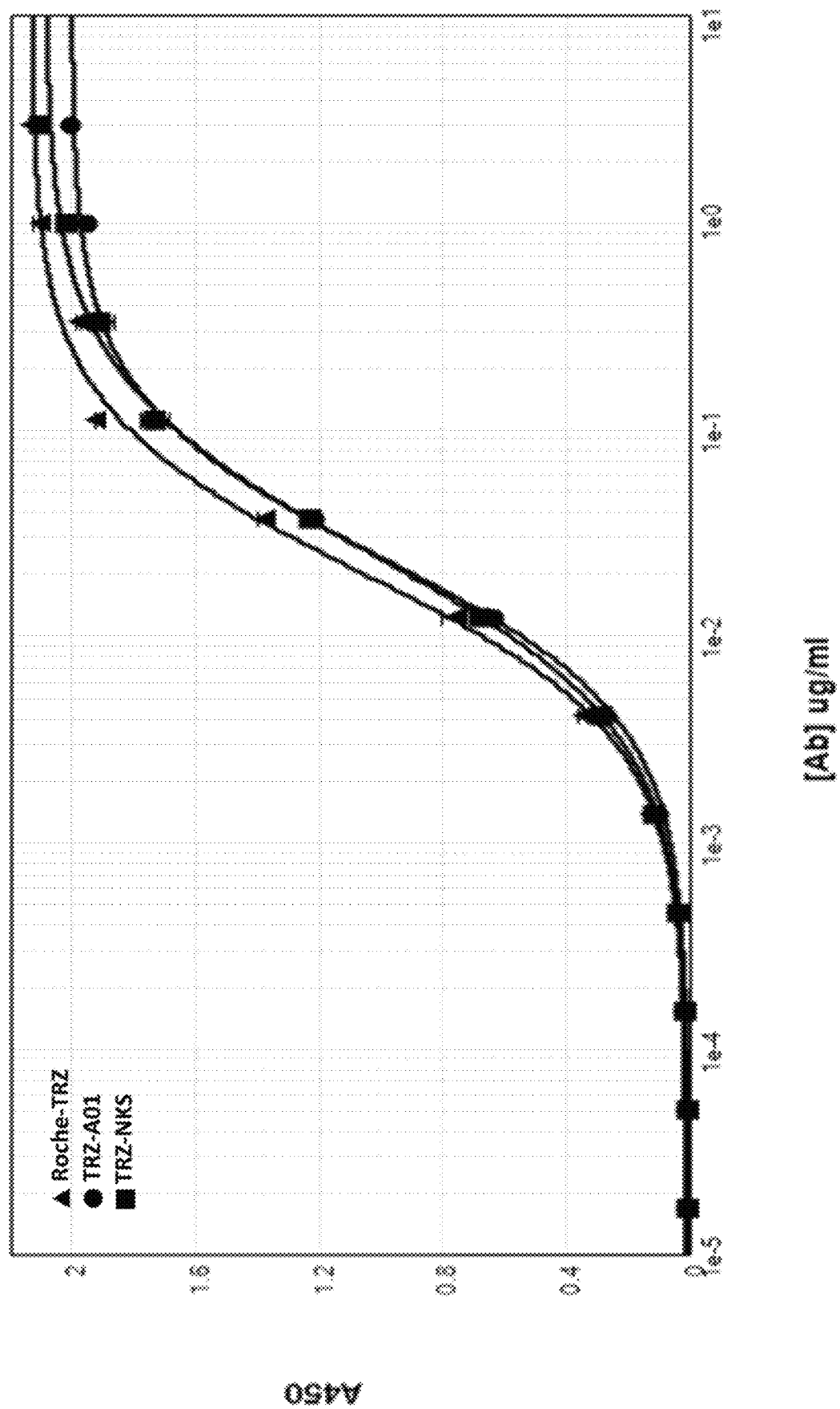
FIG. 8 shows binding affinity evaluation of TRZ-A01 to HER2 in comparison with Roche-TRZ in accordance with embodiments of the invention.

As shown in FIG. 8, the antibody-drug conjugate (i.e., CHO-A01) retains the binding properties as the commercial antibody (i.e., Roche-TRZ; IgG1κ anti-HER2 trastuzumab TRZ; Herceptin, Roche), indicating that the conjugation did not alter the conformation of the antibody in ADC.

Example 5. Cytotoxicity Assay

BT474 cells (2.5×10$^3$ cells/100 μL/well) were grown and maintained in 90% Hybri-Care Medium (Modified Dulbecco's medium) with 30 ng/mL EGF and 10% fetal bovine serum. Next day, antibody, ADC (TRZ or TRZ-A01) or payload were diluted in the medium and added to the final concentration range from 20.5-0.0031 nM or 1000-0.00001 nM, respectively. The incubation continued for 5d and the cell viability was estimated with CellTiter-Glo (Promega Inc.), by measuring the luminescence, which parallels the amount of ATP. Data were collected by a Spectra Max M5 microplate reader (Molecular Devices) and were analyzed by the four-parameter nonlinear regression equation (4PL) for curve fitting. The number of BT474 cells in the medium was set to 100% cell viability, and medium alone was set to 0% cell viability.

TABLE 4

A summary table of cytotoxicity increment of TRZ versus ADCs (EC$_{50}$ value of TRZ/ADC) in Her2 positive BT-474 cells Fold of EC50 improvement
(TRZ/TRZ-A01) in BT-474 ADCs

| ≈1 | A03, A04, A06, A07, A12 |
|---|---|
| 5~10 folds | A08, A10, A13, A16, A19, A01-D2, A11-D2 |
| >10 folds | A01, A02, A05, A09, A11, A14, A15, A17, A18, A20, A21, A22, A23, A24 |

Figure 9:
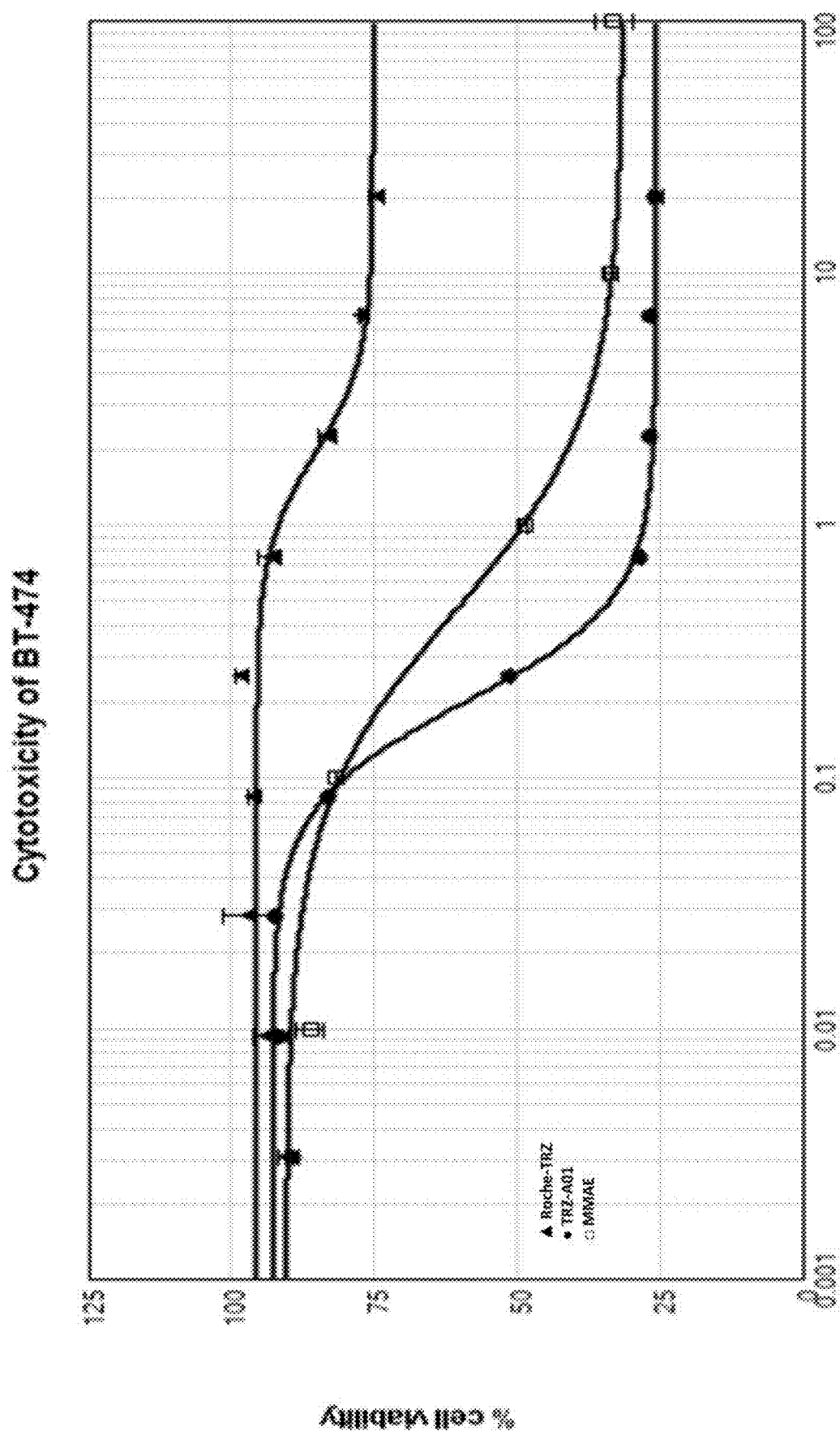
FIG. 9 shows comparison of the cytotoxicity of TRZ-A01 on a HER2-positive cell line BT474 with antibody or toxin in accordance with embodiments of the invention.

As shown in FIG. 9, TRZ-A01 induced cytotoxicity in a dose dependent manner. In contrast, with the tested concentrations TRZ alone exhibited minimal cytotoxicity. In addition, no cytotoxicity was observed in MDA-MB231 cells which are Her2 antigen negative. This result indicates that the ADC achieves the advantages of both binding specificity and cell cytotoxicity. The relative potencies of TRZ-A01-TRZ-A25, as compared with TRZ, were calculated using the following formula: relative potency=(EC50 of TRZ)/(EC50 of ADC), and the results were summarized in Table 4.

The other Her2-positive cancer cell lines, such as SKBR3, NCI-N87, JIMT-1, and MCF-7, and Her2-negative MDA-MB-231 were also used to test the cytotoxicity induced by TRZ-A01 and TRZ. The results showed that all these Her2-positive cell lines have higher response to TRZ-A01 than TRZ (Table 5).

TABLE 5

Comparing the cytotoxicity of TRZ-A01 on HER2-positives cell lines or HER2-negative cell line.

| Cell lines | Fold of EC50 improvement (TRZ/TRZ-A01) | Maximal viability (TRZ) | Maximal viability (TRZ-A01) |
|---|---|---|---|
| BT-474 | 17 | 70% | 16% |
| SKBR3 | 9.2 | 50% | 4% |
| NCI-N87 | 12 | 81% | 15% |
| JIMT-1 | >100 | 100% | 6% |
| MCF-7 | NA | 100% | 100% |
| MDA-MB-231 | NA | 100% | 100% |

Example 6. In Vivo Efficacy Animal Model

Six weeks old female C.B-17 SCID mice were obtained from BioLasco Taiwan. All mice were inoculated subcutaneously 5×10$^6$ NCI-N87 cells into the right flank region. Tumor growth was measured with calipers and volumes were calculated using the formula: ½[length (mm)]×[width (mm)]$^2$. When tumor size had reached a volume of ~300 mm$^3$ (at Day28), the animals were randomly assigned to two groups of 3 mice, treatment with TRZ-A01 or vehicle control. TRZ-A01 was given intraperitoneally at the concentration of 5 mg/kg in sterile saline once per week for 4 weeks, and the vehicle control was saline. Tumor size, body weight and mortality were recorded twice weekly for the whole study period. All of the animal protocols were approved and performed by the IACUC at Fountain Biopharma.

Statistical analyses of the difference between tumor volumes in two groups was conducted using unpaired t test of tumor volumes at the end of study (day 71). TRZ-A01 demonstrated a significant inhibitory effect on tumor growth in vivo compared with the vehicle control group.

Figure 10:
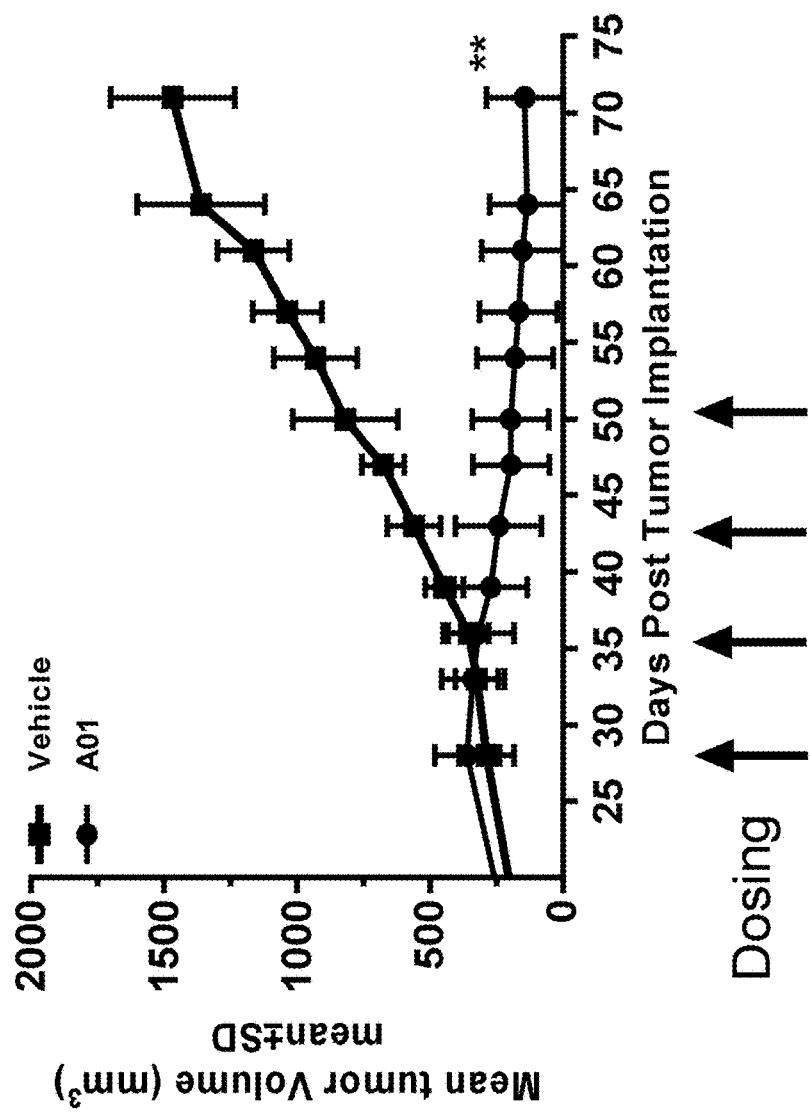
FIG. 10 shows antitumor activity of A01 in NCI-N87 xenograft model in accordance with embodiments of the invention. Tumor growth of was inhibited by 5 mg/kg TRZ-A01 Q7D×4 treatments. Data is expressed as meant SD. **, P<0.01 versus vehicle control group.

As shown in FIG. 10, the antitumor activity of A01 in the NCI-N87 xenograft model is markedly effective, as compared with the vehicle control group. Tumor growth of NCI-N87 was inhibited by 5 mg/kg TRZ-A01 every 7 days for 4 treatments. Data show that tumor not only did not grow, but in fact shrank. In contrast, the control group tumor continued to grow. This impressive results validate the efficacies of ADCs of the invention. Such impressive results likely arise from the fact that ADCs of the invention have more payload molecules per antibody molecule (i.e., DAR is 3.0 or higher in most embodiments). Drug-Antibody ratio (DAR) refers to the number of drug molecules per antibody molecule in the antibody-drug conjugate. DAR numbers may be calculated based on the intensity of each ADC species in the MS spectra of the ADC conjugate.

The above results clearly indicate that ADCs of the invention are effective and specific therapeutic agents. Some embodiments of the invention relate to methods for treating a disease or condition using an ADC of the invention, wherein the antibody moiety in ADC can bind to the specific target, while the drug moiety in the ADC exerts its therapeutic or cytotoxic effects.

A method in accordance with embodiments of the invention may comprise administering to a subject in need of such treatments an effective amount of an ADC of the invention. One skilled in the art would appreciate that an effective amount of a particular ADC would depend on the diseases, the patient conditions, routes of administration, etc. One skilled in the art would be able to determine an effective amount without inventive efforts.

143

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An antibody-drug conjugate (ADC) having a structure represented by Formula (I):

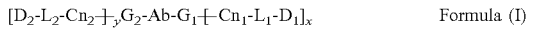   Formula (I)

or a pharmaceutically acceptable salt thereof, wherein
Ab is an antibody without glycans;
$G_1$ and $G_2$ are each a glycan moiety;
$Cn_1$ and $Cn_2$ are each a conjugation moiety;
$L_1$ and $L_2$ are each a direct bond or a linker moiety, which may be the same or different;
$D_1$ and $D_2$ are each a drug unit which may be the same or different; and
each of x and y is an integer of 2;
wherein,
the glycan moiety has a structure shown as Formula (II-1b):

Formula (II-1b)

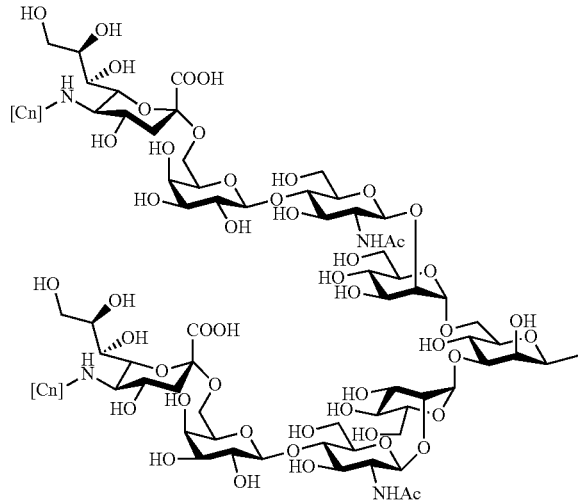

144

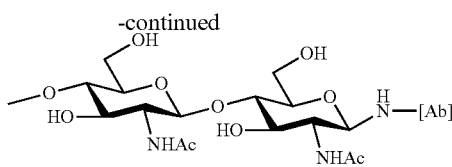
-continued wherein
[Ab] indicates an attachment site for the antibody; and
[Cn] indicates an attachment site for the conjugation moiety; and
the conjugation moiety has the structure of Formula (III-1), Formula (III-1)

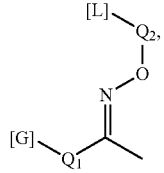

wherein
$Q_1$ is —C(O)(CH$_2$)$_2$—, and $Q_2$ is —(CH$_2$)$_2$O—;
[G] indicates an attachment site for the glycan moiety; and
[L] indicated an attachment site for the linker moiety.

2. The antibody-drug conjugate according to claim 1, wherein the antibody binds to a target selected from the group consisting of CD19, CD22, CD27, CD30, CD33, CD37, CD70, CD74, CD79b, CD138, CD142, CA6, p-Cadherin, CEACAM5, C4.4a, DLL3, EGFR, EGFRVIII, ENPP3, EphA2, EphrinA, FLOR1, FGFR2, GCC, HER2, cKIT, LIV1, MSLN, MUC16, NaPi2b, Nectin4, gpNMB, PSMA, SLITRK6, STEAP1, TROP2, 5T4, SSEA4, GloboH, Gb5, STn, and Tn.

3. The antibody-drug conjugate according to claim 1, wherein the linker is selected from the group consisting of the structures of Formula (IV-1), Formula (IV-2), Formula (IV-3), Formula (IV-4), and Formula (IV-5):

Formula (IV-1)

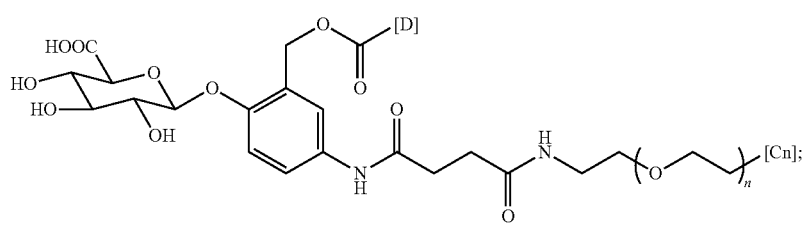

-continued

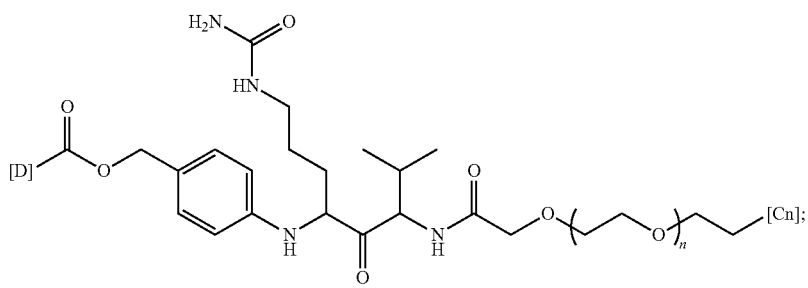

Formula (IV-2)

Formula (IV-3)

Formula (IV-4)

Formula (IV-5)

wherein

[Cn] indicated an attachment site for the conjugation moiety; and

[D] indicates an attachment site for the drug unit;

and each instance of m and n is an integer from 0 to 6, inclusive.

4. The antibody-drug conjugate according to claim 1, wherein the drug is selected from the group consisting of Monomethyl auristatin E (MMAE), Monomethyl auristatin F (MMAF), Monomethyl auristatin D (MMAD), Mertansine (Maytansinoid DM1/DM4), Paclitaxel, Docetaxel, Epothilone B, Epothilone A, CYT997, Auristatin tyramine phosphate, Auristatin aminoquinoline, Halocombstatins, Calicheamicin theta, 7-Ethyl-10-hydroxy-camptothecin (SN-38), Pyrrolobenzodiazepine (PBD), Pancratistatin, Cyclophosphate, Cribrostatin-6, Kitastatin, Turbostatin 1-4, Halocombstatins, and Silstatins.

5. The antibody-drug conjugate according to claim 1, wherein the ADC is synthesized using a reagent selected from the group consisting of:

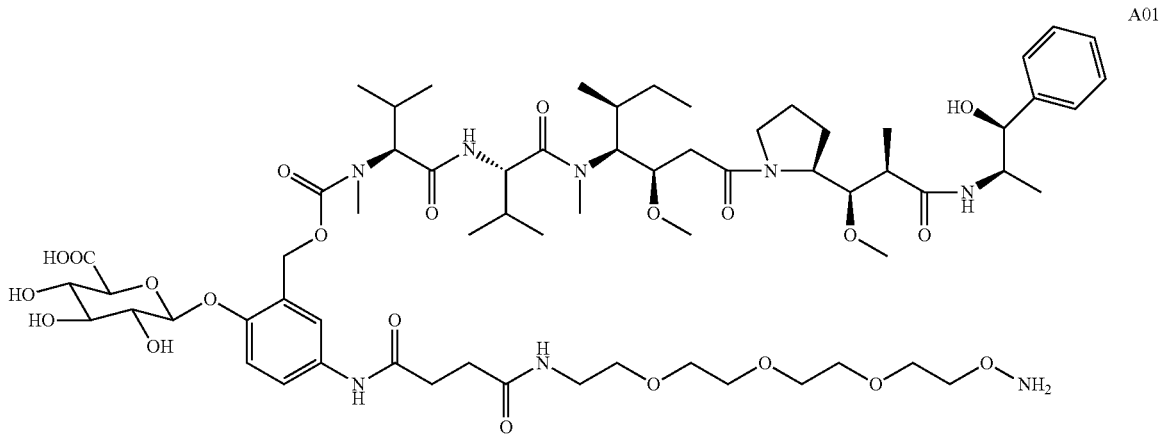

A01

-continued
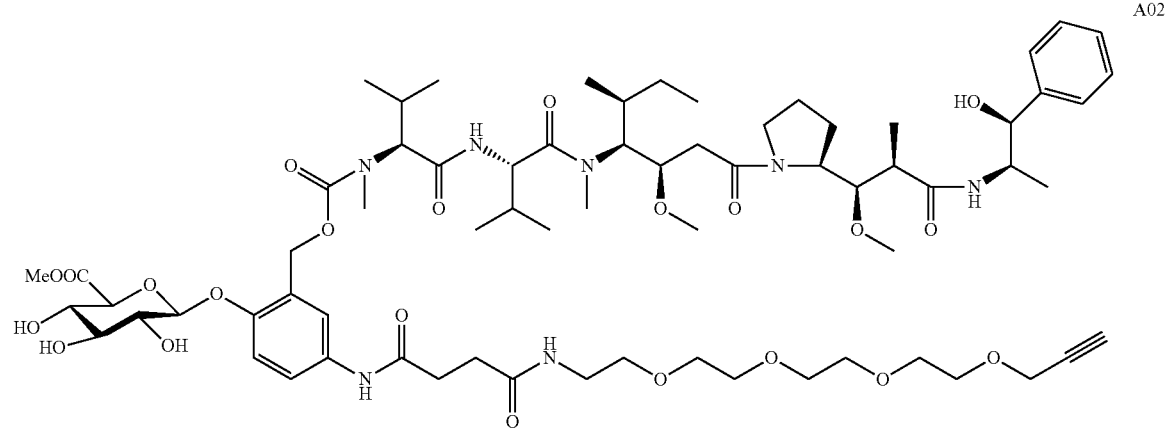
A02
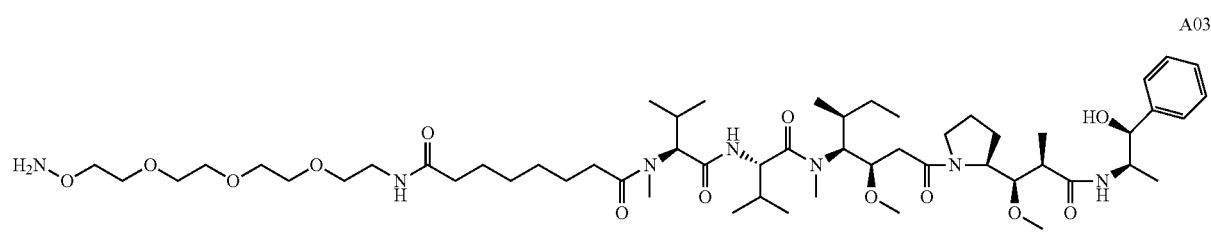
A03
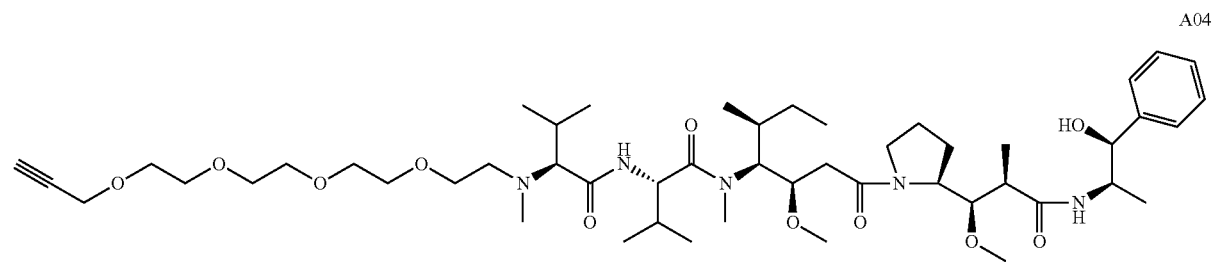
A04
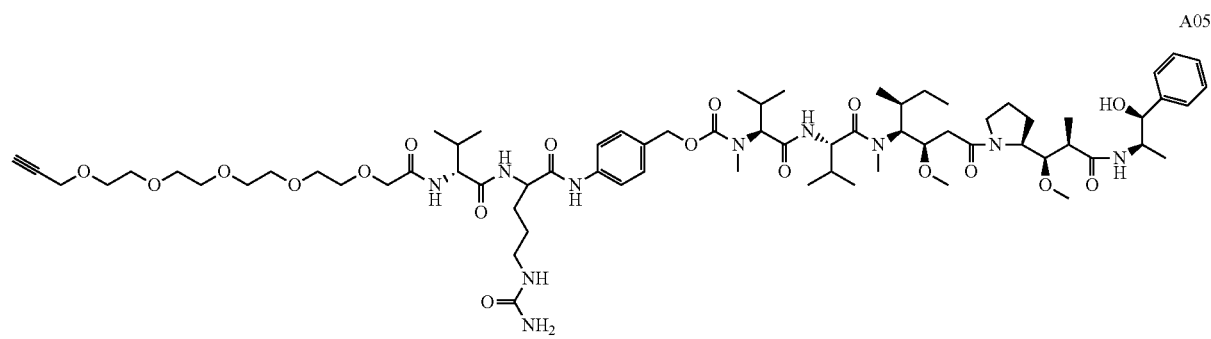
A05
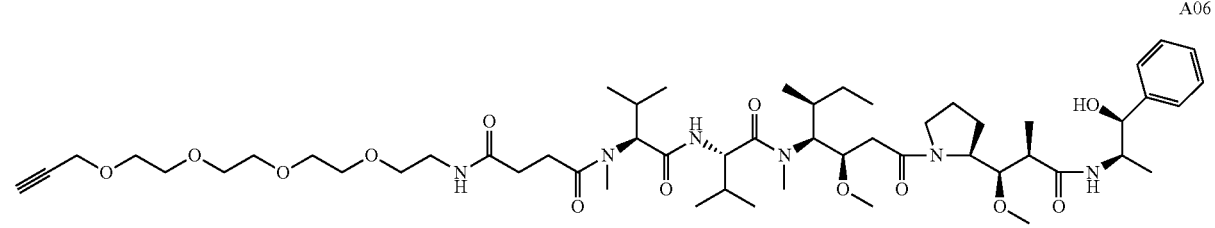
A06

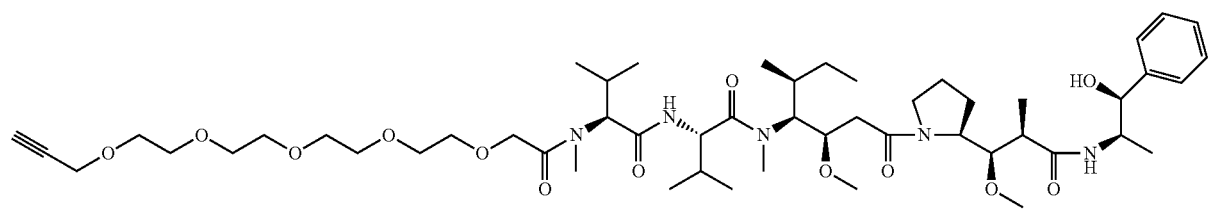 [SMILES: C#CCOCCOCCOCCOCCOCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]
A07
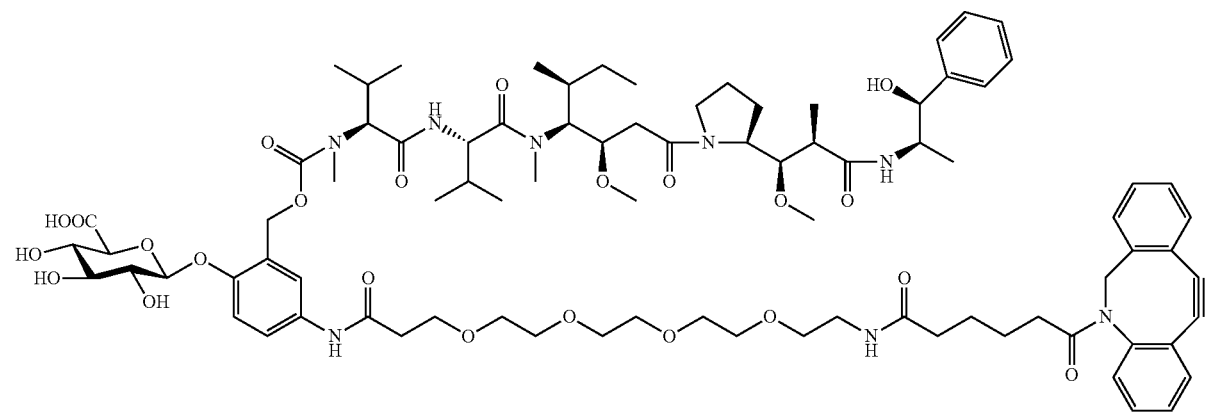
A08
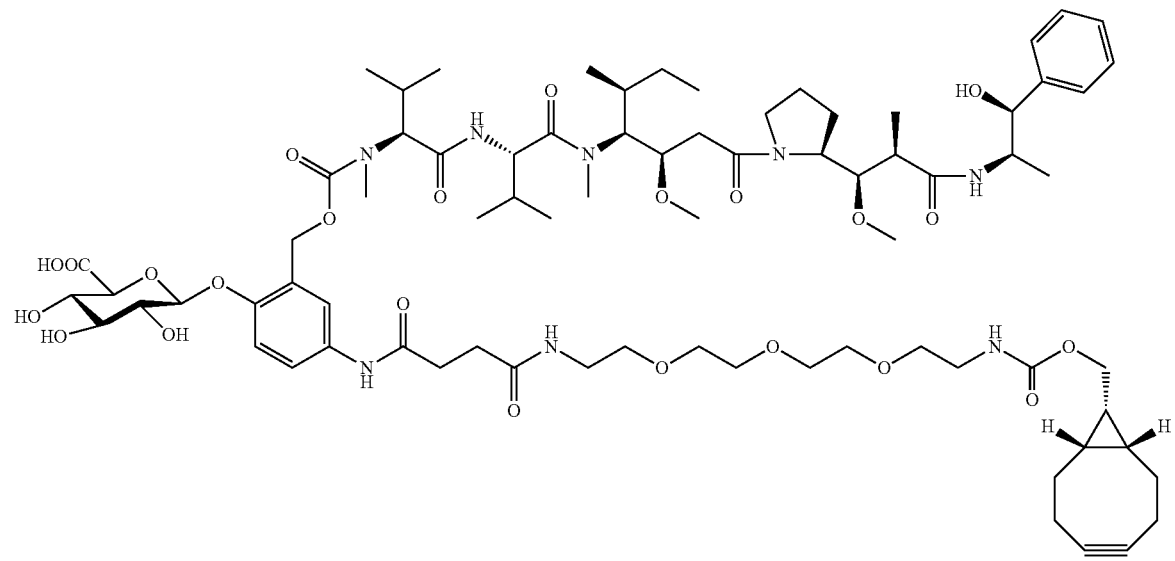
A09
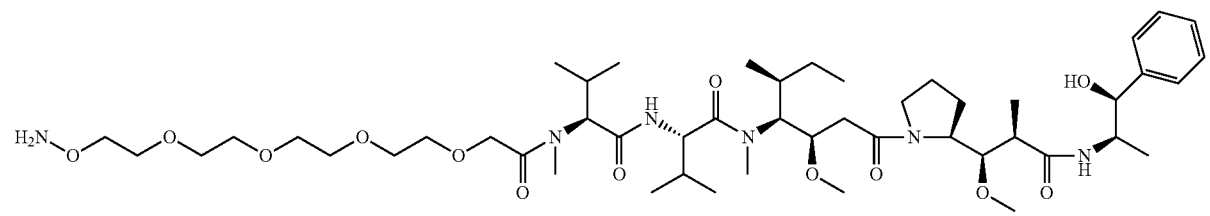 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)COCCOCCOCCOCCON)C(C)C]
A10

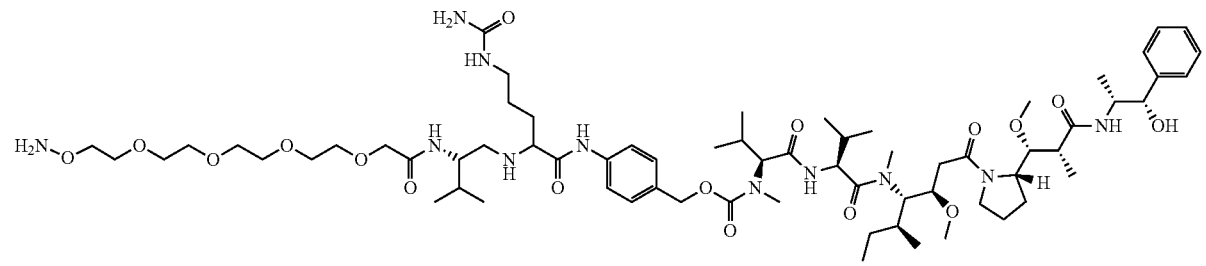
A11
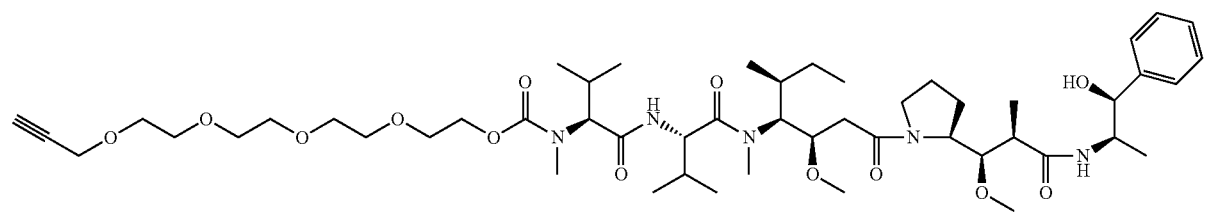 [SMILES: C#CCOCCOCCOCCOCCOC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]
A12
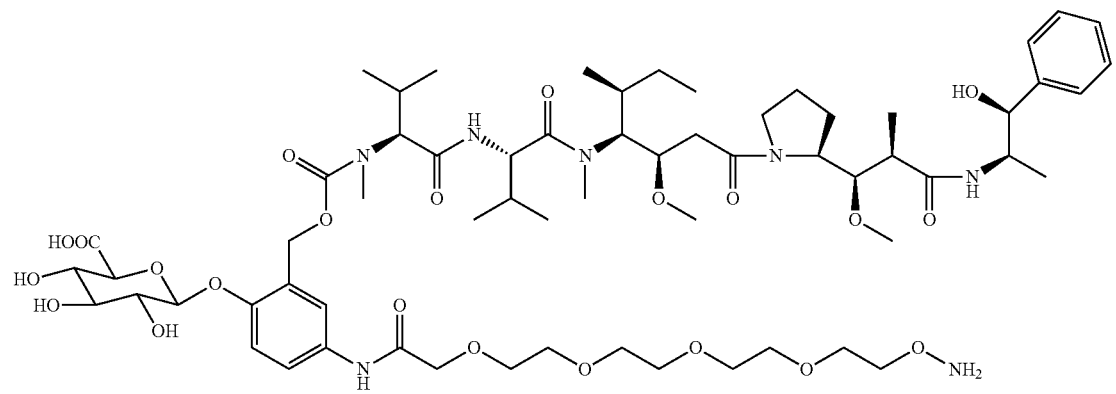 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1cc(NC(=O)COCCOCCOCCOCCON)ccc1OC1OC(C(=O)O)C(O)C(O)C1O)C(C)C]
A13
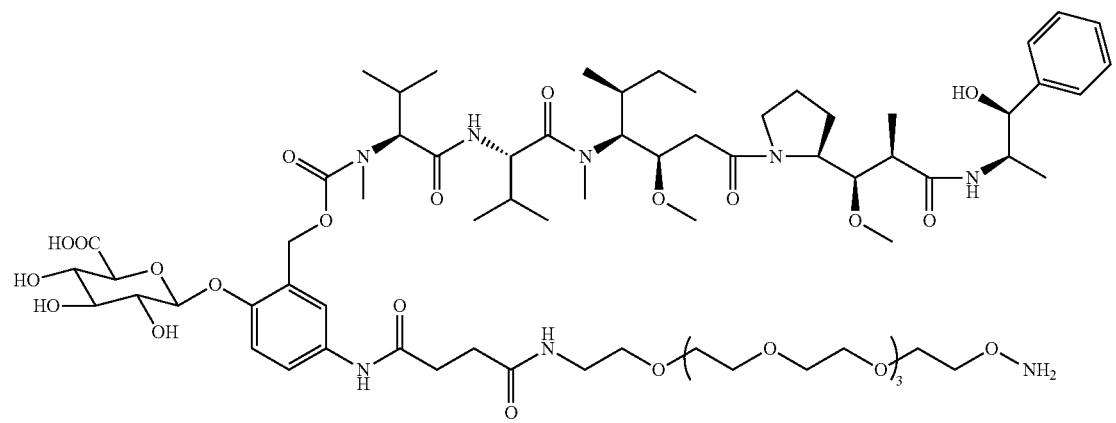
A14

A15
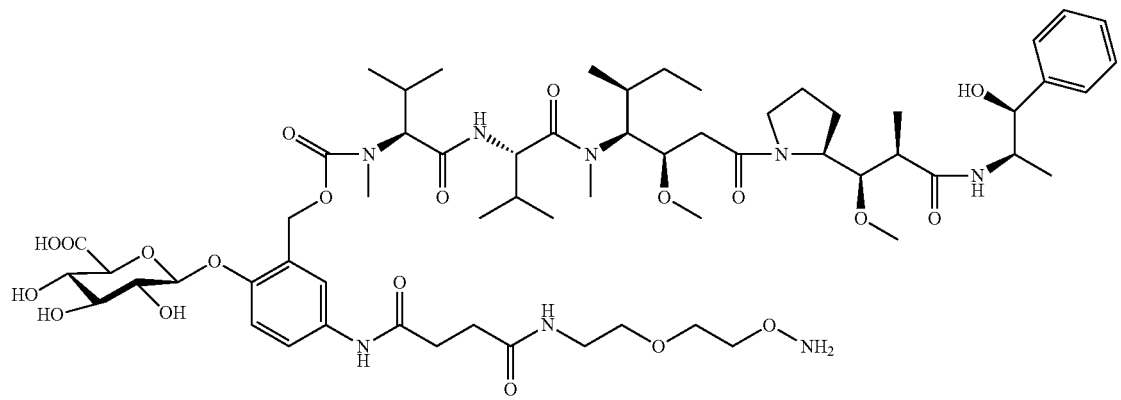
A16
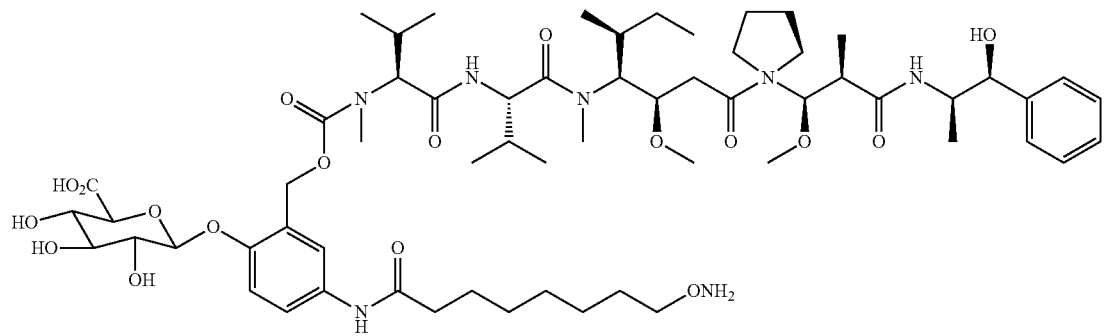
A17
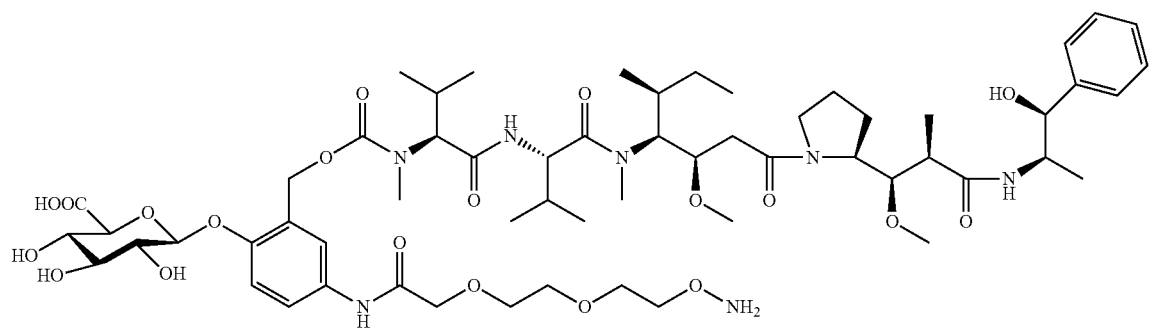
A18
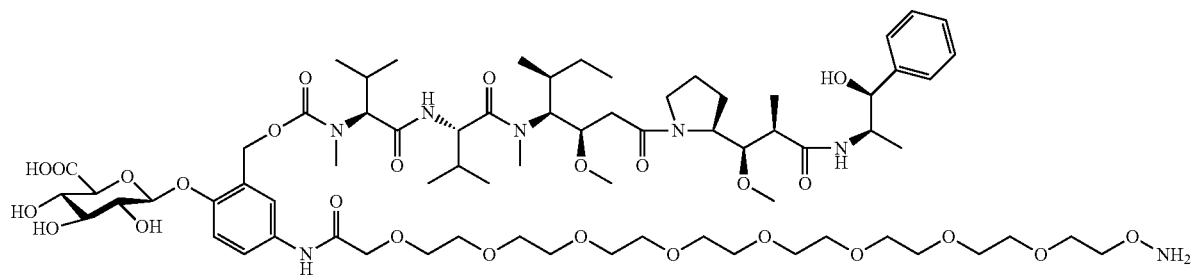

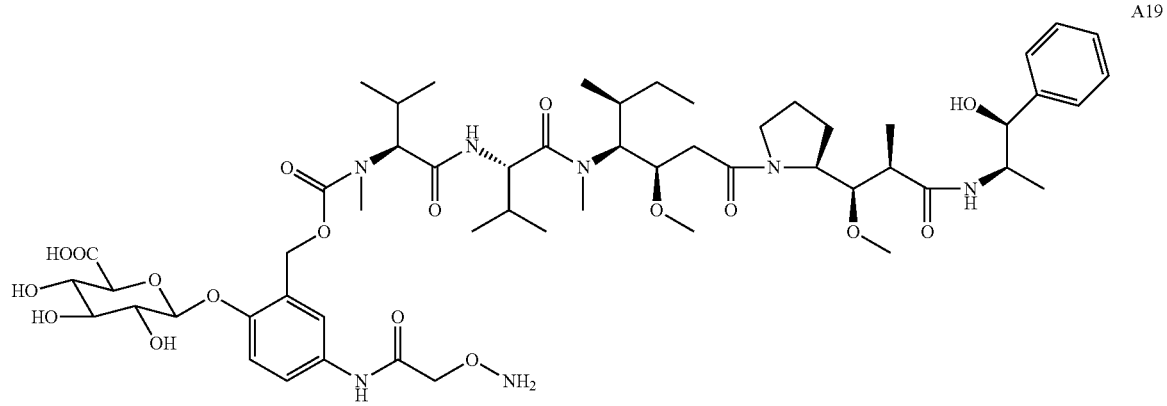
A19
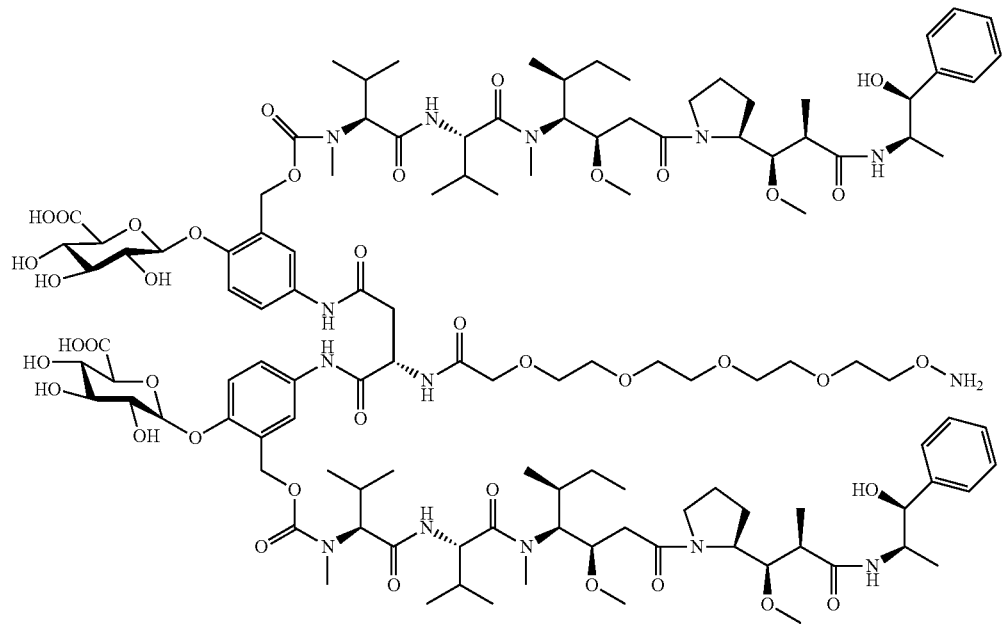
A20
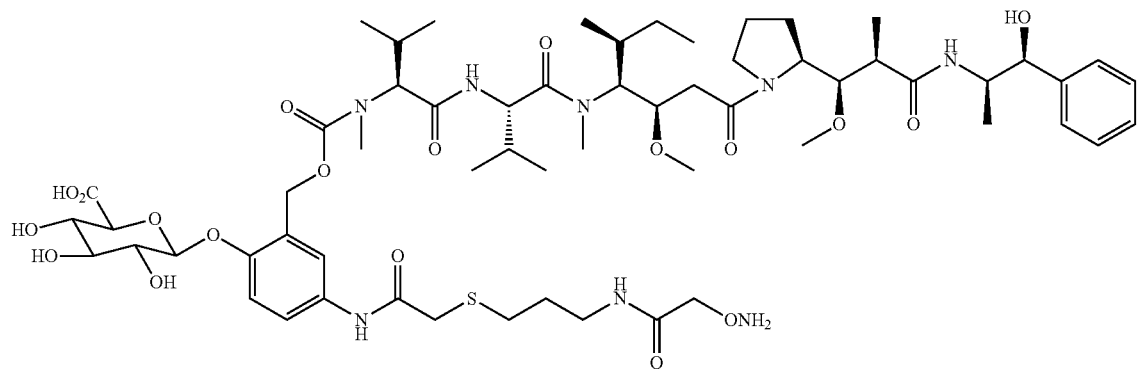
A21

-continued

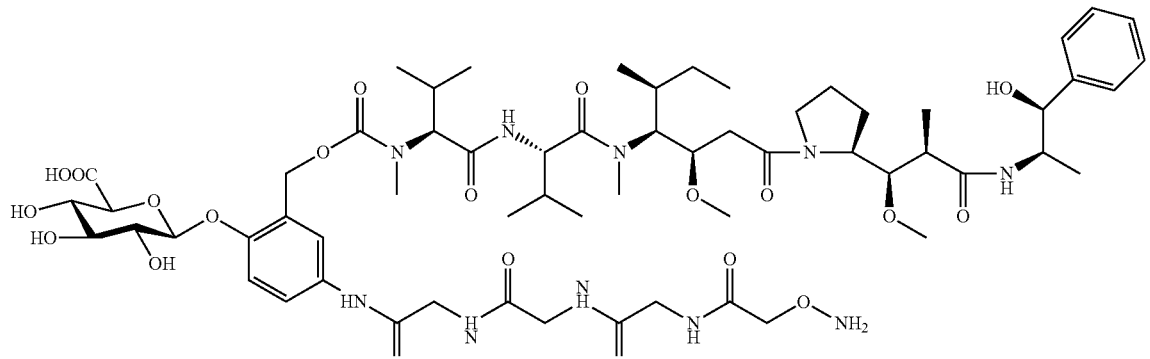

A22

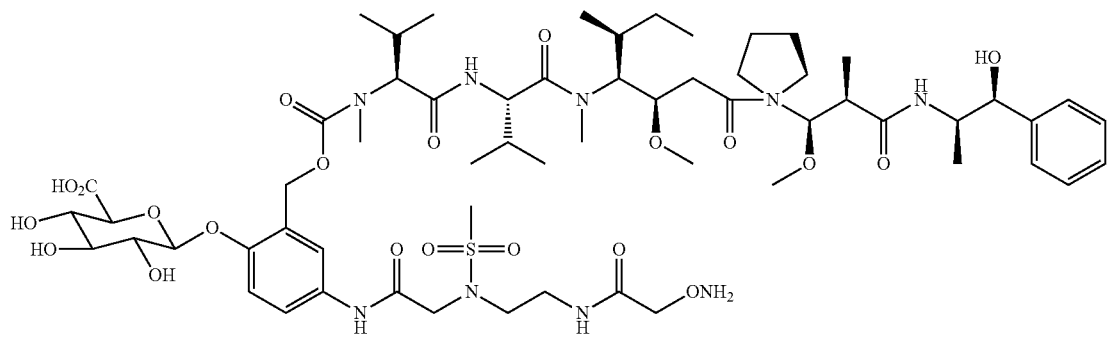

A23

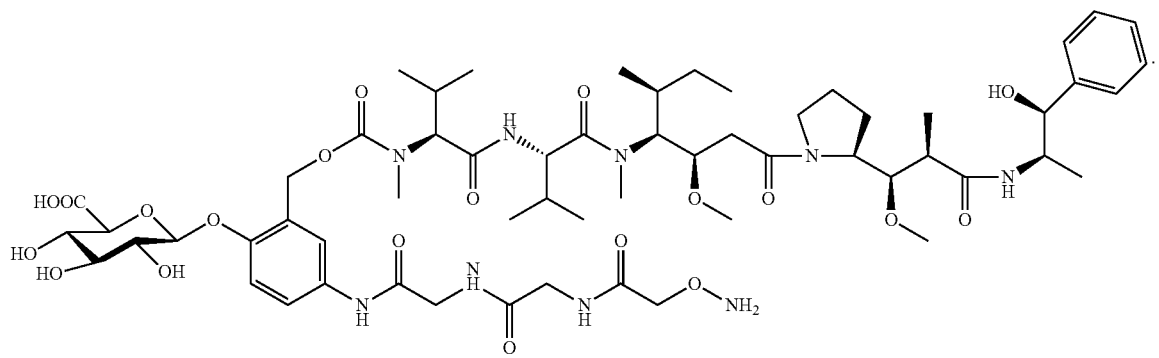

A24

6. A method for treating cancer, comprising administering to a subject in need thereof a composition comprising the antibody-drug conjugate according to claim 1.

7. The method according to claim 6, wherein the cancer is brain, lung, breast, oral, esophageal, stomach, liver, bile duct, pancreatic, colon, kidney, gastric, cervical, ovarian, or prostate cancer.

8. The method according to claim 7, wherein the cancer is breast cancer or gastric cancer.

* * * * *